(12) United States Patent
Zhou et al.

(10) Patent No.: US 9,670,231 B2
(45) Date of Patent: Jun. 6, 2017

(54) FUSED TRICYCLIC AMIDE COMPOUNDS AS MULTIPLE KINASE INHIBITORS

(71) Applicant: BEIGENE, LTD., Camana Bay, KY (US)

(72) Inventors: Changyou Zhou, Princeton, NJ (US); Gouliang Zhang, Beijing (CN)

(73) Assignee: BeiGene, Ltd., Grand Cayman (KY)

( * ) Notice: Subject to any disclaimer, the term of this patent is extended or adjusted under 35 U.S.C. 154(b) by 0 days.

(21) Appl. No.: 14/901,556

(22) PCT Filed: Jun. 27, 2014

(86) PCT No.: PCT/CN2014/080986
§ 371 (c)(1),
(2) Date: Dec. 28, 2015

(87) PCT Pub. No.: WO2014/206344
PCT Pub. Date: Dec. 31, 2014

(65) Prior Publication Data
US 2016/0159820 A1 Jun. 9, 2016

(30) Foreign Application Priority Data
Jun. 28, 2013 (WO) ............... PCT/CN2013/078317

(51) Int. Cl.
*C07D 519/00* (2006.01)
*C07D 405/12* (2006.01)
*C07D 471/04* (2006.01)
*C07D 498/04* (2006.01)

(52) U.S. Cl.
CPC ......... *C07D 519/00* (2013.01); *C07D 405/12* (2013.01); *C07D 471/04* (2013.01); *C07D 498/04* (2013.01)

(58) Field of Classification Search
CPC .. C07D 519/00; C07D 405/12; C07D 471/04; C07D 498/04
See application file for complete search history.

(56) References Cited

U.S. PATENT DOCUMENTS

2010/0197924 A1   8/2010   Gould et al.

FOREIGN PATENT DOCUMENTS

| WO | WO 02/070516 A2 | 9/2002 |
|----|---|---|
| WO | WO 2004/021969 A2 | 3/2004 |
| WO | WO 2005/062795 A2 | 7/2005 |
| WO | WO 2006/066913 A2 | 6/2006 |
| WO | WO 2007/067444 A1 | 6/2007 |
| WO | WO 2007/136572 A2 | 11/2007 |
| WO | WO 2008/028617 A1 | 3/2008 |
| WO | WO 2008/079906 A1 | 7/2008 |
| WO | WO 2008/079909 A1 | 7/2008 |
| WO | WO 2009/012283 A1 | 1/2009 |
| WO | WO 2010/064722 A1 | 6/2010 |
| WO | WO 2011/092088 A1 | 8/2011 |
| WO | WO 2013/097224 | 7/2013 |
| WO | WO 2014/206343 A1 | 12/2014 |
| WO | WO 2014/206344 A1 | 12/2014 |

OTHER PUBLICATIONS

International Search Report and Written Opinion for International Application No. PCT/CN2014/080986, mailed Sep. 30, 11 pages.
International Preliminary Report on Patentability for International Application No. PCT/CN2014/080986, mailed Dec. 29, 2015, 8 pages.
International Search Report and Written Opinion for International Application No. PCT/CN2014/080983, mailed Oct. 9, 2014, 12 pages.
International Preliminary Report on Patentability for Internatonal Application No. PCT/CN2014/080983, mailed Dec. 29, 2015, 8 pages.
Supplementary European Search Report for European Application No. 14818636.4, mailed Jan. 10, 2017, 4 pages.
Supplementary European Search Report for European Application No. 14816633.3, mailed Nov. 7, 2016, 4 pages.

*Primary Examiner* — Rebecca Anderson
(74) *Attorney, Agent, or Firm* — Cooley LLP

(57) ABSTRACT

Provided are fused tricyclic amide compounds, pharmaceutical compositions comprising at least one such fused tricyclic compound, processes for the preparation thereof, and the use thereof in therapy. Disclosed herein are certain tricyclic amide compounds that can be useful for inhibiting multiple (specifically BRAF and/or EGFR-T790M) kinases and for treating disorders mediated thereby.

37 Claims, No Drawings

FUSED TRICYCLIC AMIDE COMPOUNDS AS MULTIPLE KINASE INHIBITORS

CROSS-REFERENCE TO RELATED APPLICATION

This application is a U.S. National Stage Application under 35 U.S.C. 371 of International Application No. PCT/CN2014/080986, filed on Jun. 27, 2014 and entitled "FUSED TRICYCLIC AMIDE COMPOUNDS AS MULTIPLE KINASE INHIBITORS", which claims the benefit of priority to International Application No. PCT/CN2013/078317, filed Jun. 28, 2013.

Disclosed herein are fused tricyclic amide compounds, pharmaceutical compositions comprising at least one such fused tricyclic amide compound, processes for the preparation thereof, and the use thereof in therapy. Disclosed herein are certain tricyclic amide compounds that can be useful for inhibiting multiple (specifically BRAF and/or EGFR-T790M) kinases and for treating disorders mediated thereby.

The EGFR/RAF/MEK/ERK pathway is of interest for cell survival, growth, proliferation and tumorigenesis (Zebisch et al., Curr Med Chem. 14(5): 601-623, 2007; Roberts and Der, Oncogene 26 (22): 3291-3310, 2007; Montagut and Settleman, Cancer Lett. 283(2): 125-134, 2009). Stimulation of the EGFR/RAF/MEK/ERK signal transduction pathway may occur after binding of a ligand to the membrane-bound receptor tyrosine kinase. GTP-bound RAS can be activated, which can subsequently promote the activation of the Raf family proteins (A-Raf, B-Raf and Rafl, formerly known as C-Raf) (Wellbrock et al., Nat. Rev. Mol. Cell Biol. 5: 875-885, 2004). Mutations in various RAS GTPases and B-Raf kinase in the EGFR/RAF/MEK/ERK signal pathway have been reported to constitutively activate the MAPK pathway, resulting in increased cell division and survival (Bos, Cancer Res. 49: 4682-4689, 1989; Hoshino et al., Oncogene. 18(3): 813-822, 1999). For example, B-Raf mutations are reportedly found in a large percentage of human melanomas and thyroid cancers (Davies et al., Nature 417: 949-954, 2002) (Cohen et al., J. Nat. Cancer Inst. 95(8): 625-627, 2003; Kimura et al., Cancer Res. 63(7): 1454-1457, 2003; Pollock and Meltzer, Cancer Cell 2: 5-7, 2002). In addition, lower, but still significant frequency of B-Raf mutations have been reported in Barret's adenocarcinoma (Garnett et al., Cancer Ce116:313-319, 2004; Sommerer et al., Oncogene 23(2): 554-558, 2004), breast cancer (Davies et al., Nature 417: 949-954, 2002), cervical cancer (Moreno-Bueno et al., Clin. Cancer Res. 12(12): 365-3866, 2006), cholangiocarcinoma (Tannapfel et al., Gut. 52(5): 706-712, 2003), glioblastoma (Knobbe et al., Acta Neuropathol. (Berl.). 108(6): 467-470, 2004), colorectal cancer (Yuen et al., Cancer Res. 62(22): 6451-6455, 2002; Davies et al., Nature 417: 949-954, 2002), gastric cancer (Lee et al., Oncogene 22(44): 6942-6945), lung cancer (Brose et al., Cancer Res. 62(23): 6997-7000, 2002), ovarian cancer (Russell and McCluggage, J. Pathol. 203(2): 617-619, 2004; Davies et al., Nature 417: 949-954, 2002), pancreatic cancer (Ishimura et al., Cancer Lett. 199(2): 169-173, 2003), prostate cancer (Cho et al., Int. J. Cancer. 119(8): 1858-1862, 2006), and hematologic cancers (Garnett and Marais, Cancer Cell 6: 313-319, 2004). These reports suggest that B-Raf is one of the most frequently mutated genes in human cancers. B-Raf kinase can represent an excellent target for anticancer therapy based on preclinical target validation, epidemiology and drugability.

Inhibitors of Raf kinases have been discussed for use in disruption of tumor cell growth and hence in the treatment of cancers, e.g. melanoma, colorectal cancer including large intestinal colon carcinoma, histiocytic lymphoma, lung adenocarcinoma, small cell lung cancer, and pancreatic and breast carcinoma (Crump, Current Pharmaceutical Design 8: 2243-2248, 2002; Sebastien et al., Current Pharmaceutical Design 8: 2249-2253, 2002), and/or in the treatment or prophylaxis of disorders associated with neuronal degeneration resulting from ischemic events, including cerebral ischemia after cardiac arrest, stroke and multi-infarct dementia. Inhibitors of Raf kinases have also been discussed for use after cerebral ischemic events such as those resulting from head injury, surgery and/or during childbirth (York et al., Mol. and Cell. Biol. 20(21): 8069-8083, 2000; Chin et al., Neurochem. 90: 595-608, 2004), as well as in polycystic kidney disease (Nagao et al., Kidney Int. 63(2): 427-437, 2003).

In addition, certain hyperproliferative disorders may be characterized by the over activation of Raf kinase functions, for example, by mutations or over expression of the protein. Accordingly, inhibitors of Raf kinases can be useful in the treatment of hyperproliferative disorders, such as cancer.

Small molecule inhibitors of B-Raf kinases are being developed for anticancer therapy. Nexavar® (sorafenib tosylate) is a multikinase inhibitor, which includes inhibition of B-Raf kinases, and is approved for the treatment of patients with advanced renal cell carcinoma and unresectable hepatocellular carcinoma. More selective smal molecule inhibitors of B-Raf kinases such as venumrafenib and dabrafenib have recently approved for the treatment of patients with metastatic melanoma with B-Raf V600E mutations. Other Raf inhibitors have also been disclosed or have entered clinical trials, for example SB-590885, RAF-265, PLX-4032, GSK2118436 and XL-281.

Other B-Raf inhibitors are also known. See, for example, U.S. Patent Application Publication 2006/0189627, U.S. Patent Application Publication 2006/0281751, U.S. Patent Application Publication 2007/0049603, International Patent Application Publication WO 2007/002325, International Patent Application Publication WO 2007/002433, International Patent Application Publication WO 03/068773, International Patent Application Publication WO 2007/013896, International Patent Application Publication WO 2011/097526, International Patent Application Publication WO 2011/117382 and International Patent Application Publication WO2012/118492.

Certain nitrogen-containing heteroaryl-substituted aryl bicyclic compounds have been identified as Raf inhibitors. See, for example, International Patent Application Publication WO 2007/067444 and U.S. Patent Application Publication 2010/0197924.

Certain Raf kinase inhibitors have also been identified. See, for example, International Patent Application Publication WO 2005/062795, International Patent Application Publication WO 2008/079906, International Patent Application Publication WO 2008/079909, International Patent Application Publication WO 2006/066913, International Patent Application Publication WO 2008/028617, International Patent Application Publication WO 2009/012283, International Patent Application Publication WO 2010/064722 and International Patent Application Publication WO 2011/092088.

Despite the enormous success has been achieved in the treatment of Braf-V600E mutant melanoma with the recently approved Braf inhibitors such as vemurafenib and dabrafenib, the treatment of Braf-V600E mutant CRCs with Braf inhibitors has been elusive. In a study published in 2012, investigators conducted a synthetic lethal screen of BRAF-mutant colorectal cancer cells that were resistant to vemurafenib and ultimately revealed that BRAF inhibition by vemurafenib caused rapid feedback activation of epidermal growth factor receptor (EGFR), which supported continued proliferation in the presence of BRAF inhibition (Prahallad A, et al, Nature 483:100-103, 2012). The researchers showed that if you suppressed EGFR with cetuximab, erlotinib (Tarceva), or gefitinib (Iressa), added to vemurafanib, BRAF-mutant colorectal cancer was inhibited in both in vitro and in vivo models, suggesting that combination therapy with BRAF and EGFR inhibitors may be more effective in this patient population. This was corroborated by another group, which showed that the combination of vemurafenib and erlotinib led to tumor regression in colorectal cancer cell line xenografts and reduction of the proliferative marker Ki67 (Corcoran R B, et al, Cancer Discovery 3:227-235, 2012).

Data are becoming consistent, therefore, that EGFR or other receptor tyrosine kinases may mediate resistance to vemurafenib, and that combinations with an EGFR or MEK inhibitor may produce greater suppression of tumor growth.

Many human tumors are characterized by hyperactivity of protein kinases. The inhibition of these enzymes has been established as a cancer treatment in recent years. Given the great success of this therapeutic strategy, the search for additional protein kinase inhibitors is one of the major research topics in the oncology drug development area (S. Grant, Cell. Mol. Life Sci. 66 (2009) 1163-1177; J. Zhang, P. Yang, N. Gray, Nat. Rev. Cancer 9 (2009) 28-39). While in the beginning of the protein kinase inhibitor era selectivity towards a single target enzyme appeared desirable, it is now generally accepted that inhibiting more than one tumor-related protein kinase at a time offers the advantage of hitting the tumour in multiple aspects (L. Gossage, T. Eisen, Clin. Cancer Res. 16 (2010) 1973-1978; A. Petrelli, S. Giordano, Curr. Med. Chem. 15 (2008) 422-432). Among other advantages, the aspecificity of drugs targeting several kinases may lead to a lower risk of drug-resistance development (L. Gossage, T. Eisen, Clin. Cancer Res. 16 (2010) 1973-1978; A. Petrelli, S. Giordano, Curr. Med. Chem. 15 (2008) 422-432). Multikinase inhibitors launched recently as anticancer drugs comprise sunitinib (D. B. Mendel, et al, Clin. Cancer Res. 9 (2003) 327-337), sorafenib (S. Wilhelm, et al, Nat. Rev. Drug Discov. 5 (2006) 835-844) and dasatinib (Yeatman T J, Nat Rev Cancer 2004; 4:470-480). Albeit namely the latter was reported as an inhibitor of human protein kinases with high promiscuity, the undesired side effects of the drug are tolerable.

A single compound which inhibits a combination of several targets, such as RAFs and EGFRs (in particular EGFR-T790M), offer the advantage of inhibiting a combination of several signal transduction pathways, thereby interfering with several oncogenic processes, while making the treatment easier and improving the patients comfort. It would be desirable to generate small molecule kinase inhibitor molecules able to simultaneously inhibit RAFs and EGFRs (in particular EGFR-T790M).

By combining a dual inhibitory activity, such as RAFs and EGFRs (in particular EGFR-T790M), in a single molecule, the advantage resides in (i) reducing the risks related to off-target toxicity encountered when two or more different kinase inhibitors targeting RAFs and EGFRs (in particular EGFR-T790M) are administered, (ii) reducing the costs of treatment, (iii) increasing the patients compliance.

Accordingly, the present invention aims to provide compounds which simultaneously inhibit several key signal transduction pathways.

Disclosed herein are compounds that can inhibit multiple kinases, such as RAFs and/or EGFR-T790M kinases. Provided is at least one compound selected from compounds of Formula I:

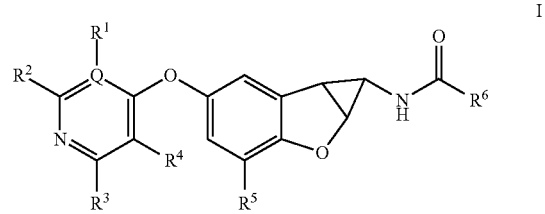

stereoisomers thereof, and pharmaceutically acceptable salts thereof,
wherein:
Q is selected from C and N;
$R^1$, $R^2$, $R^3$ and $R^4$ which may be the same or different, are each selected from hydrogen, halogen, haloalkyl, alkyl, alkenyl, cycloalkyl, aryl, heterocyclyl, heteroaryl, alkynyl, —CN, —NR$^{10}$R$^{11}$, —OR$^{10}$, —COR$^{10}$, —CO$_2$R$^{10}$, —CONR$^{10}$R$^{11}$, —C(=NR$^{10}$)NR$^{11}$R$^{12}$, —NR$^{10}$COR$^{11}$, —NR$^{10}$CONR$^{11}$R$^{12}$, —NR$^{10}$CO$_2$R$^{11}$, —SO$_2$R$^{10}$, —NR$^{10}$SO$_2$NR$^{11}$R$^{12}$, and —NR$^{10}$SO$_2$R$^{11}$, wherein the alkyl, alkenyl, alkynyl, cycloalkyl, heteroaryl, aryl, and heterocyclyl are optionally substituted with at least one substituent $R^{13}$, or ($R^1$ and $R^2$), and/or ($R^3$ and $R^4$), together with the ring to which they are attached, form a fused ring selected from heterocyclyl, and heteroaryl rings optionally substituted with at least one substituent $R^{14}$; provided that $R^1$ is absent when Q is N;
$R^5$ is selected from hydrogen, halogen and CH$_3$;
$R^6$ is selected from haloalkyl, alkyl, alkenyl, cycloalkyl, aryl, heterocyclyl, heteroaryl, alkynyl, wherein the alkyl, alkenyl, cycloalkyl, heteroaryl, aryl, and heterocyclyl are optionally substituted with at least one substituent $R^{15}$;
$R^{10}$, $R^{11}$, $R^{12}$, $R^{13}$ and $R^{14}$ are each selected from hydrogen, halogen, haloalkyl, alkyl, alkenyl, cycloalkyl, aryl, heteroaryl, heterocyclyl, alkynyl, oxo, —CN, —OR', —NR'R'', —COR', —CO$_2$R', —CONR'R'', —C(=NR') NR''R''', —NR'COR'', —NR'CONR'R'', —NR'CO$_2$R'', —SO$_2$R', —SO$_2$aryl, —NR'SO$_2$NR''R''', and NR'SO$_2$R'', wherein R', R'', and R''' are independently selected from H, haloalkyl, alkyl, alkenyl, alkynyl, cycloalkyl, heterocyclyl, aryl, and heteroaryl, or (R' and R''), and/or (R'' and R''') together with the atoms to which they are attached, form a ring selected from heterocyclyl, and heteroaryl rings;
$R^{15}$ is selected from hydrogen, halogen, haloalkyl, alkyl, cycloalkyl, aryl, heteroaryl, heterocyclyl, —CN, —OR', —O—(CH$_2$)$_{0-2}$-(heterocyclyl), —NR'R'', CH$_2$NR'R'', C(Me)$_2$NR'R'', CH$_2$<CNR'R'' (i.e.

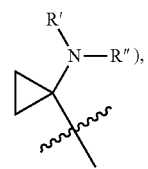

wherein R' and R'' are independently selected from H, haloalkyl, alkyl, cycloalkyl, heterocyclyl, aryl, and heteroaryl, or (R' and R'') together with the atoms to which they are attached, form a ring selected from heterocyclyl, and heteroaryl rings, wherein any of the alkyl, cycloalkyl, aryl, heteroaryl and heterocyclyl groups in $R^{15}$, R' and R" is optionally substituted.

Also provided is a pharmaceutical composition comprising at least one pharmaceutically acceptable carrier and at least one compound selected from compounds of Formula (I), stereoisomers thereof, and pharmaceutically acceptable salts thereof described herein.

Also provided is a method of treating cancer responsive to inhibition of Raf kinas comprising administering to a subject in need of treating for such cancer an amount of at least one compound selected from compounds of Formula (I), stereoisomers thereof, and pharmaceutically acceptable salts thereof described herein effective to treat the cancer.

Also provided is a use of at least one compound selected from compounds of Formula (I), stereoisomers thereof, and pharmaceutically acceptable salts thereof described herein in manufacture of a medicament for inhibiting multiple (specifically EGFR-T790M) kinases.

Also provided is a use of at least one compound selected from compounds of Formula (I), stereoisomers thereof, and pharmaceutically acceptable salts thereof described herein in the manufacture of a medicament for treating cancer.

As used herein, the following words, phrases and symbols are generally intended to have the meanings as set forth below, except to the extent that the context in which they are used indicates otherwise. The following abbreviations and terms have the indicated meanings throughout:

The term "alkyl" herein refers to a hydrocarbon group selected from linear and branched saturated hydrocarbon groups comprising from 1 to 18, such as from 1 to 12, further such as from 1 to 6, carbon atoms. Examples of the alkyl group can be selected from methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group can be selected from 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$) and 3,3-dimethyl-2-butyl (—$CH(CH_3)C(CH_3)_3$ groups.

The term "alkenyl" herein refers to a hydrocarbon group selected from linear and branched hydrocarbon groups comprising at least one C=C double bond and from 2 to 18, such as from 2 to 6, carbon atoms. Examples of the alkenyl group may be selected from ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as from 2 to 6, carbon atoms. Examples of the alkynyl group include ethynyl (—C≡CH), 1-propynyl (—C≡$CCH_3$), 2-propynyl (propargyl, —$CH_2$C≡CH), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as 3 to 8, further such as 3 to 6, 3 to 5, or 3 to 4 carbon atoms. Even further for example, the cycloalkyl group may be selected from monocyclic group comprising from 3 to 12, such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "Aryl" herein refers to a group selected from:
5- and 6-membered carbocyclic aromatic rings, for example, phenyl;
bicyclic ring systems such as 7 to 12 membered bicyclic ring systems wherein at least one ring is carbocyclic and aromatic, selected, for example, from naphthalene, indane, and 1,2,3,4-tetrahydroquinoline; and
tricyclic ring systems such as 10 to 15 membered tricyclic ring systems wherein at least one ring is carbocyclic and aromatic, for example, fluorene.

For example, the aryl group is selected from 5 and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" herein refers to F, Cl, Br or I.

The term "heteroaryl" herein refers to a group selected from:
5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;

8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In the group comprising a wavy line, such as

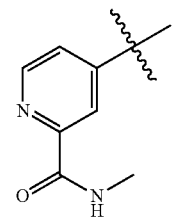

the wavy line indicates the point of attachment.

Compounds described herein may contain an asymmetric center and may thus exist as enantiomers. Where the compounds described herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoiosomer(s).

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)_n$—COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "pharmaceutically acceptable salts thereof" include salts of at least one compound of Formulae I and II, and salts of the stereoisomers of at least one compound of Formulae I and II, such as salts of enantiomers, and/or salts of diastereomers.

"Treating," "treat," or "treatment" or "alleviation" refers to administering at least one compound and/or at least one stereoisomer thereof, and/or at least one pharmaceutically acceptable salt thereof disclosed herein to a subject in recognized need thereof that has, for example, cancer.

The term "effective amount" refers to an amount of at least one compound and/or at least one stereoisomer thereof, and/or at least one pharmaceutically acceptable salt thereof disclosed herein effective to "treat," as defined above, a disease or disorder in a subject.

The term "at least one substituent" disclosed herein includes, for example, from 1 to 4, such as from 1 to 3, further as 1 or 2, substituents, provided that the valency allows. For example, "at least one substituent $R^{13}$" disclosed herein includes from 1 to 4, such as from 1 to 3, further as 1 or 2, substituents selected from the list of $R^{13}$ as described herein.

Provided is at least one compound selected from compounds of Formula I:

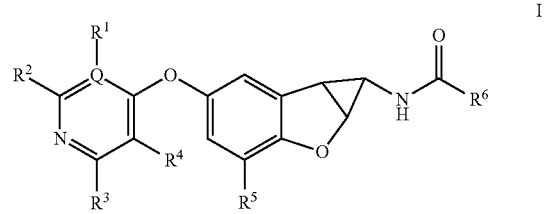

stereoisomers thereof, and pharmaceutically acceptable salts thereof, wherein:

Q is selected from C and N;

R¹, R², R³ and R⁴ which may be the same or different, are each selected from hydrogen, halogen, haloalkyl, alkyl, alkenyl, cycloalkyl, aryl, heterocyclyl, heteroaryl, alkynyl, —CN, —NR¹⁰R¹¹, —OR¹⁰, —COR¹⁰, —CO₂R¹⁰, —CONR¹⁰R¹¹, —C(=NR¹⁰)NR¹¹R¹², —NR¹⁰COR¹¹, —NR¹⁰CONR¹¹R¹², —NR¹⁰CO₂R¹¹, —SO₂R¹⁰, —NR¹⁰SO₂NR¹¹R¹², and —NR¹⁰SO₂R¹¹, wherein the alkyl, alkenyl, alkynyl, cycloalkyl, heteroaryl, aryl, and heterocyclyl are optionally substituted with at least one substituent R¹³, or (R¹ and R²), and/or (R³ and R⁴), together with the ring to which they are attached, form a fused ring selected from heterocyclyl, and heteroaryl rings optionally substituted with at least one substituent R¹⁴; provided that R¹ is absent when Q is N;

R⁵ is selected from hydrogen, halogen and CH₃;

R⁶ is selected from haloalkyl, alkyl, alkenyl, cycloalkyl, aryl, heterocyclyl, heteroaryl, alkynyl, wherein the alkyl, alkenyl, cycloalkyl, heteroaryl, aryl, and heterocyclyl are optionally substituted with at least one substituent R¹⁵;

R¹⁰, R¹¹, R¹², R¹³ and R¹⁴ are each selected from hydrogen, halogen, haloalkyl, alkyl, alkenyl, cycloalkyl, aryl, heteroaryl, heterocyclyl, alkynyl, oxo, —CN, —OR', —NR'R", —COR', —CO₂R', —CONR'R", —C(=NR') NR"R''', —NR'COR", —NR'CONR'R", —NR'CO₂R", —SO₂R', —SO₂aryl, —NR'SO₂NR"R''', and NR'SO₂R", wherein R', R", and R''' are independently selected from H, haloalkyl, alkyl, alkenyl, alkynyl, cycloalkyl, heterocyclyl, aryl, and heteroaryl, or (R' and R"), and/or (R" and R''') together with the atoms to which they are attached, form a ring selected from heterocyclyl, and heteroaryl rings;

R¹⁵ is selected from hydrogen, halogen, haloalkyl, alkyl, cycloalkyl, aryl, heteroaryl, heterocyclyl, —CN, —OR', —O—(CH₂)₀₋₂-(heterocyclyl), —NR'R", CH₂NR'R", C(Me)₂NR'R", CH₂<CNR'R" (i.e.

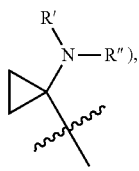

wherein R' and R" are independently selected from H, haloalkyl, alkyl, cycloalkyl, heterocyclyl, aryl, and heteroaryl, or (R' and R") together with the atoms to which they are attached, form a ring selected from heterocyclyl, and heteroaryl rings, wherein any of the alkyl, cycloalkyl, aryl, heteroaryl and heterocyclyl groups in R¹⁵, R' and R" is optionally substituted.

In some embodiments of Formula I, Q is C.

In some embodiments of Formula I, R¹ is H.

In some embodiments of Formula I, R² is H.

In some embodiments of Formula I, both R¹ and R² are H.

In some embodiments of Formula I, R³ is —NR¹⁰R¹¹ or —CONR¹⁰R¹¹.

In some embodiments of Formula I, R⁴ is H.

In some embodiments of Formula I, R³ is —NR¹⁰R¹¹ or —CONR¹⁰R¹¹, and R⁴ is hydrogen.

In some embodiments of Formula I, R¹⁰ and R¹¹ are each selected from H and alkyl (e.g. CH₃).

In some embodiments of Formula I, the moiety

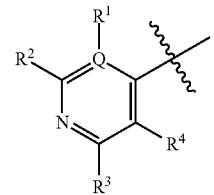

in Formula I is:

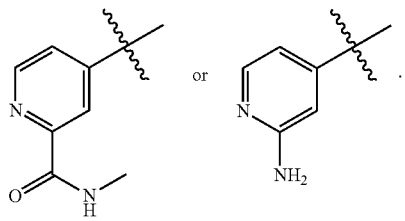 [SMILES: *c1ccnc(C(=O)NC)c1 ; *c1ccnc(N)c1]

In some embodiments of Formula I, R³ and R⁴, together with the ring to which they are attached, form a fused heterocyclyl or heteroaryl ring (e.g. naphthyridinyl, pyridooxazinyl and pyridopyrimidinyl which are optionally hydrogenated and optionally substituted with at least one substituent R¹⁴, such as 1,2,3,4-tetrahydro-[1,8]naphthyridinyl, 1,4-dihydro-2H-pyrido[2,3-d][1,3]oxazinyl and 1,2,3,4-tetrahydro-pyrido[2,3-d]pyrimidinyl which are optionally substituted with at least one substituent R¹⁴).

In some embodiments of Formula I, R¹⁴ is oxo.

In some embodiments of Formula I, R³ and R⁴, together with the ring to which they are attached, form a fused ring selected from:

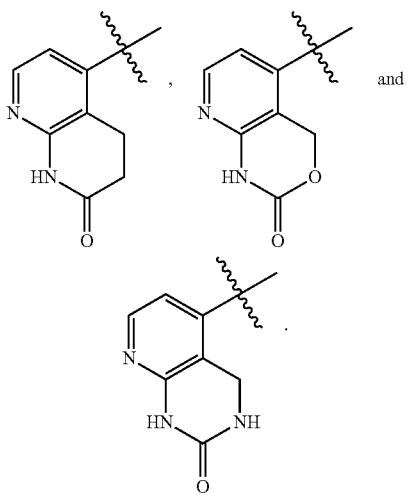

In some embodiments of Formula I, R⁵ is H.

In some embodiments of Formula I, R⁵ is CH₃.

In some embodiments of Formula I, R⁶ is selected from alkyl (e.g. C₁₋₉ alkyl), alkenyl (e.g. vinyl), aryl (e.g. phenyl) and heteroaryl (e.g. a 5- or 6-membered heteroaryl comprising 1, 2 or 3 heteroatoms selected from the group consisting of N, O and S, such as pyridinyl or furanyl), wherein the alkyl, alkenyl, aryl and heteroaryl are optionally substituted with at least one substituent R¹⁵.

In some embodiments of Formula I, R⁶ is phenyl substituted with one, two or three substituent R¹⁵.

In some embodiments of Formula I, R⁶ is heteroaryl, which is a 5- or 6-membered heteroaryl comprising 1, 2 or 3 heteroatoms selected from the group consisting of N, O and S and substituted with one, two or three substituent R¹⁵.

In some embodiments of Formula I, R⁶ is pyridinyl or furanyl substituted with one, two or three substituent R¹⁵.

In some embodiments of Formula I, R¹⁵ is selected from halogen (e.g. F, Cl or Br), haloalkyl (e.g. CF₃), optionally substituted alkyl (e.g. CH₃, HO—CH₂— or NC—C(CH₃)₂—), optionally substituted cycloalkyl (e.g. cyclopropyl optionally substituted with NH₂ or CN), optionally substituted aryl (e.g. phenyl optionally substituted with CF₃), —OR' (e.g. CH₃—O— or —CF₃O—), —O—(CH₂)₀₋₂-(optionally substituted heterocyclyl) (e.g. —O—(CH₂)₀₋₂-(piperazinyl or piperidyl optionally substituted with one or more alkyl groups such as CH₃ or CH₂CH₃)), —NR'R'', CH₂NR'R'' and C(Me)₂NR'R''.

In some embodiments of Formula I, R' and R'' are independently selected from H and alky (e.g. CH₃) and haloalkyl (e.g., CF₃).

In some embodiments of Formula I, (R' and R'') together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a]pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).

In some embodiments of Formula I, (R' and R'') together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.

In some embodiments of Formula I, (R' and R'') together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.

In some embodiments of Formula I, in the definitions of R¹⁵, R' and R'', any of the groups defined with "optionally substituted" is independently and optionally substituted with at least one group selected from HO—, NC—, NH₂, NH(alkyl) (e.g. NH(CH₃)), N(alkyl)₂ (e.g. N(CH₃)₂), haloalkyl (e.g. CF₃ or CF₃CH₂), alkyl (e.g. CH₃ or CH₃CH₂), HO-alkyl- (e.g. HO—CH₂CH₂—) and alkyl-heterocyclyl- (e.g., CH₃CH₂-piperidyl-) and heterocyclylidin (e.g. piperidinylidene or piperidin-4-ylidene).

In some embodiments of Formula I, the compound is in the following configuration:

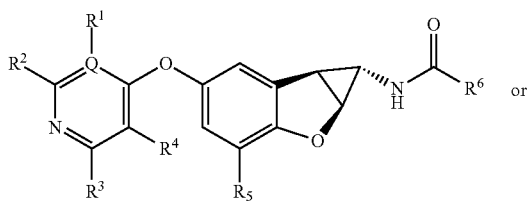

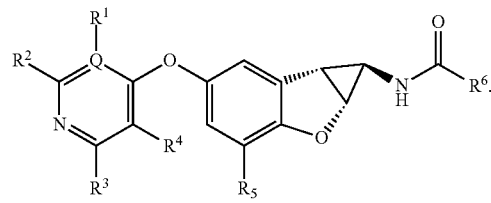

In some embodiments of Formula I, the compound has Formula Ia:

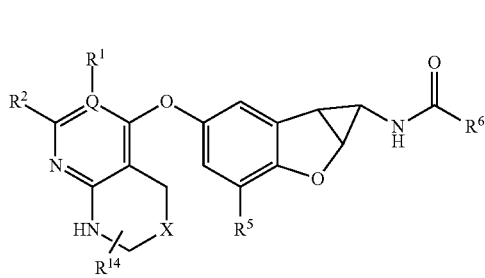

Ia stereoisomers thereof, and pharmaceutically acceptable salts thereof, wherein X is selected from the group consisting of C(R¹⁶)₂, N(R¹⁶) and O;

R¹⁶ is selected from the group consisting of H and alkyl; and

R¹, R², R⁵, R⁶ and R¹⁴ are defined as in the above Formula I.

In some embodiments of Formula Ia, Q is C.

In some embodiments of Formula Ia, R¹ is H.

In some embodiments of Formula Ia, R² is H.

In some embodiments of Formula Ia, both R¹ and R² are H.

In some embodiments of Formula Ia, X is C(R¹⁶)₂.

In some embodiments of Formula Ia, X is CH.

In some embodiments of Formula Ia, X is N(R¹⁶).

In some embodiments of Formula Ia, X is NH.

In some embodiments of Formula Ia, X is O.

In some embodiments of Formula Ia, R¹⁴ is oxo.

In some embodiments of Formula Ia, the moiety

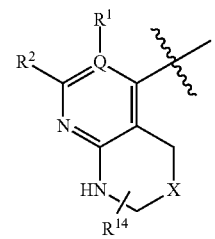

in Formula Ia is:

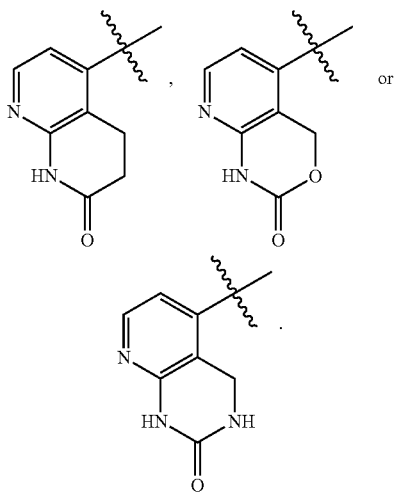

In some embodiments of Formula Ia, $R^5$ is H.

In some embodiments of Formula Ia, $R^5$ is $CH_3$.

In some embodiments of Formula Ia, $R^6$ is selected from alkyl (e.g. $C_{1-9}$ alkyl), alkenyl (e.g. vinyl), aryl (e.g. phenyl) and heteroaryl (e.g. a 5- or 6-membered heteroaryl comprising 1, 2 or 3 heteroatoms selected from the group consisting of N, O and S, such as pyridinyl or furanyl), wherein the alkyl, alkenyl, aryl and heteroaryl are optionally substituted with at least one substituent $R^{15}$.

In some embodiments of Formula Ia, $R^6$ is phenyl substituted with one, two or three substituent $R^{15}$.

In some embodiments of Formula Ia, $R^6$ is heteroaryl, which is a 5- or 6-membered heteroaryl comprising 1, 2 or 3 heteroatoms selected from the group consisting of N, O and S and substituted with one, two or three substituent $R^{15}$.

In some embodiments of Formula Ia, $R^6$ is pyridinyl or furanyl substituted with one, two or three substituent $R^{15}$.

In some embodiments of Formula Ia, $R^{15}$ is selected from halogen (e.g. F, Cl or Br), haloalkyl (e.g. $CF_3$), optionally substituted alkyl (e.g. $CH_3$, $HO-CH_2-$ or $NC-C(CH_3)_2-$), optionally substituted cycloalkyl (e.g. cyclopropyl optionally substituted with $NH_2$ or CN), optionally substituted aryl (e.g. phenyl optionally substituted with $CF_3$), —OR' (e.g. $CH_3-O-$ or $CF_3-O-$), —O—$(CH_2)_{0-2}$-(optionally substituted heterocyclyl) (e.g. —O—$(CH_2)_{0-2}$-(piperazinyl or piperidyl optionally substituted with one or more alkyl group such as $CH_3$ and $CH_2CH_3$)), —NR'R", $CH_2NR'R"$ and $C(Me)_2NR'R"$.

In some embodiments of Formula Ia, R' and R" are independently selected from H and alky (e.g. $CH_3$) and haloalkyl (e.g., $CF_3$).

In some embodiments of Formula Ia, (R' and R") together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a]pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).

In some embodiments of Formula Ia, (R' and R") together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.

In some embodiments of Formula Ia, (R' and R") together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.

In some embodiments of Formula Ia, in the definitions of $R^{15}$, R' and R", any of the groups defined with "optionally substituted" is independently and optionally substituted with at least one group selected from HO—, NC—, $NH_2$, NH(alkyl) (e.g. $NH(CH_3)$), $N(alkyl)_2$ (e.g. $N(CH_3)_2$), haloalkyl (e.g. $CF_3$ or $CF_3CH_2$), alkyl (e.g. $CH_3$ or $CH_3CH_2$), HO-alkyl- (e.g. $HO-CH_2CH_2-$) and alkyl-heterocyclyl- (e.g., $CH_3CH_2$-piperidyl-) and heterocyclylidin (e.g. piperidinylidene or piperidin-4-ylidene).

In some embodiments of Formula Ia, the compound is in the following configuration:

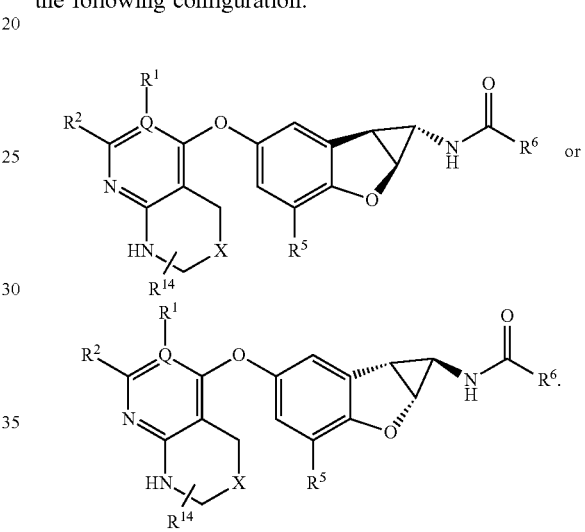

In some embodiments of Formula I, the compound has Formula Ia-1:

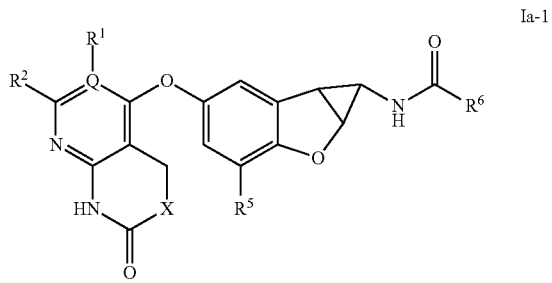

Ia-1 stereoisomers thereof, and pharmaceutically acceptable salts thereof, wherein $R^1$, $R^2$, $R^5$, $R^6$ and X are defined as in the above Formula Ia.

In some embodiments of Formula Ia-1, Q is C.

In some embodiments of Formula Ia-1, $R^1$ is H.

In some embodiments of Formula Ia-1, $R^2$ is H.

In some embodiments of Formula Ia-1, both $R^1$ and $R^2$ are H.

In some embodiments of Formula Ia-1, X is $C(R^{16})_2$.

In some embodiments of Formula Ia-1, X is CH.
In some embodiments of Formula Ia-1, X is $N(R^{16})$.
In some embodiments of Formula Ia-1, X is NH.
In some embodiments of Formula Ia-1, X is O.
In some embodiments of Formula Ia-1, $R^5$ is H.
In some embodiments of Formula Ia-1, $R^5$ is $CH_3$.

In some embodiments of Formula Ia-1, $R^6$ is selected from alkyl (e.g. $C_{1-9}$ alkyl), alkenyl (e.g. vinyl), aryl (e.g. phenyl) and heteroaryl (e.g. a 5- or 6-membered heteroaryl comprising 1, 2 or 3 heteroatoms selected from the group consisting of N, O and S, such as pyridinyl or furanyl), wherein the alkyl, alkenyl, aryl and heteroaryl are optionally substituted with at least one substituent $R^{15}$.

In some embodiments of Formula Ia-1, $R^6$ is phenyl with one, two or three substituent $R^{15}$.

In some embodiments of Formula Ia-1, $R^6$ is heteroaryl, which is a 5- or 6-membered heteroaryl comprising 1, 2 or 3 heteroatoms selected from the group consisting of N, O and S and substituted with one, two or three substituent $R^{15}$.

In some embodiments of Formula Ia-1, $R^6$ is pyridinyl or furanyl substituted with one, two or three substituent $R^{15}$.

In some embodiments of Formula Ia-1, $R^{15}$ is selected from halogen (e.g. F, Cl or Br), haloalkyl (e.g. $CF_3$), optionally substituted alkyl (e.g. $CH_3$, HO—$CH_2$— or NC—$C(CH_3)_2$—), optionally substituted cycloalkyl (e.g. cyclopropyl optionally substituted with $NH_2$ or CN), optionally substituted aryl (e.g. phenyl optionally substituted with $CF_3$), —OR' (e.g. $CH_3$—O— or $CF_3$), —O—$(CH_2)_{0-2}$-(optionally substituted heterocyclyl) (e.g. —O—$(CH_2)_{0-2}$-(piperazinyl or piperidyl optionally substituted with one or more alkyl groups such as $CH_3$ and $CH_2CH_3$)), —NR'R", $CH_2NR'R"$ and $C(Me)_2NR'R"$.

In some embodiments of Formula Ia-1, R' and R" are independently selected from H and alky (e.g. $CH_3$) and haloalkyl (e.g., $CF_3$).

In some embodiments of Formula Ia-1, (R' and R") together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a]pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).

In some embodiments of Formula Ia-1, (R' and R") together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.

In some embodiments of Formula Ia-1, (R' and R") together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.

In some embodiments of Formula Ia-1, in the definitions of $R^{15}$, R' and R", any of the groups defined with "optionally substituted" is independently and optionally substituted with at least one group selected from HO—, NC—, $NH_2$, NH(alkyl) (e.g. $NH(CH_3)$), $N(alkyl)_2$ (e.g. $N(CH_3)_2$), haloalkyl (e.g. $CF_3$ or $CF_3CH_2$), alkyl (e.g. $CH_3$ or $CH_3CH_2$), HO-alkyl- (e.g. HO—$CH_2CH_2$—) and alkyl-heterocyclyl- (e.g., $CH_3CH_2$-piperidyl-) and heterocyclylidin (e.g. piperidinylidene or piperidin-4-ylidene).

In some embodiments of Formula Ia-1, the compound is in the following configuration:

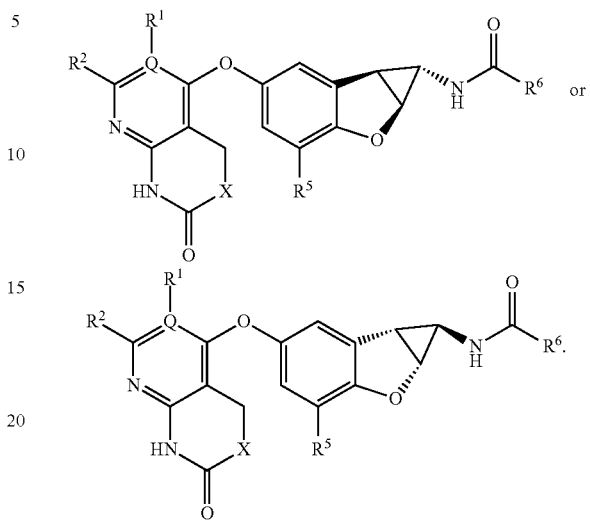

In some embodiments of Formula I, the compound has Formula Ia-1a:

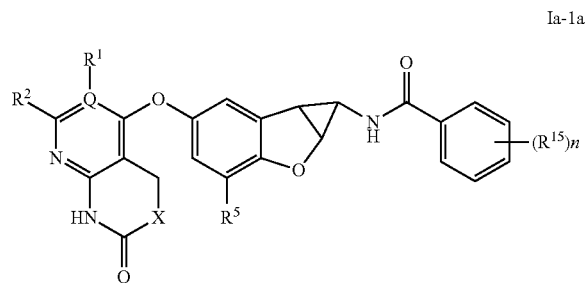

Ia-1a stereoisomers thereof, and pharmaceutically acceptable salts thereof,
wherein
n=1, 2 or 3; and
$R^1$, $R^2$, $R^5$, $R^{15}$ and X are defined as in the above Formula Ia.

In some embodiments of Formula Ia-1a, Q is C.
In some embodiments of Formula Ia-1a, $R^1$ is H.
In some embodiments of Formula Ia-1a, $R^2$ is H.
In some embodiments of Formula Ia-1a, both $R^1$ and $R^2$ are H.
In some embodiments of Formula Ia-1a, X is $C(R^{16})_2$.
In some embodiments of Formula Ia-1a, X is CH.
In some embodiments of Formula Ia-1a, X is $N(R^{16})$.
In some embodiments of Formula Ia-1a, X is NH.
In some embodiments of Formula Ia-1a, X is O.
In some embodiments of Formula Ia-1a, $R^5$ is H.
In some embodiments of Formula Ia-1a, $R^5$ is $CH_3$.
In some embodiments of Formula Ia-1a, n=1.
In some embodiments of Formula Ia-1a, n=2, and the two $R^{15}$ groups are independent from each other.
In some embodiments of Formula Ia-1a, n=3, and the three $R^{15}$ groups are independent from each other.
In some embodiments of Formula Ia-1a, $R^{15}$ is selected from halogen (e.g. F, Cl or Br), haloalkyl (e.g. $CF_3$), optionally substituted alkyl (e.g. $CH_3$, HO—$CH_2$— or NC—C(CH$_3$)$_2$—), optionally substituted cycloalkyl (e.g. cyclopropyl optionally substituted with NH$_2$ or CN), optionally substituted aryl (e.g. phenyl optionally substituted with CF$_3$), —OR' (e.g. CH$_3$—O— or —CF$_3$), —O—(CH$_2$)$_{0-2}$-(optionally substituted heterocyclyl) (e.g. —O—(CH$_2$)$_{0-2}$-(piperazinyl or piperidyl optionally substituted with one ore more alkyl groups such as CH$_3$ and CH$_2$CH$_3$)), —NR'R", CH$_2$NR'R" and C(Me)$_2$NR'R".

In some embodiments of Formula Ia-1a, R' and R" are independently selected from H and alky (e.g. CH$_3$) and haloalkyl (e.g., CF$_3$).

In some embodiments of Formula Ia-1a, (R' and R") together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a]pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).

In some embodiments of Formula Ia-1a, (R' and R") together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.

In some embodiments of Formula Ia-1a, (R' and R") together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.

In some embodiments of Formula Ia-1a, in the definitions of R$^{15}$, R' and R", any of the groups defined with "optionally substituted" is independently and optionally substituted with at least one group selected from HO—, NC—, NH$_2$, NH(alkyl) (e.g. NH(CH$_3$)), N(alkyl)$_2$ (e.g. N(CH$_3$)$_2$), haloalkyl (e.g. CF$_3$ or CF$_3$CH$_2$), alkyl (e.g. CH$_3$ or CH$_3$CH$_2$), HO-alkyl- (e.g. HO—CH$_2$CH$_2$—) and alkyl-heterocyclyl- (e.g., CH$_3$CH$_2$-piperidyl-) and heterocyclylidin (e.g. piperidinylidene or piperidin-4-ylidene).

In some embodiments of Formula Ia-1a, the compound is in the following configuration:

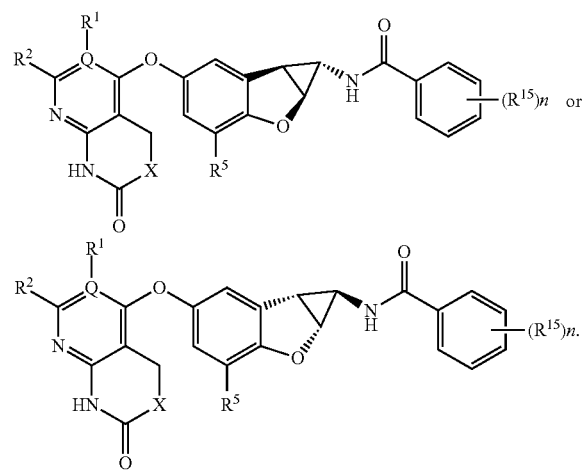

In some embodiments of Formula I, the compound has Formula Ia-1b:

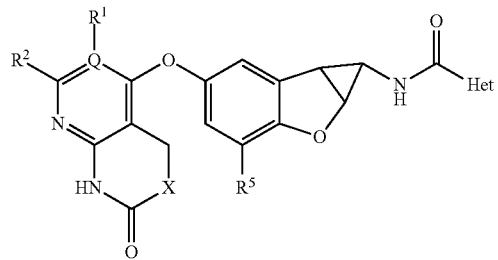

stereoisomers thereof, and pharmaceutically acceptable salts thereof, wherein

Het is a 5- or 6-membered heteroaryl comprising 1, 2 or 3 heteroatoms selected from the group consisting of N, O and S and substituted with one, two or three substituent R$^{15}$; and R$^1$, R$^2$, R$^5$, R$^{15}$ and X are defined as in the above Formula Ia.

In some embodiments of Formula Ia-1b, Q is C.
In some embodiments of Formula Ia-1b, R$^1$ is H.
In some embodiments of Formula Ia-1b, R$^2$ is H.
In some embodiments of Formula Ia-1b, both R$^1$ and R$^2$ are H.
In some embodiments of Formula Ia-1b, X is C(R$^{16}$)$_2$.
In some embodiments of Formula Ia-1b, X is CH.
In some embodiments of Formula Ia-1b, X is N(R$^{16}$).
In some embodiments of Formula Ia-1b, X is NH.
In some embodiments of Formula Ia-1b, X is O.
In some embodiments of Formula Ia-1b, R$^5$ is H.
In some embodiments of Formula Ia-1b, R$^5$ is CH$_3$.
In some embodiments of Formula Ia-1b, Het is pyridinyl or furanyl substituted with one, two or three substituent R$^{15}$.

In some embodiments of Formula Ia-1b, Het is substituted with one substituent R$^{15}$.

In some embodiments of Formula Ia-1b, Het is substituted with two substituents R$^{15}$, and the two R$^{15}$ groups are independent from each other.

In some embodiments of Formula Ia-1b, Het is substituted with three substituents R$^{15}$, and the three R$^{15}$ groups are independent from each other.

In some embodiments of Formula Ia-1b, R$^{15}$ is selected from halogen (e.g. F, Cl or Br), haloalkyl (e.g. CF$_3$), optionally substituted alkyl (e.g. CH$_3$, HO—CH$_2$— or NC—C(CH$_3$)$_2$—), optionally substituted cycloalkyl (e.g. cyclopropyl optionally substituted with NH$_2$ or CN), optionally substituted aryl (e.g. phenyl optionally substituted with CF$_3$), —OR' (e.g. CH$_3$—O— or CF$_3$), —O—(CH$_2$)$_{0-2}$-(optionally substituted heterocyclyl) (e.g. —O—(CH$_2$)$_{0-2}$-(piperazinyl or piperidyl optionally substituted with one or more alkyl group such as CH$_3$ and CH$_2$CH$_3$)), —NR'R", CH$_2$NR'R" and C(Me)$_2$NR'R".

In some embodiments of Formula Ia-1b, R' and R" are independently selected from H and alky (e.g. CH$_3$) and haloalkyl (e.g., CF$_3$).

In some embodiments of Formula Ia-1b, (R' and R") together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a]pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).

In some embodiments of Formula Ia-1b, (R' and R") together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.

In some embodiments of Formula Ia-1b, (R' and R") together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.

In some embodiments of Formula Ia-1b, in the definitions of $R^{15}$, R' and R", any of the groups defined with "optionally substituted" is independently and optionally substituted with at least one group selected from HO—, NC—, $NH_2$, NH(alkyl) (e.g. $NH(CH_3)$), $N(alkyl)_2$ (e.g. $N(CH_3)_2$), haloalkyl (e.g. $CF_3$ or $CF_3CH_2$), alkyl (e.g. $CH_3$ or $CH_3CH_2$), HO-alkyl- (e.g. $HO—CH_2CH_2$—) and alkyl-heterocyclyl- (e.g., $CH_3CH_2$-piperidyl-) and heterocyclylidin (e.g. piperidinylidene or piperidin-4-ylidene).

In some embodiments of Formula Ia-1b, $R^{15}$ is selected from haloalkyl (e.g. $CF_3$) or aryl (e.g. phenyl).

In some embodiments of Formula Ia-1b, the compound is in the following configuration:

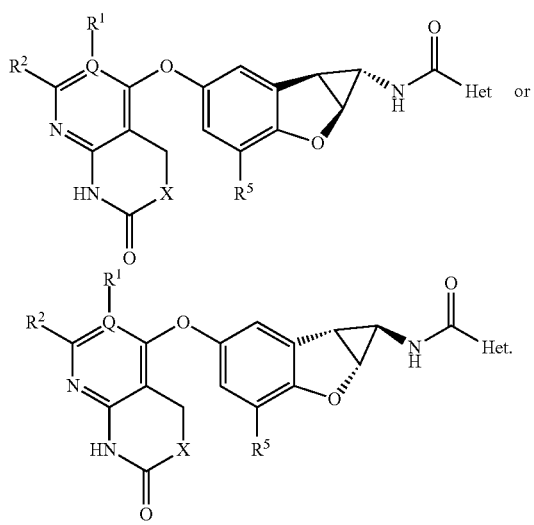

In some embodiments of Formula I, the compound has Formula Ib:

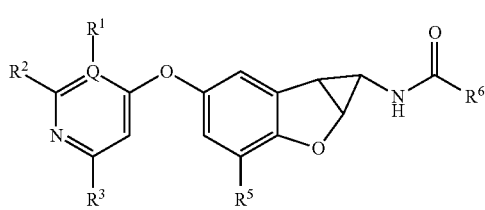

Ib stereoisomers thereof, and pharmaceutically acceptable salts thereof, wherein $R^1$, $R^2$, $R^3$, $R^5$ and $R^6$ are defined as in the above Formula I.

In some embodiments of Formula Ib, Q is C.
In some embodiments of Formula Ib, $R^1$ is H.
In some embodiments of Formula Ib, $R^2$ is H.
In some embodiments of Formula Ib, both $R^1$ and $R^2$ are H.
In some embodiments of Formula Ib, $R^3$ is —$NR^{10}R^{11}$ or —$CONR^{10}R^{11}$.
In some embodiments of Formula Ib, $R^{10}$ and $R^{11}$ are each selected from H and alkyl (e.g. $CH_3$).
In some embodiments of Formula Ib, the moiety

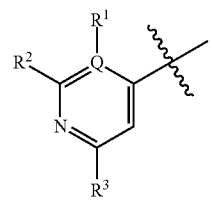

in Formula Ib is:

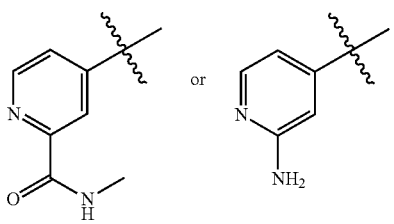

In some embodiments of Formula Ib, $R^5$ is H.
In some embodiments of Formula Ib, $R^5$ is $CH_3$.
In some embodiments of Formula Ib, $R^6$ is selected from aryl (e.g. phenyl) and heteroaryl (e.g. a 5- or 6-membered heteroaryl comprising 1, 2 or 3 heteroatoms selected from the group consisting of N, O and S, such as pyridinyl or furanyl), wherein the aryl and heteroaryl are optionally substituted with at least one substituent $R^{15}$.

In some embodiments of Formula Ib, $R^6$ is aryl (e.g. phenyl).

In some embodiments of Formula Ib, $R^6$ is phenyl substituted with one, two or three substituent $R^{15}$.

In some embodiments of Formula Ib, $R^{15}$ is selected from halogen (e.g. F, Cl or Br), haloalkyl (e.g. $CF_3$), optionally substituted alkyl (e.g. $CH_3$, $HO—CH_2$— or NC—$C(CH_3)_2$—), optionally substituted cycloalkyl (e.g. cyclopropyl optionally substituted with $NH_2$ or CN), optionally substituted aryl (e.g. phenyl optionally substituted with $CF_3$), —OR' (e.g. $CH_3$—O— or $CF_3$—O—), —O—$(CH_2)_{0-2}$-(optionally substituted heterocyclyl) (e.g. —O—$(CH_2)_{0-2}$-(piperazinyl or piperidyl optionally substituted with one or more alkyl groups such as $CH_3$ and $CH_2CH_3$)), —NR'R", $CH_2NR'R"$ and $C(Me)_2NR'R"$.

In some embodiments of Formula Ib, $R^{15}$ is selected from haloalkyl (e.g. $CF_3$) and $CH_2NR'R"$.

In some embodiments of Formula Ib, (R' and R") together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a]

pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).

In some embodiments of Formula Ib, (R' and R") together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.

In some embodiments of Formula Ib, (R' and R") together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.

In some embodiments of Formula Ib, (R' and R") together with the atoms to which they are attached, form a piperazinyl ring which is optionally substituted.

In some embodiments of Formula Ib, in the definitions of $R^{15}$, R' and R", any of the groups defined with "optionally substituted" is independently and optionally substituted with at least one group selected from HO—, CN—, $NH_2$, NH(alkyl) (e.g. $NH(CH_3)$), $N(alkyl)_2$ (e.g. $N(CH_3)_2$), haloalkyl (e.g. $CF_3$ or $CF_3CH_2$), alkyl (e.g. $CH_3$ or $CH_3CH_2$), HO-alkyl- (e.g. HO—$CH_2CH_2$—) and alkyl-heterocyclyl- (e.g., $CH_3CH_2$-piperidyl-) and heterocyclylidin (e.g. piperidinylidene or piperidin-4-ylidene).

In some embodiments of Formula Ib, the compound is in the following configuration:

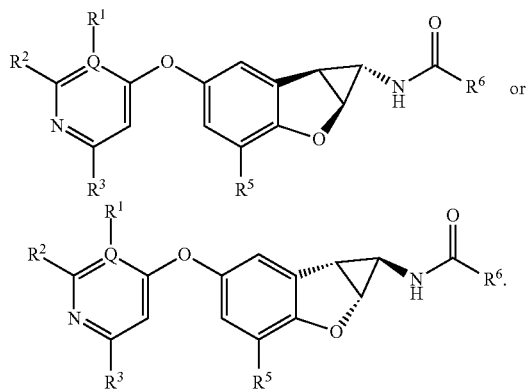

In some embodiments of Formula I, the compound has Formula Ib-1:

Ib-1

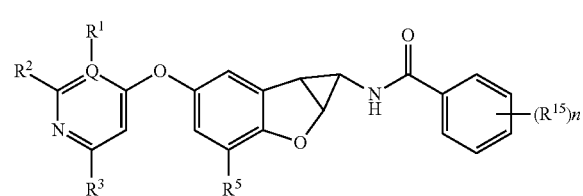

stereoisomers thereof, and pharmaceutically acceptable salts thereof, wherein
n=1, 2 or 3; and
$R^1$, $R^2$, $R^3$, $R^5$ and $R^{15}$ are defined as in the above Formula Ib.

In some embodiments of Formula Ib-1, Q is C.
In some embodiments of Formula Ib-1, $R^1$ is H.
In some embodiments of Formula Ib-1, $R^2$ is H.
In some embodiments of Formula Ib-1, both $R^1$ and $R^2$ are H.
In some embodiments of Formula Ib-1, $R^3$ is —$NR^{10}R^{11}$ or —$CONR^{10}R^{11}$.
In some embodiments of Formula Ib-1, $R^{10}$ and $R^{11}$ are each selected from H and alkyl (e.g. $CH_3$).
In some embodiments of Formula Ib-1, the moiety

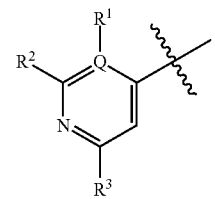

in Formula Ib-1 is:

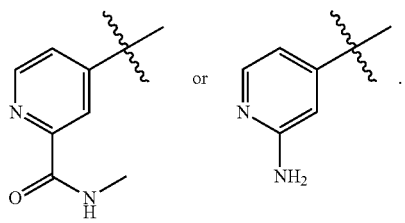 [SMILES: *c1ccnc(C(=O)NC)c1 ; *c1ccnc(N)c1]

In some embodiments of Formula Ib-1, $R^5$ is H.
In some embodiments of Formula Ib-1, $R^5$ is $CH_3$.
In some embodiments of Formula Ib-1, n=1.
In some embodiments of Formula Ib-1, n=2, and the two $R^{15}$ groups are independent from each other.
In some embodiments of Formula Ib-1, n=3, and the three $R^{15}$ groups are independent from each other.
In some embodiments of Formula Ib-1, $R^{15}$ is selected from halogen (e.g. F, Cl or Br), haloalkyl (e.g. $CF_3$), optionally substituted alkyl (e.g. $CH_3$, HO—$CH_2$— or NC—$C(CH_3)_2$—), optionally substituted cycloalkyl (e.g. cyclopropyl optionally substituted with $NH_2$ or CN), optionally substituted aryl (e.g. phenyl optionally substituted with $CF_3$), —OR' (e.g. $CH_3$—O— or $CF_3$—O—), —O—$(CH_2)_{0-2}$-(optionally substituted heterocyclyl) (e.g. —O—$(CH_2)_{0-2}$-(piperazinyl or piperidyl optionally substituted with one or more alkyl groups such as $CH_3$ and $CH_2CH_3$)), —NR'R", $CH_2NR'R"$ and $C(Me)_2NR'R"$.

In some embodiments of Formula Ib-1, $R^{15}$ is selected from haloalkyl (e.g. $CF_3$) and $CH_2NR'R"$.

In some embodiments of Formula Ib-1, (R' and R") together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a] pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).

In some embodiments of Formula Ib-1, (R' and R") together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.

In some embodiments of Formula Ib-1, (R' and R") together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.

In some embodiments of Formula Ib-1, (R' and R") together with the atoms to which they are attached, form a piperazinyl ring which is optionally substituted.

In some embodiments of Formula Ib-1, in the definitions of $R^{15}$, R' and R", any of the groups defined with "optionally substituted" is independently and optionally substituted with at least one group selected from HO—, NC—, $NH_2$, NH(alkyl) (e.g. $NH(CH_3)$), $N(alkyl)_2$ (e.g. $N(CH_3)_2$), haloalkyl (e.g. $CF_3$ or $CF_3CH_2$), alkyl (e.g. $CH_3$ or $CH_3CH_2$), HO-alkyl- (e.g. HO—$CH_2CH_2$—) and alkyl-heterocyclyl- (e.g., $CH_3CH_2$-piperidyl-) and heterocyclylidin (e.g. piperidinylidene or piperidin-4-ylidene).

In some embodiments of Formula Ib-1, the compound is in the following configuration:

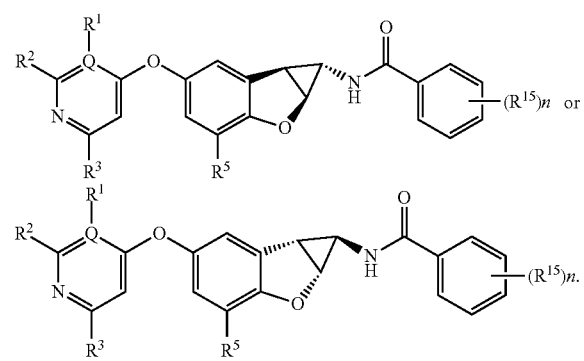

In some embodiments of Formula I, the compound has Formula Ic:

Ic

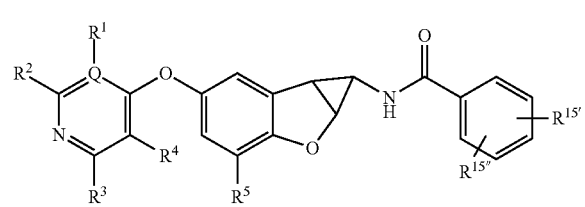

stereoisomers thereof, and pharmaceutically acceptable salts thereof,
wherein
$R^{15'}$ is —Y—NR'R";
Y is absent, or is -alkyl-, -cycloalkyl- or —O-alkyl-;
$R^{15''}$ is defined as $R^{15}$ in the above Formula I; and
$R^1$-$R^5$, R' and R" are defined as in the above Formula I.

In some embodiments of Formula Ic, Q is C.
In some embodiments of Formula Ic, $R^1$ is H.
In some embodiments of Formula Ic, $R^2$ is H.
In some embodiments of Formula Ic, both $R^1$ and $R^2$ are H.

In some embodiments of Formula Ic, $R^3$ is —$NR^{10}R^{11}$ or —$CONR^{10}R^{11}$.

In some embodiments of Formula Ic, $R^4$ is H.

In some embodiments of Formula Ic, $R^3$ is —$NR^{10}R^{11}$ or —$CONR^{10}R^{11}$, and $R^4$ is hydrogen.

In some embodiments of Formula Ic, $R^{10}$ and $R^{11}$ are each selected from H and alkyl (e.g. $CH_3$).

In some embodiments of Formula Ic, the moiety

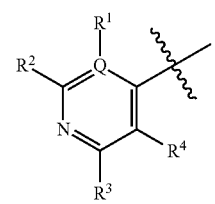

in Formula Ic is:

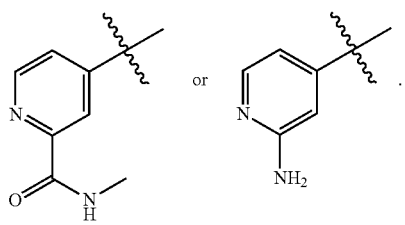 [SMILES: *c1ccnc(C(=O)NC)c1 ; *c1ccnc(N)c1]

In some embodiments of Formula Ic, $R^3$ and $R^4$, together with the ring to which they are attached, form a fused heterocyclyl or heteroaryl ring (e.g. naphthyridinyl, pyridooxazinyl and pyridopyrimidinyl which are optionally hydrogenated and optionally substituted with at least one substituent $R^{14}$, such as 1,2,3,4-tetrahydro-[1,8]naphthyridinyl, 1,4-dihydro-2H-pyrido[2,3-d][1,3]oxazinyl and 1,2,3,4-tetrahydro-pyrido[2,3-d]pyrimidinyl which are optionally substituted with at least one substituent $R^{14}$).

In some embodiments of Formula Ic, $R^{14}$ is oxo.

In some embodiments of Formula Ic, $R^3$ and $R^4$, together with the ring to which they are attached, form a fused ring selected from:

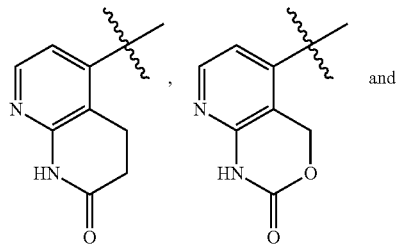

-continued

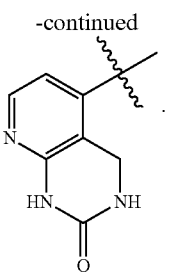

In some embodiments of Formula Ic, $R^5$ is H.
In some embodiments of Formula Ic, $R^5$ is $CH_3$.
In some embodiments of Formula Ic, Y is absent.
In some embodiments of Formula Ic, Y is -alkyl- (e.g. $CH_2$ or $C(CH_3)_2$).
In some embodiments of Formula Ic, Y is -cycloalkyl- (e.g. -cyclopropyl-).
In some embodiments of Formula Ic, Y is —O-alkyl- (e.g. —O—$CH_2CH_2$—).
In some embodiments of Formula Ic, R' and R" are independently selected from H and alky (e.g. $CH_3$) and haloalkyl (e.g. $CF_3$).
In some embodiments of Formula Ic, (R' and R") together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a]pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).
In some embodiments of Formula Ic, (R' and R") together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.
In some embodiments of Formula Ic, (R' and R") together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.
In some embodiments of Formula Ic, in the definitions of R' and R", any of the groups defined with "optionally substituted" is independently and optionally substituted with at least one group selected from HO—, NC—, $NH_2$, NH(alkyl) (e.g. NH($CH_3$)), N(alkyl)$_2$ (e.g. N($CH_3$)$_2$), haloalkyl (e.g. $CF_3$ or $CF_3CH_2$), alkyl (e.g. $CH_3$ or $CH_3CH_2$), HO-alkyl- (e.g. HO—$CH_2CH_2$—) and alkyl-heterocyclyl- (e.g., $CH_3CH_2$-piperidyl-) and heterocyclylidin (e.g. piperidinylidene or piperidin-4-ylidene).
In some embodiments of Formula Ic, $R^{15''}$ is halogen (e.g. F, Cl or Br), haloalkyl (e.g. $CF_3$), optionally substituted alkyl (e.g. $CH_3$, HO—$CH_2$— or NC—$C(CH_3)_2$—), optionally substituted cycloalkyl (e.g. cyclopropyl optionally substituted with CN), optionally substituted aryl (e.g. phenyl optionally substituted with $CF_3$), —OR' (e.g. $CH_3$—O— or $CF_3$—O—), and —O—$(CH_2)_{0-2}$-(optionally substituted heterocyclyl) (e.g. —O—$(CH_2)_{0-2}$-(piperazinyl or piperidyl optionally substituted with one or more alkyl groups such as $CH_3$ and $CH_2CH_3$)).
In some embodiments of Formula Ic, $R^{15''}$ is halogen (e.g. F, Cl or Br) or haloalkyl (e.g. $CF_3$).

In some embodiments of Formula Ic, the compound is in the following configuration:

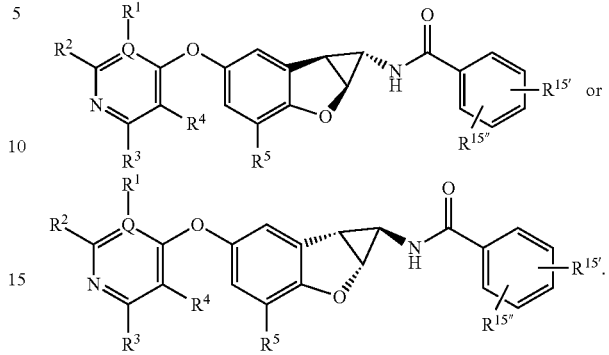

In some embodiments, the at least one compound selected from compounds of Formula (I), stereoisomers thereof, and pharmaceutically acceptable salts thereof, is selected from compounds of Formula (II) below:

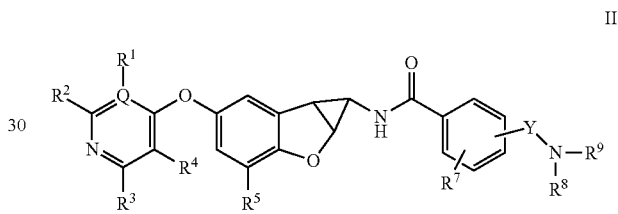

II stereoisomers thereof, and pharmaceutically acceptable salts thereof,
wherein:
Q is selected from C and N;
Y is selected from $CH_2$, $C(CH_3)_2$, C>$CH_2$ (cyclopropane), $CH_2$-alkyl, $CH_2$-cycloalkyl, $CH_2$-heterocyclyl, O-alkyl, O-cycloalkyl, O-heterocyclyl or absent;
$R^1$, $R^2$, $R^3$ and $R^4$ which may be the same or different, are each selected from hydrogen, halogen, haloalkyl, alkyl, alkenyl, cycloalkyl, aryl, heterocyclyl, heteroaryl, alkynyl, —CN, —$NR^{10}R^{11}$, —$OR^{10}$, —$COR^{10}$, —$CO_2R^{10}$, —$CONR^{10}R^{11}$, —$C(=NR^{10})NR^{11}R^{12}$, —$NR^{10}COR^{11}$, —$NR^{10}CONR^{11}R^{12}$, —$NR^{10}CO_2R^{11}$, —$SO_2R^{10}$, —$NR^{10}SO_2NR^{11}R^{12}$, and —$NR^{10}SO_2R^{11}$, wherein the alkyl, alkenyl, alkynyl, cycloalkyl, heteroaryl, aryl, and heterocyclyl are optionally substituted with at least one substituent $R^{13}$, or ($R^1$ and $R^2$), and/or ($R^3$ and $R^4$), together with the ring to which they are attached, form a fused ring selected from heterocyclyl, and heteroaryl rings optionally substituted with at least one substituent $R^{14}$; provided that $R^1$ is absent when Q is N.
$R^7$ is selected from hydrogen, halogen, alkyl, cycloalkyl, haloalkyl, cyanoalkyl, halocycloalkyl and cyanoacycloalkyl;
$R^8$ and $R^9$ which may be the same or different, are each selected from hydrogen, haloalkyl, alkyl, cycloalkyl, heterocyclyl, wherein the alkyl, cycloalkyl, and heterocyclyl are optionally substituted with at least one substituent $R^{13}$, or ($R^8$ and $R^9$) together with the ring to which they are attached, form a fused ring selected from heterocyclyl, and heteroaryl rings optionally substituted with at least one substituent $R^{14}$;

$R^{10}$, $R^{11}$, $R^{12}$, $R^{13}$ and $R^{14}$ are each selected from hydrogen, halogen, haloalkyl, alkyl, alkenyl, cycloalkyl, aryl, heteroaryl, heterocyclyl, alkynyl, oxo, —CN, —OR', —NR'R", —COR', —CO$_2$R', —CONR'R", —C(=NR')NR"R''', —NR'COR", —NR'CONR'R''', —NR'CO$_2$R", —SO$_2$R', —SO$_2$aryl, —NR'SO$_2$NR"R''', and NR'SO$_2$R", wherein R', R", and R''' are independently selected from H, haloalkyl, alkyl, alkenyl, alkynyl, cycloalkyl, heterocyclyl, aryl, and heteroaryl, or (R' and R"), and/or (R" and R''') together with the atoms to which they are attached, form a ring selected from heterocyclyl, and heteroaryl rings.

In some embodiments of Formula (II), Q is C.

In some embodiments of Formula (II), Q is N and $R^1$ is absent.

In some embodiments of Formula (II), each of $R^1$ and $R^2$ is hydrogen.

In some embodiments of Formula (II), $R^3$ and $R^4$ together with the ring to which they are attached, form a fused ring selected from a heterocycle or heteroaryl ring, such as naphthyridinyl (e.g., dihydronaphthyridinyl), pyrrolopyridinyl (e.g., pyrrolo[2,3-b]pyridin-4-yl), and purinyl, said ring being optionally substituted with at least one substituent $R^{14}$, such as oxo.

In some embodiments of Formula (II), $R^3$ and $R^4$, which may be the same or different, are each selected from hydrogen, —CONR$^{11}$R$^{12}$, such as —CONHCH$_3$, and heteroaryl (e.g. imdazole) optionally substituted with at least one substituent $R^{14}$, such as at least one haloalkyl, wherein the haloalkyl is, for example, —CF$_3$.

In some embodiments of Formula (II), $R^3$ is —NR$^{10}$R$^{11}$ or —CONR$^{10}$R$^{11}$.

In some embodiments of Formula (II), $R^4$ is H.

In some embodiments of Formula (II), $R^3$ is —NR$^{10}$R$^{11}$ or —CONR$^{10}$R$^{11}$, and $R^4$ is hydrogen.

In some embodiments of Formula (II), $R^{10}$ and $R^{11}$ are each selected from H and alkyl (e.g. CH$_3$).

In some embodiments of Formula (II), the moiety

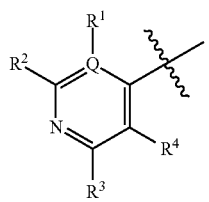

in Formula Ic is:

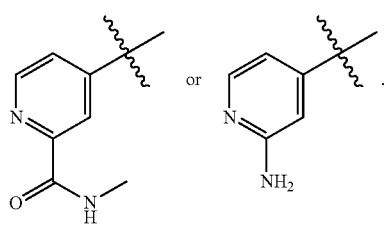 [SMILES: *c1ccnc(C(=O)NC)c1 ; *c1ccnc(N)c1]

In some embodiments of Formula (II), $R^3$ and $R^4$, together with the ring to which they are attached, form a fused heterocyclyl or heteroaryl ring (e.g. naphthyridinyl, pyridooxazinyl and pyridopyrimidinyl which are optionally hydrogenated and optionally substituted with at least one substituent $R^{14}$, such as 1,2,3,4-tetrahydro-[1,8]naphthyridinyl, 1,4-dihydro-2H-pyrido[2,3-d][1,3]oxazinyl and 1,2,3,4-tetrahydro-pyrido[2,3-d]pyrimidinyl which are optionally substituted with at least one substituent $R^{14}$).

In some embodiments of Formula (II), $R^{14}$ is oxo.

In some embodiments of Formula (II), $R^3$ and $R^4$, together with the ring to which they are attached, form a fused ring selected from:

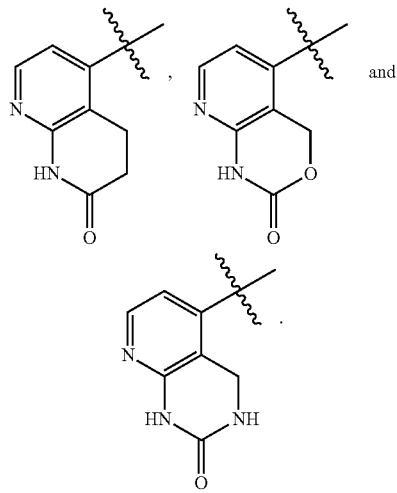

In some embodiments of Formula (II), $R^5$ is H.
In some embodiments of Formula (II), $R^5$ is CH$_3$.
In some embodiments of Formula (II), $R^7$ is H.
In some embodiments of Formula (II), $R^7$ is F.
In some embodiments of Formula (II), $R^7$ is Cl.
In some embodiments of Formula (II), $R^7$ is Br.
In some embodiments of Formula (II), $R^7$ is I.
In some embodiments of Formula (II), $R^7$ is CH$_3$.
In some embodiments of Formula (II), $R^7$ is CF$_3$.
In some embodiments of Formula (II), Y is absent.
In some embodiments of Formula (II), Y is -alkyl-.
In some embodiments of Formula (II), Y is CH$_2$.
In some embodiments of Formula (II), Y is C(CH$_3$)$_2$.
In some embodiments of Formula (II), Y is -cycloalkyl-.
In some embodiments of Formula (II), Y is cyclopropyl.
In some embodiments of Formula (II), Y is O-alkyl.
In some embodiments of Formula (II), Y is —O—CH$_2$CH$_2$—.
In some embodiments of Formula (II), Y is O-cycloalkyl.
In some embodiments of Formula (II), Y is O-heterocyclyl.
In some embodiments of Formula (II), Y is CH$_2$-alkyl.
In some embodiments of Formula (II), Y is CH$_2$-cycloalkyl.
In some embodiments of Formula (II), Y is CH$_2$-heterocyclyl.
In some embodiments of Formula (II), Y is absent.
In some embodiments of Formula (II), $R^8$ and $R^9$, which may be the same or different, are each selected from hydrogen, alkyl, cyclalkyl, heterocyclyl, or ($R^8$ and $R^9$) together forms pyrrolidine, or piperidine, or piperazene or morpholine ring optionally substituted with at least one substituent $R^{14}$, such as at least one functional group, wherein the functional group is, for example, —CH$_3$, —CH$_2$CH$_3$, —CH$_2$CF$_3$, —CH$_2$CH$_2$OH, CH$_2$CH$_2$F, —OH, —NH$_2$, —NHCH$_3$, N(CH$_3$)$_2$.

In some embodiments of Formula (II), $R^8$ and $R^9$ are independently selected from H and alky (e.g. CH$_3$).

In some embodiments of Formula (II), (R⁸ and R⁹) together with the atoms to which they are attached, form a ring selected from optionally substituted heterocyclyl, and optionally substituted heteroaryl rings (e.g. piperazinyl, morpholinyl, piperidyl, pyrolidinyl, pyrrolopyrazinyl optionally hydrogenated such as octahydro-pyrrolo[1,2-a]pyrazinyl, triazolopyrazinyl optionally hydrogenated such as 5,6,7,8-tetrahydro-[1,2,4]triazolo[4,3-a]pyrazinyl and pyrrolopyrrolyl optionally hydrogenated such as octahydro-pyrrolo[3,4-c]pyrrolyl which are optionally substituted).

In some embodiments of Formula (II), (R⁸ and R⁹) together with the atoms to which they are attached, form a ring selected from piperazinyl, morpholinyl, piperidyl, pyrolidinyl, pyrrolopyrazinyl optionally hydrogenated, triazolopyrazinyl optionally hydrogenated and pyrrolopyrrolyl optionally hydrogenated which are optionally substituted.

In some embodiments of Formula (II), (R⁸ and R⁹) together with the atoms to which they are attached, form a ring selected from piperazinyl, morpholinyl, piperidyl, pyrolidinyl, octahydro-pyrrolo[1,2-a]pyrazinyl, 5,6,7,8-tetrahydro-[1,2,4]triazolo[4,3-a]pyrazinyl and octahydro-pyrrolo[3,4-c]pyrrolyl which are optionally substituted.

In some embodiments of Formula (II), $R^{13}$ and $R^{14}$ are independently selected from the group consisting of HO—, NC—, NH₂, NH(alkyl) (e.g. NH(CH₃)), N(alkyl)₂ (e.g. N(CH₃)₂), haloalkyl (e.g. CF₃ or CF₃CH₂), alkyl (e.g. CH₃ or CH₃CH₂), HO-alkyl- (e.g. HO—CH₂CH₂—) and alkyl-heterocyclyl- (e.g., CH₃CH₂-piperidyl-).

In some embodiments of Formula (II), in the definitions of R⁸ and R⁹, any of the groups defined with "optionally substituted" is independently and optionally substituted with at least one group selected from HO—, NC—, NH₂, NH(alkyl) (e.g. NH(CH₃)), N(alkyl)₂ (e.g. N(CH₃)₂), haloalkyl (e.g. CF₃ or CF₃CH₂), alkyl (e.g. CH₃ or CH₃CH₂), HO-alkyl- (e.g. HO—CH₂CH₂—) and alkyl-heterocyclyl- (e.g., CH₃CH₂-piperidyl-) and heterocyclylidin (e.g. piperidinylidene or piperidin-4-ylidene).

In some embodiments of Formula (II), the compound is in the following configuration:

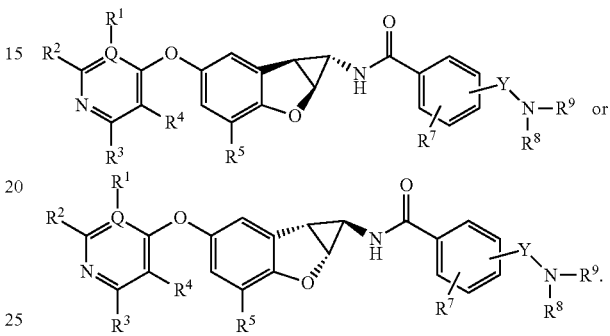

Also provided herein is at least one compound selected from the following compounds, Compound 1.1

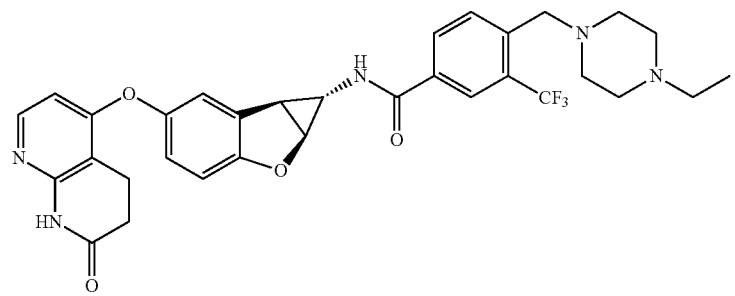

Compound 1.2

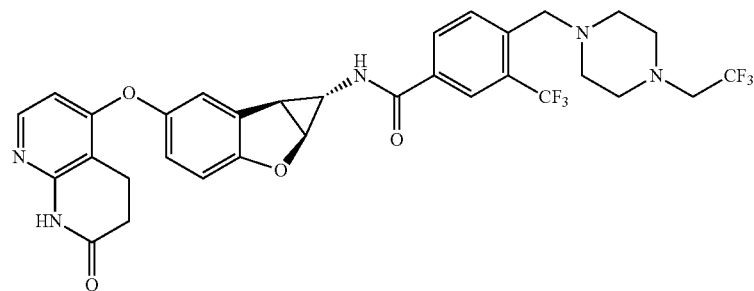

Compound 1.3

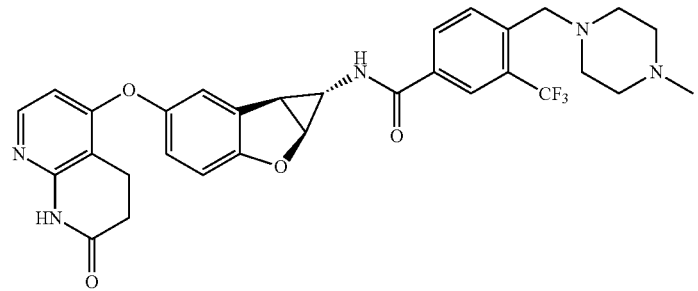

-continued
Compound 1.4
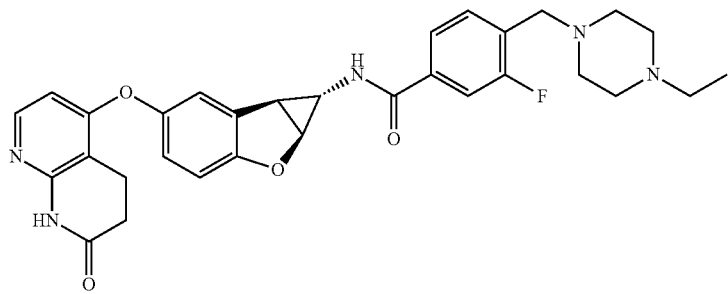
Compound 1.5
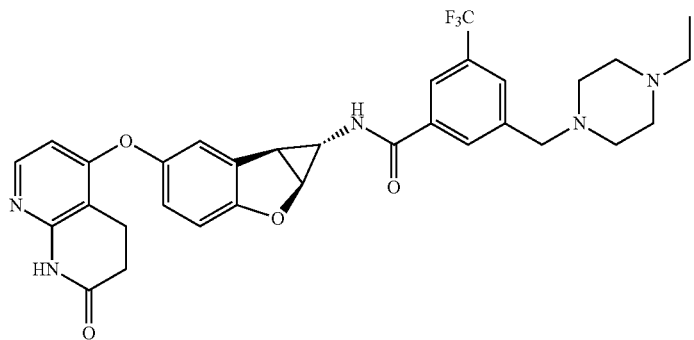
Compound 1.6
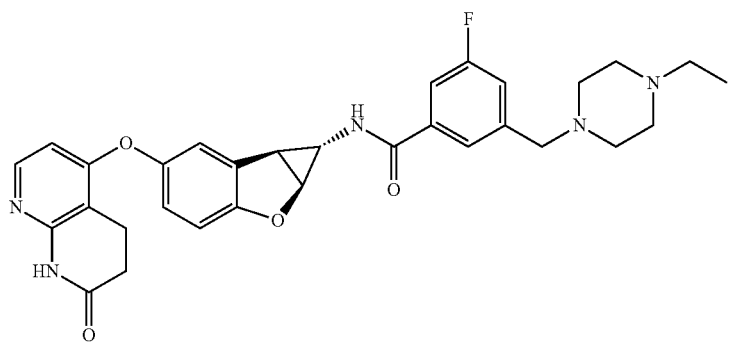
Compound 1.7
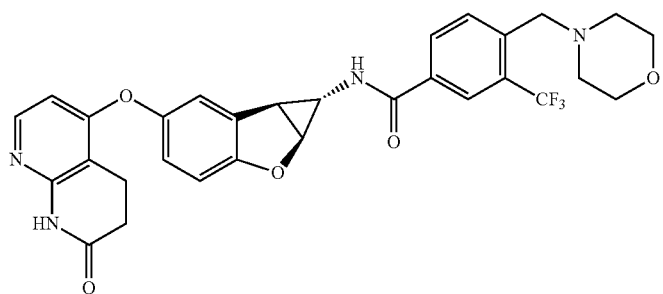
Compound 1.8
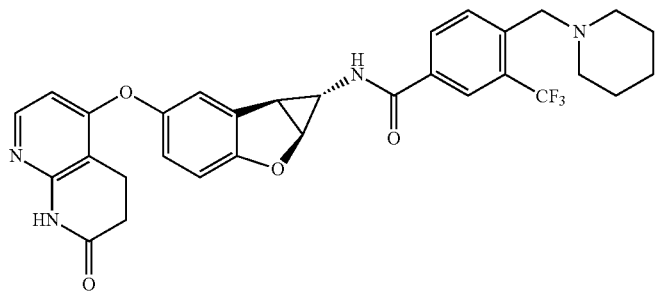

Compound 1.9
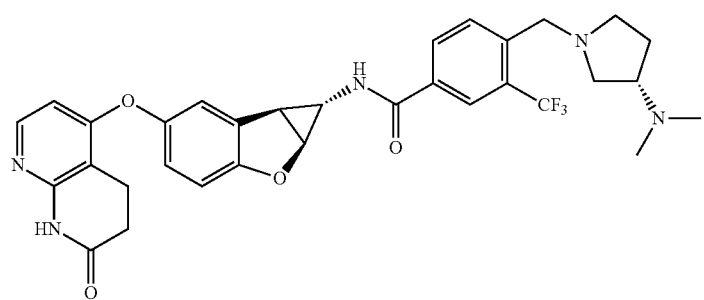
Compound 1.10
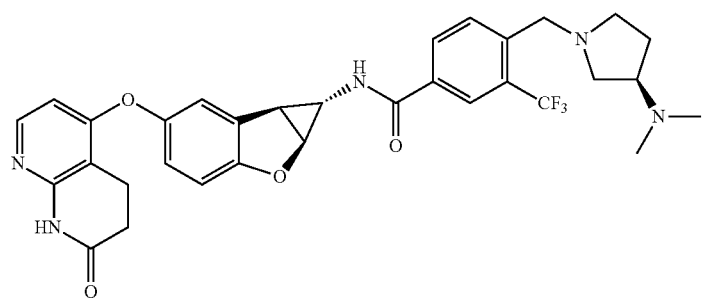
Compound 1.11
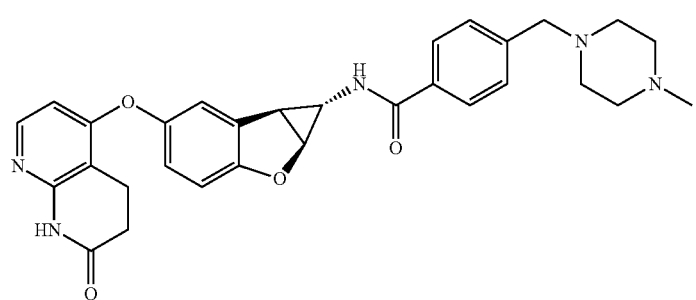
Compound 1.12
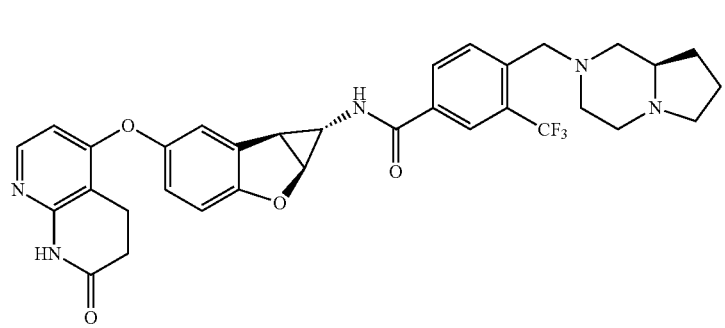
Compound 1.13
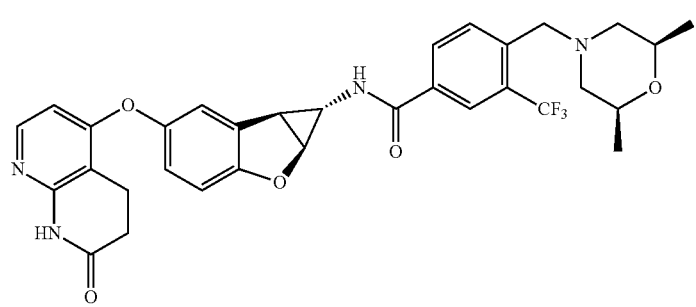

-continued
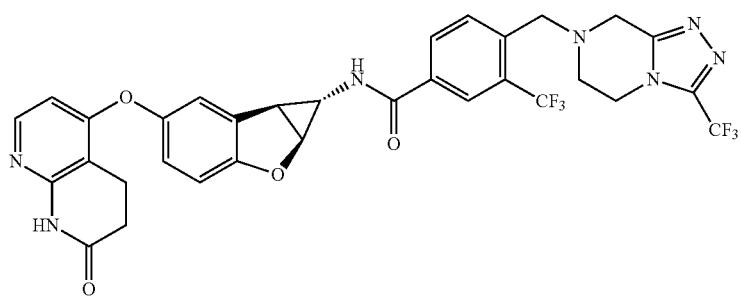
Compound 1.14
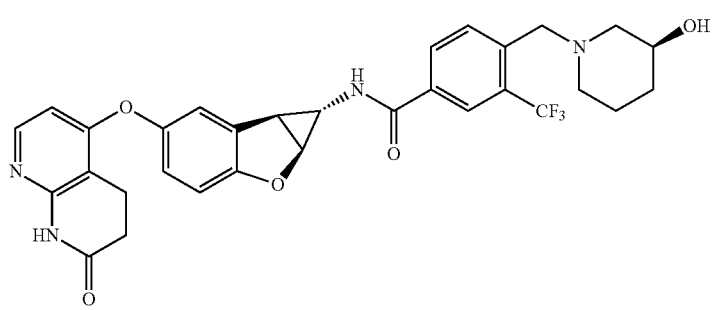
Compound 1.15
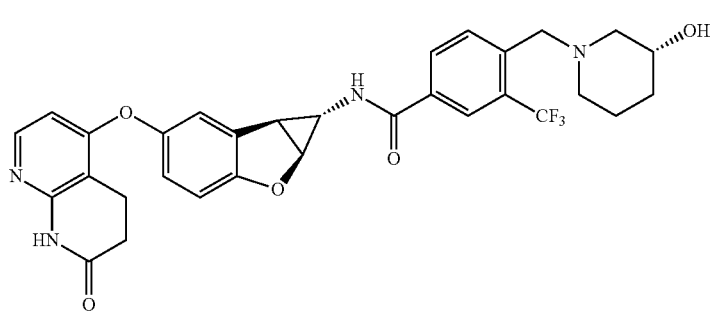
Compound 1.16
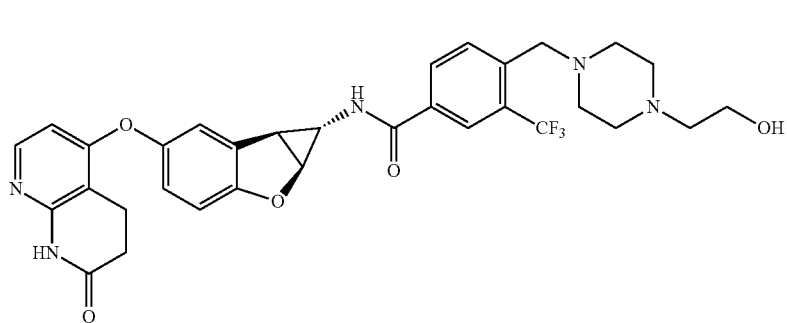
Compound 1.17
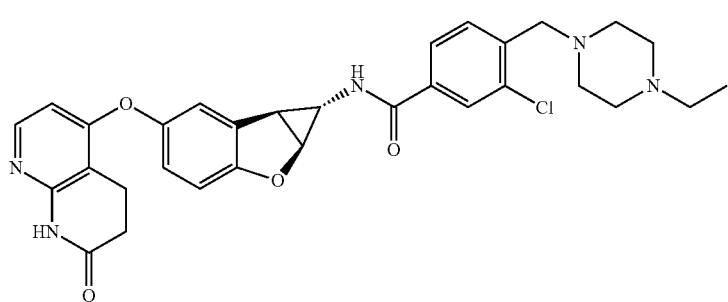
Compound 1.18

-continued
Compound 1.19
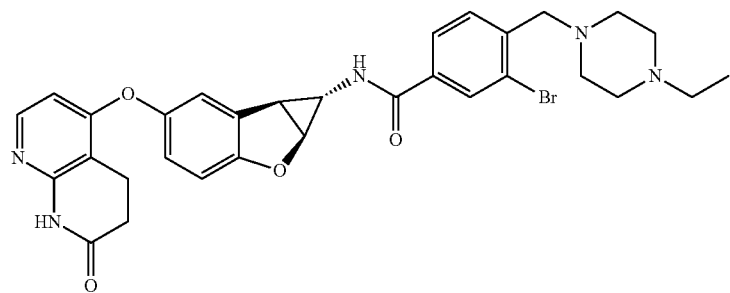
Compound 1.20
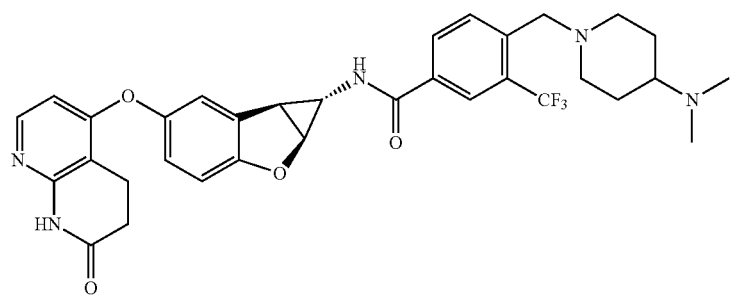
Compound 1.21
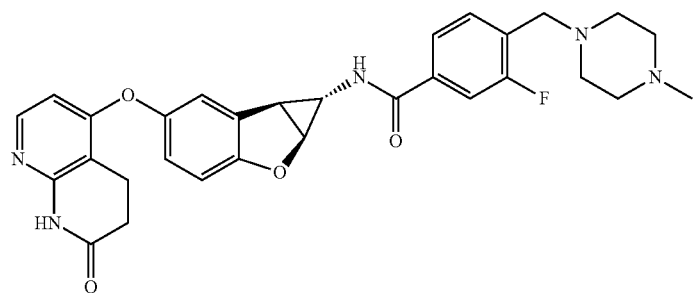
Compound 1.22
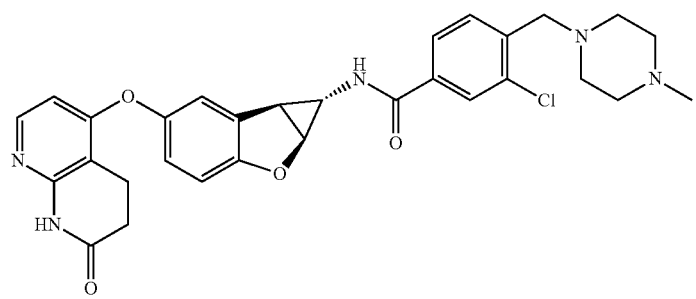
Compound 1.23
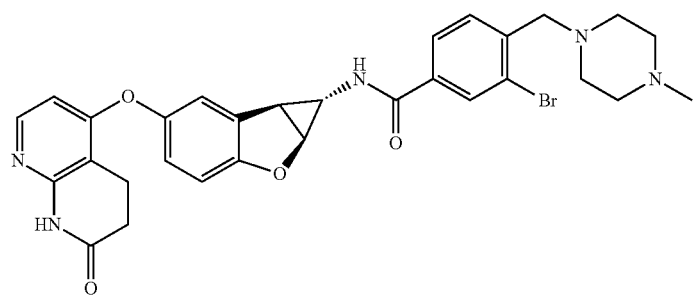

-continued
Compound 1.24
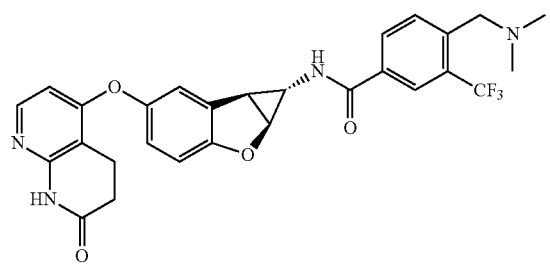
Compound 1.25
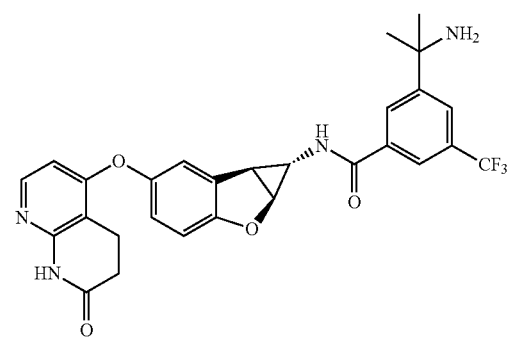
Compound 1.26
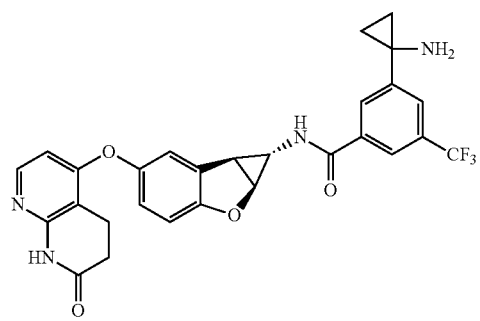
Compound 1.27
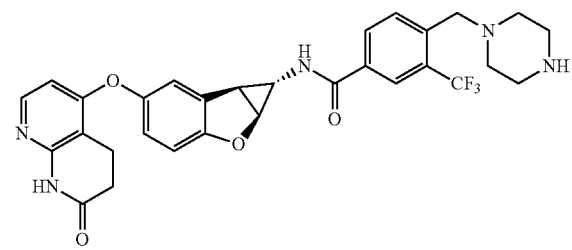
Compound 1.28
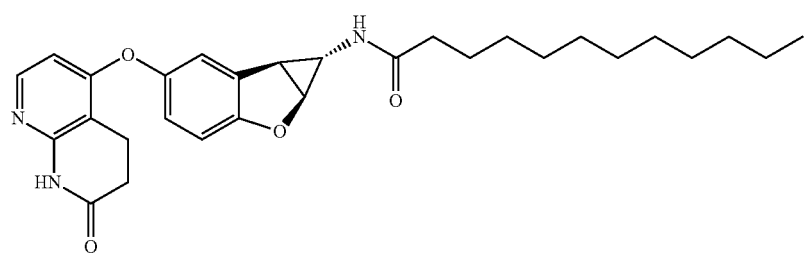
Compound 1.29
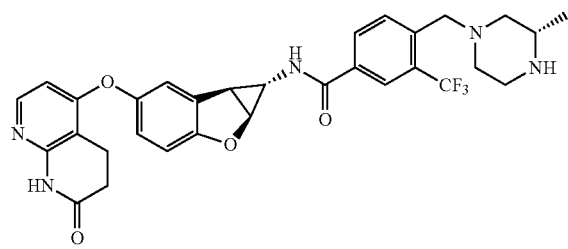
Compound 1.30
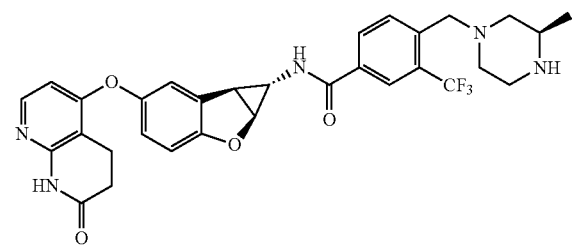
Compound 1.31
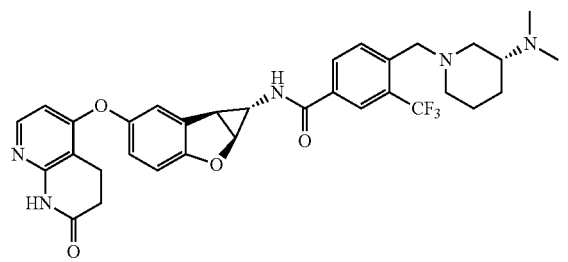
Compound 1.32
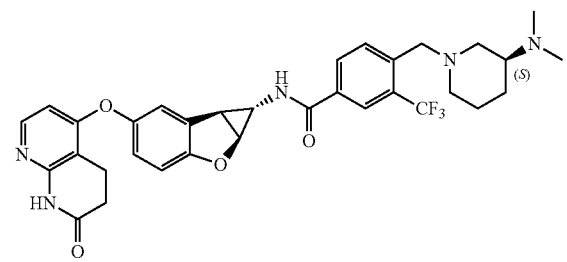

-continued
Compound 1.33
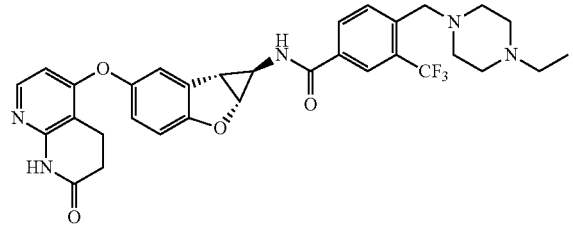
Compound 1.34
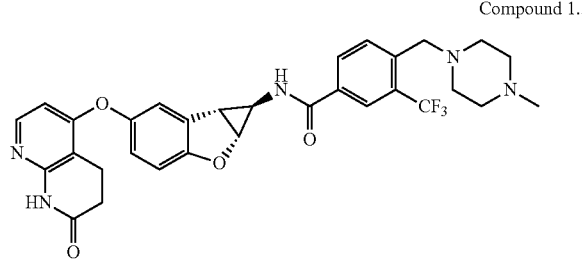
Compound 1.35
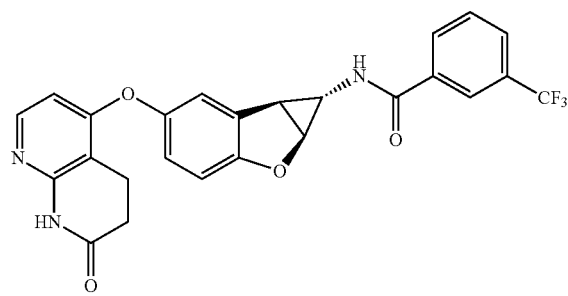
Compound 1.36
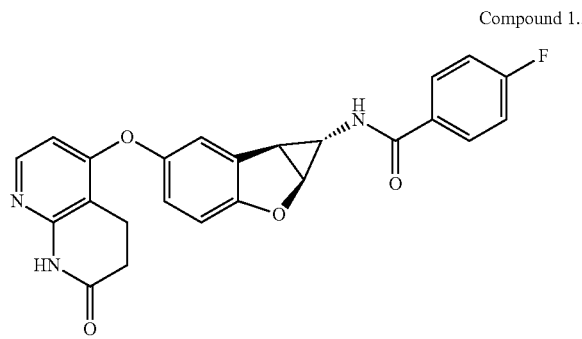
Compound 1.37
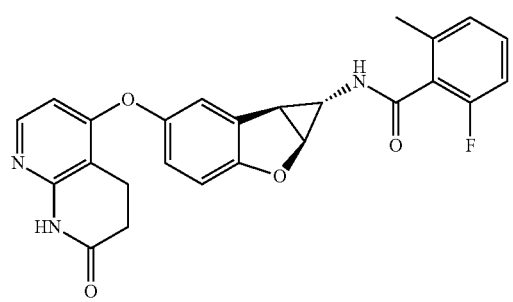
Compound 1.38
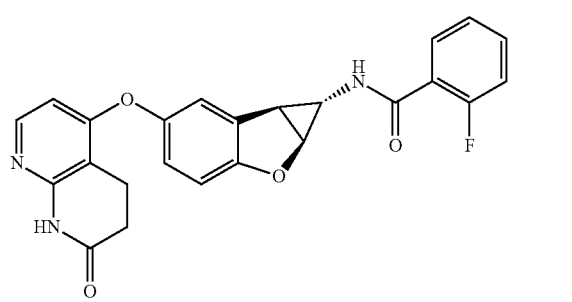
Compound 1.39
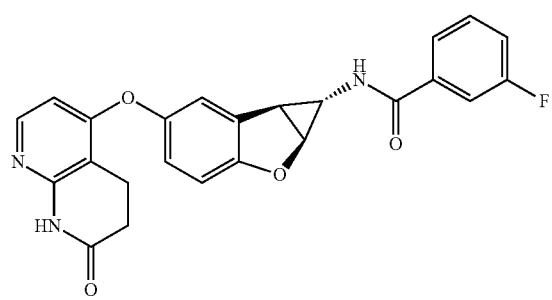
Compound 1.40
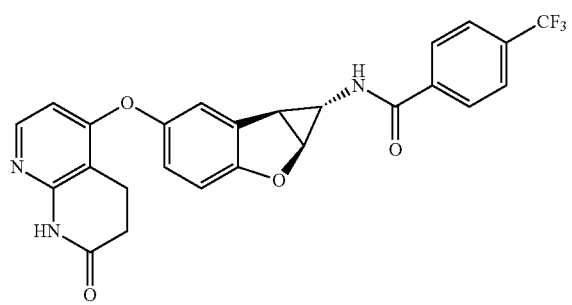
Compound 1.41
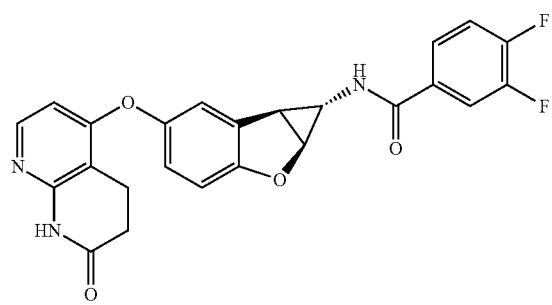
Compound 1.42
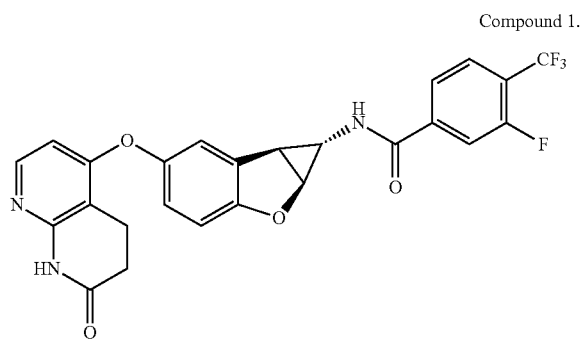

-continued
Compound 1.43
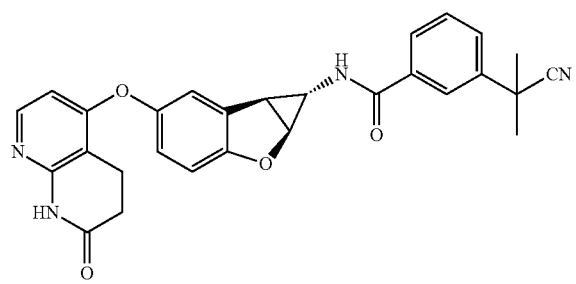
Compound 1.44
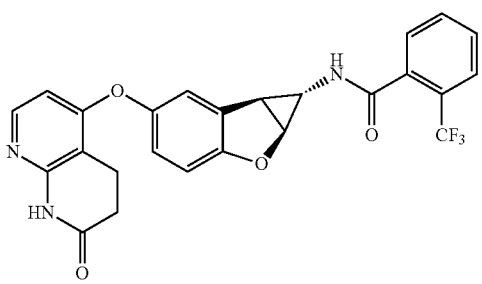
Compound 1.45
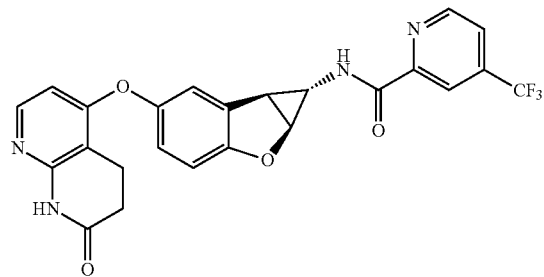
Compound 1.46
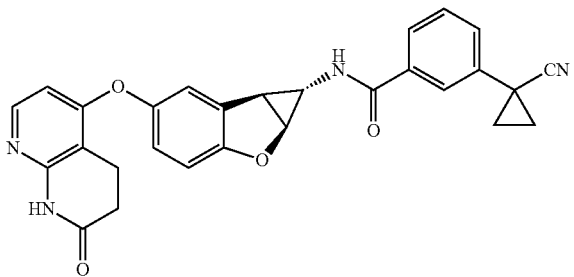
Compound 1.47
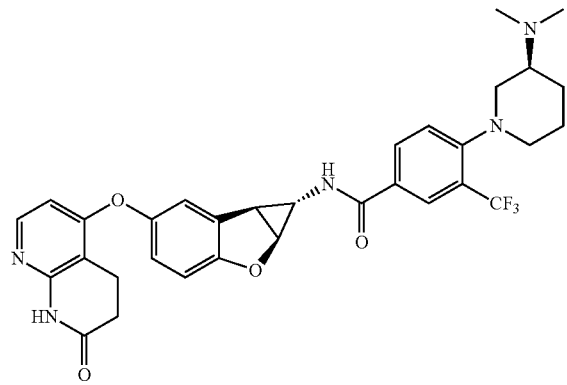
Compound 1.48
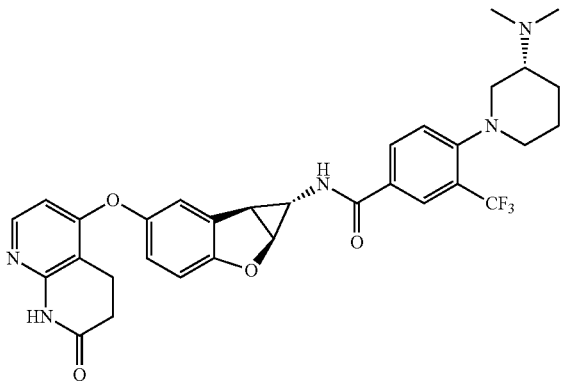
Compound 1.49
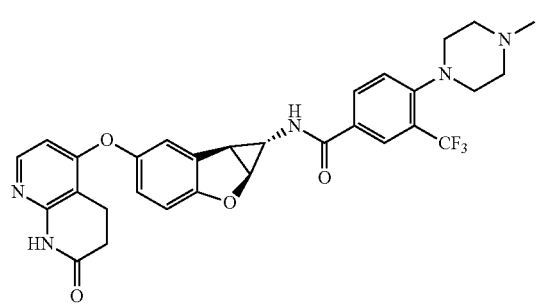
Compound 1.50
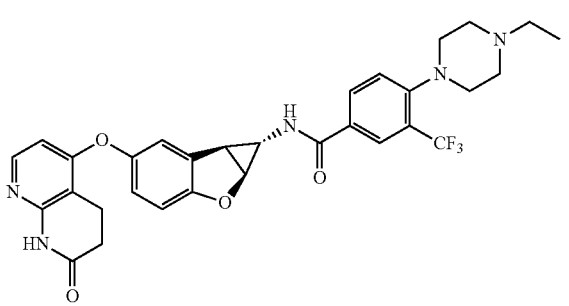
Compound 1.51
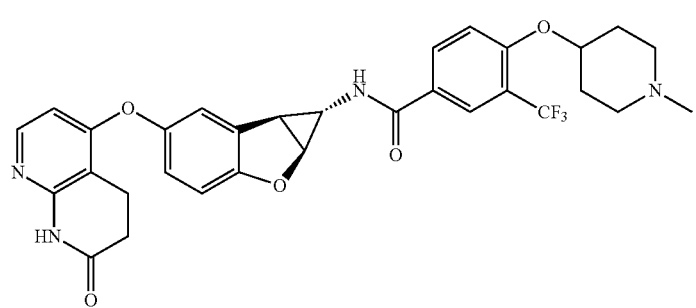

Compound 1.52
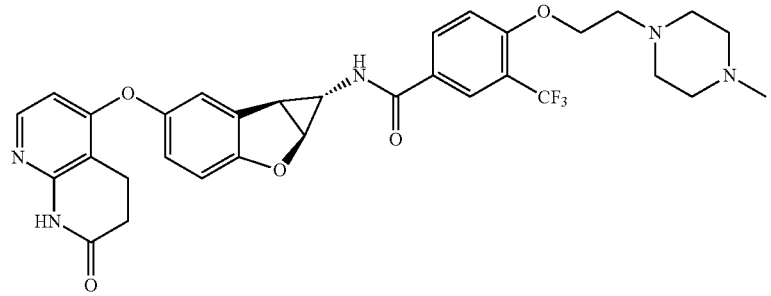
Compound 1.53
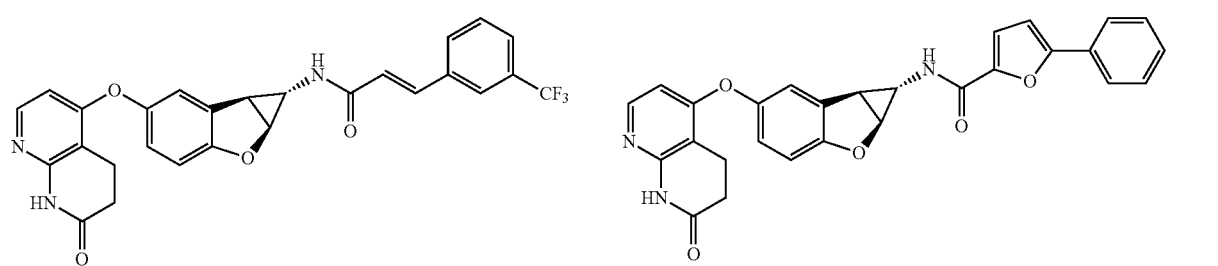
Compound 1.54
Compound 1.55
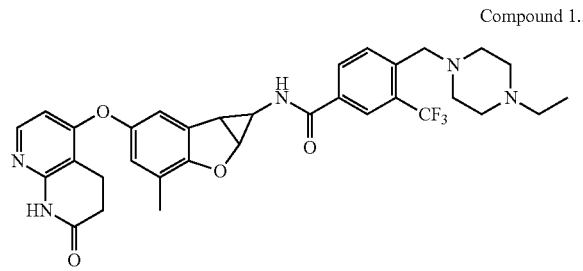
Compound 1.56
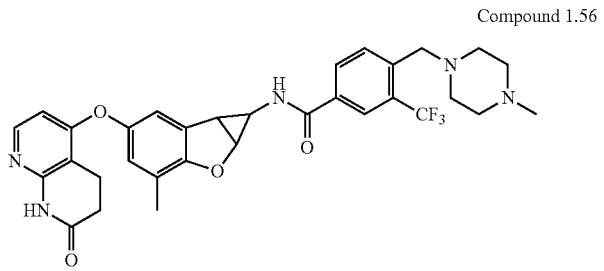
Compound 1.57
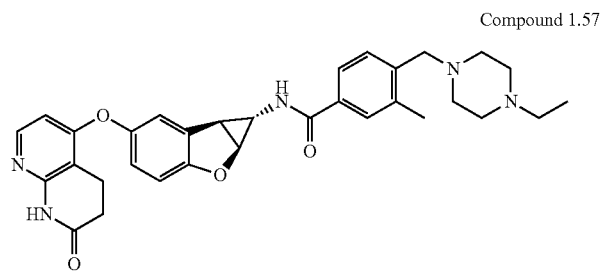
Compound 1.58
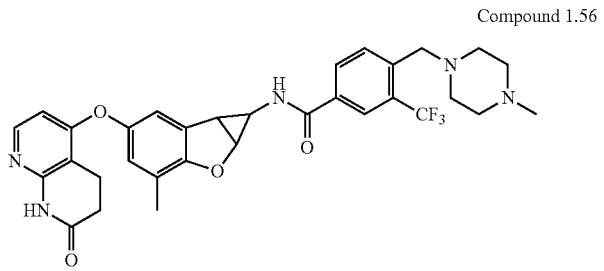
Compound 1.59
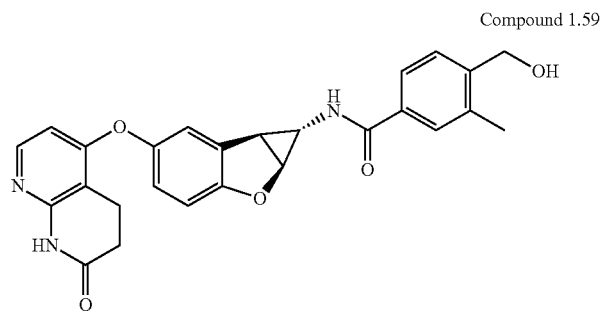
Compound 1.60
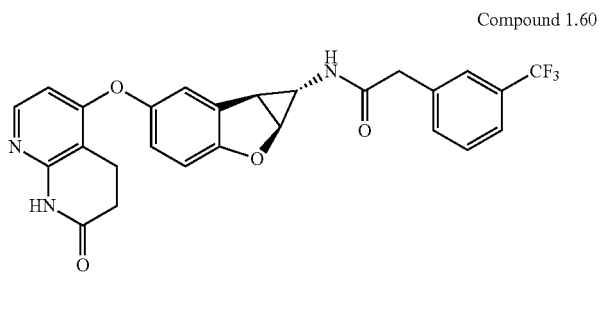

-continued
Compound 1.61
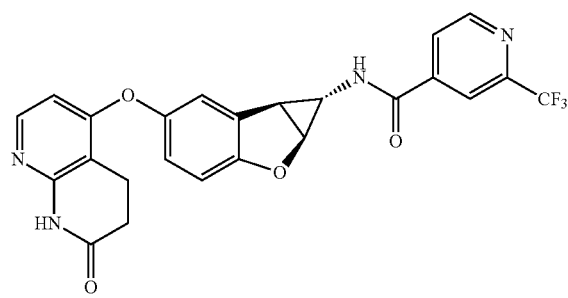
Compound 1.62
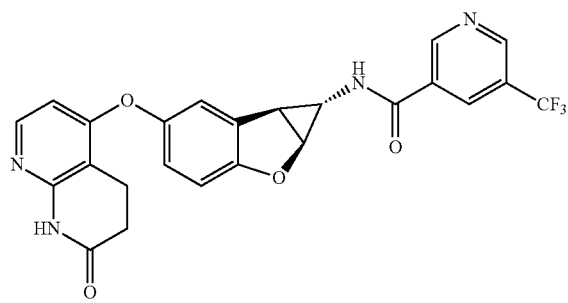
Compound 1.63
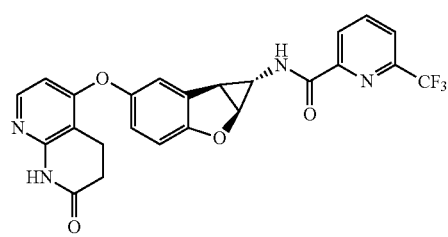
Compound 1.64
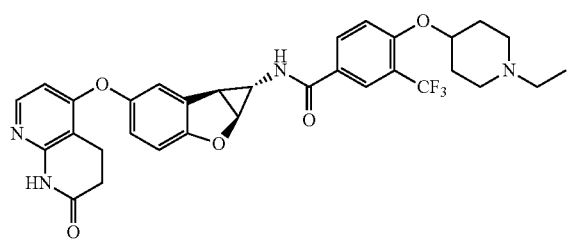
Compound 1.65
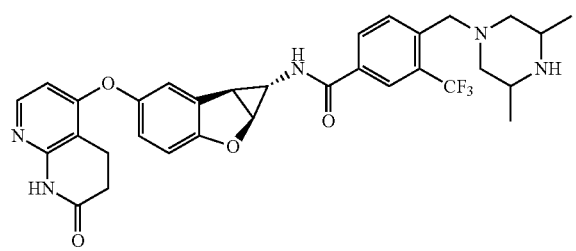
Compound 1.66
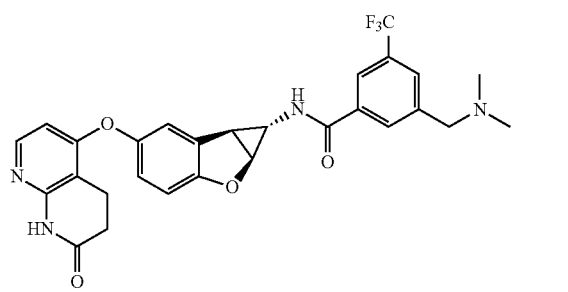
Compound 1.67
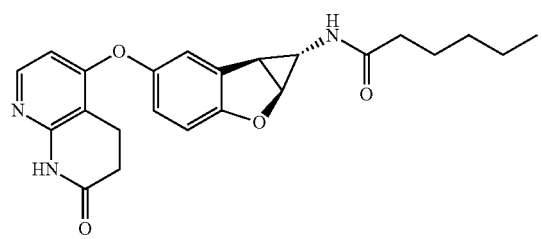
Compound 1.68
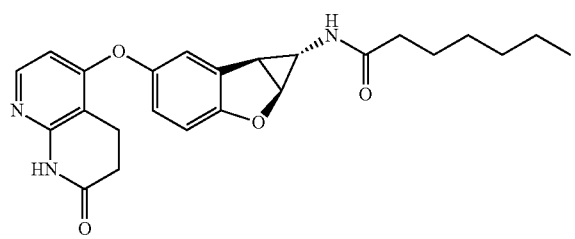
Compound 1.69
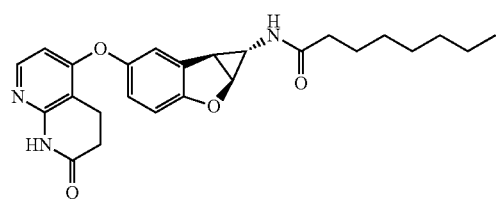
Compound 1.70
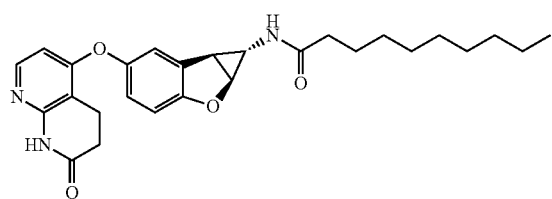

-continued
Compound 1.71
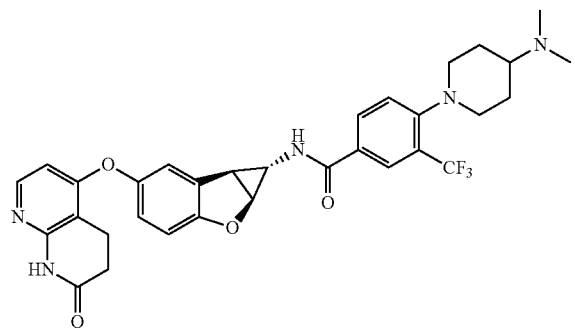
Compound 1.72
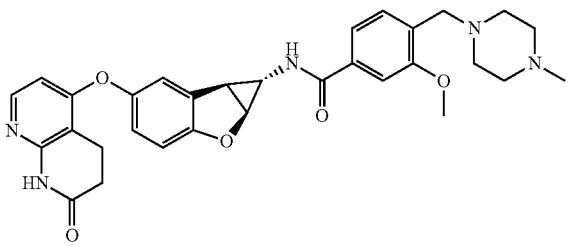
Compound 1.73
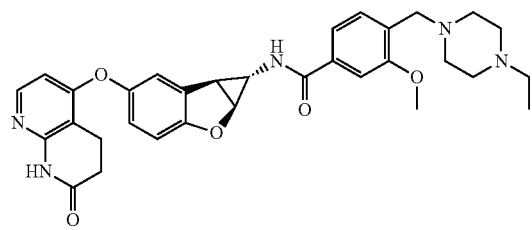
Compound 1.74
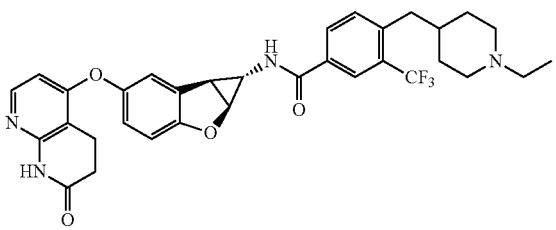
Compound 1.75
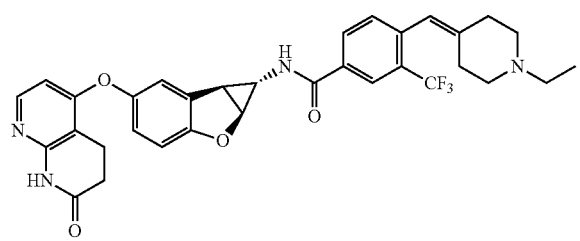
Compound 1.76
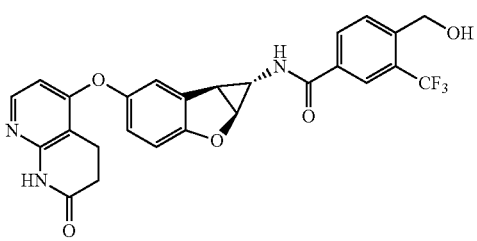
Compound 1.77
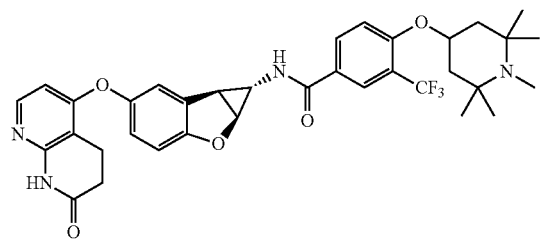
Compound 1.78
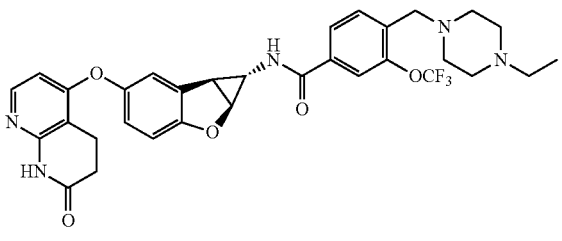
Compound 2.1
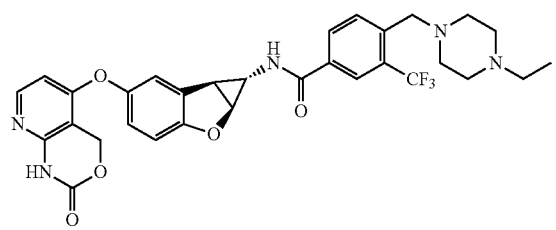
Compound 2.2
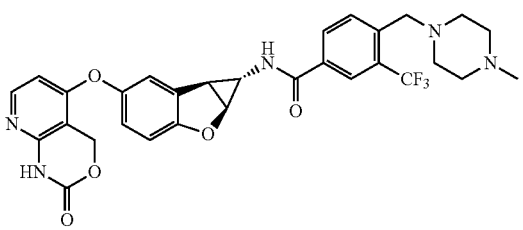
Compound 2.3
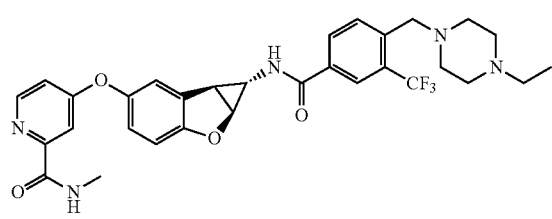
Compound 2.4
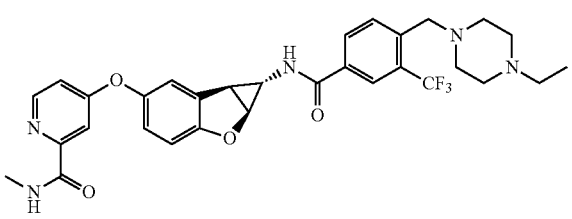

-continued

Compound 2.5

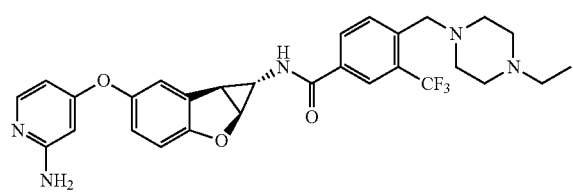

Compound 2.6

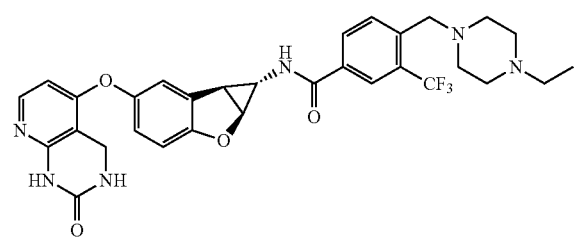

Compound 2.7

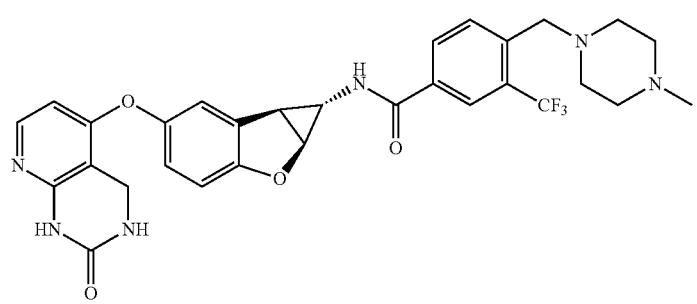

stereoisomers thereof, and pharmaceutically acceptable salts thereof:

The compounds disclosed herein, and/or the pharmaceutically acceptable salts thereof, can be synthesized from commercially available starting materials taken together with the disclosure herein. The following scheme illustrates methods for preparation of some of the compounds disclosed herein.

Scheme I

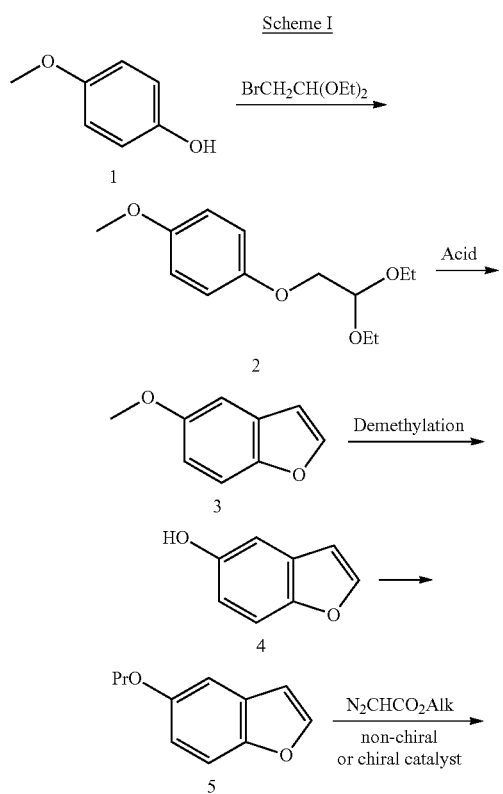

-continued

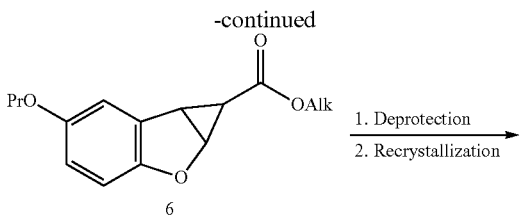

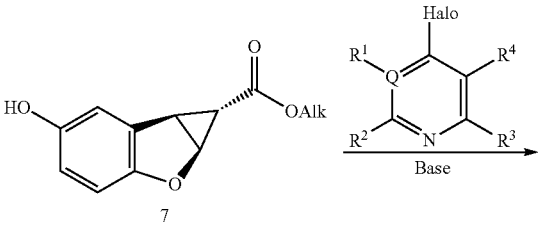

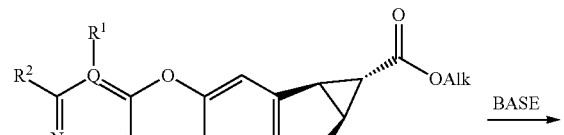

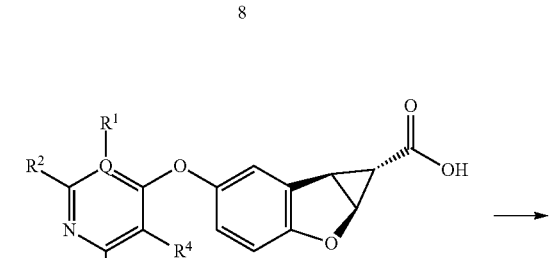

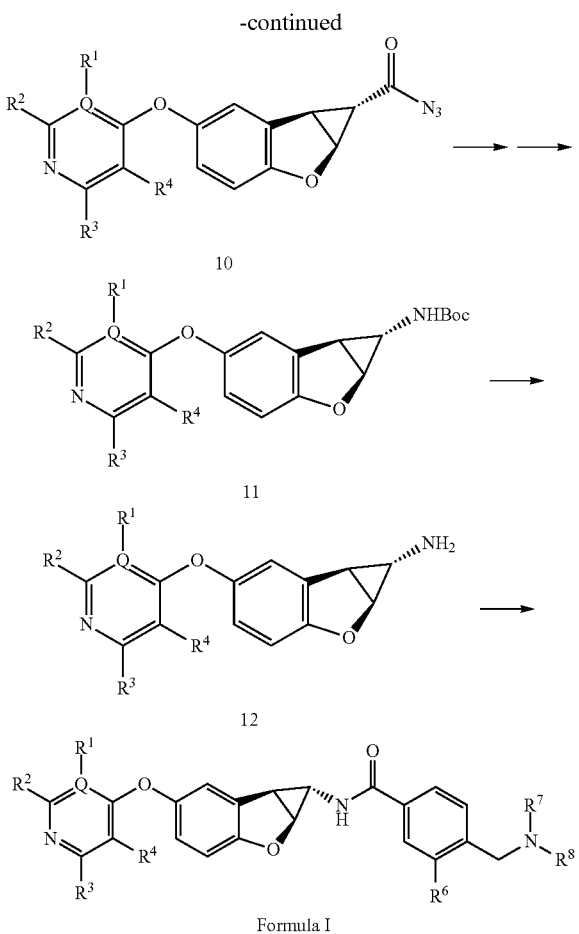

Formula I

In this scheme, a commercially available 4-methoxyphenol is reacted with 2-bromo-1,1-diethoxyethane to form formula 2, then the ring is closed in the presence of acidic condition to give 5-methoxybenzofuran. Then the methyl group is removed and the hydroxy group of formula 4 is protected with a hydroxy protecting group (such as methyl, ethyl, isopropyl, benzyl, p-methoxybenzyl, trityl, methoxymethyl, tetrahydropyranyl acetyl, benzoate, trimethylsilyl, triethylsilyl, tri-isopropylsilyl, tert-butyldimethylsilyl or tert-butyldiphenylsilyl, further such as benzyl from benzyl bromide, and tert-butyldiphenylsilyl from TBSCl) to provide a protected hydroxybenzofuran of formula 5. The compound of formula 5 is reacted with alkyl diazo-acetate (such as ethyl diazo-acetate) in the presence of a Rh or Cu catalyst to provide a cyclopropane derivative of formula 6. The chiral derivative of formula 6 may be obtained by using a chiral catalyst formed in situ from $Cu(OOCCF_3)_2$ and a chiral amino alcohol or by using a commercially available chiral Rh catalyst. The compound of formula 6 is deprotected as described above to provide a phenol derivative (for example, the TMS protecting group may be removed by treating with HCl/EtOH). Formula 7 can be obtained using simple recrystallization. The resulting phenol derivative of formula 7 is reacted with haloheteroaryl derivative (such as fluoro-substituted teroaryl derivative) to provide a compound of formula 8, which subsequently is hydrolyzed into the free acid of formula 9 by using a base such as sodium hydroxide. A compound of formula 9 is reacted with DPPA (diphenylphosphoryl azide) to form formula 10, which is rearranged to afford the Boc protected amine 11 in the presence of tert-butanol. Then Boc group is removed under acidic condition such as TFA or HCl. The further coupling of the amine 12 is accomplished under standard conditions known in the art to provide a compound of Formula I.

Also provided is a method for treating or preventing hyperproliferative disorders, such as cancer, comprising administrating to a subject, such as a mammal or human in need thereof pharmaceutically-effective amount of at least one compound selected from compounds of Formula (I) (such as Formulae (Ia), (Ib), (Ic) and (II)), stereoisomers thereof, and pharmaceutically accept salts thereof described herein.

Also provided is a method for treating or preventing hyperproliferative disorders, such as cancer by inhibiting multiple (specifically BRAF and/or EGFR-T790M) kinases, comprising administrating to a subject, such as a mammal or human in need thereof pharmaceutically-effective amount of at least one compound selected from compounds of Formula (I) (such as Formulae (Ia), (Ib), (Ic) and (II)), stereoisomers thereof, and pharmaceutically accept salts thereof described herein.

Also provided is a method for treating or preventing cancer including but not limiting to, for example, melanomas and thyroid cancers, Barret's adenocarcinoma, breast cancer, cervical cancer, cholangiocarcinoma, glioblastoma, colorectal cancer, gastric cancer, lung cancer, ovarian cancer, pancreatic cancer, prostate cancer, and hematologic cancers, comprising administrating to a subject, such as a mammal or human in need thereof pharmaceutically-effective amount of at least one compound selected from compounds of Formula (I) (such as Formulae (Ia), (Ib), (Ic) and (II)), stereoisomers thereof, and pharmaceutically accept salts thereof described herein.

Also provided is a method for treating or preventing disorders associated with neuronal degeneration resulting from ischemic events, including cerebral ischemia after cardiac arrest, stroke and multi-infarct dementia, comprising administrating to a subject, such as a mammal or human in need thereof pharmaceutically-effective amount of at least one compound selected from compounds of Formula (I) (such as Formulae (Ia), (Ib), (Ic) and (II)), stereoisomers thereof, and pharmaceutically accept salts thereof described herein.

Also provided is a method for treating or preventing disorders associated with those after cerebral ischemic events such as those resulting from head injury, surgery and/or during childbirth, as well as in polycystic kidney disease, comprising administrating to a subject, such as a mammal or human in need thereof pharmaceutically-effective amount of at least one compound selected from compounds of Formula (I) (such as Formulae (Ia), (Ib), (Ic) and (II)), stereoisomers thereof, and pharmaceutically accept salts thereof described herein.

Also provided is a pharmaceutical composition comprising at least one compound selected from compounds of Formula (I) (such as Formulae (Ia), (Ib), (Ic) and (II)), stereoisomers thereof, and pharmaceutically accept salts thereof described herein and pharmaceutically-acceptable carriers, diluents, or adjuvants.

Also provided herein is a method of treating cancer responsive to inhibition of Raf kinase comprising administering to a subject, such as a mammal or human, in need of treating for the cancer an effective amount of at least one compound selected from compounds of Formula (I) (such as Formulae (Ia), (Ib), (Ic) and (II)), stereoisomers thereof, and pharmaceutically acceptable salts thereof described herein.

The at least one compound selected from compounds of Formula (I) (such as Formulae (Ia), (Ib), (Ic) and (II)), stereoisomers thereof, and pharmaceutically acceptable salts thereof may be employed alone or in combination with at least one other therapeutic agent for treatment. In some embodiments, the at least one compound selected from compounds of Formula (I) (such as Formulae (Ia), (Ib), (Ic) and (II)), stereoisomers thereof, and pharmaceutically acceptable salts thereof can be used in combination with at least one additional therapeutic agent. The at least one additional therapeutics agent can be, for example, selected from anti-hyperproliferative, anti-cancer, and chemotherapeutic agents. The at least one compound and/or at least one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the at least one compound and/or at least one pharmaceutically acceptable salt disclosed hereinA "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anti-cancer drugs, toxins, and/or radionuclides; biological response modifiers (e.g., interferons, such as IFN-a and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); Trametinib; Selumetinib; Binimetinib; Pimasertib; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB1-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, such as calicheamicin gammaI1 and calicheamicin omegaI1 (Angew Chem. Intl. Ed. Engl. (1994) 33:183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; and rogens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ib and ronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal gl and s, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti- and rogens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, such asthose which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER$^2$ expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the at least one compound selected from compounds of Formula (I) (such as Formulae (Ia), (Ib), (Ic) and (II)), stereoisomers thereof, and pharmaceutically acceptable salt thereofmay, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, visilizumab, nivolumab and pembroluzimab.

Also provided herein is a composition comprising at least one compound selected from compounds of Formula (I) (such as Formulae (Ia), (Ib), (Ic) and (II)), stereoisomers thereof, and pharmaceutically acceptable salts thereof, and at least one pharmaceutically acceptable carrier.

The composition comprising at least one compound selected from compounds of Formula (I) (such as Formulae (Ia), (Ib), (Ic) and (II)), stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositionsdisclosed herein may be conveniently presented in unit dosage form and prepared by any of the methods well known in the art.

The at least one compound selected from Formula (I) (such as Formulae (Ia), (Ib), (Ic) and (II)), stereoisomers thereof, and pharmaceutically acceptable salts thereofcan be administered orally in solid dosage forms, such as capsules, tablets, troches, dragées, granules and powders, or in liquid dosage forms, such as elixirs, syrups, emulsions, dispersions, and suspensions. The at least one compound selected from compounds of Formula (I) (such as Formulae (Ia), (Ib), (Ic) and (II)), stereoisomers thereof, and pharmaceutically acceptable salts thereof disclosed herein can also be administered parenterally, in sterile liquid dosage forms, such as dispersions, suspensions or solutions. Other dosages forms that can also be used to administer the at least one compound selected from Formula (I) (such as Formulae (Ia), (Ib), (Ic) and (II)), stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the at least one compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration maycomprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

The at least one compound selected from compounds of Formula (I) (such as Formulae (Ia), (Ib), (Ic) and (II)), stereoisomers thereof, and pharmaceutically acceptable salts thereof disclosed herein can further be examined for efficacy in treating cancer by in vivo assays. For example, the at least one compound and/or the at least one pharmaceutically acceptable salts thereof disclosed herein can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the at least one compound selected from compounds of Formula (I) (such as Formulae (Ia), (Ib), (Ic) and (II)), stereoisomers thereof, and pharmaceutically acceptable salts thereof disclosed herein may be conveniently delivered in the form of an aerosol spray presentation from pressurized packs or nebulisers. The at least one compound selected from compounds of Formula (I) (such as Formulae (Ia), (Ib), (Ic) and (II)), stereoisomers thereof, and pharmaceutically acceptable salts thereof disclosed herein may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of at least one compound selected from compounds of Formula (I) (such as Formulae (Ia), (Ib), (Ic) and (II)), stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the at least one compound selected from compounds of Formula (I) (such as Formulae (Ia), (Ib), (Ic) and (II)), stereoisomers thereof, and pharmaceutically acceptable salts thereof disclosed herein in an appropriate ophthalmic vehicle, such that the at least one compound selected from compounds of Formula (I) (such as Formulae (Ia), (Ib), (Ic) and (II)), stereoisomers thereof, and at least one pharmaceutically acceptable salts thereof disclosed herein is maintained in contact with the ocular surface for a sufficient time period to allow the compound to penetrate the corneal and internal regions of the eye.

Useful pharmaceutical dosage-forms for administration of the at least one compound selected from compounds of Formula (I) (such as Formulae (Ia), (Ib), (Ic) and (II)), stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the at least one compound selected from compounds of Formula (I) (such as Formulae (Ia), (Ib), (Ic) and (II)), stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the at least one compound selected from compounds of Formula (I) (such as Formulae (Ia), (Ib), (Ic) and (II)), stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the at least one compound selected from compounds of Formula (I) (such as Formulae (Ia), (Ib), (Ic) and (II)), stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the at least one compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided at least one compound selected from compounds of Formula (I) (such as Formulae (Ia), (Ib), (Ic) and (II)), stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the at least one compound selected from compounds of Formula (I) (such as Formulae (Ia), (Ib), (Ic) and (II)), stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term "coadministration" is understood to include the administration of at least two agents concomitantly or sequentially, or alternatively as a fixed dose combination of the at least two active components.

The at least one compound selected from compounds of Formula (I) (such as Formulae (Ia), (Ib), (Ic) and (II)), stereoisomers thereof, and pharmaceutically acceptable salt thereof disclosed herein can be administered as the sole active ingredient or in combination with at least one second active ingredient, selected, for example, from other active ingredients known to be useful for treating cancers in a patient.

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using pre-packed silica gel cartridges.

$^1$H NMR spectra were recorded on a Varian instrument operating at 400 MHz. $^1$H-NMR spectra were obtained using CDCl$_3$, CD$_2$Cl$_2$, CD$_3$OD, D$_2$O, d$_6$-DMSO, d$_6$-acetone or (CD$_3$)$_2$CO as solvent and tetramethylsilane (0.00 ppm) or residual solvent (CDCl$_3$: 7.25 ppm; CD$_3$OD: 3.31 ppm; D$_2$O: 4.79 ppm; d$_6$-DMSO: 2.50 ppm; d$_6$-acetone: 2.05; (CD$_3$)$_2$CO: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by ChemDraw version 12.0.

In the following examples, the abbreviations below are used:
AcOH Acetic acid
Aq Aqueous
Brine Saturated aqueous sodium chloride solution
Bn Benzyl
BnBr Benzyl Bromide
CH$_2$Cl$_2$ Dichloromethane
DMF N,N-Dimethylformamide
Dppf 1,1'-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMSO Dimethyl sulfoxide
EtOAc Ethyl acetate
EtOH Ethanol
Et$_2$O or ether Diethyl ether
g grams
h or hr hour
HATU O-(7-Azabenzotriazol-1-yl)-N,N,N',N'-tetramethyluronium hexafluorophosphate
HCl Hydrochloric acid
HPLC High-performance liquid chromatography
IPA 2-propanol
i-PrOH Isopropyl alcohol
mg milligrams
mL milliliters
mmol millimole
MeCN Acetonitrile
MeOH Methanol
min minutes
ms or MS Mass spectrum
Na$_2$SO$_4$ Sodium sulfate
PE petroleum ether
PPA Polyphosphoric acid
Rt Retention time
Rt or rt Room temperature
TBAF Tetra-butyl ammonium fluoride
TBSCl tert-Butyldimethylsilyl chloride
TFA Trifluoroacetic acid
THF tetrahydrofuran
TLC thin layer chromatography
μL microliters

EXAMPLE 1: SYNTHESIS OF COMPOUNDS 1.1-1.78

Intermediate I: 5-(((1S,1aS,6bS)-1-amino-1a,6b-dihydro-1H-cyclopropa[b]benzofuran-5-yl)oxy)-3,4-dihydro-1,8-naphthyridin-2(1H)-one

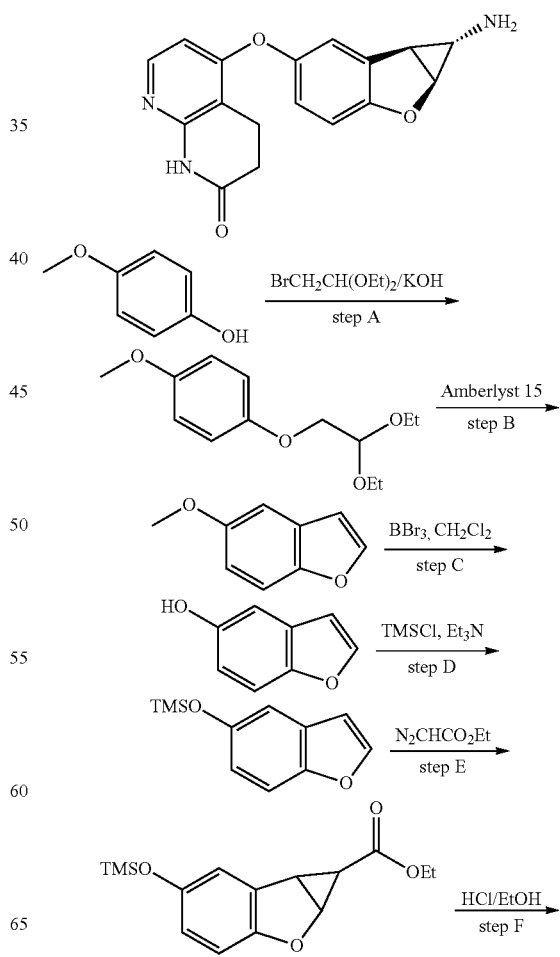

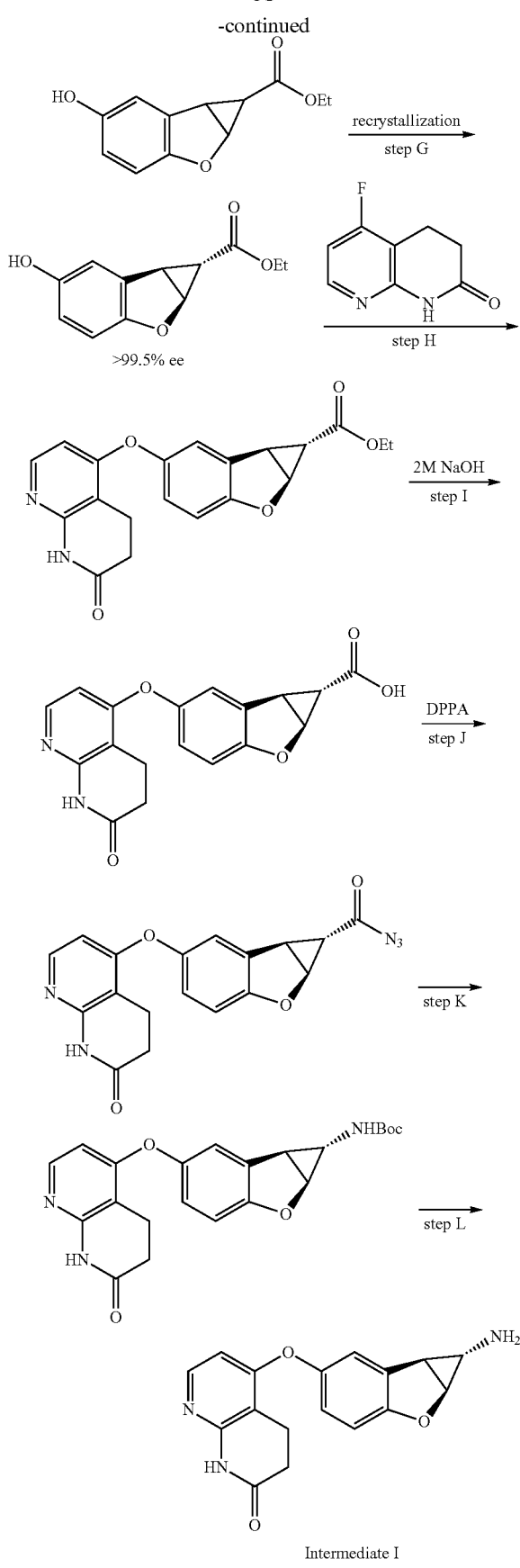

Intermediate I

Step A: 1-(2,2-diethoxyethoxy)-4-methoxybenzene

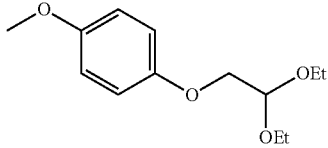 [SMILES: CCOC(COc1ccc(OC)cc1)OCC]

To a stirred solution of 4-methoxyphenol (500 g, 4 mol) in DMSO (500 mL) was added KOH (400 g, 7.1 mol, 1.78 eq) at room temperature. After stirring for 20 min, the resulted mixture was heated to 120° C. 2-bromo-1,1-diethoxyethane (850 g, 4.3 mol) was added in drops within 2 hour at this temperature and stirred for another 2 hours. The mixture was treated with water (1000 mL) and PE (1000 mL), filtered through a celite pad. The liquid phase was extracted with PE (500 mL×2). The combined organics was washed with aqueous NaOH (2 N, 300 mL×2), brine (500 mL×3), dried over anhydrate sodium sulfate and concentrated under reduced pressure to give the title compound (850 g, 88%) as a light yellow oil which was used into next step directly. $^1$H NMR (400 MHz, DMSO-d6) δ 6.98-6.78 (m, 4H), 4.76 (t, J=5.2 Hz, 1H), 3.88 (d, J=5.2 Hz, 2H), 3.71-3.68 (m, 3H), 3.69-3.61 (m, 2H), 3.60-3.50 (m, 2H), 1.17-1.10 (m, 6H) ppm.

Step B: 5-methoxybenzofuran

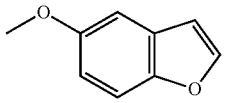

The mixture of the product of Step A (420 g, 1.87 mmol) and Amberlyst 15 (42 g) in toluene (2 L) was stirred at reflux for 6 hrs with concomitant azeotrope removal of EtOH generated in the reaction (keep the solvent more than 1.5 L). The resulting reaction mixture was filtered and the resin was washed with an excess of toluene. The combined filtrates were concentrated to dryness under reduced pressure. The crude product was distilled at 100° C. under reduced pressure through a lab oil pump to afford (105 g, 74° C. fraction). The solid was diluted with 1000 mL of PE and washed with NaOH (3 M, 200 mL×2), brine (500 mL×3), dried over anhydrate sodium sulfate and concentrated under reduced pressure to give the title compounds (85 g, 33%) as a white solid. $^1$H NMR (400 MHz, CDCl$_3$) δ 7.59 (d, J=2.0 Hz, 1H), 7.39 (d, J=9.0 Hz, 1H), 7.05 (d, J=2.4 Hz, 1H), 6.90 (dd, J=9.0, 2.4 Hz, 1H), 6.73-6.68 (m, 1H), 3.84 (s, 3H) ppm.

Step C: benzofuran-5-ol

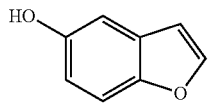

To a solution of the product of Step B (50 g, 0.34 mol) in CH$_2$Cl$_2$ (1200 mL) was added BBr$_3$ (32.5 mL, 0.34 mol) in drops at −20° C. under N₂. After the addition, the mixture was warmed to 20° C. and stirred for 2 hrs. The reaction mixture was cooled to 0° C. and added into a solution of NH₃/MeOH (3 mol/L, 500 mL) using a canula at −20° C. over a period of 15 min carefully. The mixture was concentrated and the residue was added EA (500 mL). The solid was filtered off through a silica pad and the filtrate was concentrated under reduced pressure to give the crude product (crude, 48 g) as a oil which was used for the next step directly. ¹H NMR (400 MHz, DMSO-d6) δ 9.14 (s, 1H), 7.86 (d, J=2.0 Hz, 1H), 7.36 (d, J=8.8 Hz, 1H), 6.94 (d, J=2.4 Hz, 1H), 6.79 (dd, J=2.0, 0.9 Hz, 1H), 6.74 (dd, J=8.8, 2.4 Hz, 1H) ppm. MS: M/e 135 (M+1)⁺.

Step D: (benzofuran-5-yloxy)trimethylsilane

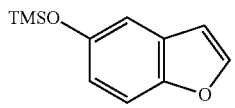

To a stirred solution of the product of Step C (350 g, 2.6 mol) and Et₃N (400 g, 3.9 mol) in DCM (2000 mL) was added a solution of trimethylsilanyl chloride (290 g, 2.6 mol) in DCM (300 mL) at 0° C. The mixture was stirred at ambient temperature for 3 hours. Large amount of white solid precipitated and it was filtered with a silica-gel pad and the filter cake was washed with PE. The combined filtrates was concentrated and the resulted oil was distilled under high vacuum to give product (290 g, yield: 62% for 2 steps) as a colorless oil. ¹H NMR (400 MHz, DMSO-d6) δ 7.69 (d, J=2.0 Hz, 1H), 7.21 (d, J=8.8 Hz, 1H), 6.84 (d, J=2.5 Hz, 1H), 6.61 (d, J=2.0 Hz, 1H), 6.56 (dd, J=8.8, 2.5 Hz, 1H), 0.00 (s, 9H) ppm.

Step E: ethyl 5-((trimethylsilyl)oxy)-1a,6b-dihydro-1H-cyclopropa[b]benzo furan-1-carboxylate

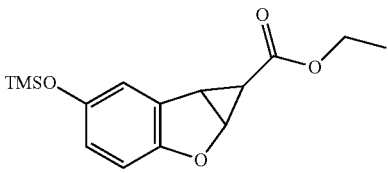

Copper (I) triflate (2:1 complex with toluene, 600 mg, 0.5%) and (S,S)-2,2'-Isopropylidene-bis(4-phenyl-2-oxazoline) (760 mg, 1%) were stirred in dichloromethane (10 mL) at ambient temperature under N₂ atmosphere for 1 hour. the product of Step D (47.2 g, 0.23 mol) was added, followed by a slow addition of ethyl diazoethanoate (78 g, 0.69 mol) in DCM (400 mL) during a period of 12 hours using a syringe pump. A solution of EDTA disodium (0.05 mol/L, 100 mL×2) was added to the reaction mixture and stirred at room temperature for 1 hr. The organic phase was concentrated and the residue was distilled under reduced pressure (lab oil pump). The fraction of the title compound (43.5 g, 65%, light yellow oil) was collected at 125~140° C. ¹H NMR (400 MHz, DMSO-d6) δ 6.79 (d, J=2.4 Hz, 1H), 6.59 (d, J=8.4 Hz, 1H), 6.42 (dd, J=8.4, 2.4 Hz, 1H), 4.95 (dd, J=5.4, 1.0 Hz, 1H), 3.08 (dd, J=5.4, 3.2 Hz, 1H), 1.02 (dd, J=3.1, 1.2 Hz, 1H), 0.00 (s, 9H) ppm.

Step F: ethyl 5-hydroxy-1a,6b-dihydro-1H-cyclopropa[b]benzofuran-1-carboxylate

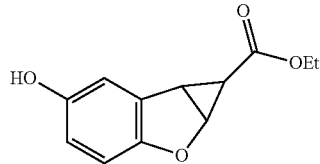 [SMILES: CCOC(=O)C1C2Oc3ccc(O)cc3C21]

A solution of the product of Step E (35 g, 0.12 mol) in MeOH (100 mL) was added a solution of HCl/EtOH (1 M, 0.1 mL) at ambient temperature and stirred for 1 hour. The mixture was concentrated and the resulted oil was diluted with 100 mL of PE/EA (3:1) and concentrated again to give the title compound (26.3 g, yield: >99%, ee %: 85%) as a light yellow solid.

¹H-NMR (600 MHz, CDCl₃) δ 7.01 (s, 1H), 6.89 (d, J=2.6 Hz, 1H), 6.68 (d, J=8.6 Hz, 1H), 6.63 (dd, J=8.6, 2.6 Hz, 1H), 5.02 (dd, J=5.6, 1.2 Hz, 1H), 4.15 (q, J=7.2 Hz, 2H), 3.19 (dd, J=5.4, 3.0 Hz, 1H), 1.26 (dd, J=3.0, 1.2 Hz, 1H), 1.26-1.23 (m, 3H) ppm.

Step G: (1S,1aS,6bR)-ethyl 5-hydroxy-1a,6b-dihydro-1H-cyclopropa[b]benzofuran-1-carboxylate

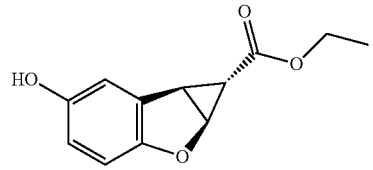 [SMILES: CCOC(=O)[C@@H]1[C@H]2Oc3ccc(O)cc3[C@H]21]

The phenol the product of Step F (46.0 g, purity: 100%; ee: 85.1%) in n-hexane/ethyl acetate (12/1, total 1400 mL) was stirred at reflux. After all solids dissolved and a homogenous solution was obtained, the solution was stirred at reflux for 0.5 h more. Then the solution was cooled to room temperature and phenol compound crystallized out as needle form crystals over 2 h time period. The mixture was filtered and the crystals (26.5 g, ee: 98.0%) were collected. 26 g of the 98.0% ee compound was subjected to a second round of re-crystallization (n-hexane/ethyl acetate 11/1, total 1000 mL) to give 18.3 g of crystals (the title compound) with 99.9% ee after filtration and drying. ¹H NMR (400 MHz, DMSO-d6) δ 9.06 (s, 1H), 6.89 (d, J=2.8 Hz, 1H), 6.72 (d, J=8.8 Hz, 1H), 6.55 (dd, J=8.8, 2.4 Hz, 1H), 5.12 (d, J=5.6 Hz, 1H), 4.09 (q, J=7.2 Hz, 2H), 3.27 (dd, J=5.6, 2.8 Hz, 1H), 1.25-1.15 (m, 4H). MS: M/e 221 (M+1)⁺.

Step H: (1S,1aS,6bR)-ethyl 5-((7-oxo-5,6,7,8-tetrahydro-1,8-naphthyridin-4-yl)oxy)-1a,6b-dihydro-1H-cyclopropa[b]benzofuran-1-carboxylate

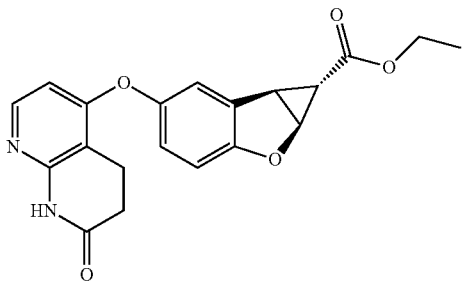 [SMILES: CCOC(=O)[C@@H]1[C@H]2Oc3ccc(Oc4ccnc5c4CCC(=O)N5)cc3[C@H]21]

To the mixture of the product of Step G (66.3 g, 0.3 mol) and 5-fluoro-3,4-dihydro-1,8-naphthyridin-2(1H)-one (50 g, 0.3 mol) in DMF (850 mL) was added Potassium tert-butoxide (35.4 g, 0.32 mol) and the mixture was stirred at 120° C. under nitrogen for 2 hrs. The reaction was cooled to room temperature and filtered through a celite pad and the filtrate was removed half of the solvent. The residue was added into stirred 2 L water in drops. A solid was precipitated out of the solution. The solid was filtered, washed with water and dried in air. The dried title compound (108.2 g, 98%) as a gray solid was used into next step directly. $^1$H NMR (400 MHz, DMSO-d6) δ 10.43 (s, 1H), 7.92 (d, J=5.8 Hz, 1H), 7.30 (d, J=2.4 Hz, 1H), 6.98 (d, J=8.8 Hz, 1H), 6.94 (dd, J=8.8, 2.4 Hz, 1H), 6.21 (d, J=5.8 Hz, 1H), 5.26 (dd, J=5.4, 1.0 Hz, 1H), 4.08 (q, J=7.0 Hz, 2H), 3.34 (dd, J=5.4, 3.2 Hz, 1H), 2.89 (t, J=7.8 Hz, 2H), 2.51 (t, J=7.8 Hz, 2H), 1.34 (dd, J=3.2, 1.0 Hz, 1H), 1.18 (t, J=7.0 Hz, 3H) ppm. MS: M/e 367 (M+1)$^+$.

Step I: (1S,1aS,6bR)-5-((7-oxo-5,6,7,8-tetrahydro-1,8-naphthyridin-4-yl)oxy)-1a,6b-dihydro-1H-cyclopropa[b]benzofuran-1-carboxylic acid

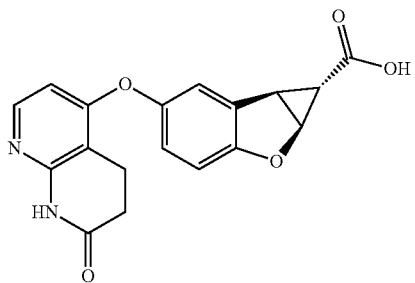

Sodium hydroxide aqueous solution (450 mL, 2 M, 0.9 mol) was added to a stirred solution of the product of Step H (216.4 g, 0.59 mol) in ethanol (1 L) at room temperature. The mixture was stirred at room temperature for 2 hours and 60° C. for 2 hours. The solvent was removed under reduced pressure and the residue was dissolved into water (1.2 L). The solution was neutralized with HCl (1 mol/L) to pH=7 and white solid precipitated out of solution. The white solid was collected by filtration and dried in air to give the title compound (164 g, 82%). $^1$H NMR (400 MHz, DMSO-d6) δ 12.59 (s, 1H), 10.43 (s, 1H), 7.92 (d, J=5.8 Hz, 1H), 7.29 (d, J=2.4 Hz, 1H), 6.97 (d, J=8.8 Hz, 1H), 6.93 (dd, J=8.8, 2.4 Hz, 1H), 6.21 (d, J=5.8 Hz, 1H), 5.21 (dd, J=5.4, 1.0 Hz, 1H), 3.27-3.25 (m, 1H), 2.89 (t, J=7.8 Hz, 2H), 2.51 (d, J=8.8 Hz, 2H), 1.19 (dd, J=3.0, 1.0 Hz, 1H) ppm. MS: M/e 339 (M+1)$^+$.

Step J: (1S,1aS,6bR)-5-((7-oxo-5,6,7,8-tetrahydro-1,8-naphthyridin-4-yl)oxy)-1a,6b-dihydro-1H-cyclopropa[b]benzofuran-1-carbonylazide

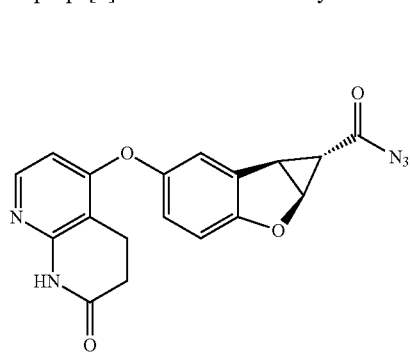

To a 0° C. solution of the product of Step I (6.0 g, 17.7 mmol) in DMF (40 mL) was added Et$_3$N (4.5 g, 45 mmol) and followed by DPPA (5.9 g, 21.5 mmol). The resulted mixture was allowed warm to ambient temperature and stirred for 5 hours. 150 mL of H$_2$O was added and the mixture was extracted with EA (100 mL×3). The combined extracts was washed with brine (100 mL×3), dried over Na$_2$SO$_4$, concentrated under vacuum until about 30 mL of EA remained. 150 mL of PE was added and the mixture was stirred for 30 minutes. The white solid was filtered and washed with PE/EA (5:1, 100 mL), dried under high vacuum to give the title compound (6.17 g, yield: 95%) as a white solid. $^1$H NMR (400 MHz, CDCl$_3$) δ 8.80 (s, 1H), 8.02 (d, J=6.0 Hz, 1H), 7.15 (d, J=2.0 Hz, 1H), 7.00-6.85 (m, 2H), 6.26 (d, J=6.0 Hz, 1H), 5.22 (d, J=5.2 Hz, 1H), 3.43 (dd, J=5.2, 2.8 Hz, 1H), 3.07 (t, J=7.6 Hz, 2H), 2.71 (t, J=7.6 Hz, 2H), 1.36 (d, J=2.0 Hz, 1H). MS: M/e 364 (M+1)$^+$.

Step K: tert-butyl ((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)carbamate

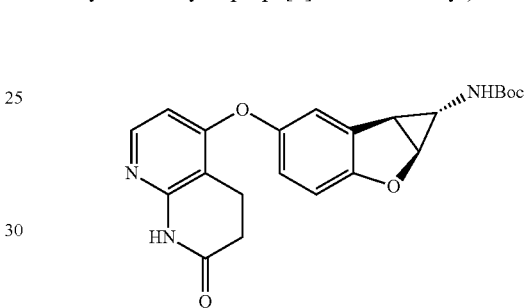

A solution of the product of Step J, 2.0 g, 5.5 mmol) in anhydrous t-BuOH (20 mL) was refluxed for 5 hours. The mixture was concentrated to dryness and 50 mL of anhydrous CH$_2$Cl$_2$ was added and the mixture was stirred for 10 min. The white solid was filtered and the filtrate was concentrated to obtain the desired compound (2.16 g, 96%) as a light yellow solid. $^1$H NMR (400 MHz, CDCl$_3$) δ 8.66 (s, 1H), 8.00 (d, J=6.0 Hz, 1H), 7.11 (s, 1H), 6.87-6.78 (m, 2H), 6.26 (d, J=6.0 Hz, 1H), 4.80 (d, J=5.6 Hz, 1H), 3.06 (t, J=7.6 Hz, 2H), 2.96-2.85 (m, 1H), 2.70 (t, J=7.6 Hz, 2H), 2.25 (s, 1H), 1.47 (s, 9H).

Step L: 5-(((1S,1aS,6bS)-1-amino-1a,6b-dihydro-1H-cyclopropa[b]benzofuran-5-yl)oxy)-3,4-dihydro-1,8-naphthyridin-2(1H)-one (Intermediate I)

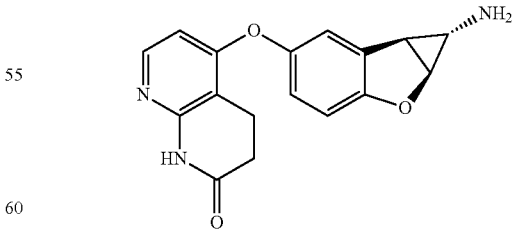

The product from Step K (2.16 g, 5.3 mmol) was added into a solution of HCl in EA (3 M, 40 mL) in portions at ambient temperature. After the addition finished, the mixture was stirred for 30 min. A white solid was filtered and washed with EA (50 mL), dried and concentrated under high vacuum to obtain the desired compound (1.75 g, 96%) as a white solid. $^1$H NMR (400 MHz, DMSO-d6) δ 10.62 (s, 1H), 8.70 (s, 3H), 7.99 (d, J=6.0 Hz, 1H), 7.31 (s, 1H), 7.04-6.94 (m, 2H), 6.27 (d, J=6.0 Hz, 1H), 5.21 (d, J=6.0 Hz, 1H), 3.29 (d, J=6.0 Hz, 1H), 2.94 (t, J=7.6 Hz, 2H), 2.56 (t, J=7.6 Hz, 2H), 2.47 (s, 1H). MS: M/e 310 (M+1)$^+$.

Compound 1.1: 4-((4-ethylpiperazin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

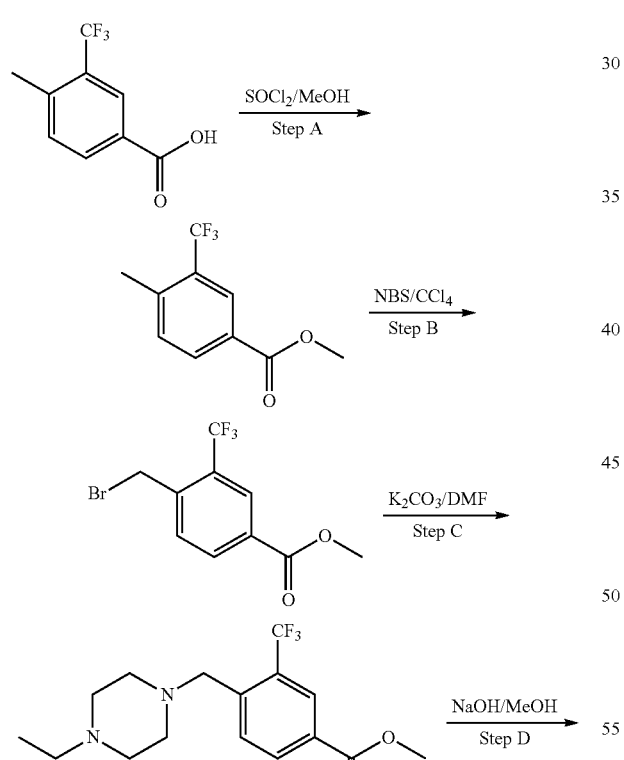

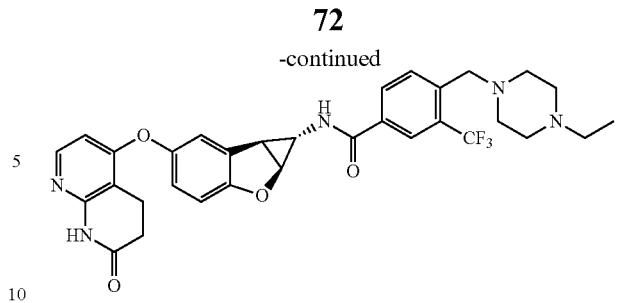

Step A: methyl 4-methyl-3-(trifluoromethyl)benzoate

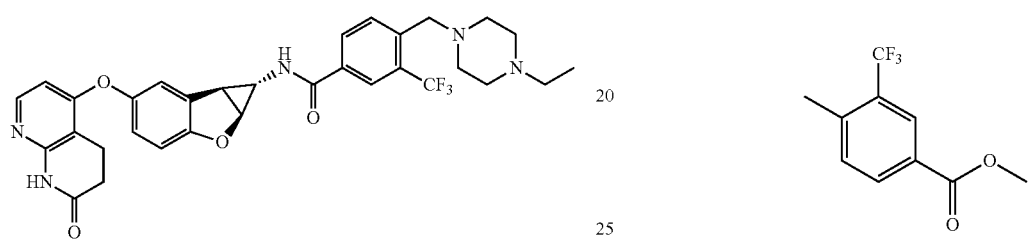

To a stirred methanol (300 mL) was added dropwisely sulfurous dichloride (30 mL) at 0° C. The reaction mixture was stirred at room temperature for 1 hour. To this stirred solution was added 4-methyl-3-(trifluoromethyl)benzoic acid (30 g, 0.15 mol) in one portion at room temperature. The mixture was stirred at 80° C. for 5 hrs. The solvent was removed under reduced pressure. The residue was diluted with ethyl acetate (300 mL) and washed with saturated sodium bicarbonate and brine. The organic phase was dried over sodium sulfate anhydrous and concentrated. The residue (28.3 g, yield: 88.4%) was used into next step directly. $^1$H NMR (400 MHz, CDCl$_3$) δ 8.24 (s, 1H), 8.03 (d, J=8.0 Hz, 1H), 7.32 (d, J=8.0 Hz, 1H), 3.90 (s, 3H), 2.50 (s, 3H) ppm.

Step B: methyl 4-(bromomethyl)-3-(trifluoromethyl)benzoate

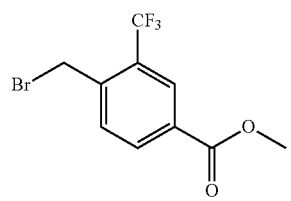 [SMILES: COC(=O)c1ccc(CBr)c(C(F)(F)F)c1]

The mixture of the product of Step A (5 g, 22.9 mmol), N-bromosuccinimide (4.49 g, 25.2 mmol) and benzoyl peroxide (0.56 g, 2.3 mmol) was stirred at 80° C. for 3 hours. The solvent was concentrated under reduced pressure. The residue was purified by silica gel chromatography (silica weight: 60 g, elute: ethyl acetate/Petroleum ether: 1/100~1/50) to afford the title compound (2.2 g, yield: 32.4%). $^1$H NMR (400 MHz, CDCl$_3$) δ 8.31 (s, 1H), 8.20 (dd, J=8.0, 1.2 Hz, 1H), 7.69 (d, J=8.0 Hz, 1.2H), 4.64 (s, 2H), 3.96 (s, 3H) ppm.

Step C: methyl 4-((4-ethylpiperazin-1-yl)methyl)-3-(trifluoromethyl)benzoate

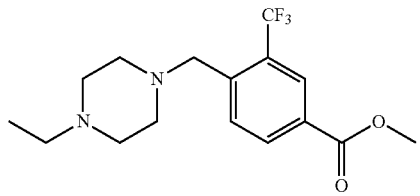 [SMILES: CCN1CCN(Cc2ccc(C(=O)OC)cc2C(F)(F)F)CC1]

The mixture of the product of Step B (613 mg, 2.06 mmol), 1-ethylpiperazine (282 mg, 2.48 mg) and Cesium-carbonate (1.35 g, 4.12 mmol) in N,N-Dimethyl formamide (10 mL) was stirred at 80° C. for 3 hours. The reaction mixture was filtered through a silica pad and the filtrate was concentrated under reduced pressure. The residue was diluted with ethyl acetate (40 mL) and washed with brine (20 mL). The organic phase was dried over sodium sulfate anhydrous and concentrated. The residue (681 mg, yield: 99%) was used into next step directly. MS: M/e 331 (M+1)+.

Step D: 4-((4-ethylpiperazin-1-yl)methyl)-3-(trifluoromethyl)benzoic acid

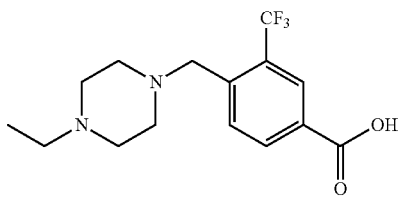 [SMILES: CCN1CCN(Cc2ccc(C(=O)O)cc2C(F)(F)F)CC1]

To the stirred solution of product of Step C (1.53 g, 4.64 mmol) in MeOH (10 mL) was added sodium hydroxide aqueous solution (2 mL, 5 mol/L). The solution was stirred at room temperature for 0.5 hour. The solution was concentrated under reduced pressure. The residue was dissolved in water (2 mL) and added HCl aqueous solution (2 mol/L) till pH about 5~6. The resulting solution was concentrated, the residue was washed by DCM/MeOH (2/1). The solid was formed and filtered off, the filtrate was concentrated to get the title compound (1.46 g, yield: 100%) as yellow solid, which was used into next step directly. $^1$H NMR (400 MHz, DMSO-d6) δ 8.18 (d, J=5.2 Hz, 2H), 7.88 (d, J=8.4 Hz, 1H), 3.70 (s, 2H), 2.92-2.51 (m, 10H), 1.11 (t, J=7.2 Hz, 3H) ppm. MS: M/e 317 (M+1)+.

Step E: 4-((4-ethylpiperazin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide (Compound 1.1)

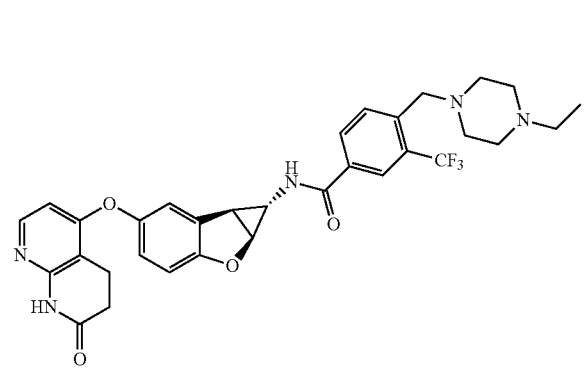

A mixture of the product of Step D (800 mg, 2.52 mmol), HATU (930 mg, 3.02 mmol) and DIPEA (974 mg, 7.56 mmol) in DMF (10 mL) was stirred at room temperature for 10 min. Then Intermediate I (938 mg, 3.02 mmol) was added to this solution. The final solution was stirred at room temperature for 1.2 hours. TLC (DCM/MeOH=10/1) showed the reaction was finished. The resulting solution was concentrated under reduced pressure and the residue was washed by water (20 mL). The white solid was formed, filtered and purified by silica gel chromatography (silica weight: 30 g, elute: DCM/MeOH: 20/1~10/1) to afford the title compound (800 mg, yield: 52%) as a white solid. $^1$H NMR (400 MHz, DMSO-d6) δ 10.50 (s, 1H), 8.96 (d, J=3.6 Hz, 1H), 8.15 (s, 1H), 8.11 (d, J=8.0 Hz, 1H), 7.96 (d, J=5.6 Hz, 1H), 7.88 (d, J=8.0 Hz, 1H), 7.27 (d, J=2.0 Hz, 1H), 7.04-6.87 (m, 2H), 6.25 (d, J=5.6 Hz, 1H), 5.08 (d, J=5.6 Hz, 1H), 3.65 (s, 2H), 3.09 (dd, J=5.6, 2.0 Hz, 1H), 2.94 (t, J=7.6 Hz, 2H), 2.59-2.52 (m, 4H), 2.49-2.17 (m, 9H), 0.98 (t, J=7.2 Hz, 3H) ppm. MS: M/e 608 (M+1)+.

Compounds 1.2-1.24 were prepared according to the procedures described for Compound 1.1 under appropriate conditions that could be recognized by one skilled in the art.

Compound 1.2

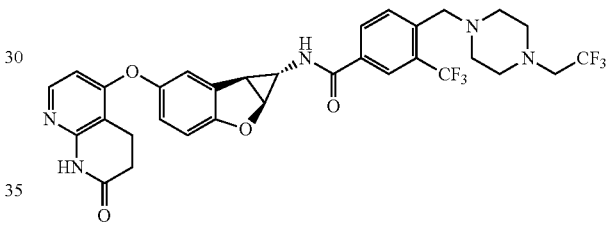

$^1$H NMR (400 MHz, DMSO-d6) δ 10.48 (s, 1H), 8.95 (d, J=3.6 Hz, 1H), 8.16 (s, 1H), 8.11 (d, J=8.4 Hz, 1H), 7.96 (d, J=5.6 Hz, 1H), 7.88 (d, J=8.0 Hz, 1H), 7.27 (d, J=2.0 Hz, 1H), 7.02-6.86 (m, 2H), 6.25 (d, J=5.6 Hz, 1H), 5.08 (d, J=5.6 Hz, 1H), 3.66 (s, 2H), 3.17 (q, J=10.4 Hz, 2H), 3.09 (dd, J=5.6, 2.0 Hz, 1H), 2.94 (t, J=7.6 Hz, 2H), 2.74-2.59 (m, 4H), 2.58-2.53 (m, 3H), 2.48-2.32 (m, 4H) ppm. MS: M/e 662 (M+1)+.

Compound 1.3

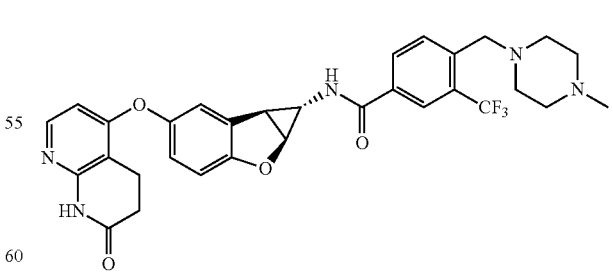

$^1$H NMR (400 MHz, CD$_3$OD) δ 8.14 (s, 1H), 8.04 (d, J=8.0 Hz, 1H), 7.92 (d, J=6.0 Hz, 2H), 7.21 (s, 1H), 6.89 (s, 2H), 6.32 (d, J=6.0 Hz, 1H), 5.01 (d, J=6.0 Hz, 1H), 3.72 (s, 2H), 3.06 (t, J=8.0 Hz, 3H), 2.65 (t, J=7.6 Hz, 3H), 2.60-2.43 (m, 8H), 2.31 (s, 3H) ppm. MS: M/e 594 (M+1)+

Compound 1.4

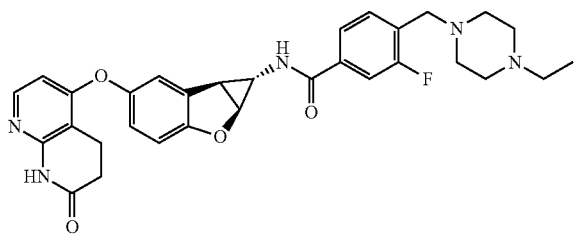 [SMILES: CCN1CCN(Cc2ccc(C(=O)N[C@@H]3[C@H]4Oc5ccc(Oc6ccnc7c6CCC(=O)N7)cc5[C@@H]34)cc2F)CC1]

¹H NMR (400 MHz, DMSO-d6) δ 10.57 (br.s, 1H), 9.21 (br.s, 1H), 8.84 (s, 1H), 7.98 (d, J=5.6 Hz, 1H), 7.72-7.67 (m, 2H), 7.58 (d, J=7.6 Hz, 1H), 7.27 (s, 1H), 6.99-6.94 (m, 2H), 6.29 (d, J=5.6 Hz, 1H), 5.07 (d, J=5.6 Hz, 1H), 3.97-3.70 (m, 2H), 3.49 (s, 2H), 3.25-2.90 (m, 9H), 2.60-2.51 (m, 5H), 1.20 (t, J=7.2 Hz, 3H) ppm. MS: M/e 558 (M+1)⁺.

Compound 1.5

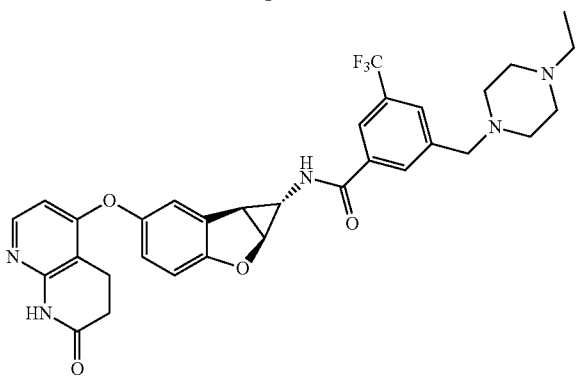

¹H NMR (400 MHz, DMSO-d6) δ 10.57 (s, 1H), 9.03 (d, J=2.8 Hz, 1H), 8.16 (s, 2H), 7.97-7.88 (m, 2H), 7.24 (s, 1H), 6.97-6.87 (m, J=8.8 Hz, 2H), 6.25 (d, J=6.0 Hz, 1H), 5.06 (d, J=5.6 Hz, 1H), 3.97 (s, 2H), 3.49 (brs, 2H), 3.26-2.98 (m, 7H), 2.92 (t, J=7.6 Hz, 2H), 2.76-2.48 (m, 5H), 1.16 (t, J=7.2 Hz, 3H) ppm. MS: M/e 608 (M+1)⁺.

Compound 1.6

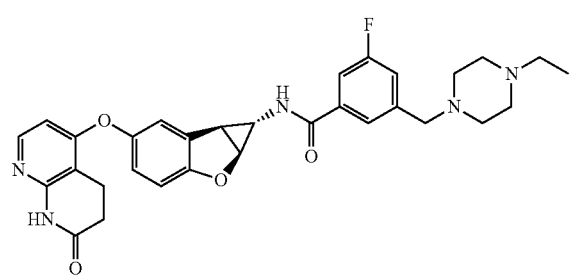 [SMILES: CCN1CCN(Cc2cc(F)cc(C(=O)N[C@@H]3[C@H]4Oc5ccc(Oc6ccnc7c6CCC(=O)N7)cc5[C@@H]34)c2)CC1]

¹H NMR (400 MHz, DMSO-d6) δ 10.45 (s, 1H), 8.78 (d, J=3.6 Hz, 1H), 8.12 (s, 1H), 7.92 (d, J=5.6 Hz, 1H), 7.61 (s, 1H), 7.50 (d, J=9.2 Hz, 1H), 7.29 (d, J=9.2 Hz, 1H), 7.21 (d, J=2.0 Hz, 1H), 6.95-6.82 (m, 2H), 6.21 (d, J=5.6 Hz, 1H), 5.04 (d, J=5.6 Hz, 1H), 3.49 (s, 3H), 3.05 (dd, J=5.6, 2.0 Hz, 1H), 2.90 (t, J=7.6 Hz, 2H), 2.55-2.48-2.46 (m, 6H), 2.40-2.30 (m, 6H), 0.96 (t, J=7.2 Hz, 3H) ppm. MS: M/e 558 (M+1)⁺.

Compound 1.7

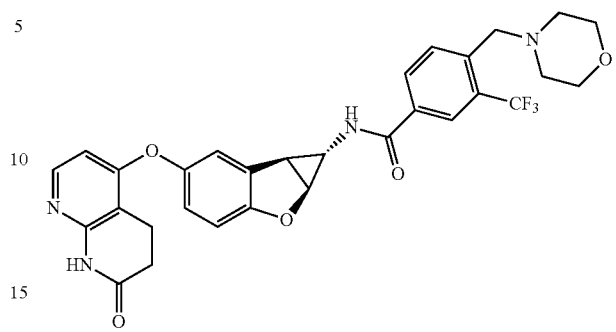

¹H NMR (400 MHz, DMSO-d6) δ 10.53 (d, J=4.0 Hz, 1H), 9.08 (s, 1H), 8.35-8.19 (m, 2H), 8.02 (d, J=8.4 Hz, 1H), 7.97 (d, J=6.0 Hz, 1H), 7.27 (d, J=2.0 Hz, 1H), 7.01-6.91 (m, 2H), 6.27 (d, J=6.0 Hz, 1H), 5.09 (d, J=5.6 Hz, 1H), 4.48-4.40 (m, 5H), 3.80 (s, 3H), 3.28-3.09 (m, 3H), 2.95 (t, J=7.6 Hz, 2H), 2.59-2.52 (m, 3H) ppm. MS: M/e 581 (M+1)⁺.

Compound 1.8

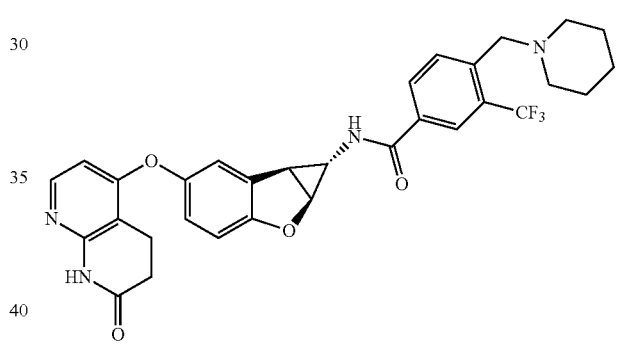

¹H NMR (400 MHz, DMSO-d6) δ 10.51 (d, J=4.0 Hz, 1H), 9.41 (br.s, 1H, CF₃COOH), 9.10 (s, 1H), 8.36-8.21 (m, 2H), 8.04 (d, J=7.6 Hz, 1H), 7.97 (d, J=5.6 Hz, 1H), 7.27 (d, J=2.0 Hz, 1H), 7.04-6.89 (m, 2H), 6.26 (d, J=5.6 Hz, 1H), 5.09 (d, J=5.6 Hz, 1H), 4.51 (s, 2H), 3.35 (d, J=10.9 Hz, 2H), 3.19-3.02 (m, 3H), 2.94 (t, J=7.6 Hz, 2H), 2.62-2.52 (m, 3H), 1.88-1.36 (m, 6H) ppm. MS: M/e 579 (M+1)⁺.

Compound 1.9

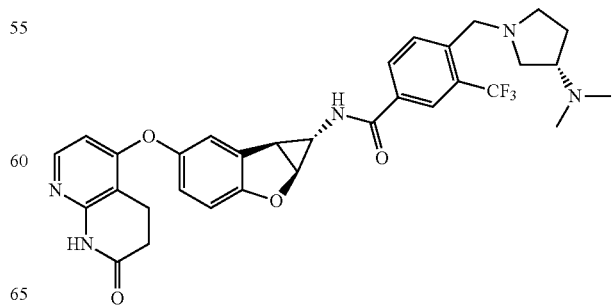

¹H NMR (400 MHz, CD₃OD) δ 8.16 (s, 1H), 8.06 (d, J=8.0 Hz, 1H), 7.92 (d, J=6.0 Hz, 1H), 7.88 (d, J=8.0 Hz, 1H), 7.21 (s, 1H), 6.89 (d, J=1.2 Hz, 2H), 6.32 (d, J=6.0 Hz, 1H), 5.02 (d, J=5.6 Hz, 1H), 3.86 (q, J=14.8 Hz, 2H), 3.67 (br.s, 1H), 3.15-3.00 (m, 3H), 2.92-2.83 (m, 2H), 2.80-2.60 (m, 9H), 2.56-2.45 (m, 2H), 2.32-2.20 (m, 1H), 2.02-1.89 (m, 1H) ppm. MS: M/e 304.6 (M/2+1)⁺

Compound 1.10

Compound 1.12

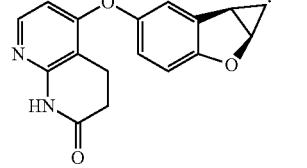

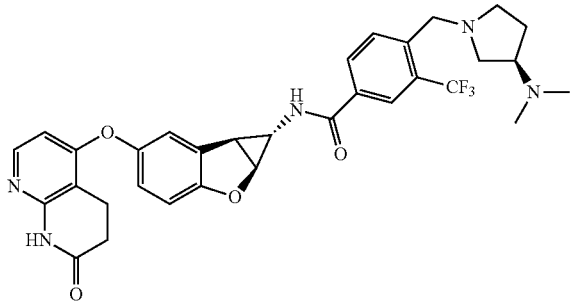 [SMILES: CN(C)[C@@H]1CCN(Cc2ccc(C(=O)N[C@@H]3[C@H]4Oc5ccc(Oc6ccnc7c6CCC(=O)N7)cc5[C@@H]34)cc2C(F)(F)F)C1]

¹H NMR (400 MHz, CD₃OD) δ 8.06 (s, 1H), 7.96 (d, J=8.4 Hz, 1H), 7.89-7.79 (m, 2H), 7.12 (s, 1H), 6.86-6.75 (m, 2H), 6.23 (d, J=6.0 Hz, 1H), 4.93 (d, J=6.0 Hz, 1H), 3.68 (s, 2H), 3.10-2.91 (m, 5H), 2.84 (d, J=10.4 Hz, 1H), 2.69 (d, J=11.2 Hz, 1H), 2.56 (t, J=7.6 Hz, 2H), 2.47-2.21 (m, 5H), 2.00 (t, J=10.4 Hz, 1H), 1.84-1.69 (m, 3H), 1.47-1.33 (m, 1H) ppm. MS: M/e 620 (M+1)⁺.

Compound 1.13

¹H NMR (400 MHz, CD₃OD) δ 8.23 (s, 1H), 8.13 (d, J=8.4 Hz, 1H), 8.03 (d, J=6.8 Hz, 1H), 7.92 (d, J=8.0 Hz, 1H), 7.30 (d, J=2.4 Hz, 1H), 7.03-6.91 (m, 2H), 6.61 (d, J=6.8 Hz, 1H), 5.06 (d, J=5.6 Hz, 1H), 4.25 (q, J=14.8 Hz, 2H), 4.09-3.97 (m, 1H), 3.45-3.35 (m, 1H), 3.31-3.29 (m, 1H), 3.27-3.22 (m, 1H), 3.21-3.12 (m, 2H), 3.09 (dd, J=5.6, 2.0 Hz, 1H), 3.01-2.84 (m, 7H), 2.77 (t, J=7.6 Hz, 2H), 2.54 (d, J=1.6 Hz, 1H), 2.52-2.40 (m, 1H), 2.24-2.11 (m, 1H) ppm. MS: M/e 304.6 (M/2+1)⁺

Compound 1.11

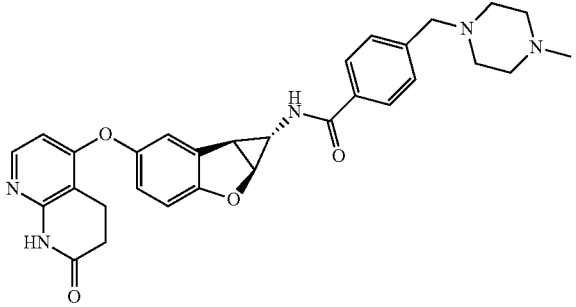 [SMILES: CN1CCN(Cc2ccc(C(=O)N[C@@H]3[C@H]4Oc5ccc(Oc6ccnc7c6CCC(=O)N7)cc5[C@@H]34)cc2)CC1]

¹H NMR (400 MHz, DMSO-d6) δ 10.49 (s, 1H), 8.96 (d, J=3.6 Hz, 1H), 8.16 (s, 1H), 8.11 (d, J=8.0 Hz, 1H), 7.96 (d, J=5.6 Hz, 1H), 7.89 (d, J=8.0 Hz, 1H), 7.27 (d, J=2.0 Hz, 1H), 7.02-6.89 (m, 2H), 6.25 (d, J=5.6 Hz, 1H), 5.08 (d, J=5.6 Hz, 1H), 3.70-3.51 (m, 4H), 3.09 (dd, J=5.6, 2.0 Hz, 1H), 2.94 (t, J=7.6 Hz, 2H), 2.65 (d, J=10.8 Hz, 2H), 2.59-2.52 (m, 3H), 1.73 (t, J=10.8 Hz, 2H), 1.03 (d, J=6.4 Hz, 6H) ppm. MS: M/e 609 (M+1)⁺.

Compound 1.14

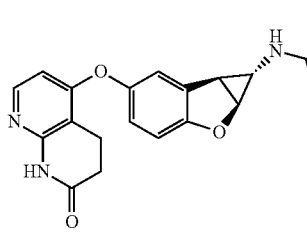

¹H NMR (400 MHz, DMSO-d6) δ 10.47 (s, 1H), 8.69 (d, J=3.6 Hz, 1H), 7.96 (d, J=6.0 Hz, 1H), 7.80 (d, J=8.4 Hz, 2H), 7.38 (d, J=8.4 Hz, 2H), 7.25 (d, J=2.0 Hz, 1H), 6.98-6.89 (m, 2H), 6.25 (d, J=6.0 Hz, 1H), 5.06 (d, J=5.2 Hz, 1H), 3.49 (s, 2H), 3.06 (dd, J=6.0, 2.0 Hz, 1H), 2.94 (t, J=7.6 Hz, 2H), 2.56-2.52 (m, 3H), 2.48-2.18 (m, 8H), 2.14 (s, 3H) ppm. MS: M/e 526 (M+1)⁺.

¹H NMR (400 MHz, DMSO-d6) δ 10.48 (s, 1H), 8.99 (d, J=3.6 Hz, 1H), 8.20 (s, 1H), 8.14 (d, J=8.0 Hz, 1H), 7.96 (d, J=6.0 Hz, 2H), 7.27 (d, J=2.4 Hz, 1H), 6.98-6.93 (m, 2H), 6.25 (d, J=6.0 Hz, 1H), 5.08 (d, J=5.6 Hz, 1H), 4.19 (t, J=5.2 Hz, 2H), 4.00 (s, 2H), 3.95 (s, 2H), 3.10 (dd, J=5.6, 2.0 Hz, 1H), 2.94 (t, J=7.6 Hz, 4H), 2.61-2.52 (m, 3H) ppm. MS: M/e 686 (M+1)⁺.

Compound 1.15

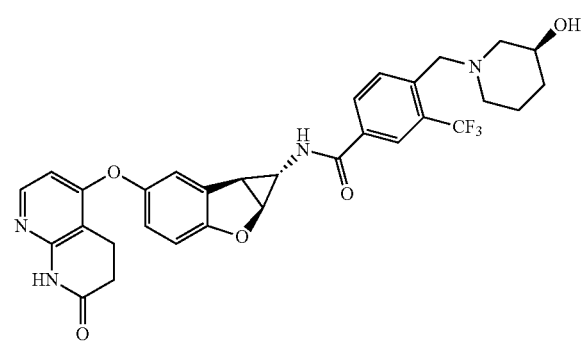 [SMILES: O=C1CCc2c(Oc3ccc4c(c3)[C@H]3[C@H](NC(=O)c5ccc(CN6CCC[C@H](O)C6)c(C(F)(F)F)c5)[C@H]3O4)ccnc2N1]

¹H NMR (400 MHz, DMSO-d6) δ 10.52 (s, 1H), 9.64-9.17 (m, 1H, CF₃COOH), 9.09 (d, J=3.6 Hz, 1H), 8.28 (d, J=6.4 Hz, 2H), 8.19-7.99 (m, 1H), 7.97 (d, J=5.6 Hz, 1H), 7.28 (d, J=2.4 Hz, 1H), 7.02-6.90 (m, 2H), 6.26 (d, J=5.6 Hz, 1H), 5.09 (d, J=5.6 Hz, 1H), 4.70-3.67 (m, 4H), 3.47-3.17 (m, 2H), 3.17-2.99 (m, 2H), 2.94 (t, J=7.6 Hz, 3H), 2.62-2.52 (m, 4H), 2.19-1.19 (m, 5H) ppm. MS: M/e 298 (M/2+1)⁺.

Compound 1.16

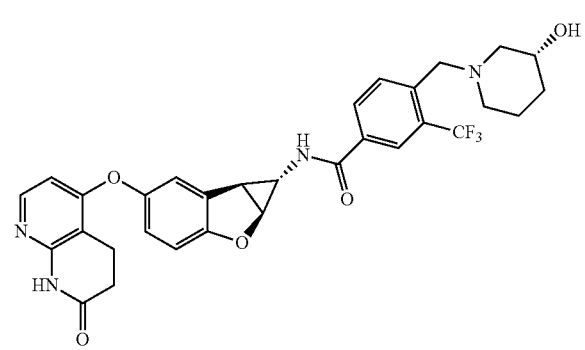 [SMILES: O=C1CCc2c(Oc3ccc4c(c3)[C@H]3[C@H](NC(=O)c5ccc(CN6CCC[C@@H](O)C6)c(C(F)(F)F)c5)[C@H]3O4)ccnc2N1]

¹H NMR (400 MHz, DMSO-d6) δ 10.55 (s, 1H), 9.40 (br.s, 1H, CF₃COOH), 8.99 (s, 1H), 8.19 (s, 1H), 8.14 (d, J=6.0 Hz, 1H), 7.97 (d, J=6.0 Hz, 1H), 7.88 (d, J=6.0 Hz, 1H), 7.28 (d, J=2.1 Hz, 1H), 7.01-6.91 (m, 2H), 6.25 (d, J=6.0 Hz, 1H), 5.08 (d, J=5.6 Hz, 1H), 4.73-3.70 (m, 4H), 3.47-3.17 (m, 2H), 3.17-3.01 (m, 2H), 2.99-2.79 (m, 3H), 2.63-2.52 (m, 4H), 2.20-1.22 (m, 4H), 1.16 (t, J=5.6 Hz, 1H) ppm. MS: M/e 298 (M/2+1)⁺

Compound 1.17

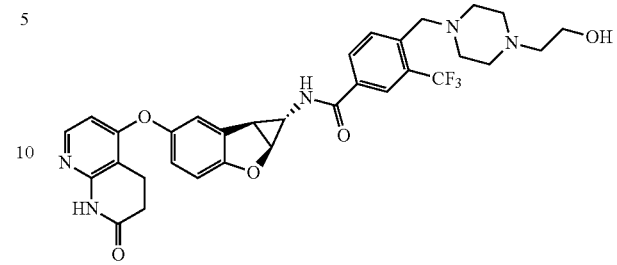

¹H NMR (400 MHz, DMSO-d6) δ10.50 (s, 1H), 9.40 (br.s, 1H, CF₃COOH), 8.99 (s, 1H), 8.19 (s, 1H), 8.14 (d, J=8.4 Hz, 1H), 7.96 (d, J=5.6 Hz, 1H), 7.88 (d, J=8.4 Hz, 1H), 7.27 (d, J=2.4 Hz, 1H), 7.00-6.92 (m, 2H), 6.25 (d, J=5.6 Hz, 1H), 5.08 (d, J=5.6 Hz, 1H), 3.84-3.69 (m, 4H), 3.47 (d, J=10.9 Hz, 2H), 3.20 (s, 2H), 3.16-3.02 (m, 3H), 3.00-2.82 (m, 4H), 2.59-2.52 (m, 4H), 1.16 (t, J=7.2 Hz, 1H) ppm. MS: M/e 312.5 (M/2+1)⁺

Compound 1.18

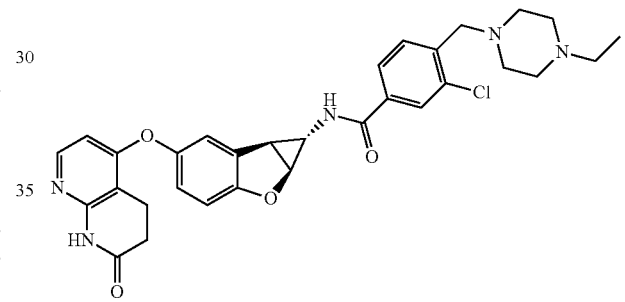

¹H NMR (400 MHz, DMSO-d6+D₂O) δ 8.01 (d, J=6.0 Hz, 1H), 7.95 (s, 1H), 7.84 (d, J=8.0 Hz, 1H), 7.66 (d, J=8.0 Hz, 1H), 7.29 (s, 1H), 7.05-6.92 (m, 2H), 6.34 (d, J=6.0 Hz, 1H), 5.09 (d, J=5.6 Hz, 1H), 3.90 (s, 2H), 3.48 (s, 2H), 3.26-2.92 (m, 8H), 2.83-2.54 (m, 6H), 1.22 (t, J=7.2 Hz, 3H). MS: M/e 574 (M+1)⁺.

Compound 1.19

¹H NMR (400 MHz, DMSO-d6) δ 10.53 (s, 1H), 9.31 (s, 1H, CF₃COOH), 8.85 (s, 1H), 8.10 (d, J=1.6 Hz, 1H), 7.97 (d, J=6.0 Hz, 1H), 7.87 (d, J=8.0 Hz, 1H), 7.60 (d, J=8.0 Hz, 1H), 7.26 (d, J=2.0 Hz, 1H), 7.03-6.85 (m, 2H), 6.26 (dd, J=6.0, 2.4 Hz, 1H), 5.07 (d, J=5.6 Hz, 1H), 3.72 (d, J=4.8 Hz, 2H), 3.47 (d, J=11.2 Hz, 2H), 3.14 (q, J=7.2 Hz, 2H), 3.08 (dd, J=5.6, 2.0 Hz, 1H), 3.06-2.87 (m, 6H), 2.60-2.51 (m, 4H), 2.48-2.38 (m, 1H), 1.21 (t, J=7.2 Hz, 3H) ppm. MS: M/e 618 (M+1)⁺.

Compound 1.20

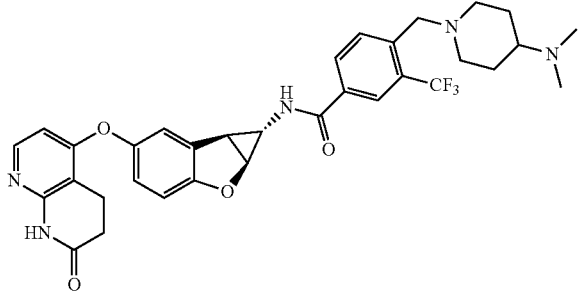 [SMILES: CN(C)C1CCN(Cc2ccc(C(=O)N[C@@H]3[C@H]4Oc5ccc(Oc6ccnc7c6CCC(=O)N7)cc5[C@@H]34)cc2C(F)(F)F)CC1]

¹H NMR (400 MHz, CD₃OD) δ 8.28 (s, 1H), 8.18 (d, J=8.0 Hz, 1H), 8.04-7.94 (m, 2H), 7.26 (d, J=1.6 Hz, 1H), 6.99-6.88 (m, 2H), 6.47 (d, J=6.4 Hz, 1H), 5.05 (d, J=5.6 Hz, 1H), 4.39 (s, 2H), 3.62-3.41 (m, 3H), 3.17-3.05 (m, 3H), 3.01 (t, J=12.0 Hz, 2H), 2.88 (s, 6H), 2.71 (t, J=7.6 Hz, 2H), 2.54 (d, J=1.6 Hz, 1H), 2.27 (d, J=12.4 Hz, 2H), 2.14-1.98 (m, 2H) ppm. MS: M/e 311.5 (M/2+1)⁺.

Compound 1.21

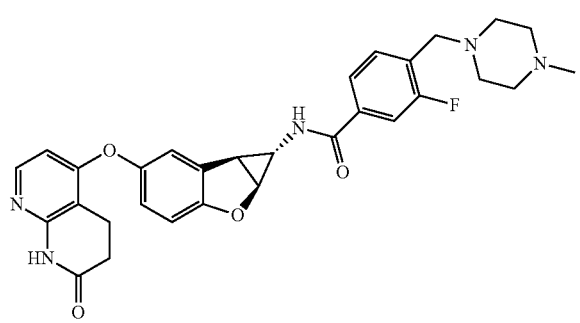 [SMILES: CN1CCN(Cc2ccc(C(=O)N[C@@H]3[C@H]4Oc5ccc(Oc6ccnc7c6CCC(=O)N7)cc5[C@@H]34)cc2F)CC1]

¹H NMR (400 MHz, DMSO-d6) δ 10.47 (s, 1H), 8.79 (d, J=3.2 Hz, 1H), 8.15 (s, 1H, HCOOH), 7.96 (d, J=5.6 Hz, 1H), 7.68 (d, J=8.0 Hz, 1H), 7.63 (d, J=10.4 Hz, 1H), 7.51 (t, J=7.6 Hz, 1H), 7.26 (d, J=2.0 Hz, 1H), 7.00-6.88 (m, 2H), 6.25 (d, J=5.6 Hz, 1H), 5.06 (d, J=5.6 Hz, 1H), 3.57 (s, 2H), 3.07 (dd, J=5.6, 2.0 Hz, 1H), 2.94 (t, J=7.6 Hz, 2H), 2.59-2.52 (m, 5H), 2.49-2.36 (m, 5H), 2.27 (s, 3H) ppm. MS: M/e 544 (M+1)⁺.

Compound 1.22

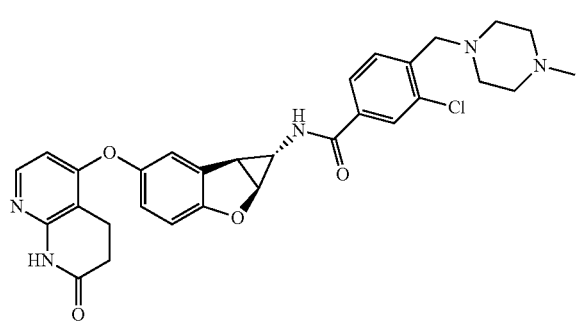

¹H NMR (400 MHz, DMSO-d6, D2O) δ 7.99 (d, J=6.0 Hz, 1H), 7.93 (s, 1H), 7.82 (d, J=8.0 Hz, 1H), 7.63 (d, J=8.0 Hz, 1H), 7.27 (s, 1H), 7.02-6.90 (m, 2H), 6.30 (d, J=6.0 Hz, 1H), 5.08 (d, J=5.6 Hz, 1H), 3.79 (s, 2H), 3.52-3.29 (m, 2H), 3.24-2.90 (m, 7H), 2.81 (s, 3H), 2.63-2.53 (m, 5H) ppm. MS: M/e 560 (M+1)+.

Compound 1.23

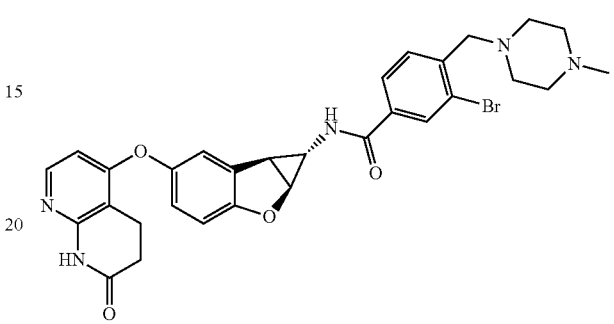

¹H NMR (400 MHz, DMSO-d6) δ 10.52 (s, 1H), 9.47 (s, 1H, CF₃COOH), 8.85 (d, J=3.6 Hz, 1H), 8.10 (d, J=1.6 Hz, 1H), 7.96 (d, J=6.0 Hz, 1H), 7.87 (dd, J=8.0, 2.0 Hz, 1H), 7.59 (d, J=8.0 Hz, 1H), 7.26 (d, J=2.4 Hz, 1H), 7.01-6.89 (m, 2H), 6.26 (d, J=6.0 Hz, 1H), 5.07 (d, J=5.6 Hz, 1H), 3.69 (s, 2H), 3.40 (d, J=11.2 Hz, 2H), 3.12-2.88 (m, 7H), 2.80 (s, 3H), 2.58-2.52 (m, 3H), 2.49-2.38 (m, 2H) ppm. MS: M/e 604 (M+1)⁺.

Compound 1.24

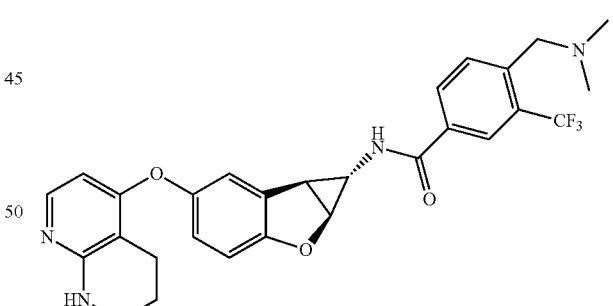

¹H NMR (400 MHz, CD₃OD) δ 8.33 (s, 1H), 8.24 (d, J=8.0 Hz, 1H), 7.95 (d, J=6.0 Hz, 1H), 7.88 (d, J=8.0 Hz, 1H), 7.24 (s, 1H), 6.97-6.86 (m, 2H), 6.39 (d, J=6.2 Hz, 1H), 5.04 (d, J=5.6 Hz, 1H), 4.58 (s, 2H), 3.13-3.05 (m, 3H), 2.95 (s, 6H), 2.68 (t, J=7.6 Hz, 2H), 2.54 (d, J=1.6 Hz, 1H) ppm. MS: M/e 539 (M+1)⁺

Compound 1.25: 3-(2-aminopropan-2-yl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-5-(trifluoromethyl)benzamide

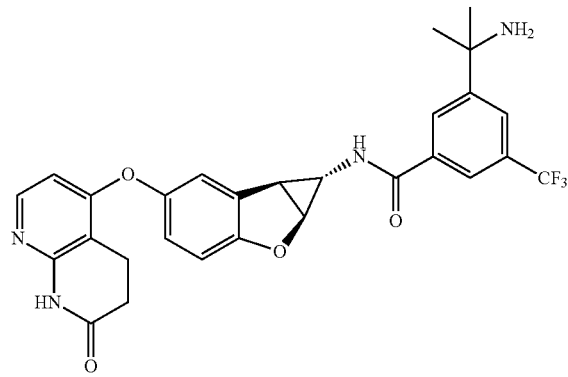

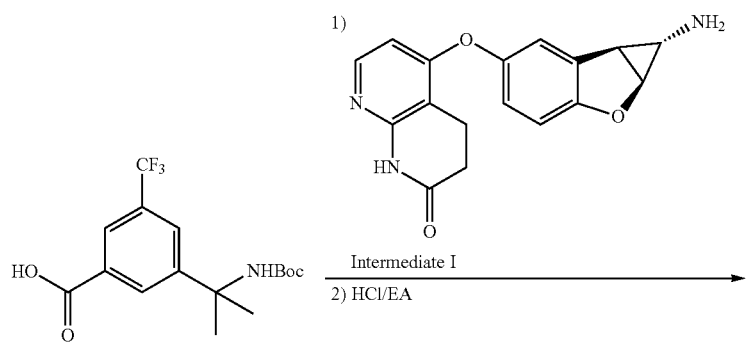

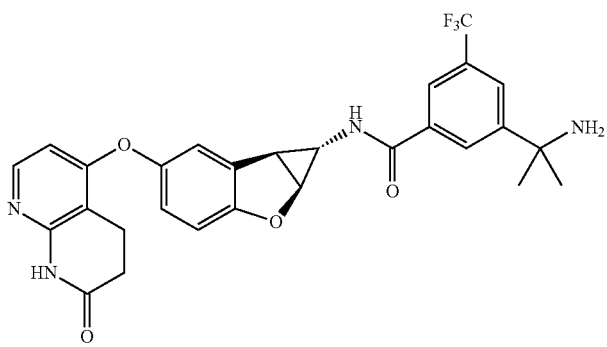

To a mixture of 3-(2-((tert-butoxycarbonyl)amino)propan-2-yl)-5-(trifluoromethyl)benzoic acid (50 mg, 0.144 mmol) and DIEA (120 mg, 0.93 mmol) in DMF (2 mL) was added HATU (65 mg, 0.17 mmol) and followed by Intermediate I (50 mg, 0.145 mmol) at ambient temperature and the resulted mixture was stirred for 3 hours. The mixture was added to H$_2$O (10 mL) and extracted with EA (10 mL×3). The combined extracts were washed with brine (10 mL×2), dried over Na$_2$SO$_4$, concentrated under reduced pressure to give a brown oil (120 mg) which was dissolved in EA (5 mL), and the resulted solution was added HCl/EA (6M, 5 mL) at rt and the mixture was stirred at rt for 2 hours. The mixture was concentrated and the residue was purified by prep-HPLC to obtain the desired product (39 mg, 46%) as a white solid in the form of formic acid salt. $^1$H NMR (400 MHz, DMSO-d6) δ 10.48 (s, 1H), 9.03 (s, 1H), 8.29 (s, 1H), 8.23 (s, 1H), 8.09 (s, 1H), 8.06 (s, 1H), 7.96 (d, J=6.0 Hz, 1H), 7.27 (d, J=2.0 Hz, 1H), 7.01-6.90 (m, 2H), 6.25 (d, J=6.0 Hz, 1H), 5.10 (d, J=5.6 Hz, 1H), 3.12 (dd, J=5.6, 2.0 Hz, 1H), 2.94 (t, J=7.6 Hz, 2H), 2.58-2.51 (m, 3H), 1.49 (s, 6H). MS: M/e 539 (M+1)$^+$.

Compound 1.26: 3-(1-aminocyclopropyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-5-(trifluoromethyl)benzamide

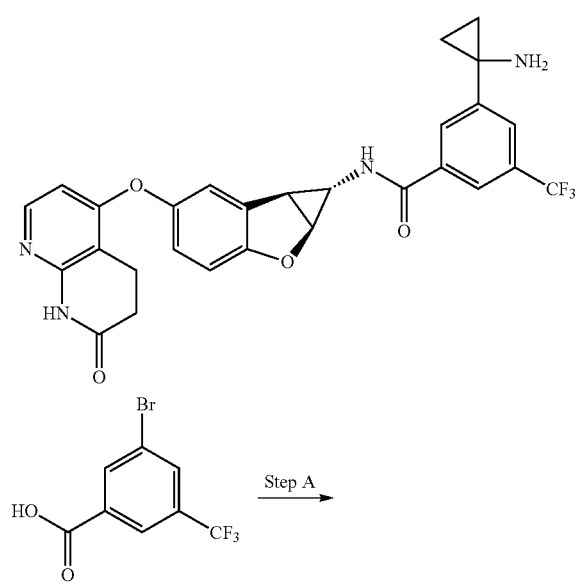

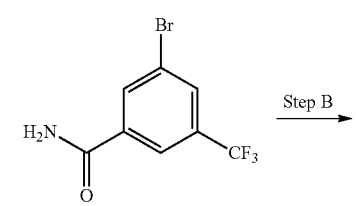

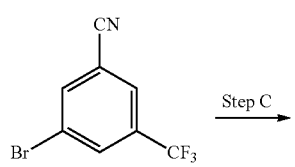

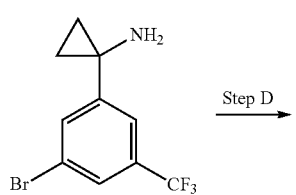

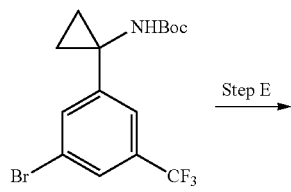

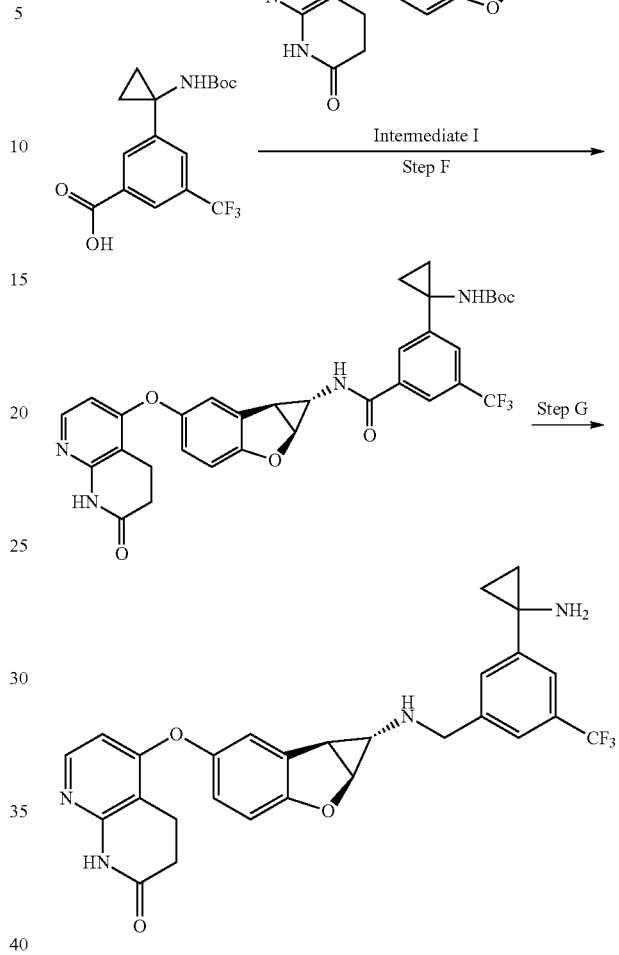

Step A: 3-bromo-5-(trifluoromethyl)benzamide

To a solution of 3-bromo-5-(trifluoromethyl)benzoic acid (807 mg, 3 mmol) and EDCI (633 mg, 3.3 mmol) in DMF (10 mL) was added 1-hydroxypyrrolidine-2,5-dione (380 mg, 3.3 mmol) and the mixture was stirred at ambient temperature for 6 hours. Then ammonia solution (25-28%, 1.5 mL) was added and the mixture was stirred at ambient temperature overnight. Water (10 mL) was added and a white precipitate was formed. The solid was filtered, washed with water (10 mL), and dried to give the desired compound (420 mg, 50%) as a white solid. $^1$H NMR (400 MHz, CDCl$_3$) δ 8.14 (s, 1H), 7.99 (s, 1H), 7.93 (s, 1H), 6.17-5.76 (m, 2H). MS: M/e 268 (M+1)$^+$.

Step B: 3-bromo-5-(trifluoromethyl)benzonitrile

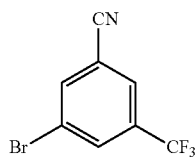

A solution of the product from Step A (420 mg, 1.56 mmol) and 2,4,6-trichloro-1,3,5-triazine (437 mg, 2.35 mmol) in DMF (4 mL) was stirred at ambient temperature overnight. A white precipitate was formed. Water (10 mL) was added, and the mixture was extracted with EA (20 mL×2). The extract was washed with brine (30 mL), dried over $Na_2SO_4$, filtered and concentrated to give the desired compound (330 mg, 84%) as a brown oil. 1H NMR (400 MHz, $CDCl_3$) δ 7.99 (s, 1H), 7.98 (s, 1H), 7.85 (s, 1H).

Step C: 1-(3-bromo-5-(trifluoromethyl)phenyl)cyclopropanamine

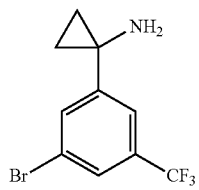

To a solution of the product from Step B (1.41 g, 5.24 mmol) and $Ti(Oi-Pr)_4$ (1.65 g, 5.76 mmol) in dry ether (30 mL) at −70° C. was added a solution of ethylmagnesium bromide in 2-methyltetrahydrofuran (3.4 mL, 11.53 mmol) dropwise. The reaction was warmed to ambient temperature over 0.5 h and stirred at ambient temperature for 1 h. $BF_3.Et_2O$ (1.3 mL, 10.5 mmol) was added and the mixture was stirred for another one hour. The mixture was quenched with 2N HCl (8 mL) to pH 3, extracted with EA (30 mL). The aqueous layer was treated with 2N NaOH solution to pH 9, extracted with EA (20 mL×3). The extract was washed with brine (30 mL), dried over $Na_2SO_4$, filtered and concentrated to give the title product (680 mg, 46.5%) as a brown oil. $^1H$ NMR (400 MHz, $CDCl_3$) δ 7.61 (s, 1H), 7.58 (s, 1H), 7.47 (s, 1H), 2.47-1.86 (m, 2H), 1.19-1.16 (m, 2H), 1.06-1.02 (m, 2H). MS: M/e 280 (M+1)$^+$.

Step D: tert-butyl (1-(3-bromo-5-(trifluoromethyl)phenyl)cyclopropyl)carbamate

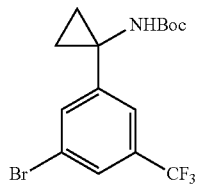

To a solution of the product from Step C (540 mg, 1.93 mmol) and $K_2CO_3$ (0.53 g, 3.86 mmol) in THF/$H_2O$ (13 mL, V:V) was added di-tert-butyl dicarbonate (0.5 g, 2.31 mmol). The reaction was stirred at ambient temperature for 6 h. The mixture was diluted with water (20 mL), extracted with EA (20 mL×3). The extract was washed with brine (40 mL), dried over $Na_2SO_4$, filtered and concentrated. The residue was purified by silica-gel column chromatography (PE/EA=20:1) to obtain the desired compound (450 mg, 61%) as a white solid. $^1H$ NMR (400 MHz, $CDCl_3$) δ 7.56 (s, 1H), 7.47 (s, 1H), 7.35 (s, 1H), 5.25 (s, 1H), 1.44-1.25 (m, 13H). MS: M/e 324 (M−tBu+1)$^+$.

Step E: 3-(1-((tert-butoxycarbonyl)amino)cyclopropyl)-5-(trifluoromethyl)benzoic acid

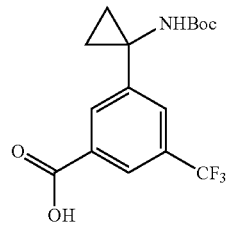 [SMILES: CC(C)(C)OC(=O)NC1(c2cc(C(=O)O)cc(C(F)(F)F)c2)CC1]

To a solution of the product from Step D (38 mg, 0.1 mmol) and $K_2CO_3$ (68 mg, 0.5 mmol) in DMF (2 mL) was added $Pd(OAc)_2$ (2.24 mg, 0.01 mmol) and 4,5-Bis(diphenylphosphino)-9,9-dimethylxanthene (Xantphos) (1.2 mg, 0.02 mmol). The reaction was stirred at 80° C. for 5 h under CO (balloon). The mixture was cooled to ambient temperature, diluted with water (20 mL), extracted with EA (20 mL). The aqueous layer was treated with saturated citric acid solution to pH 4. The mixture was extracted with EA (20 mL×2). The extract was washed with brine (10 mL), dried over $Na_2SO_4$, filtered and concentrated to obtain the desired compound (28 mg, 82% for crude yield) as colorless oil. MS: M/e 344 (M−1)$^-$.

Step F: tert-butyl (1-(3-(((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)carbamoyl)-5-(trifluoromethyl)phenyl)cyclopropyl)carbamate

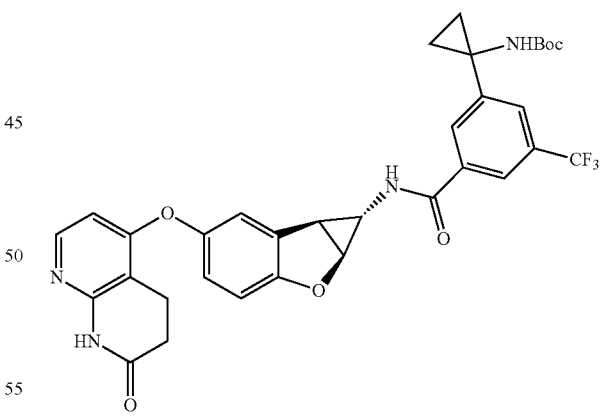

To a mixture of the product from Step E (28 mg, 0.08 mmol), Intermediate I (35 mg, 0.1 mmol) and DIEA (51 mg, 0.4 mmol) in DMF (2 mL) was added HATU (38 mg, 0.1 mmol). The mixture was stirred at ambient temperature overnight. The mixture was added $H_2O$ (10 mL) and extracted with EA (20 mL×3). The combined extracts were washed with brine (30 mL), dried over $Na_2SO_4$, concentrated to give the desired product (70 mg, crude) as a brown residue which used directly for next step without further purification. MS: M/e 637 (M+1)$^+$.

Step G: 3-(1-aminocyclopropyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-5-(trifluoromethyl)benzamide (Compound 1.26)

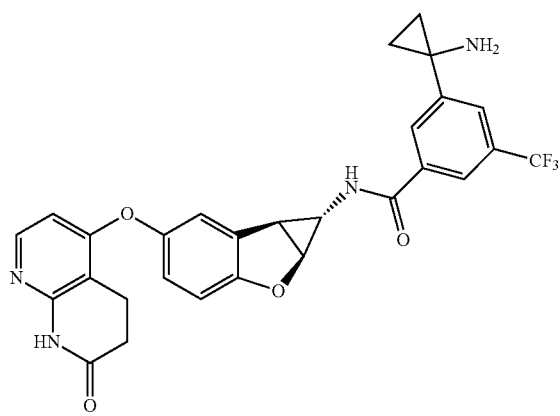 [SMILES: NC1(c2cc(C(=O)N[C@@H]3[C@H]4Oc5ccc(Oc6ccnc7c6CCC(=O)N7)cc5[C@@H]34)cc(C(F)(F)F)c2)CC1]

To a mixture of the product from Step F (70 mg, 0.1 mmol) in EA (4 mL) was added HCl/EA (6M, 3 mL) and the mixture was stirred at ambient temperature for 4 hours. The mixture was concentrated and the residue was purified by prep-HPLC to obtain the desired product (28 mg, 40%) as a white solid in the form of 2,2,2-trifluoro acetic acid salt. 1H NMR (400 MHz, DMSO-d6) δ 10.46 (s, 1H), 9.02 (d, J=2.0 Hz, 1H), 8.68 (br.s, 3H), 8.15 (s, 1H), 8.10 (s, 1H), 7.95-7.91 (m, 2H), 7.24 (d, J=2 Hz, 1H), 6.95-6.89 (m, 2H), 6.22 (d, J=5.6 Hz, 1H), 5.05 (d, J=5.6 Hz, 1H), 3.08 (dd, J=5.6, 2.0 Hz, 1H), 2.91 (t, J=7.6 Hz, 2H), 2.58-2.51 (m, 3H), 1.36 (s, 4H). MS: M/e 537 (M+1)$^+$.

Compound 1.27: N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-4-(piperazin-1-ylmethyl)-3-(trifluoromethyl)benzamide

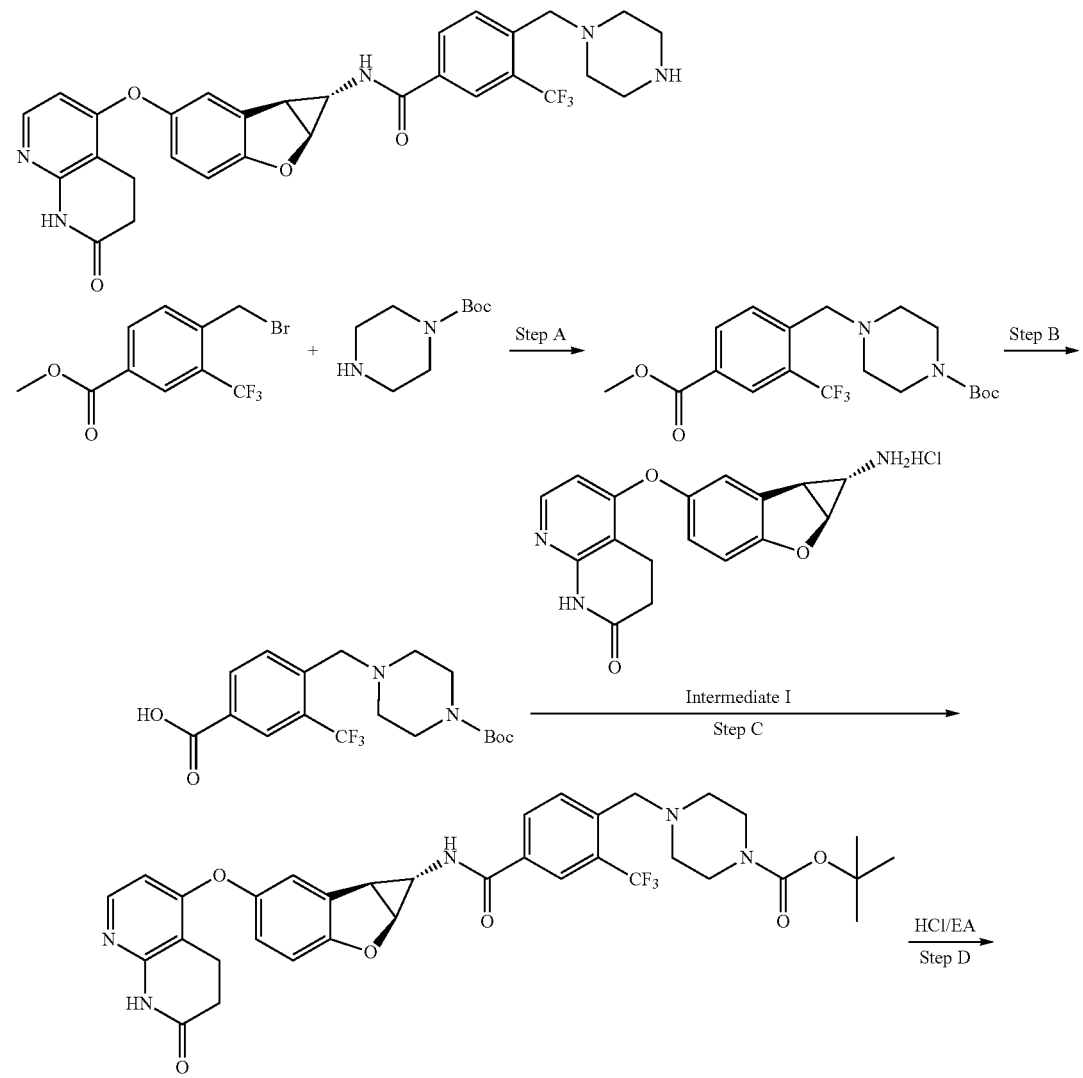

-continued

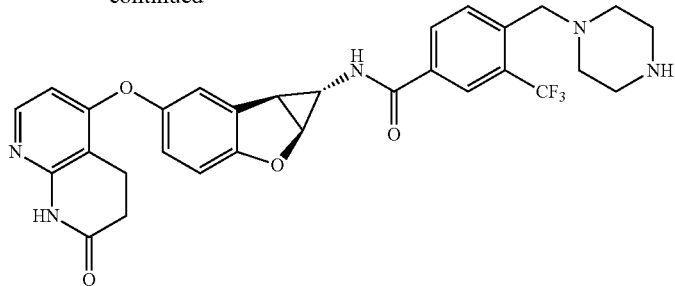

Step A: tert-butyl 4-(4-(methoxycarbonyl)-2-(trifluoromethyl)benzyl)piperazine-1-carboxylate

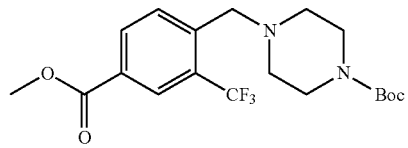 [SMILES: COC(=O)c1ccc(CN2CCN(C(=O)OC(C)(C)C)CC2)c(C(F)(F)F)c1]

A mixture of methyl 4-(bromomethyl)-3-(trifluoromethyl)benzoate (1.0 g, 3.4 mmol), tert-butyl piperazine-1-carboxylate (630 mg, 3.4 mmol) and Cs$_2$CO$_3$ (1.5 g, 4.6 mmol) in DMF (10 mL) was stirred at 60° C. for 3 hours. The mixture was cooled to room temperature, added H$_2$O (30 mL) and extracted with EA (30 mL×3). The combined extracts were washed with brine (30 mL×2), dried over Na$_2$SO$_4$ and concentrated under reduced pressure. The resulted residue was purified by column chromatography (silica gel weight: 50 g, eluted with PE/EA: 30/1-10/1) to obtain the title product (780 mg, 57%) as a light yellow oil. $^1$H NMR (400 MHz, CDCl$_3$) δ 8.30 (s, 1H), 8.18 (d, J=8.0 Hz, 1H), 7.93 (d, J=8.0 Hz, 1H), 3.94 (s, 3H), 3.70 (s, 2H), 3.45 (s, 4H), 2.42 (s, 4H), 1.46 (s, 9H) ppm. MS: M/e 403 (M+1)$^+$.

Step B: 4-((4-(tert-butoxycarbonyl)piperazin-1-yl)methyl)-3-(trifluoromethyl)benzoic acid

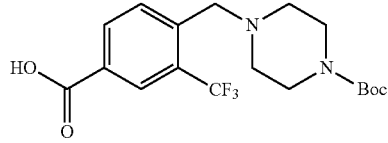 [SMILES: CC(C)(C)OC(=O)N1CCN(Cc2ccc(C(=O)O)cc2C(F)(F)F)CC1]

To a stirred solution of the product from Step A (550 mg, 1.37 mmol) in THF (5 mL) was added aqueous solution of NaOH (2 M, 5 mL) at ambient temperature and the mixture was stirred at ambient temperature for 3 hours. LC_MS traced the reaction. Only a little of SM was transferred to product and most of the SM remained. 5 mL of MeOH was then added and the resulted mixture was stirred for another 1 hour. The reaction was completed. The reaction mixture was acidified by sat. citric acid to pH about 3 and extracted with EA (10 mL×3). The combined extracts were washed with brine (15 mL×2), dried over anhydrous sodium sulfate and concentrated under reduced pressure to obtain the title product (500 mg, 94%) as a white solid. $^1$H NMR (400 MHz, DMSO-d6) δ 13.28 (s, 1H), 8.20 (d, J=8.0 Hz, 1H), 8.17 (s, 1H), 7.95 (d, J=8.0 Hz, 1H), 3.70 (s, 2H), 3.40-3.25 (m, 4H), 2.42-2.31 (m, 4H), 1.39 (s, 9H). MS: M/e 389 (M+1)$^+$.

Step C: tert-butyl 4-(4-(((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)carbamoyl)-2-(trifluoromethyl)benzyl)piperazine-1-carboxylate

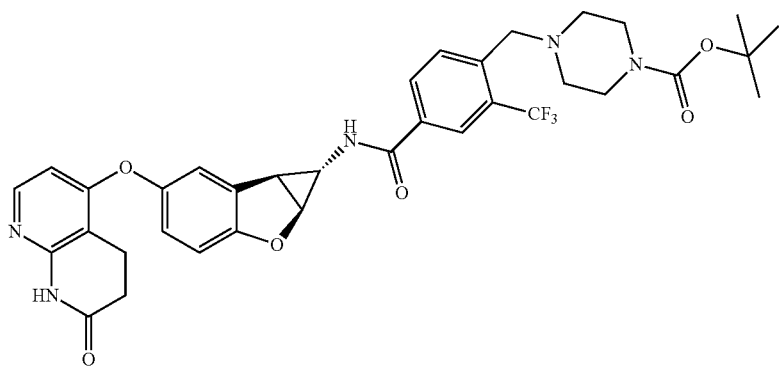 [SMILES: CC(C)(C)OC(=O)N1CCN(Cc2ccc(C(=O)N[C@@H]3[C@H]4Oc5ccc(Oc6ccnc7c6CCC(=O)N7)cc5[C@@H]34)cc2C(F)(F)F)CC1]

To a mixture of the Intermediate I (450 mg, 1.29 mmol), the product from Step B (500 mg, 1.29 mmol) and DIEA in DMF (10 mL) was added HATU (540 mg, 1.42 mmol) at ambient temperature and the resulted mixture was stirred at ambient temperature for 16 hours. 30 mL of H₂O was added and the mixture was extracted with EA (30 mL×3). The combined extracts were washed with brine (30 mL×2), dried over anhydrous sodium sulfate and concentrated under reduced pressure. The resulted oil was purified by prep-HPLC to obtain a TFA salt which was added 5 mL aqueous NaHCO₃ and extracted with EA (10 mL×3). The combined extracts were washed with brine (10 mL×2), dried over anhydrous sodium sulfate, concentrated under reduced pressure and lyophilized to give the title product (580 mg, 66%) as a white solid. ¹H NMR (400 MHz, DMSO-d6) δ 10.47 (s, 1H), 8.96 (d, J=3.6 Hz, 1H), 8.16 (s, 1H), 8.12 (d, J=8.0 Hz, 1H), 7.96 (d, J=6.0 Hz, 1H), 7.91 (d, J=8.0 Hz, 1H), 7.26 (d, J=2.0 Hz, 1H), 7.00-6.88 (m, 2H), 6.25 (d, J=6.0 Hz, 1H), 5.08 (d, J=5.6 Hz, 1H), 3.68 (s, 2H), 3.09 (dd, J=5.6, 2.0 Hz, 1H), 2.94 (t, J=7.6 Hz, 2H), 2.57-2.51 (m, 7H), 2.38-2.32 (m, 4H), 1.39 (s, 9H). MS: M/e 680 (M+1)⁺.

Step D: N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-4-(piperazin-1-ylmethyl)-3-(trifluoromethyl)benzamide (Compound 1.27)

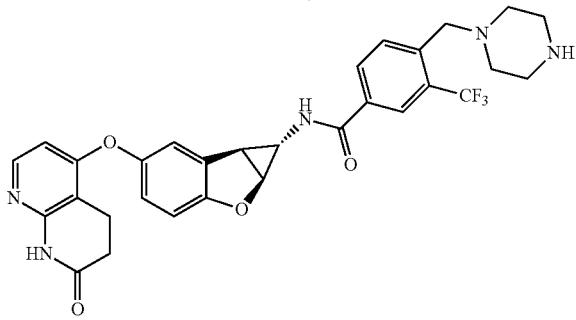 [SMILES: O=C1CCc2c(Oc3ccc4c(c3)[C@H]3[C@H](NC(=O)c5ccc(CN6CCNCC6)c(C(F)(F)F)c5)[C@H]3O4)ccnc2N1]

To a solution of HCl in EA (3 M, 5 mL) was added a solution of the product from Step C (240 mg, 0.35 mmol) in 2 mL of EA at ambient temperature and the resulted mixture was stirred at this temperature for 3 hours. A precipitated white solid was filtered and the filter cake was washed with 5 mL of EA. The resulted solid was lyophilized to obtain the title product (105 mg, 51%) as a light yellow solid. ¹H NMR (400 MHz, DMSO-d6+D₂O) 68.22 (s, 1H), 8.20 (d, J=8.4 Hz, 1H), 8.04 (d, J=8.4 Hz, 1H), 8.01 (d, J=6.0 Hz, 1H), 7.29 (d, J=2.4 Hz, 1H), 7.02-6.92 (m, 2H), 6.34 (d, J=6.0 Hz, 1H), 5.13 (d, J=5.6 Hz, 1H), 4.00 (s, 2H), 3.30-3.18 (m, 4H), 3.14 (dd, J=5.6, 2.0 Hz, 1H), 2.98 (t, J=7.6 Hz, 2H), 2.94-2.81 (m, 4H), 2.61-2.55 (m, 3H). MS: M/e 580 (M+1)⁺.

Compound 1.28 was prepared according to the procedures described for Compound 1.1 under appropriate conditions that could be recognized by one skilled in the art.

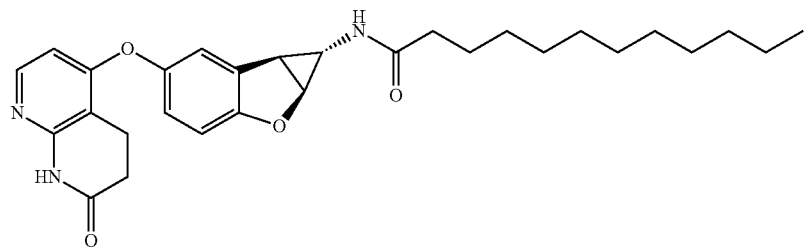 [SMILES: CCCCCCCCCCCC(=O)N[C@@H]1[C@H]2Oc3ccc(Oc4ccnc5c4CCC(=O)N5)cc3[C@@H]12]

¹H NMR (400 MHz, DMSO-d6) δ 10.49 (s, 1H), 8.12 (d, J=3.6 Hz, 1H), 7.95 (d, J=6.0 Hz, 1H), 7.21 (s, 1H), 6.94-6.88 (m, 2H), 6.24 (d, J=6.0 Hz, 1H), 4.87 (d, J=6.0 Hz, 1H), 2.93 (t, J=8.0 Hz, 2H), 2.86 (dd, J=5.6, 2.0 Hz, 1H), 2.54 (t, J=8.0 Hz, 2H), 2.30-2.26 (m, 1H), 2.05 (t, J=7.6 Hz, 2H), 1.52-1.41 (m, 2H), 1.32-1.14 (m, 16H), 0.85 (t, J=6.8 Hz, 3H) ppm. MS: M/e 492 (M+1)⁺.

Compound 1.29: 4-(((S)-3-methylpiperazin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

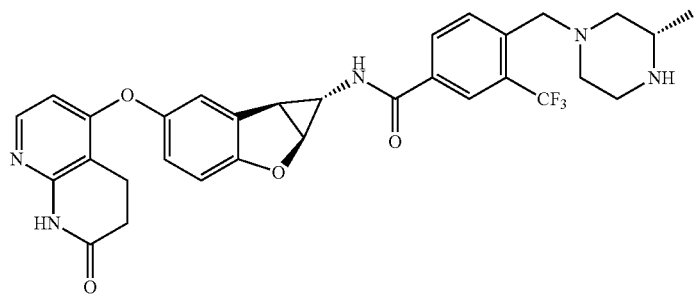

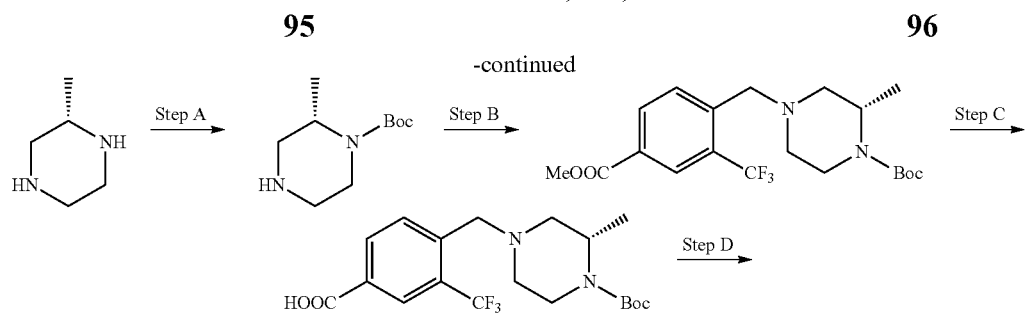

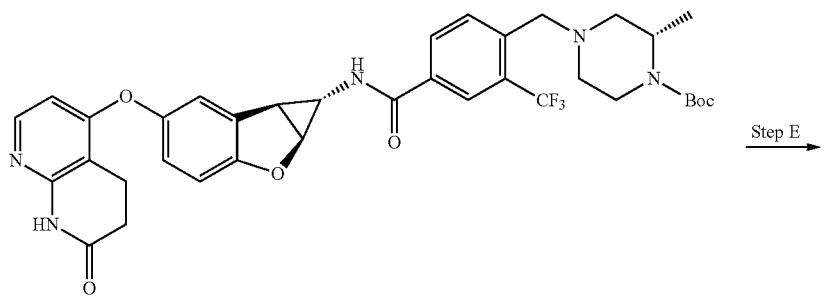

Step A: (S)-tert-butyl 2-methylpiperazine-1-carboxylate

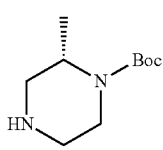

A solution of (S)-2-methylpiperazine (3.0 g, 30 mmol) in THF (300 mL) was added n-BuLi (2.4M, 25 mL, 60 mmol) dropwisely at room temperature. After the solution was stirred at room temperature for 30 min, TBSCl (4.5 g, 30 mmol) was added to the solution. The mixture was stirred for 1 hour and (Boc)$_2$O (7.8 g, 36 mmol) was added at room temperature. The resulting mixture was stirred at room temperature for 1 hour and quenched with H$_2$O (30 mL). The mixture was concentrated and then diluted with EA (300 mL), washed with brine (100 mL), dried over anhydrous sodium sulfate and concentrated under reduced pressure. The residue was purified by column chromatography (silica weight: 20 g, eluted with EtOAc/MeOH 10:1, Et$_3$N 5%) to give the title compound (1.15 g, 19%) as oil.

Step B: (S)-tert-butyl 4-(4-(methoxycarbonyl)-2-(trifluoromethyl)benzyl)-2-methylpiperazine-1-carboxylate

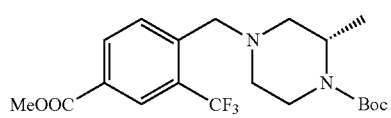

A mixture of the product of step A (500 mg, 2.5 mmol), methyl 4-(bromomethyl)-3-(trifluoromethyl)benzoate (891 mg, 3.0 mmol) and Et$_3$N (505 mg, 5.0 mmol) in DCM (20 mL) was stirred at room temperature for 2 hours. The reaction mixture was diluted with DCM (100 mL), washed with brine (30 mL), dried over anhydrous sodium sulfate and concentrated under reduced pressure. The residue was purified by column chromatography (silica weight: 10 g, eluted with petroleum ether/EA: 10/1) to give the title compound (700 mg, 70%) as oil. $^1$H NMR (400 MHz, CDCl$_3$) δ 8.31 (s, 1H), 8.19 (d, J=8.0 Hz, 1H), 7.95 (d, J=8.0 Hz, 1H), 4.26-4.16 (m, 1H), 3.95 (s, 3H), 3.86-3.80 (m, 1H), 3.66 (s, 2H), 3.18-3.07 (m, 1H), 2.76-2.68 (m, 1H), 2.58-2.51 (m, 1H), 2.30-2.23 (m, 1H), 2.18-2.08 (m, 1H), 1.46 (s, 9H), 1.28-1.25 (m, 3H) ppm.

Step C: (S)-4-((4-(tert-butoxycarbonyl)-3-methyl-piperazin-1-yl)methyl)-3-(trifluoromethyl)benzoic acid

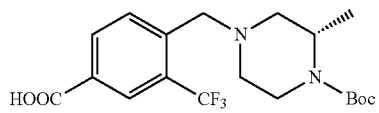

A mixture of the product from step B (210 mg, 0.5 mmol) and NaOH (2N, 1.5 mL, 3 mmol) in THF (5 mL) was stirred at 60° C. for 2 hours. The solvent was removed under reduced pressure and the residue was diluted with water (5 mL). The mixture was adjusted to pH about 5 by 2N HCl. The solid was collected and dried in air to afford the title product (160 mg, 80%) as a white solid. $^1$HNMR (400 MHz, DMSO-d6) δ 8.18 (d, J=7.2 Hz, 2H), 7.90 (d, J=7.2 Hz, 1H), 4.09 (s, 1H), 3.74-3.58 (m, 3H), 3.01 (t, J=11.6 Hz, 1H), 2.73 (d, J=11.2 Hz, 1H), 2.60-2.54 (m, 1H), 2.17-2.10 (m, 1H), 2.03-1.94 (m, 1H), 1.39 (s, 9H), 1.20 (d, J=6.8 Hz, 3H) ppm.

Step D: (S)-tert-butyl 2-methyl-4-(4-(((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)carbamoyl)-2-(trifluoromethyl)benzyl)piperazine-1-carboxylate

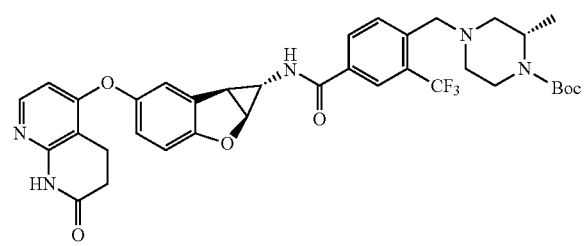 [SMILES: C[C@H]1CN(Cc2ccc(C(=O)N[C@@H]3[C@H]4Oc5ccc(Oc6ccnc7c6CCC(=O)N7)cc5[C@@H]34)cc2C(F)(F)F)CCN1C(=O)OC(C)(C)C]

A mixture of Intermediate I (120 mg, 0.35 mmol), the product from step C (155 mg, 0.385 mmol), HATU (160 mg, 0.42 mmol) and DIEA (181 mg, 1.4 mmol) in DMF (3 mL) was stirred at room temperature for 2 hours. The reaction was concentrated and water (10 mL) was added to the residue. The precipitate was collected and purified by prep-HPLC to get the title compound (90 mg, 37%) as a white solid. $^1$H NMR (400 MHz, DMSO-d6) δ 10.51 (s, 1H), 8.97 (s, 1H), 8.27-8.10 (m, 2H), 8.03-7.86 (m, 2H), 7.27 (d, J=2.0 Hz, 1H), 7.03-6.89 (m, 2H), 6.26 (d, J=6.0 Hz, 1H), 5.09 (d, J=6.0 Hz, 1H), 4.19-4.04 (m, 1H), 3.77-3.59 (m, 3H), 3.15-3.07 (m, 1H), 2.94 (t, J=7.2 Hz, 2H), 2.58-2.51 (m, 6H), 2.23-1.90 (m, 2H), 1.40 (s, 9H), 1.20 (d, J=6.0 Hz, 3H) ppm. MS: M/e 694 (M+1)$^+$.

Step E: 4-(((S)-3-methylpiperazin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide (Compound 1.29)

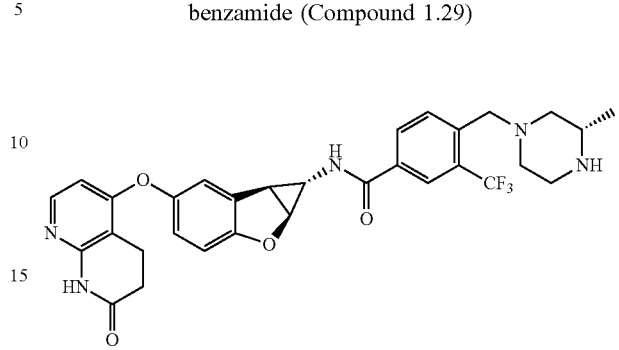

A mixture of the product from step D (85 mg, 0.12 mmol) in HCl (g)/EA (6N, 6 mL) was stirred at room temperature for 30 min. The reaction mixture was concentrated and purified by prep-HPLC to get the title compound (30 mg, 42%) as a white solid. $^1$H NMR (400 MHz, CD$_3$OD) δ 8.45 (s, 1H), 8.17 (s, 1H), 8.07 (d, J=8.0 Hz, 1H), 7.94-7.90 (m, 2H), 7.21 (s, 1H), 6.90-6.88 (m, 2H), 6.32 (d, J=6.0 Hz, 1H), 5.01 (d, J=5.6 Hz, 1H), 3.80 (s, 2H), 3.40-3.30 (m, 2H), 3.20-3.12 (m, 1H), 3.09-3.03 (m, 3H), 2.98-2.88 (m, 2H), 2.65 (t, J=8.0 Hz, 2H), 2.52 (d, J=1.6 Hz, 1H), 2.46-2.38 (m, 1H), 2.31-2.14 (m, 1H), 1.27 (d, J=6.4 Hz, 3H) ppm. MS: M/e 594 (M+1)$^+$ Compound 1.30 was prepared according to the procedures described for Compound 1.29 under appropriate conditions that could be recognized by one skilled in the art.

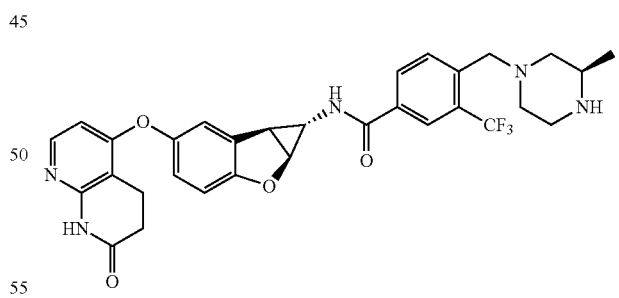

$^1$H NMR (400 MHz, CD$_3$OD) δ 8.49 (s, 1H), 8.17 (s, 1H, HCOOH), 8.07 (d, J=8.0 Hz, 1H), 7.95-7.90 (m, 2H), 7.21 (s, 1H), 6.91-6.88 (m, 2H), 6.32 (d, J=6.0 Hz, 1H), 5.01 (d, J=5.6 Hz, 1H), 3.80 (s, 2H), 3.41-3.33 (m, 2H), 3.19-3.10 (m, 1H), 3.06 (t, J=8.0 Hz, 3H), 2.97-2.87 (m, 2H), 2.65 (t, J=8.0 Hz, 2H), 2.52 (d, J=1.6 Hz, 1H), 2.45-2.35 (m, 1H), 2.23-2.15 (m, 1H), 1.25 (d, J=6.8 Hz, 3H) ppm. MS: M/e 594 (M+1)$^+$.

Compound 1.31: 4-(((R)-3-(dimethylamino)piperidin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide
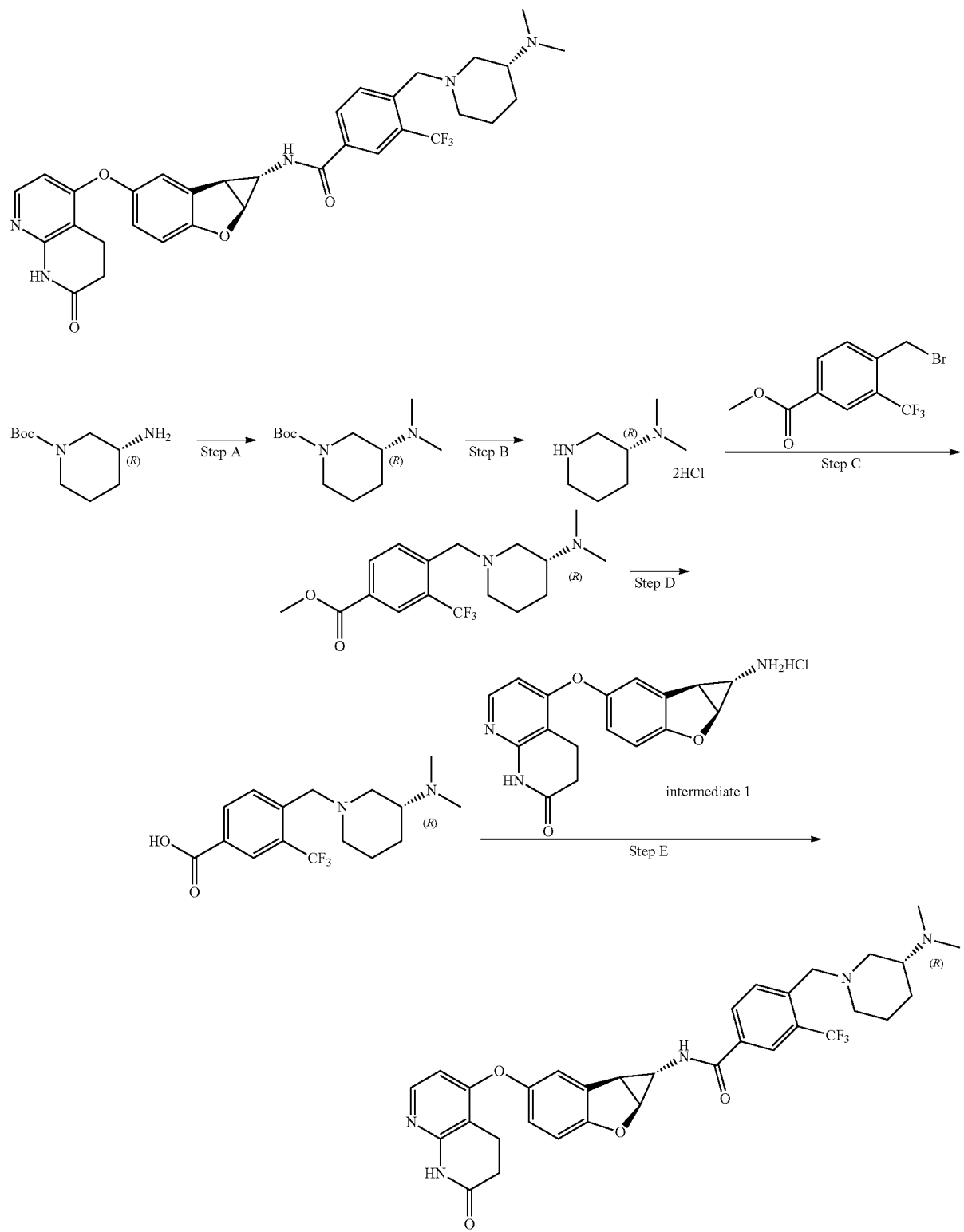

Step A: (R)-tert-butyl 3-(dimethylamino)piperidine-1-carboxylate

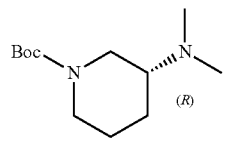

To a stirred solution of (R)-tert-butyl 3-aminopiperidine-1-carboxylate (2.0 g, 10 mmol) in methanol (40 mL) was added aqueous solution of formaldehyde (4 mL, 40 mmol) and followed by NaBH$_3$CN (1.6 g, 25 mmol) at ambient temperature and the mixture was stirred at ambient temperature for 16 hours. The mixture was added 100 mL of CH$_2$Cl$_2$, washed with aqueous solution of NaHCO$_3$ (50 mL×2), brine (50 mL×2). The organic layer was separated and dried over MgSO$_4$ and filtered. The filtrate was concentrated under reduced pressure to obtain the title product (2.1 g, yield: 90%) as a colorless oil. MS: M/e 229 (M+1)$^+$.

Step B: (R)—N,N-dimethylpiperidin-3-amine dihydrochloride

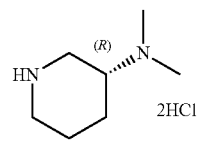

To a stirred solution of HCl/EA (15 mL, 6 mol/L) was added a solution of the product from step A (2.1 g, 9.2 mmol) in EA (15 mL) at ambient temperature in drops. The resulted mixture was stirred for 16 hours. The mixture was concentrated to dryness to obtain the title product (1.6 g, yield: 86%) as a white solid. MS: M/e 129 (M+1)$^+$.

Step C: (R)-methyl 4-((3-(dimethylamino)piperidin-1-yl)methyl)-3-(trifluoromethyl)benzoate

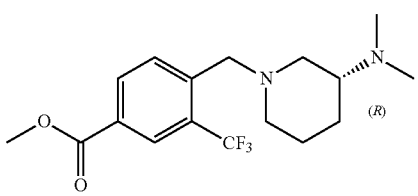

To a mixture of methyl 4-(bromomethyl)-3-(trifluoromethyl)benzoate (600 mg, 2.03 mmol), the product from step B (400 mg, 2 mmol) and Cs$_2$CO$_3$ (2.0 g, 6.15 mmol) in DMF (10 mL) was heated at 60° C. for 3 hours. 20 mL of H$_2$O was added and the mixture was extracted with EA (20 mL×3). The combined extracts were washed with brine (20 mL×3), dried over Na$_2$SO$_4$, and concentrated to obtain the title product (690 mg, crude) as light brown oil which was used for the next step directly. MS: M/e 345 (M+1)$^+$.

Step D: (R)-4-((3-(dimethylamino)piperidin-1-yl)methyl)-3-(trifluoromethyl)benzoic acid

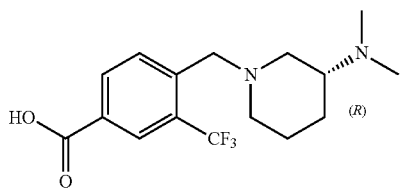

To a solution of the product from step C (690 mg, crude) in methanol (3 mL) was added aqueous solution of NaOH (5 mL, 2 M) at ambient temperature and the mixture was stirred for 3 hours. HCl (1 M) was added to pH-7. The mixture was concentrated to dryness. 50 mL of CH$_2$Cl$_2$/MeOH (10:1) was added and the mixture was stirred for 10 min. The solid (salt) was filtered off and the filtrate was concentrated to obtain the title product (550 mg, yield: 83% for 2 steps) as a white solid. MS: M/e 331 (M+1)$^+$.

Step E: 4-(((R)-3-(dimethylamino)piperidin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

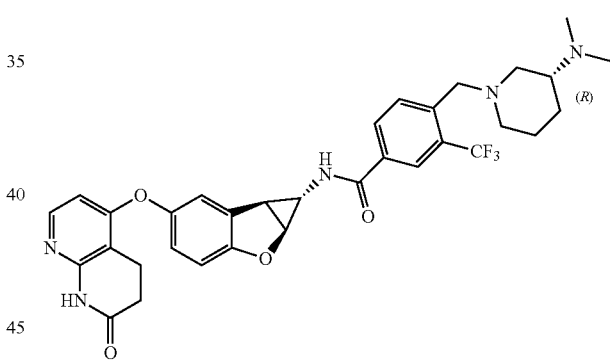

To a mixture of Intermediate I (100 mg, 0.29 mmol), the product from step D (100 mg, 0.30 mmol) and DIEA (95 mg) in DMF (2 mL) was added HATU (122 mg, 0.78 mmol) at ambient temperature and the resulted mixture was stirred at ambient temperature for 16 hours. The mixture was added into 10 mL of H$_2$O. A precipitated white solid was filtered. The filter cake was washed with 10 mL of H$_2$O and purified by prep-HPLC to obtain the title (25 mg, yield: 13%) as a white solid in a form of formic acid salt. $^1$H NMR (400 MHz, CD$_3$OD) δ 8.46 (br, 1H, HCOOH), 8.17 (s, 1H), 8.08 (d, J=8.4 Hz, 1H), 7.96 (d, J=8.4 Hz, 1H), 7.92 (d, J=6.0 Hz, 1H), 7.21 (s, 1H), 6.94-6.83 (m, 2H), 6.32 (d, J=6.0 Hz, 1H), 5.01 (d, J=6.0 Hz, 1H), 3.79 (s, 2H), 3.22 (s, 1H), 3.10-3.02 (m, 3H), 2.94-2.84 (m, 1H), 2.77 (s, 6H), 2.65 (t, J=7.6 Hz, 2H), 2.62-2.46 (m, 3H), 2.42-2.28 (m, 1H), 2.05-1.90 (m, 1H), 1.87-1.58 (m, 3H). MS: M/e 622 (M+1)$^+$.

Compound 1.32 was prepared according to the procedures described for Compound 1.31 under appropriate conditions that could be recognized by one skilled in the art.

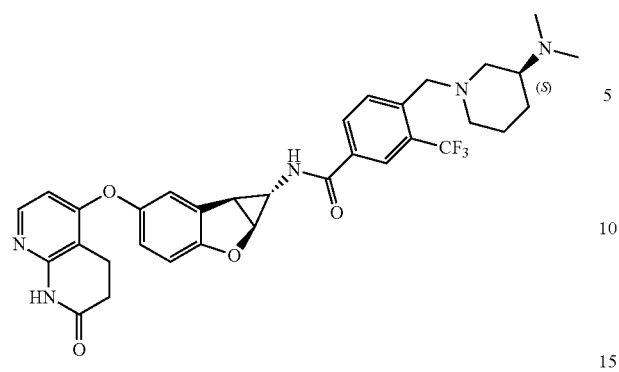
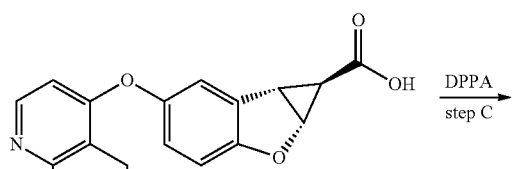
¹H NMR (400 MHz, DMSO-d6) δ 10.51 (s, 1H), 9.38 (s, 1H, CF₃COOH), 9.00 (d, J=3.2 Hz, 1H), 8.19 (s, 1H), 8.15 (d, J=8.0 Hz, 1H), 7.97 (d, J=6.0 Hz, 1H), 7.93 (d, J=8.0 Hz, 1H), 7.27 (d, J=2.4 Hz, 1H), 7.00-6.91 (m, 2H), 6.26 (d, J=6.0 Hz, 1H), 5.08 (d, J=5.6 Hz, 1H), 3.81 (s, 2H), 3.40-3.23 (m, 1H), 3.10 (dd, J=6.0, 2.0 Hz, 1H), 3.05-2.89 (m, 3H), 2.77 (s, 6H), 2.64-2.52 (m, 5H), 2.30-2.11 (m, 1H), 2.05-1.90 (m, 1H), 1.85-1.70 (m, 1H), 1.65-1.45 (m, 2H). MS: M/e 622 (M+1)⁺.
Compound 1.33: 4-((4-ethylpiperazin-1-yl)methyl)-N-((1R,1aR,6bR)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide
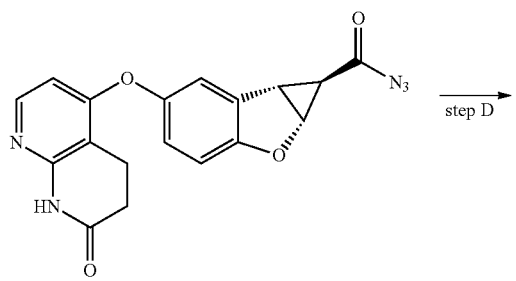
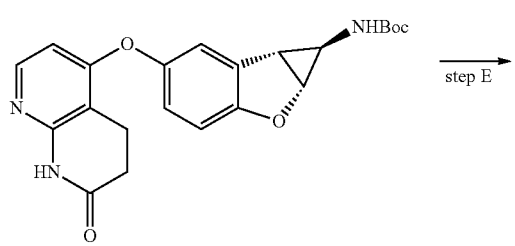
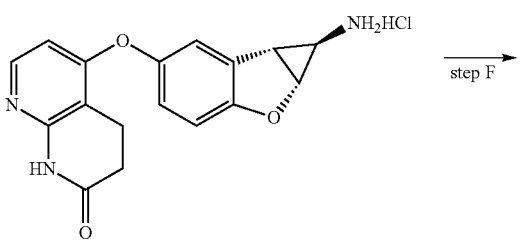
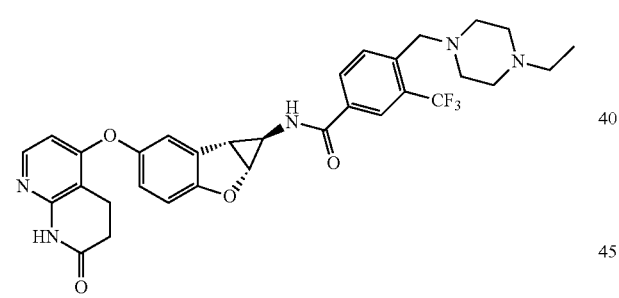
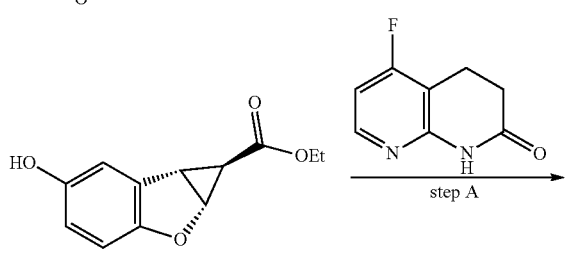
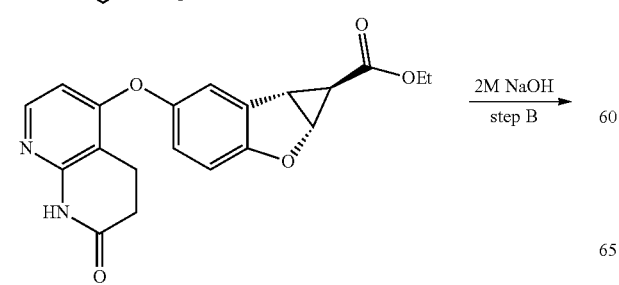
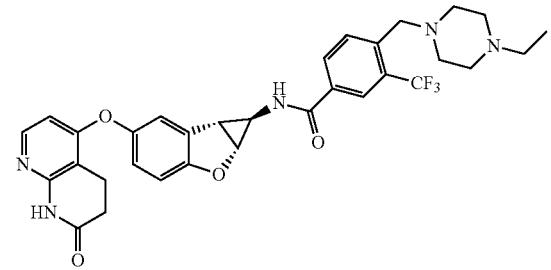

Step A: (1R,1aR,6bS)-ethyl 5-((7-oxo-5,6,7,8-tetrahydro-1,8-naphthyridin-4-yl)oxy)-1a,6b-dihydro-1H-cyclopropa[b]benzofuran-1-carboxylate

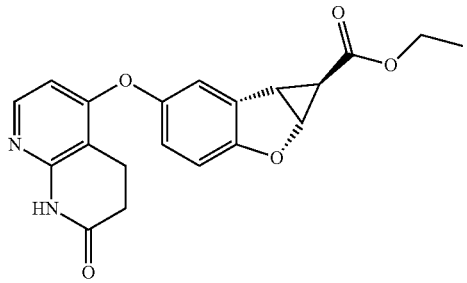

The mixture of (1R,1aR,6bS)-ethyl 5-hydroxy-1a,6b-dihydro-1H-cyclopropa[b]benzofuran-1-carboxylate (2.2 g, 0.01 mol) which was the product from Step G in synthesis of Intermediate I by Chiral SFC (column: Chiralpak AD-H), 5-fluoro-3,4-dihydro-1,8-naphthyridin-2(1H)-one (1.67 g, 0.01 mol) and t-BuOK (1.45 g, 0.013 mol) in DMF (10 mL) was stirred at 100° C. for 5 hours. The reaction was cooled to room temperature and filtered through a celite pad. The filtrate was concentrated to half of original volume. Water (30 mL) was added dropwise and a solid was precipitated out of the solution. The solid was filtered and dried in air. The title compound (3.5 g, crude) was obtained as a black solid. MS: M/e 367 (M+1)+.

Step B: (1R,1aR,6bS)-5-((7-oxo-5,6,7,8-tetrahydro-1,8-naphthyridin-4-yl)oxy)-1a,6b-dihydro-1H-cyclopropa[b]benzofuran-1-carboxylic acid

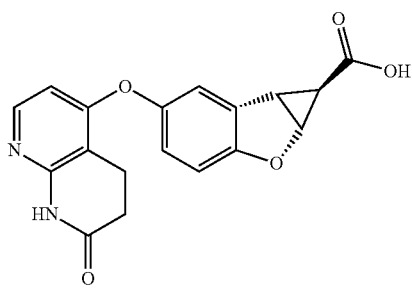

Sodium hydroxide aqueous solution (10 mL, 2 mol/L, 20 mmol) was added to a stirred solution of the crude product from Step A (2.8 g, 7.7 mmol) in methanol (20 mL) at room temperature. The mixture was stirred at 60° C. for 3 hours. The solvent was removed under reduced pressure and the residue was dissolved into water (20 mL), extracted with dichloromethane (2×20 mL). The aqueous layer was collected and neutralized with HCl (2 mol/L) to pH about 3 and white solid was precipitated out of solution. The white solid was collected by filtration and dried in air to give the title compound (2.1 g, 66% for two steps). $^1$H-NMR (400 MHz, DMSO-$d_6$) δ 12.60 (brs 1H), 10.49 (s, 1H), 7.95 (d, J=5.6 Hz, 1H), 7.33 (d, J=2.4 Hz, 1H), 7.02-6.95 (m, 2H), 6.24 (d, J=5.6 Hz, 1H), 5.27-5.23 (m, 1H), 3.34-3.29 (m, 1H), 2.93 (t, J=7.6 Hz, 2H), 2.53 (t, J=7.6 Hz, 2H), 1.24-1.21 (m, 1H) ppm. MS: M/e 339 (M+1)+.

Step C: (1R,1aR,6bS)-5-((7-oxo-5,6,7,8-tetrahydro-1,8-naphthyridin-4-yl)oxy)-1a,6b-dihydro-1H-cyclopropa[b]benzofuran-1-carbonyl azide

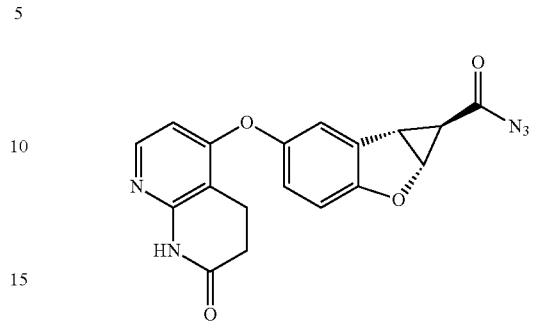

To a 0° C. solution of the product from Step B (0.5 g, 1.48 mmol) in DMF (1 mL) was added Et$_3$N (0.3 mL) and followed by DPPA (0.5 g, 1.82 mmol). The resulted mixture was allowed warm to ambient temperature and stirred for 5 hours. 10 mL of H$_2$O was added and the mixture was extracted with EA (10 mL×3). The combined extracts were washed with brine (10 mL×3), dried over Na$_2$SO$_4$, concentrated under vacuum until about 2 mL of EA remained. 10 mL of PE was added and the mixture was stirred for 30 minutes. The white solid was filtered and washed with PE/EA (5:1, 100 mL), dried under high vacuum to give the title compound (0.5 g, yield: 93.1%) as a white solid. $^1$H NMR (400 MHz, DMSO-$d_6$) δ 10.49 (s, 1H), 7.95 (d, J=5.6 Hz, 1H), 7.34 (d, J=2.4 Hz, 1H), 7.10-6.96 (m, 2H), 6.25 (d, J=5.6 Hz, 1H), 5.42 (dd, J=5.2, 0.8 Hz, 1H), 3.56 (dd, J=5.2, 3.2 Hz, 1H), 2.92 (t, J=8.0 Hz, 2H), 2.54 (t, J=8.0 Hz, 2H), 1.51 (dd, J=3.2, 0.8 Hz, 1H) ppm. MS: M/e 364 (M+1)+.

Step D: tert-butyl ((1R,1aR,6bR)-5-((7-oxo-5,6,7,8-tetrahydro-1,8-naphthyridin-4-yl)oxy)-1a,6b-dihydro-1H-cyclopropa[b]benzofuran-1-yl)carbamate

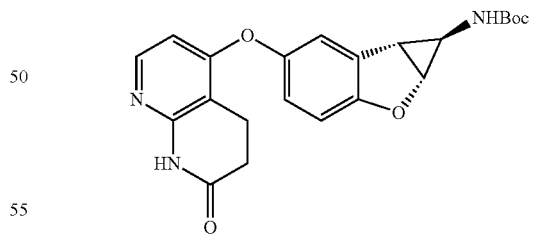

The mixture of the product from Step C (400 mg, 1.1 mmol) in t-butanol (5 mL) was stirred at 100° C. for 5 hours. The solvent was removed under reduced pressure and the residue was used into next step directly. The residue (360 mg, yield: 80%) as yellow oil was used into next step directly. MS: M/e 410 (M+1)+.

Step E: 5-(((1R,1aR,6bR)-1-amino-1a,6b-dihydro-1H-cyclopropa[b]benzofuran-5-yl)oxy)-3,4-dihydro-1,8-naphthyridin-2(1H)-one hydrochloride

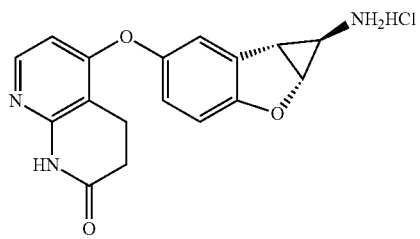

To a stirred solution of the product from Step D (100 mg, 0.24 mmol) in EA (3 mL) was added dropwise HCl/EA (1 mL, 6N) at room temperature. The white solid was precipitated from the solution immediately. The mixture was filtered. The solid (45 mg, yield: 54.9%) was dried in air and used into next step directly.

Step F: 4-((4-ethylpiperazin-1-yl)methyl)-N-((1R,1aR,6bR)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide (Compound 1.33)

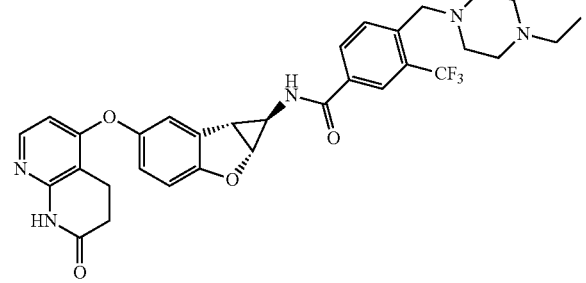

The mixture of the product from step E (50 mg, 0.14 mmol), the product obtained from Step D in synthesis of Compound 1.1 (45.8 mg, 0.14 mmol), DIEA (0.2 mL) and HATU (55 mg, 0.14 mmol) in DMF (2 mL) was stirred at room temperature of 3 hours. The solvent was removed under reduced pressure. The residue was added water (4 mL) and the solid was precipitated from the solution. The solid was purified by prep-HPLC to afford the title compound as a white solid (19 mg, yield: 21.6%). $^1$H NMR (400 MHz, DMSO-d6) δ 10.51 (s, 1H), 9.33 (br.s, 1H, CF$_3$COOH), 9.00 (d, J=3.2 Hz, 1H), 8.19 (s, 1H), 8.15 (d, J=8.0 Hz, 1H), 7.96 (d, J=6.0 Hz, 1H), 7.89 (d, J=8.0 Hz, 1H), 7.27 (d, J=2.0 Hz, 1H), 7.01-6.85 (m, 2H), 6.26 (d, J=6.0 Hz, 1H), 5.08 (d, J=5.6 Hz, 1H), 3.77 (s, 2H), 3.46 (d, J=12.0 Hz, 2H), 3.25-2.87 (m, 9H), 2.60-2.52 (m, 3H), 2.41 (t, J=12.0 Hz, 2H), 1.21 (t, J=7.2 Hz, 3H) ppm. MS: M/e 608 (M+1)$^+$.

Compound 1.34 was prepared according to the procedures described for Compound 1.33 under appropriate conditions that could be recognized by one skilled in the art.

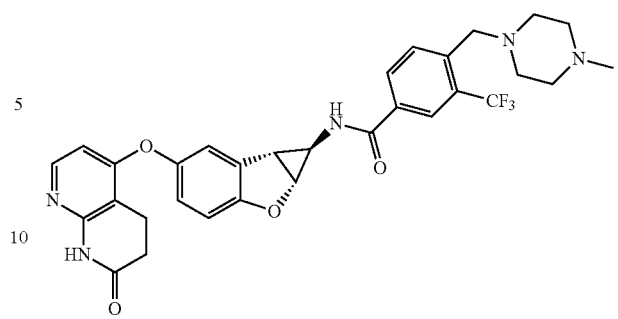

$^1$H NMR (400 MHz, DMSO-d6) δ 10.51 (s, 1H), 9.50 (br.s, 1H, CF$_3$COOH), 8.99 (s, 1H), 8.19 (s, 1H), 8.14 (d, J=8.0 Hz, 1H), 7.96 (d, J=6.0 Hz, 1H), 7.88 (d, 1H), 7.27 (d, J=2.0 Hz, 1H), 7.00-6.91 (m, 2H), 6.26 (d, J=6.0 Hz, 1H), 5.08 (d, J=6.0 Hz, 1H), 3.76 (s, 2H), 3.40 (d, J=12.0 Hz, 2H), 3.13-2.86 (m, 7H), 2.81 (s, 3H), 2.60-2.52 (m, 3H), 2.39 (t, J=12.0 Hz, 2H) ppm. MS: M/e 594 (M+1)$^+$.

Compounds 1.35-1.44 were prepared according to the procedures described for Compound 1.1 under appropriate conditions that could be recognized by one skilled in the art.

Compound 1.35

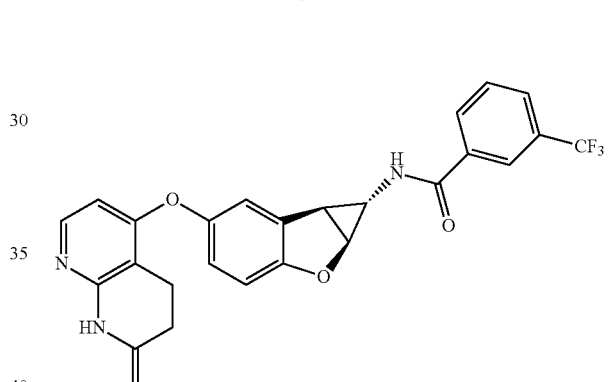

$^1$H NMR (400 MHz, DMSO-d6) δ 10.48 (s, 1H), 8.99 (d, J=3.6 Hz, 1H), 8.22-8.13 (m, 2H), 8.00-7.90 (m, 2H), 7.75 (t, J=8.0 Hz, 1H), 7.27 (d, J=2.0 Hz, 1H), 7.00-6.90 (m, 2H), 6.25 (d, J=5.6 Hz, 1H), 5.09 (d, J=6.0 Hz, 1H), 3.11 (dd, J=6.0, 2.0 Hz, 1H), 2.94 (t, J=7.6 Hz, 2H), 2.58-2.52 (m, 3H). MS: M/e 482 (M+1)$^+$

Compound 1.36

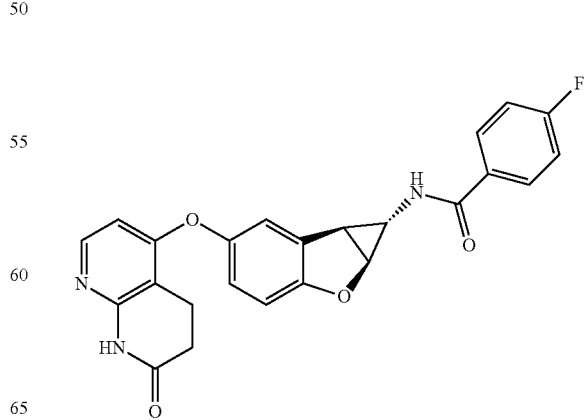

¹H NMR (400 MHz, CD₃OD) δ 7.98 (d, J=6.4 Hz, 1H), 7.92-7.83 (m, 2H), 7.25 (s, 1H), 7.18 (t, J=8.8 Hz, 2H), 6.97-6.87 (m, 2H), 6.50-6.42 (m, 1H), 5.02 (d, J=5.6 Hz, 1H), 3.11 (t, J=7.6 Hz, 2H), 3.03 (dd, J=5.6, 2.0 Hz, 1H), 2.71 (t, J=7.6 Hz, 2H), 2.49 (d, J=2.0 Hz, 1H) ppm. MS: M/e 432 (M+1)⁺

Compound 1.38

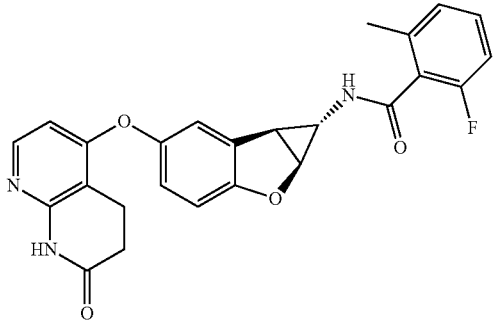 [SMILES: Cc1cccc(F)c1C(=O)N[C@@H]1[C@H]2Oc3ccc(Oc4ccnc5c4CCC(=O)N5)cc3[C@@H]12]

¹H NMR (400 MHz, CD₃OD) δ 8.05 (d, J=7.2 Hz, 1H), 7.35-7.27 (m, 2H), 7.07 (d, J=7.6 Hz, 1H), 7.02-6.92 (m, 3H), 6.67 (d, J=7.6 Hz, 1H), 4.99 (d, J=5.6 Hz, 1H), 3.19 (t, J=7.6 Hz, 2H), 3.03 (dd, J=5.6, 2.0 Hz, 1H), 2.78 (t, J=7.6 Hz, 2H), 2.54 (d, J=2.0 Hz, 1H), 2.33 (s, 3H) ppm. MS: M/e 446 (M+1)⁺

Compound 1.38

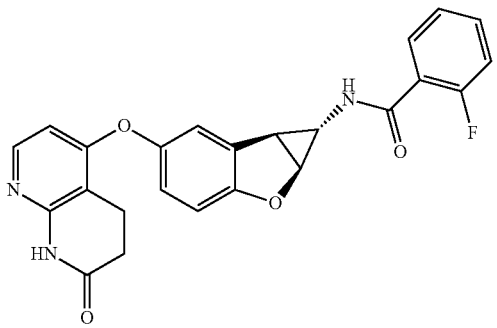 [SMILES: O=C1CCc2c(Oc3ccc4c(c3)[C@H]3[C@H](NC(=O)c5ccccc5F)[C@H]3O4)ccnc2N1]

¹H NMR (400 MHz, DMSO-d6) δ 10.55 (s, 1H), 8.66 (d, J=3.2 Hz, 1H), 8.08-7.88 (m, 1H), 7.66-7.50 (m, 2H), 7.34-7.24 (m, 3H), 6.98-6.91 (m, 2H), 6.29 (d, J=5.6 Hz, 1H), 5.05 (d, J=5.6 Hz, 1H), 3.06 (dd, J=5.6, 2.0 Hz, 1H), 2.95 (t, J=7.6 Hz, 2H), 2.60-2.51 (m, 3H). MS: M/e 432 (M+1)⁺

Compound 1.39

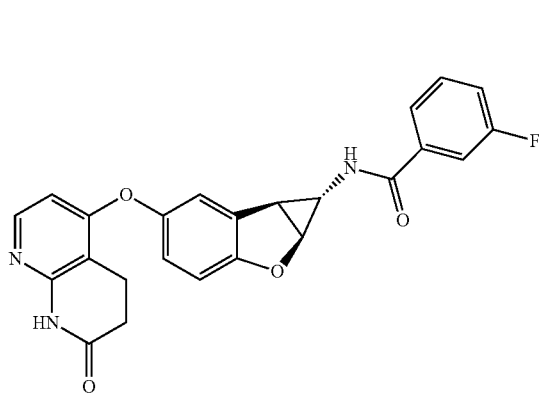 [SMILES: O=C1CCc2c(Oc3ccc4c(c3)[C@H]3[C@H](NC(=O)c5cccc(F)c5)[C@H]3O4)ccnc2N1]

¹H NMR (400 MHz, DMSO-d6) δ 10.50 (s, 1H), 8.84-8.74 (m, 1H), 7.96 (d, J=5.6 Hz, 1H), 7.94-7.29 (m, 4H), 7.28-7.24 (m, 1H), 6.98-6.90 (m, 2H), 6.26 (d, J=6.0 Hz, 1H), 5.09-5.05 (m, 1H), 3.10-3.05 (m, 1H), 2.94 (t, J=7.6 Hz, 2H), 2.58-2.51 (m, 3H). MS: M/e 432 (M+1)⁺.

Compound 1.40

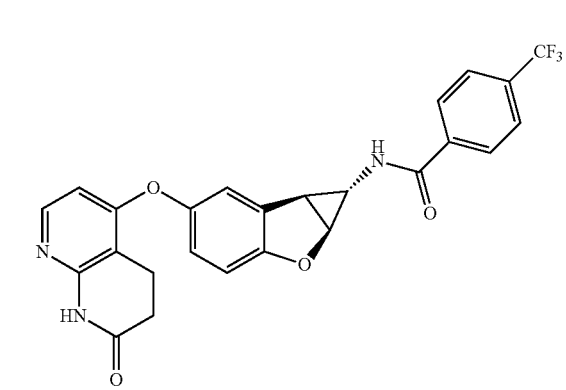 [SMILES: O=C1CCc2c(Oc3ccc4c(c3)[C@H]3[C@H](NC(=O)c5ccc(C(F)(F)F)cc5)[C@H]3O4)ccnc2N1]

¹H NMR (400 MHz, DMSO-d6) δ 10.50 (s, 1H), 8.98 (d, J=4.0 Hz, 1H), 8.05 (d, J=8.4 Hz, 2H), 7.96 (d, J=5.6 Hz, 1H), 7.88 (d, J=8.4 Hz, 2H), 7.27 (d, J=2.4 Hz, 1H), 7.00-6.89 (m, 2H), 6.27 (d, J=5.6 Hz, 1H), 5.09 (d, J=5.6 Hz, 1H), 3.10 (dd, J=5.6, 2.0 Hz, 1H), 2.94 (t, J=7.6 Hz, 2H), 2.60-2.52 (m, 3H). MS: M/e 482 (M+1)⁺.

Compound 1.41

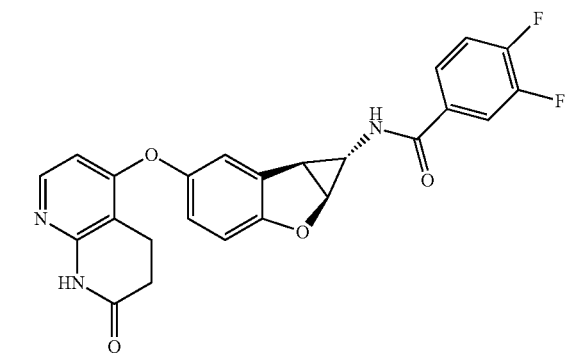 [SMILES: O=C1CCc2c(Oc3ccc4c(c3)[C@H]3[C@H](NC(=O)c5ccc(F)c(F)c5)[C@H]3O4)ccnc2N1]

¹H NMR (400 MHz, DMSO-d6) δ10.51 (s, 1H), 8.84 (d, J=3.5 Hz, 1H), 7.96 (d, J=5.6 Hz, 1H), 7.93-7.85 (m, 1H), 7.78-7.72 (m, 1H), 7.63-7.54 (m, 1H), 7.27 (d, J=2.0 Hz, 1H), 6.99-6.90 (m, 2H), 6.26 (d, J=5.6 Hz, 1H), 5.07 (d, J=5.6 Hz, 1H), 3.08 (dd, J=5.6, 2.0 Hz, 1H), 2.94 (t, J=7.6 Hz, 2H), 2.58-2.52 (m, 3H). MS: M/e 450 (M+1)⁺.

Compound 1.42

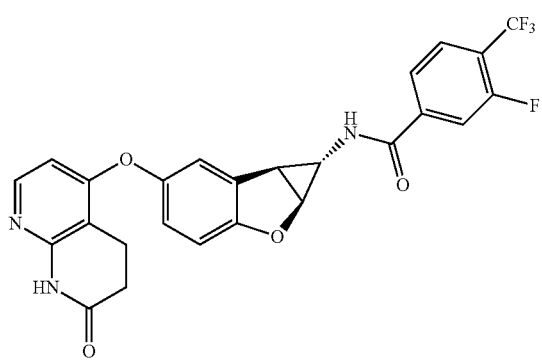 [SMILES: O=C1CCc2c(Oc3ccc4c(c3)[C@H]3[C@H](NC(=O)c5ccc(C(F)(F)F)c(F)c5)[C@H]3O4)ccnc2N1]

¹H NMR (400 MHz, DMSO-d6) δ 10.49 (s, 1H), 9.04 (d, J=3.6 Hz, 1H), 8.00-7.80 (m, 4H), 7.27 (d, J=2.4 Hz, 1H), 6.99-6.90 (m, 2H), 6.26 (d, J=5.6 Hz, 1H), 5.09 (d, J=5.6 Hz, 1H), 3.11 (dd, J=5.6, 2.0 Hz, 1H), 2.94 (t, J=7.2 Hz, 2H), 2.58-2.52 (m, 3H). MS: M/e 500 (M+1)⁺.

Compound 1.43

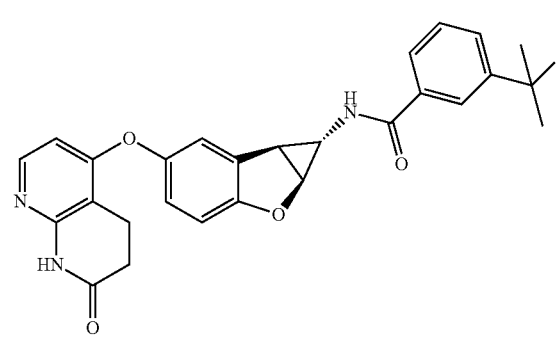

¹H NMR (400 MHz, DMSO-d6) δ 10.51 (s, 1H), 8.83 (d, J=3.2 Hz, 1H), 8.0-7.92 (m, 2H), 7.83 (d, J=8.0 Hz, 1H), 7.71 (d, J=8.0 Hz, 1H), 7.55 (t, J=8.0 Hz, 1H), 7.26 (d, J=2.0 Hz, 1H), 7.00-6.88 (m, 2H), 6.27 (d, J=5.6 Hz, 1H), 5.09 (d, J=5.6 Hz, 1H), 3.09 (dd, J=5.6, 2.0 Hz, 1H), 2.95 (t, J=7.6 Hz, 2H), 2.58-2.52 (m, 3H), 1.72 (s, 6H). MS: M/e 481 (M+1)⁺.

Compound 1.44

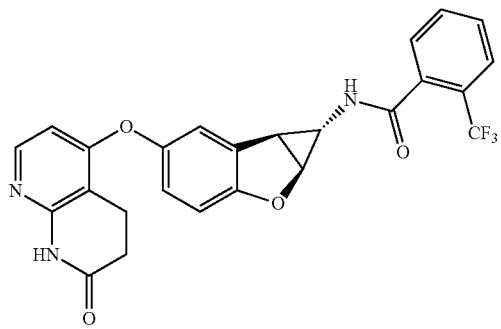 [SMILES: O=C1CCc2c(Oc3ccc4c(c3)[C@H]3[C@H](NC(=O)c5ccccc5C(F)(F)F)[C@H]3O4)ccnc2N1]

¹H NMR (400 MHz, DMSO-d6) δ 10.52 (s, 1H), 8.85 (d, J=3.6 Hz, 1H), 7.97 (d, J=6.0 Hz, 1H), 7.80 (d, J=7.6 Hz, 1H), 7.74 (t, J=7.6 Hz, 1H), 7.67 (t, J=7.6 Hz, 1H), 7.57 (d, J=7.6 Hz, 1H), 7.27 (d, J=2.0 Hz, 1H), 7.01-6.89 (m, 2H), 6.28 (d, J=6.0 Hz, 1H), 4.97 (d, J=5.6 Hz, 1H), 3.01 (dd, J=5.6, 2.0 Hz, 1H), 2.94 (t, J=7.6 Hz, 2H), 2.55 (t, J=7.6 Hz, 2H), 2.49-2.47 (m, 1H). MS: M/e 482 (M+1)⁺.

Compound 1.45: N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-4-(trifluoromethyl)picolinamide

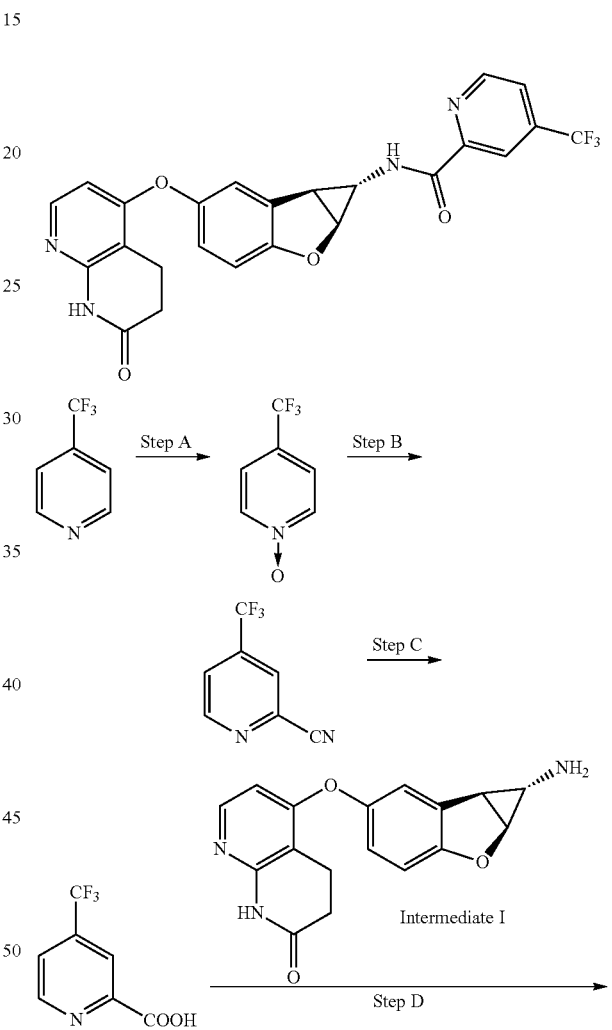

Step A: 4-(trifluoromethyl)pyridine 1-oxide

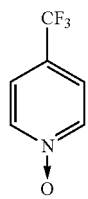 [SMILES: [O-][n+]1ccc(C(F)(F)F)cc1]

To a stirred solution of 4-(trifluoromethyl)pyridine (1 g, 6.8 mmol) in CH$_2$Cl$_2$ (15 mL) was added 3-chloroperoxybenzoic acid (m-CPBA) (1.5 g, 8.7 mmol) at 0° C. and the mixture was stirred at ambient temperature for 16 hours. The mixture was diluted with 20 mL of CH$_2$Cl$_2$ and washed with aqueous NaHSO$_3$ (10 mL), NaHCO$_3$ (10 mL×2), brine (10 mL×2), dried and concentrated to obtain the desired compound (950 mg, 86%) as a white solid.

Step B: 4-(trifluoromethyl)picolinonitrile

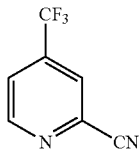

A solution of the product from Step A (500 mg, 3.07 mmol), trimethylsilyl cyanide (TMSCN) (1.0 g, 10.1 mmol) and dimethylcarbamic chloride (1.1 g, 10.3 mmol) in CH$_2$Cl$_2$ (15 mL) was heated at 50° C. in a sealed tube for 40 hours. The mixture was concentrated and purified by column chromatography eluted with PE/EA (from 20:1 to 5:1) to obtain the desired compound (1.3 g, crude) as light yellow oil. $^1$H NMR (400 MHz, CDCl$_3$) δ 8.95 (d, J=5.2 Hz, 1H), 7.92 (s, 1H), 7.77 (dd, J=5.2, 0.8 Hz, 1H).

Step C: 4-(trifluoromethyl)picolinic acid

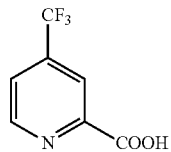 [SMILES: O=C(O)c1cc(C(F)(F)F)ccn1]

A solution of the product from Step B (1.3 g, crude) in a mixed solvent of HCl (conc.) and dioxane (20 mL, 1:1) was refluxed for 2 hours. The mixture was concentrated to obtain the title product (350 mg, 60% for 2 steps) as a brown solid which was used for the next step without any further purification. MS: M/e 192 (M+1)$^+$.

Step D: N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-4-(trifluoromethyl)picolinamide (Compound 1.45)

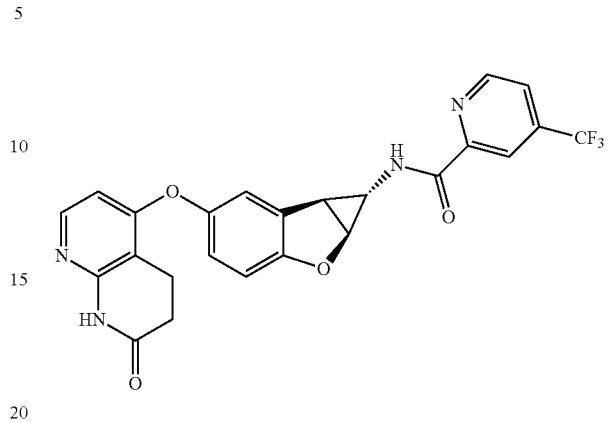

A solution of the product from Step C (35 mg, 0.18 mmol) in SOCl$_2$ (5 mL) was refluxed for 2 hours. The mixture was concentrated and 5 mL of CH$_2$Cl$_2$ was added and the solution was concentrated to obtain a light yellow oil which was diluted with CH$_2$Cl$_2$ (1 mL) and the resulted solution was added into a solution of Intermediate I (62 mg, 0.18 mmol) and DIEA (100 mg, 0.78 mmol) in CH$_2$Cl$_2$ (1 mL) in drops. The mixture was stirred at ambient temperature for 2 hours and concentrated. The resulted residue was purified by prep-HPLC to obtain the desired product (26 mg, 30%) as a light yellow solid. $^1$H NMR (400 MHz, DMSO-d6) δ 10.51 (s, 1H), 9.39 (d, J=4.8 Hz, 1H), 8.96 (d, J=4.8 Hz, 1H), 8.24 (s, 1H), 8.05 (d, J=4.8 Hz, 1H), 7.96 (d, J=5.6 Hz, 1H), 7.24 (d, J=2.4 Hz, 1H), 7.00-6.88 (m, 2H), 6.27 (d, J=5.6 Hz, 1H), 5.21 (d, J=5.6 Hz, 1H), 3.18 (dd, J=5.6, 2.0 Hz, 1H), 2.99-2.89 (m, 2H), 2.63 (dd, J=4.4, 1.6 Hz, 1H), 2.55 (t, J=8.0 Hz, 2H). MS: M/e 483 (M+1)$^+$.

Compound 1.46: 3-(1-cyanocyclopropyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)benzamide

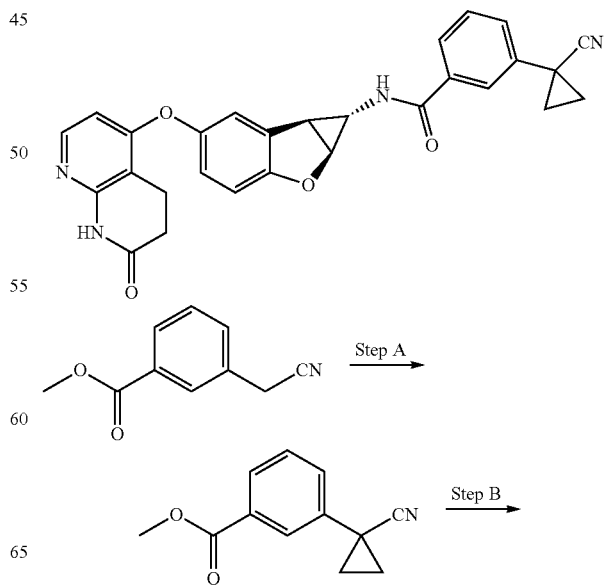

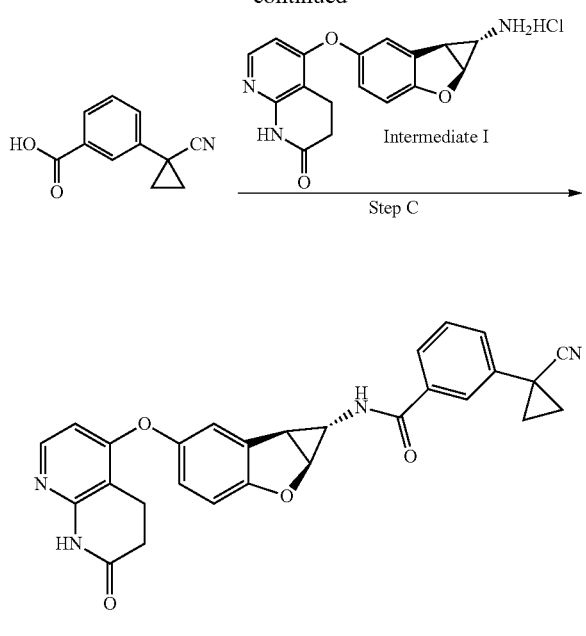

Step A: methyl 3-(1-cyanocyclopropyl)benzoate

To a stirred solution of methyl 3-(cyanomethyl)benzoate (1.5 g, 8.6 mmol) in DMSO (30 mL) was added sodium hydride (60% in oil, 1.0 g, 26 mmol) under not more than 25° C. without causing solidification. The reaction mixture was stirred at ambient temperature for 30 min. After stirring, 1,2-dibromoethane (2.4 g, 12.8 mmol) was added, and the mixture was further stirred at ambient temperature for 16 hours. The mixture was diluted with H$_2$O (100 mL), and extracted with EA (100 mL×3). The combined extracts were washed with brine (100 mL×2), dried over Na$_2$SO$_4$, concentrated under reduced pressure. The residue was purified by silica-gel column chromatography (PE/EA: from 20:1 to 1:1) to obtain the desired compound (1.45 g, crude) as a brown oil which was used for the next step without any further purification.

Step B: 3-(1-cyanocyclopropyl)benzoic acid

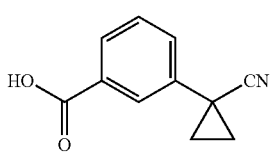 [SMILES: N#CC1(c2cccc(C(=O)O)c2)CC1]

To a solution of product from Step A (1.45 g, crude) in MeOH (15 mL) was added aqueous solution of NaOH (3 mL, 4 M). The mixture was stirred for 2 hours. The mixture was acidified by HCl (1M) to pH-3. The mixture was extracted with EA (20 mL×3). The combined extracts were washed with brine (20 mL×2), dried over Na$_2$SO$_4$, concentrated and purified by prep-HPLC to obtain the desired product (280 mg, 17% for 2 steps) as a white solid. $^1$H NMR (400 MHz, DMSO-d6) δ 13.16 (s, 1H), 7.92 (d, J=1.0 Hz, 1H), 7.90-7.85 (m, 1H), 7.56-7.49 (m, 2H), 1.87-1.74 (m, 2H), 1.64-1.51 (m, 2H).

Step C: 3-(1-cyanocyclopropyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)benzamide (Compound 1.46)

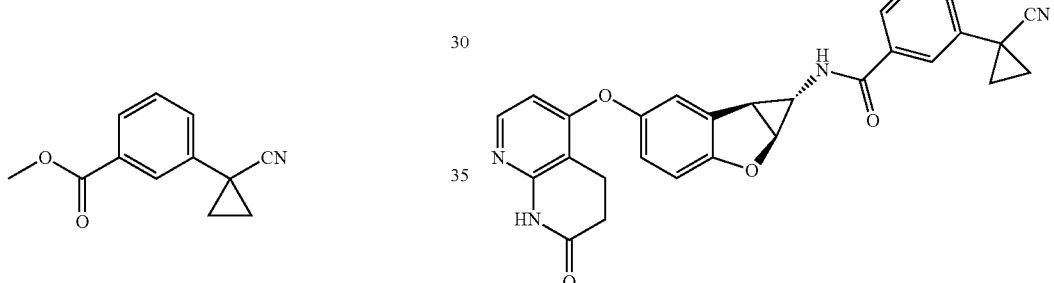

To a mixture of the product from Step B (30 mg, 0.159 mmol), Intermediate I (50 mg, 0.145 mmol) and DIEA (80 mg, 0.62 mmol) in DMF (2 mL) was added HATU (60 mg, 0.158 mmol) at ambient temperature and the mixture was stirred for 2 hours. The mixture was added 5 mL of H$_2$O and extracted with EA (5 mL×3). The combined extracts were washed with brine (5 mL×2), dried over Na$_2$SO$_4$, concentrated and purified by prep-HPLC to obtain the desired product (39 mg, 56%) as a white solid. $^1$H NMR (400 MHz, DMSO-d6) δ 10.51 (s, 1H), 8.81 (d, J=3.6 Hz, 1H), 7.97 (d, J=5.6 Hz, 1H), 7.81-7.73 (m, 2H), 7.56-7.47 (m, 2H), 7.26 (d, J=2.4 Hz, 1H), 6.99-6.91 (m, 2H), 6.27 (d, J=5.6 Hz, 1H), 5.08 (d, J=5.6 Hz, 1H), 3.08 (dd, J=5.6, 2.0 Hz, 1H), 2.95 (t, J=7.6 Hz, 2H), 2.58-2.52 (m, 3H), 1.84-1.76 (m, 2H), 1.60-1.54 (m, 2H). MS: M/e 479 (M+1)$^+$.

Compound 1.47: 4-((S)-3-(dimethylamino)piperidin-1-yl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide
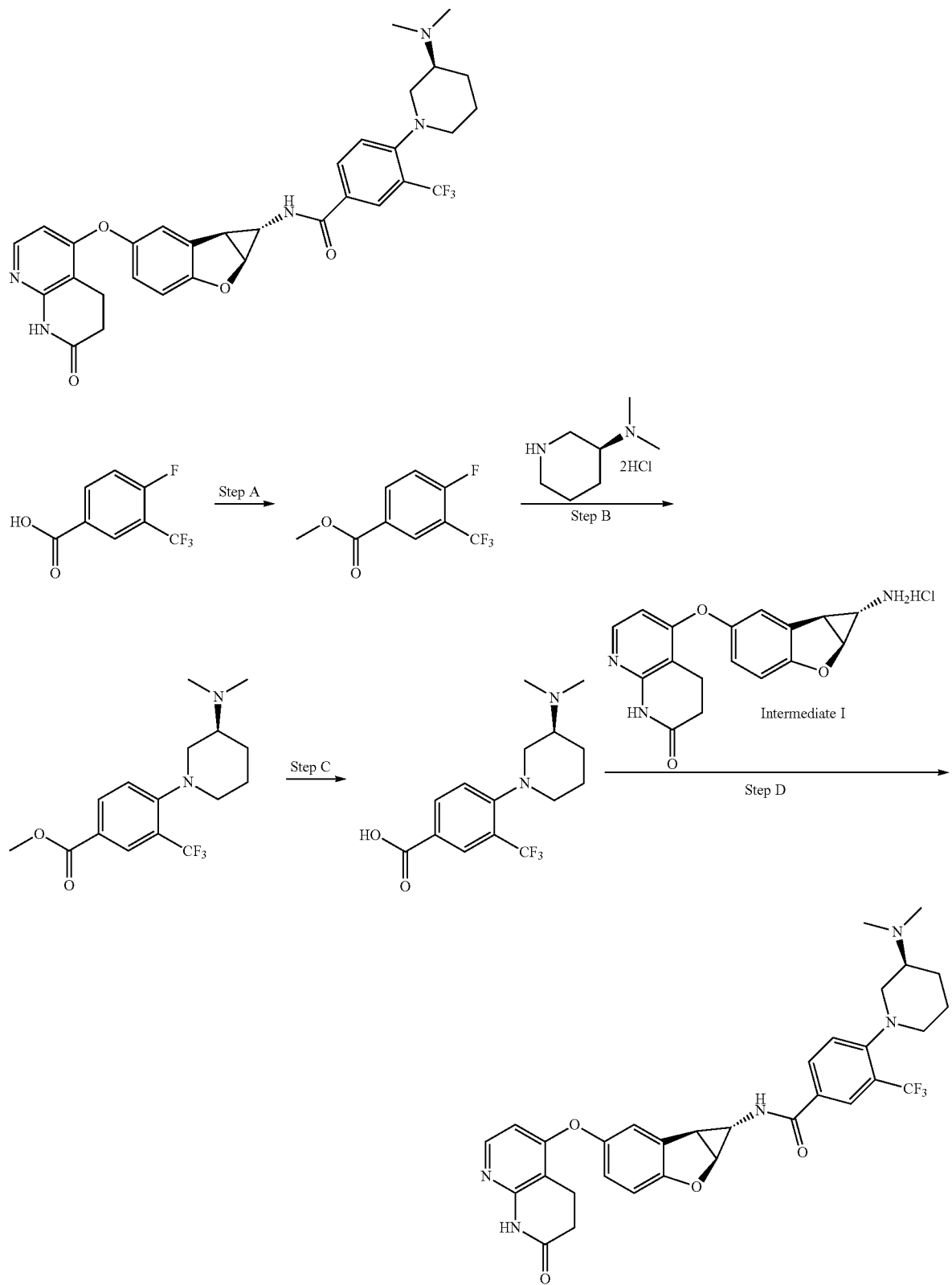

Step A: methyl 4-fluoro-3-(trifluoromethyl)benzoate

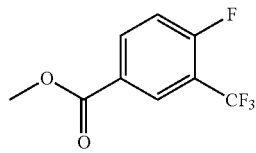

To a stirred solution of 4-fluoro-3-(trifluoromethyl)benzoic acid (10.0 g, 48.1 mmol) in MeOH (100 mL) was added conc. H$_2$SO$_4$ (4 mL, 73.4 mmol) in drops at ambient temperature and the mixture was refluxed for 5 hours. 200 mL of aqueous solution of NaHCO$_3$ was added to basified the mixture, and the resulted mixture was extracted with EA (100 mL×3). The combined extracts were washed with brine (100 mL×2), dried, concentrated to obtain the title product (9.4 g, yield: 88%) as a light yellow oil. $^1$H NMR (400 MHz, CDCl$_3$) δ 8.33 (dd, J=6.8, 1.6 Hz, 1H), 8.28-8.22 (m, 1H), 7.28 (t, 1H), 3.95 (s, 3H).

Step B: (S)-methyl 4-(3-(dimethylamino)piperidin-1-yl)-3-(trifluoromethyl)benzoate

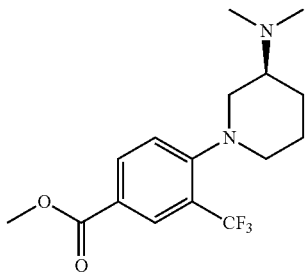

A mixture of the product from Step A (225 mg, 1 mmol), (S)—N,N-dimethyl piperidin-3-amine dihydrochloride (200 mg, 1 mmol) and Cs$_2$CO$_3$ (1.0 g, 3 mmol) in DMF (10 mL) was heated at 70° C. for 3 hours. 30 mL of H$_2$O was added and the mixture was extracted with CH$_2$Cl$_2$ (20 mL×3). The combined layers were washed with brine (20 mL×3), dried, concentrated and the residue was purified by column chromatography (5 g of silica-gel, eluting: CH$_2$Cl$_2$/MeOH from 100:1 to 30:1) to obtain the title product (105 mg, yield: 32%) as a colorless oil. MS: M/e 331 (M+1)$^+$.

Step C: (S)-4-(3-(dimethylamino)piperidin-1-yl)-3-(trifluoromethyl)benzoic acid

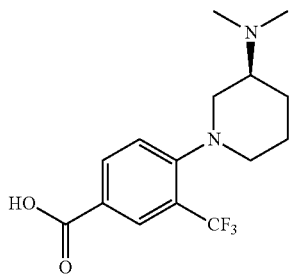 [SMILES: CN(C)[C@H]1CCCN(c2ccc(C(=O)O)cc2C(F)(F)F)C1]

To a solution of the product from Step B (105 mg, 0.32 mmol) in MeOH (2 mL) was added aqueous solution of NaOH (2 mL, 2 M) at ambient temperature and the mixture was stirred for 3 hours. HCl (1 M) was added to pH-7. The mixture was concentrated to dryness and 20 mL of CH$_2$Cl$_2$/MeOH (10:1) was added and the mixture was stirred for 10 min. The solid (salt) was filtered off and the filtrate was concentrated to obtain the title product (82 mg, yield: 81%) as a white solid. MS: M/e 317 (M+1)$^+$.

Step D: 4-((S)-3-(dimethylamino)piperidin-1-yl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide (Compound 1.47)

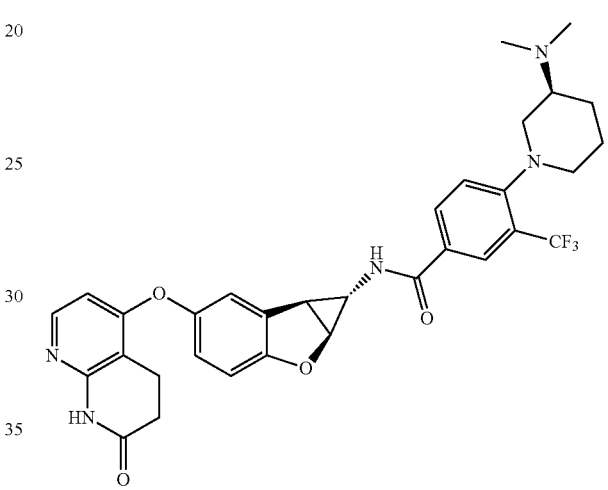

To a mixture of Intermediate I (55 mg, 0.16 mmol), the product of Step C (50 mg, 0.16 mmol) and DIEA (100 mg, 0.78 mmol) in DMF (2 mL) was added HATU (73 mg, 0.19 mmol) at ambient temperature and the resulted mixture was stirred at ambient temperature for 16 hours. The mixture was added 10 mL of H$_2$O, extracted with CH$_2$Cl$_2$ (10 mL×3). The combined layer was washed with brine (10 mL×2), dried over MgSO$_4$, filtered and concentrated and the residue was purified by prep-HPLC to obtain the title product (30 mg, yield: 22%) as a white solid and a form of CF$_3$COOH salt. $^1$H NMR (400 MHz, DMSO-d6) δ 10.49 (s, 1H), 9.60 (s, 1H, CF$_3$COOH), 8.92 (d, J=3.6 Hz, 1H), 8.21-8.10 (m, 2H), 7.96 (d, J=6.0 Hz, 1H), 7.66 (d, J=8.0 Hz, 1H), 7.26 (d, J=2.4 Hz, 1H), 6.99-6.91 (m, 2H), 6.25 (d, J=6.0 Hz, 1H), 5.07 (d, J=5.6 Hz, 1H), 3.41-3.28 (m, 2H), 3.09 (dd, J=5.6, 2.0 Hz, 1H), 3.00-2.88 (m, 4H), 2.85-2.77 (m, 6H), 2.77-2.68 (m, 1H), 2.59-2.51 (m, 3H), 2.19-2.09 (m, 1H), 1.96-1.84 (m, 1H), 1.69-1.48 (m, 2H). MS: M/e 608 (M+1)$^+$.

Compounds 1.48-1.50 were prepared according to the procedures described for Compound 1.47 under appropriate conditions that could be recognized by one skilled in the art.

121

Compound 1.48

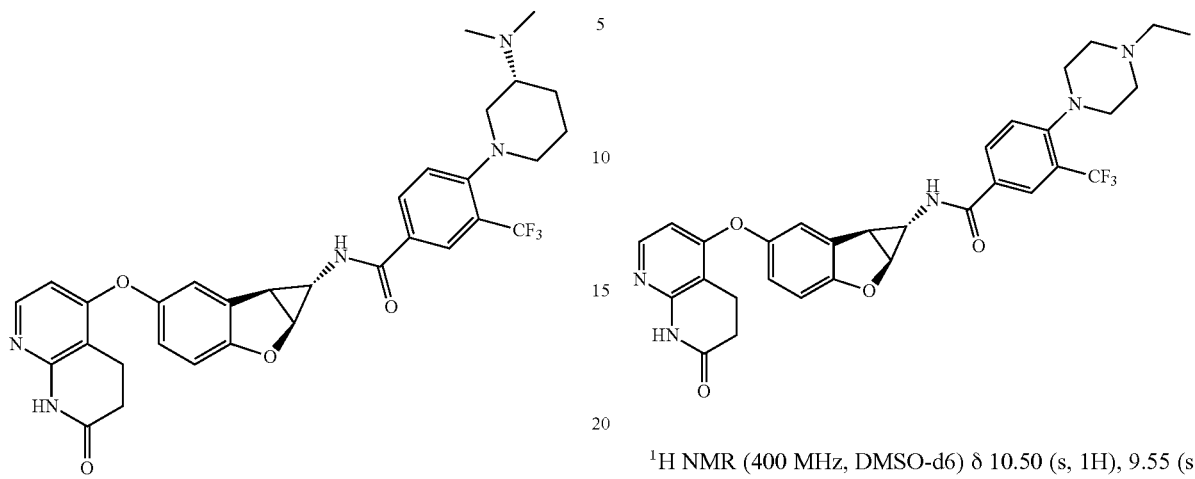

¹H NMR (400 MHz, CD₃OD) δ 8.08 (d, J=2.0 Hz, 1H), 8.00 (dd, J=8.4, 1.6 Hz, 1H), 7.84 (d, J=6.0 Hz, 1H), 7.49 (d, J=8.4 Hz, 1H), 7.13 (s, 1H), 6.85-6.77 (m, 2H), 6.23 (d, J=6.0 Hz, 1H), 4.93 (d, J=6.0 Hz, 1H), 3.33 (d, J=10.8 Hz, 1H), 3.11-3.01 (m, 1H), 3.00-2.93 (m, 4H), 2.82-2.68 (m, 2H), 2.62 (s, 6H), 2.57 (t, J=7.6, 2H), 2.42 (d, J=2.0 Hz, 1H), 2.14-2.03 (m, 1H), 1.90-1.80 (m, 1H), 1.77-1.63 (m, 1H), 1.57-1.42 (m, 1H). MS: M/e 608 (M+1)⁺.

Compound 1.49

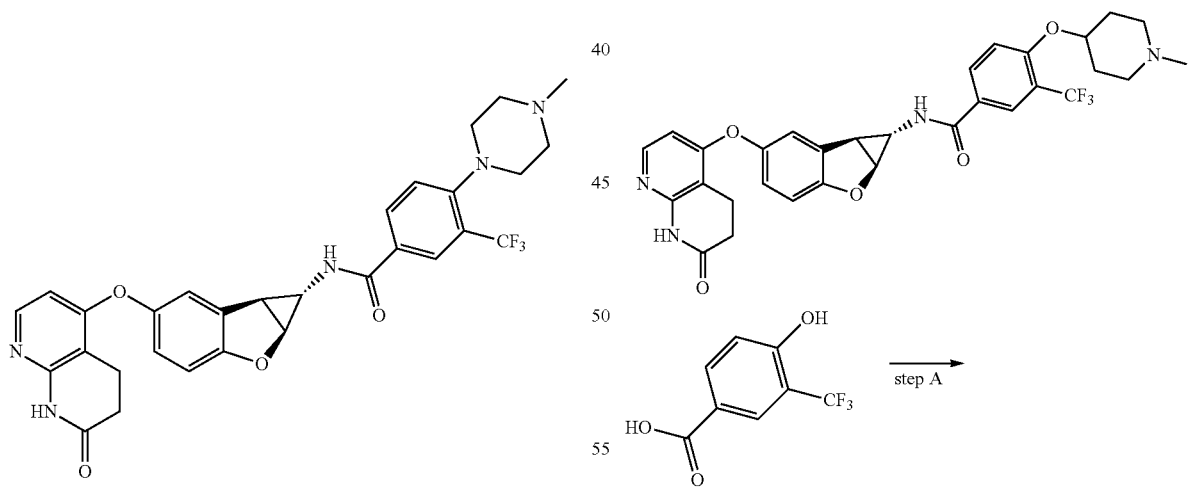

¹H NMR (400 MHz, DMSO-d6) δ 10.50 (s, 1H), 9.71 (s, 1H—CF3COOH), 8.94 (d, J=3.6 Hz, 1H), 8.21-8.10 (m, 2H), 7.96 (d, J=5.6 Hz, 1H), 7.64 (d, J=8.4 Hz, 1H), 7.26 (d, J=2.0 Hz, 1H), 7.02-6.87 (m, 2H), 6.26 (d, J=5.6 Hz, 1H), 5.07 (d, J=5.6 Hz, 1H), 3.53 (d, J=10.5 Hz, 2H), 3.24-3.06 (m, 7H), 2.97-2.88 (m, 5H), 2.58-2.52 (m, 3H) ppm. MS: M/e 580 (M+1)⁺.

122

Compound 1.50

¹H NMR (400 MHz, DMSO-d6) δ 10.50 (s, 1H), 9.55 (s, 1H—CF3COOH), 8.95 (d, J=3.2 Hz, 1H), 8.23-8.11 (m, 2H), 7.96 (d, J=5.6 Hz, 1H), 7.64 (d, J=8.4 Hz, 1H), 7.26 (d, J=2.4 Hz, 1H), 7.02-6.88 (m, 2H), 6.25 (d, J=5.6 Hz, 1H), 5.08 (d, J=5.6 Hz, 1H), 3.60 (d, J=9.6 Hz, 2H), 3.31-3.03 (m, 9H), 2.94 (t, J=7.6 Hz, 2H), 2.59-2.52 (m, 3H), 1.25 (t, J=7.2 Hz, 3H) ppm. MS: M/e 594 (M+1)⁺.

Compound 1.51: 4-((1-methylpiperidin-4-yl)oxy)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

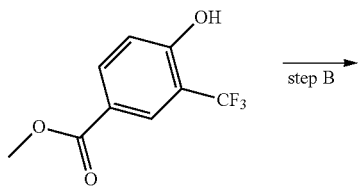

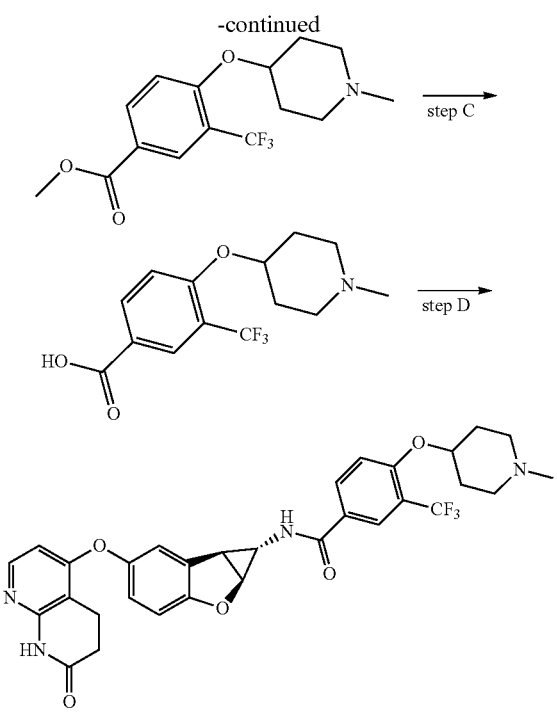

Step A: methyl 4-hydroxy-3-(trifluoromethyl)benzoate

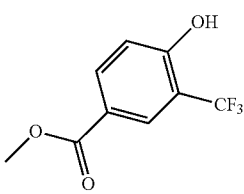

Conc. H$_2$SO$_4$ (1.5 mL) was dissolved in MeOH (20 mL) and 4-hydroxy-3-(trifluoromethyl)benzoic acid (2.0 g, 9.7 mmol) was added. After the addition, the reaction mixture was refluxed overnight. The reaction mixture was concentrated to give the residue, which was treated with EA (50 mL) and washed with aq. sat. NaHCO$_3$, brine, dried over Na$_2$SO$_4$ and concentrated to give the target compound (1.9 g, 89%) as a white solid. MS: M/e 221 (M+1)$^+$.

Step B: methyl 4-((1-methylpiperidin-4-yl)oxy)-3-(trifluoromethyl)benzoate

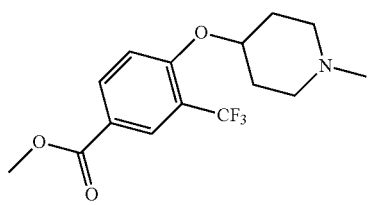

The product from Step A (0.5 g, 2.13 mmol) and 1-methylpiperidin-4-ol (0.245 mg, 2.13 mmol) were dissolved in dry CH$_2$Cl$_2$ (15 mL) and the mixture was cooled to 0° C. and DTAD (0.98 g, 4.26 mmol) and PPh$_3$ (1.1 g, 4.26 mmol) were added. After the addition, the mixture was stirred at room temperature overnight. The reaction mixture was concentrated to give the residue, which was purified by silica gel column chromatography (petroleum ether/EtOAc=1:1~CH$_2$Cl$_2$/MeOH=10:1) to give the target compound (0.32 g, 47.4%) as colorless oil. $^1$H-NMR (400 MHz, DMSO-d$_6$) δ 8.17 (dd, J=8.8, 2.0 Hz, 1H), 8.11 (d, J=2.0 Hz, 1H), 7.46 (d, J=8.8 Hz, 1H), 4.79 (s, 1H), 3.84 (s, 3H), 2.41-2.30 (m, 2H), 2.21 (s, 3H), 2.00-1.86 (m, 2H), 1.83-1.67 (m, 2H), 1.45-1.29 (m, 2H) ppm. MS: M/e 318 (M+1)$^+$.

Step C: 4-((1-methylpiperidin-4-yl)oxy)-3-(trifluoromethyl)benzoic acid

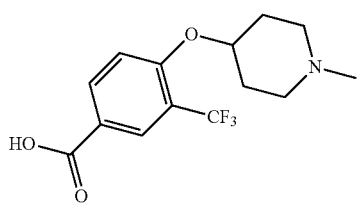 [SMILES: CN1CCC(Oc2ccc(C(=O)O)cc2C(F)(F)F)CC1]

To a stirred solution of product from Step B (50 mg, 0.158 mmol) in MeOH/H$_2$O (3 mL/3 mL) was added NaOH (12.6 mg, 0.316 mmol). After stirred for 2 hours, the reaction mixture was acidified to pH=6~7 with aq. HCl, and concentrated to give the residue, which was treated with CH$_2$Cl$_2$/MeOH (20 mL, 3/1), and filtered. The filtrate was concentrated to give target compound (48 mg, 100%) as a white solid. MS: M/e 314 (M+1)$^+$.

Step D: 4-((1-methylpiperidin-4-yl)oxy)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide (Compound 1.51)

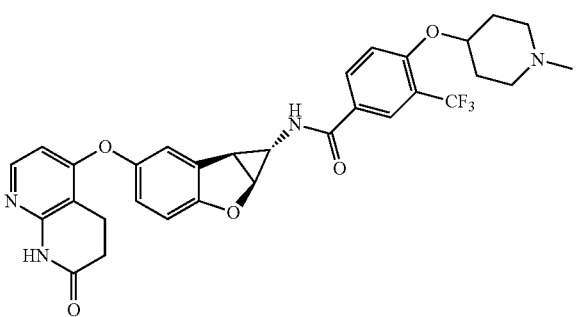 [SMILES: CN1CCC(Oc2ccc(C(=O)N[C@@H]3[C@H]4Oc5ccc(Oc6ccnc7c6CCC(=O)N7)cc5[C@@H]34)cc2C(F)(F)F)CC1]

A mixture of the product from Step C (50 mg, 0.165 mmol), Intermediate I (57 mg, 0.165 mmol), HATU (75.2 mg, 0.198 mmol) and DIPEA (0.2 mL) in DMF (2 mL) was stirred for 2 hours. The reaction mixture was concentrated to give the residue, which was purified by prep-HPLC to give the target compound (15.43 mg, 13.2%) as a white solid (TFA salt). $^1$H-NMR (400 MHz, CD$_3$OD) δ 8.25-8.10 (m, 2H), 7.99 (d, J=6.0 Hz, 1H), 7.46-7.35 (m, 1H), 7.27 (s, 1H), 7.00-6.90 (s, 2H), 6.43 (d, J=6.0 Hz, 1H), 5.12 (s, 1H), 5.05 (d, J=6.0 Hz, 1H), 3.70-3.48 (m, 2H), 3.28-3.16 (m, 2H), 3.16-3.05 (m, 3H), 2.99-2.91 (m, 3H), 2.72 (t, J=7.6 Hz, 2H), 2.54 (d, J=2.0 Hz, 1H), 2.50-2.11 (m, 3H), 2.04-1.91 (m, 1H) ppm. MS: M/e 297.9 (M/2+1)$^+$.

Compound 1.52 was prepared according to the procedures described for Compound 1.51 under appropriate conditions that could be recognized by one skilled in the art.

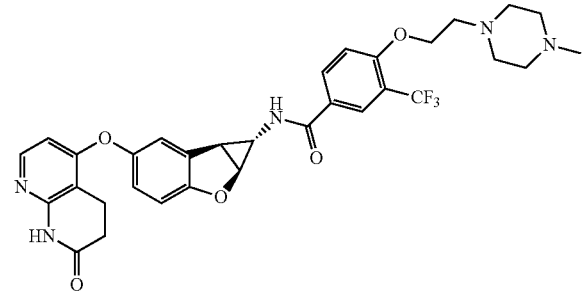 [SMILES: CN1CCN(CCOc2ccc(C(=O)N[C@@H]3[C@H]4Oc5ccc(Oc6ccnc7c6CCC(=O)N7)cc5[C@@H]34)cc2C(F)(F)F)CC1]

$^1$H-NMR (400 MHz, CD$_3$OD) δ 8.13 (s, 1H), 8.12-8.07 (m, 1H), 8.00 (d, J=6.4 Hz, 1H), 7.28 (m, 2H), 6.99-6.88 (m, 2H), 6.56-6.47 (m, 1H), 5.03 (d, J=5.6 Hz, 1H), 4.36 (t, J=4.8 Hz, 2H), 3.43-3.30 (m, 5H), 3.14 (t, J=7.6 Hz, 2H), 3.10-2.91 (m, 6H), 2.88 (s, 3H), 2.73 (t, J=7.8 Hz, 2H), 2.50 (d, J=1.6 Hz, 1H) ppm. MS: M/e 312.5 (M+1)$^+$.

Compounds 1.53-1.54 were prepared according to the procedures described for Compound 1.1 under appropriate conditions that could be recognized by one skilled in the art.

Compound 1.53

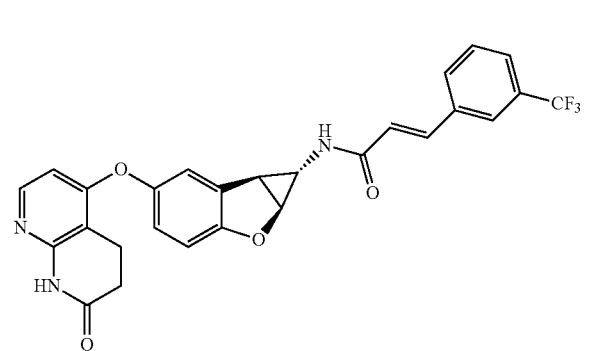 [SMILES: O=C(/C=C/c1cccc(C(F)(F)F)c1)N[C@@H]1[C@H]2Oc3ccc(Oc4ccnc5c4CCC(=O)N5)cc3[C@@H]12]

$^1$H NMR (400 MHz, CD$_3$OD) δ 7.96 (d, J=6.0 Hz, 1H), 7.84 (s, 1H), 7.81 (d, J=7.6 Hz, 1H), 7.68-7.57 (m, 3H), 7.25-7.21 (m, 1H), 6.94-6.87 (m, 2H), 6.65 (d, J=15.6 Hz, 1H), 6.41 (d, J=6.0 Hz, 1H), 4.94 (d, J=5.6 Hz, 1H), 3.09 (t, J=7.6 Hz, 2H), 2.98 (dd, J=5.6, 2.0 Hz, 1H), 2.69 (t, J=7.6 Hz, 2H), 2.46 (d, J=2.0 Hz, 1H) ppm. MS: M/e 508 (M+1)$^+$ Compound 1.54

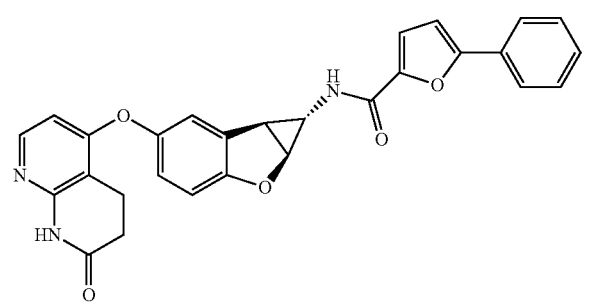 [SMILES: O=C1CCc2c(Oc3ccc4c(c3)[C@H]3[C@H](NC(=O)c5ccc(-c6ccccc6)o5)[C@H]3O4)ccnc2N1]

$^1$H NMR (400 MHz, DMSO-d6) δ 10.50 (s, 1H), 8.77 (d, J=3.6 Hz, 1H), 7.96 (d, J=5.6 Hz, 1H), 7.92 (d, J=7.6 Hz, 2H), 7.48 (t, J=7.6 Hz, 2H), 7.38 (t, J=7.6 Hz, 1H), 7.26 (d, J=2.0 Hz, 1H), 7.22 (d, J=3.6 Hz, 1H), 7.12 (d, J=3.6 Hz, 1H), 7.00-6.89 (m, 2H), 6.26 (d, J=5.6 Hz, 1H), 5.12 (d, J=6.0 Hz, 1H), 3.13 (dd, J=6.0, 2.0 Hz, 1H), 2.94 (t, J=7.6 Hz, 2H), 2.57-2.52 (m, 3H) ppm. MS: M/e 480 (M+1)$^+$ Compound 1.55: 4-((4-ethylpiperazin-1-yl)methyl)-N-(3-methyl-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

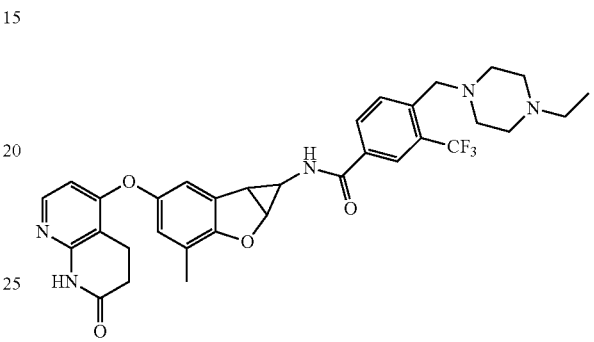

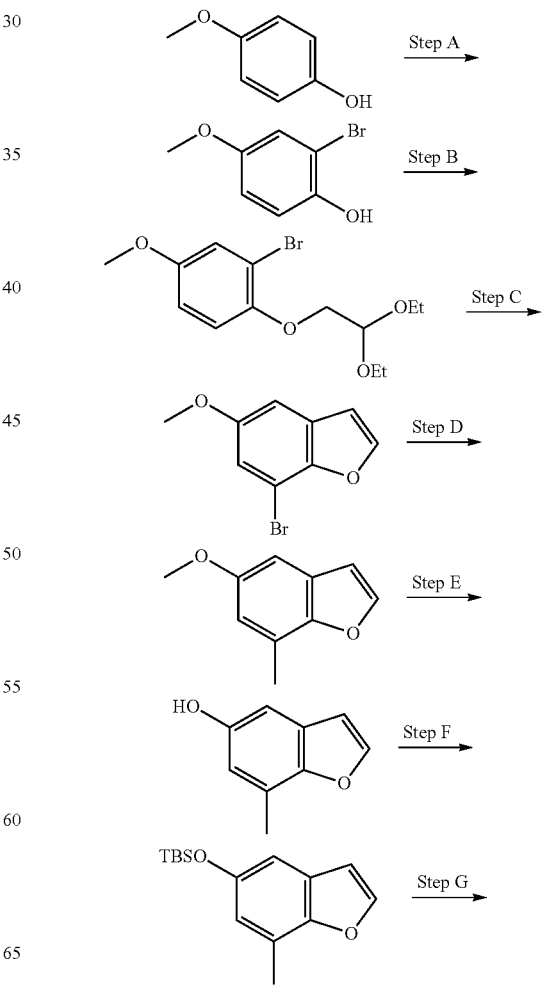

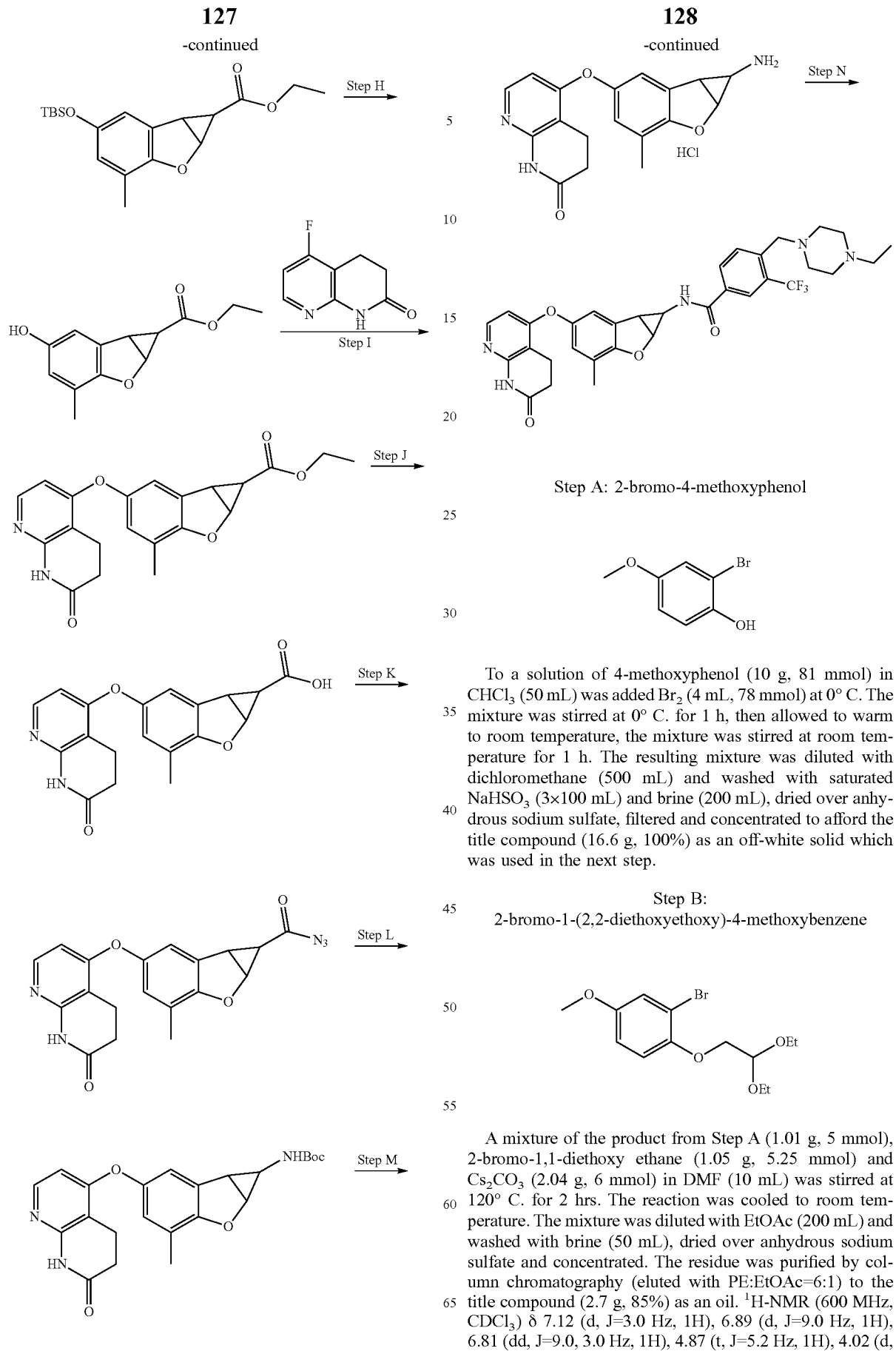

Step A: 2-bromo-4-methoxyphenol

To a solution of 4-methoxyphenol (10 g, 81 mmol) in CHCl₃ (50 mL) was added Br₂ (4 mL, 78 mmol) at 0° C. The mixture was stirred at 0° C. for 1 h, then allowed to warm to room temperature, the mixture was stirred at room temperature for 1 h. The resulting mixture was diluted with dichloromethane (500 mL) and washed with saturated NaHSO₃ (3×100 mL) and brine (200 mL), dried over anhydrous sodium sulfate, filtered and concentrated to afford the title compound (16.6 g, 100%) as an off-white solid which was used in the next step.

Step B:
2-bromo-1-(2,2-diethoxyethoxy)-4-methoxybenzene

A mixture of the product from Step A (1.01 g, 5 mmol), 2-bromo-1,1-diethoxy ethane (1.05 g, 5.25 mmol) and Cs₂CO₃ (2.04 g, 6 mmol) in DMF (10 mL) was stirred at 120° C. for 2 hrs. The reaction was cooled to room temperature. The mixture was diluted with EtOAc (200 mL) and washed with brine (50 mL), dried over anhydrous sodium sulfate and concentrated. The residue was purified by column chromatography (eluted with PE:EtOAc=6:1) to the title compound (2.7 g, 85%) as an oil. ¹H-NMR (600 MHz, CDCl₃) δ 7.12 (d, J=3.0 Hz, 1H), 6.89 (d, J=9.0 Hz, 1H), 6.81 (dd, J=9.0, 3.0 Hz, 1H), 4.87 (t, J=5.2 Hz, 1H), 4.02 (d, J=5.2 Hz, 2H), 3.84-3.78 (m, 2H), 3.77 (s, 3H), 3.73-3.67 (m, 2H), 1.27 (t, J=7.1 Hz, 6H) ppm.

Step C: 7-bromo-5-methoxybenzofuran

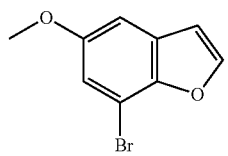

To a mixture of the product from step B (2.7 g, 8.5 mmol) in toluene (10 mL) was added PPA (1.0 mL). The reaction was heated at 70° C. for 1 hr. The reaction was cooled to room temperature. The mixture was diluted with EtOAc (200 mL) and the water phase was adjusted to pH 7-8 by NaOH (2 mol/L). The organic phase was washed with brine (50 mL), dried over anhydrous sodium sulfate and concentrated under reduced pressure. The residue was purified by silica column chromatography (eluted with PE) to afford the title compound (0.27 g, 16%) as an oil. $^1$H-NMR (600 MHz, CDCl$_3$) δ 7.68 (d, J=2.1 Hz, 1H), 7.13 (d, J=2.2 Hz, 1H), 7.04 (d, J=2.3 Hz, 1H), 6.79 (d, J=2.1 Hz, 1H), 3.86 (s, 3H) ppm.

Step D: 5-methoxy-7-methylbenzofuran

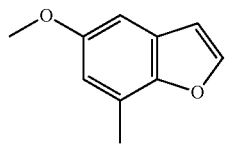

A mixture of the product from Step C (3.6 g, 16 mmol), methylboronic acid (1.4 g, 24 mmol), Pd(dppf)$_2$Cl$_2$ (0.65 g, 0.8 mmol) and Cs$_2$CO$_3$ (13.0 g, 40 mmol) in 1,4-dioxane (50 mL) and H$_2$O (10 mL) was refluxed for 3 hrs under N$_2$ atmosphere. The reaction was cooled to room temperature and filtered through a celite pad. The filtrate was diluted with EtOAc (200 mL) and washed with brine (50 mL), dried over anhydrous sodium sulfate, and concentrated under reduced pressure. The residue was purified by silica column chromatography (eluted with PE) to afford the title compound (1.0 g, 38%) as an oil. $^1$H-NMR (600 MHz, CDCl$_3$) δ 7.63 (d, J=1.6 Hz, 1H), 6.92 (d, J=2.1 Hz, 1H), 6.76 (s, 1H), 6.73 (d, J=1.8 Hz, 1H), 3.86 (s, 3H), 2.53 (s, 3H) ppm.

Step E: 7-methylbenzofuran-5-ol

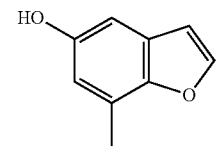

To a mixture of the product from Step D (850 mg, 5.2 mmol) and K$_2$CO$_3$ in acetonitrile (10 mL) was added Iodotrimethylsilane (TMSI) (1.1 mL). The mixture was refluxed for 2 hrs. The reaction was cooled to room temperature. The mixture was diluted with EtOAc (100 mL) and washed with brine (30 mL), dried over anhydrous sodium sulfate and concentrated under reduced pressure. The residue was purified by silica gel column chromatography (eluted with PE:EtOAc=5:1) to afford the title compound (200 mg, 25%) as an oil.

Step F: tert-butyldimethyl((7-methylbenzofuran-5-yl)oxy)silane

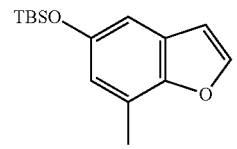 [SMILES: Cc1cc(O[Si](C)(C)C(C)(C)C)cc2ccoc12]

A solution of the product from Step E (200 mg, 1.4 mmol), TBSCl (225 mg, 1.5 mmol) and imidazole (190 mg, 2.8 mmol) in DMF (5 mL) was stirred at room temperature for 1 hr. The mixture was diluted with EtOAc (100 mL) and washed with brine (30 mL), dried over anhydrous sodium sulfate and concentrated under reduced pressure. The residue was purified by silica gel column chromatography (eluted with PE) to afford the title compound as an oil (260 mg, 71%).

Step G: (±)-exo-ethyl 5-((tert-butyldimethylsilyl)oxy)-3-methyl-1a,6b-dihydro-1H-cyclopropa[b]benzofuran-1-carboxylate

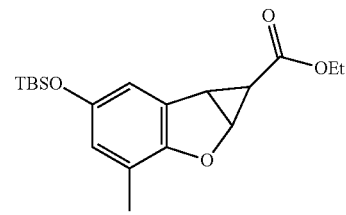 [SMILES: CCOC(=O)C1C2Oc3c(C)cc(O[Si](C)(C)C(C)(C)C)cc3C21]

To a solution of the product from Step F (260 mg, 1 mmol) and copper (I) triflate (2:1 complex with toluene, 1 mg, 0.03 mmol) in dichloromethane (2 mL) was added ethyl diazoacetate (1.0 mL, 10 mol) in dichloromethane (10 mL) through a syringe pump over a period of 10 hrs. Solvent was removed under reduced pressure, and the residue was purified by silica gel chromatography (eluted with PE) to obtain the title compound (200 mg, crude), which was used in next step without further purification.

Step H: (±)-exo-ethyl 5-hydroxy-3-methyl-1a,6b-dihydro-1H-cyclopropa[b]benzofuran-1-carboxylate

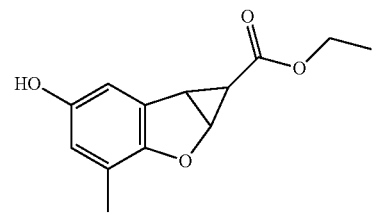 [SMILES: CCOC(=O)C1C2Oc3c(C)cc(O)cc3C21]

To a solution of the product from Step G (200 mg, 0.6 mmol) in THF (5 mL) was added TBAF in THF (0.15 mL, 1 M, 0.15 mmol) dropwise at 0° C. Then the mixture was stirred at room temperature for 10 minutes. The reaction was concentrated and purified by silica gel chromatography (eluted with EtOAc:PE=1:10) to obtain the title compound (100 mg, 43% yield for two steps) as colorless oil, which was used directly in next step.

Step I: (±)-exo-ethyl 3-methyl-5-((7-oxo-5,6,7,8-tetrahydro-1,8-naphthyridin-4-yl)oxy)-1a,6b-dihydro-1H-cyclopropa[b]benzofuran-1-carboxylate

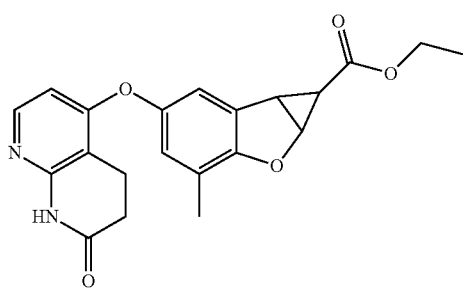 [SMILES: CCOC(=O)C1C2Oc3c(C)cc(Oc4ccnc5c4CCC(=O)N5)cc3C21]

The mixture of the product from step H (90 mg, 0.38 mmol), 5-fluoro-3,4-dihydro-1,8-naphthyridin-2(1H)-one (64 mg, 0.38 mmol) and cesium carbonate (188 mg, 0.58 mmol) in DMF (5 mL) was stirred at 120° C. for 2 hrs. The reaction was diluted with water (10 mL) and extracted with ethyl acetate (2×20 mL). The combined organic phase was washed with brine (20 mL), dried over sodium sulfate anhydrous and concentrated under reduced pressure. The residue was used in next step without further purification.

Step J: (±)-exo-3-methyl-5-((7-oxo-5,6,7,8-tetrahydro-1,8-naphthyridin-4-yl)oxy)-1a,6b-dihydro-1H-cyclopropa[b]benzofuran-1-carboxylic acid

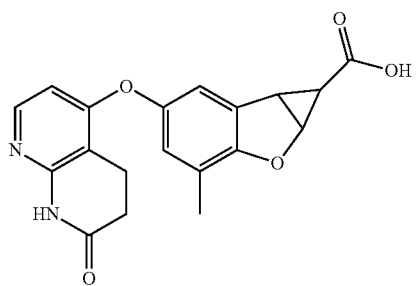 [SMILES: Cc1cc(Oc2ccnc3c2CCC(=O)N3)cc2c1OC1C(C(=O)O)C21]

Sodium hydroxide solution (3 mL, 2 M) was added to a stirred solution of ester product from Step I (60 mg, 3.8 mmol) in methanol (9 mL) at room temperature. The mixture was stirred at room temperature overnight. Solvent was removed under reduced pressure and the residue was dissolved into water (10 mL). The solution was neutralized with HCl (2 mol/L) to pH=7 and extracted with EA (2×10 mL). The combined organic phase was washed with brine (10 mL), dried over sodium sulfate anhydrous and concentrated under reduced pressure. The residue was used into next step without further purification. $^1$H-NMR (600 MHz, DMSO-d$_6$) δ 12.57 (s, 1H), 10.45 (s, 1H), 7.97-7.95 (m, 1H), 7.15 (d, J=2.5 Hz, 1H), 6.85 (d, J=2.0 Hz, 1H), 6.27 (d, J=5.8 Hz, 1H), 5.25 (dd, J=5.3, 1.0 Hz, 1H), 3.32-3.30 (m, 1H), 2.93 (t, J=7.7 Hz, 2H), 2.54 (t, J=7.7 Hz, 2H), 2.17 (s, 3H), 1.21 (dd, J=3.0, 1.0 Hz, 1H) ppm.

Step K: 3-methyl-5-((7-oxo-5,6,7,8-tetrahydro-1,8-naphthyridin-4-yl)oxy)-1a,6b-dihydro-1H-cyclopropa[b]benzofuran-1-carbonyl azide

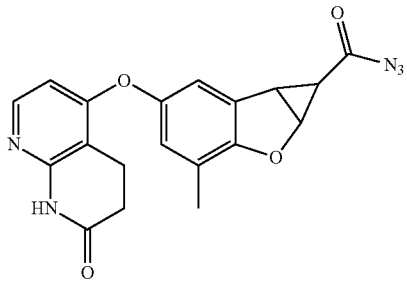 [SMILES: Cc1cc(Oc2ccnc3c2CCC(=O)N3)cc2c1OC1C(C(=O)N=[N+]=[N-])C21]

To a solution of the product of Step J (200 mg, 0.57 mmol) and Et$_3$N (144 mg, 1.43 mmol) in DMF (10 mL) was added DPPA (187 mg, 0.68 mmol) at room temperature. The reaction mixture was stirred at room temperature for 2 hours. The resulting mixture was diluted with EA (150 mL). The mixture was washed with brine (50 mL×3), dried over anhydrous sodium sulfate and concentrated under reduced pressure. The residue was purified by silica gel column chromatography (eluted with petroleum ether/EA 1:2, 300 mL) to obtain the title compound (205 mg, 96%) as a white solid. MS: M/e 378 (M+1)$^+$ Step L: tert-butyl (3-methyl-5-((7-oxo-5,6,7,8-tetrahydro-1,8-naphthyridin-4-yl)oxy)-1a,6b-dihydro-1H-cyclopropa[b]benzofuran-1-yl)carbamate

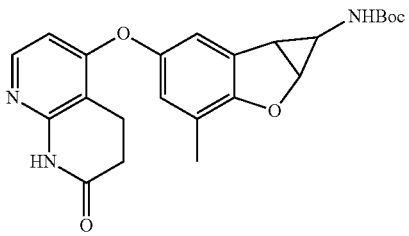 [SMILES: Cc1cc(Oc2ccnc3c2CCC(=O)N3)cc2c1OC1C(NC(=O)OC(C)(C)C)C21]

A mixture of the product of Step K (200 mg, 0.53 mmol) in t-BuOH (10 mL) was refluxed for 5 hours. The reaction was concentrated under reduced pressure and directly purified by silica column chromatography (eluted with petroleum ether/EA 1:2, 300 mL) to afford the title product (100 mg, 45%) as a white solid. $^1$H NMR (400 MHz, DMSO-d6) δ7.94 (d, J=6.0 Hz, 1H), 7.31 (s, 1H), 6.99 (s, 1H), 6.77 (d, J=2.0 Hz, 1H), 6.24 (d, J=6.0 Hz, 1H), 4.85 (d, J=6.0 Hz, 1H), 2.98-2.83 (m, 3H), 2.57-2.52 (m, 2H), 2.23-2.05 (m, 4H), 1.39 (s, 9H) ppm. MS: M/e 424 (M+1)$^+$ Step M: 5-((1-amino-3-methyl-1a,6b-dihydro-1H-cyclopropa[b]benzofuran-5-yl)oxy)-3,4-dihydro-1,8-naphthyridin-2(1H)-one hydrochloride

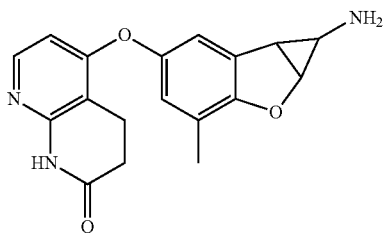 [SMILES: Cc1cc(Oc2ccnc3c2CCC(=O)N3)cc2c1OC1C(N)C21]

A mixture of the product of Step L (100 mg, 0.24 mmol) in HCl (g)/EtOAc (6M, 6 mL) was stirred at room temperature for 30 min. The reaction mixture was concentrated to afford the title product (90 mg, 100%) as a white solid. The product was directly used into the next step. MS: M/e 324 (M+1)$^+$.

Step N: 4-((4-ethylpiperazin-1-yl)methyl)-N-(3-methyl-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide (Compound 1.55)

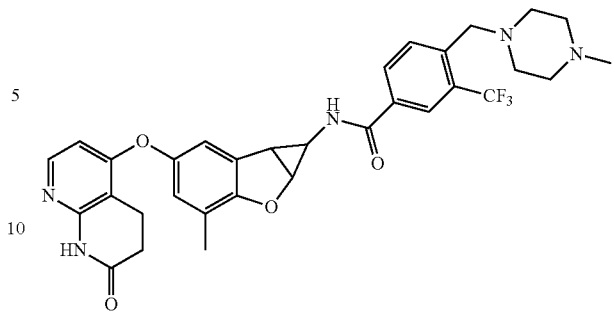

A mixture of the product of step M (45 mg, 0.125 mmol), 4-((4-ethylpiperazin-1-yl)methyl)-3-(trifluoromethyl)benzoic acid (44 mg, 0.138 mmol), HATU (57 mg, 0.15 mmol) and DIEA (65 mg, 0.5 mmol) in DMF (2 mL) was stirred at room temperature for 2 hours. The reaction was concentrated and H$_2$O (10 mL) was added to the residue. The precipitate was collected and purified by prep-HPLC to get the title compound (40 mg, 37%) as a white solid. $^1$H NMR (400 MHz, DMSO-d6) δ 10.46 (s, 1H), 8.93 (d, J=3.6 Hz, 1H), 8.25-8.05 (m, 2H, including HCOOH), 8.11 (d, J=7.6 Hz, 1H), 7.95 (d, J=5.6 Hz, 1H), 7.88 (d, J=7.6 Hz, 1H), 7.08 (d, J=2.4 Hz, 1H), 6.81 (d, J=2.4 Hz, 1H), 6.26 (d, J=5.6 Hz, 1H), 5.06 (d, J=5.6 Hz, 1H), 3.65 (s, 2H), 3.08 (dd, J=5.6, 2.0 Hz, 1H), 2.93 (t, J=7.6 Hz, 2H), 2.54-2.50 (m, 4H), 2.46-2.30 (m, 9H), 2.16 (s, 3H), 0.99 (t, J=7.2 Hz, 3H) ppm. MS: M/e 622 (M+1)$^+$ Compound 1.56 was prepared according to the procedures described for Compound 1.55 under appropriate conditions that could be recognized by one skilled in the art.

$^1$H NMR (400 MHz, DMSO-d6) δ 10.49 (s, 1H), 9.46 (s, 1H), 8.97 (d, J=3.6 Hz, 1H), 8.19 (s, 1H, HCOOH), 8.14 (d, J=8.4 Hz, 1H), 7.96 (d, J=5.6 Hz, 1H), 7.87 (d, J=8.4 Hz, 1H), 7.08 (d, J=2.4 Hz, 1H), 6.82 (d, J=2.4 Hz, 1H), 6.26 (d, J=5.6 Hz, 1H), 5.06 (d, J=5.6 Hz, 1H), 3.76 (s, 2H), 3.40 (d, J=12.0 Hz, 2H), 3.16-2.98 (m, 3H), 2.98-2.85 (m, 4H), 2.81 (s, 3H), 2.59-2.53 (m, 3H), 2.39 (t, J=12.0 Hz, 2H), 2.17 (s, 3H) ppm. MS: M/e 608 (M+1)$^+$ Compound 1.57: 4-((4-ethylpiperazin-1-yl)methyl)-3-methyl-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)benzamide

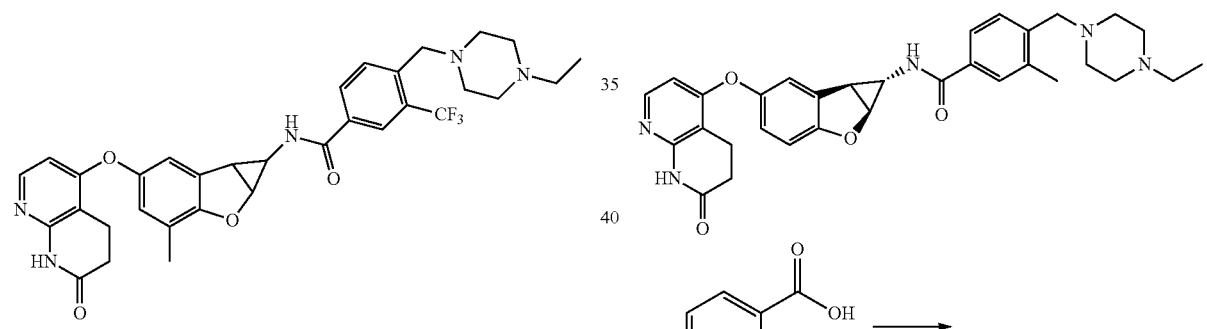

-continued

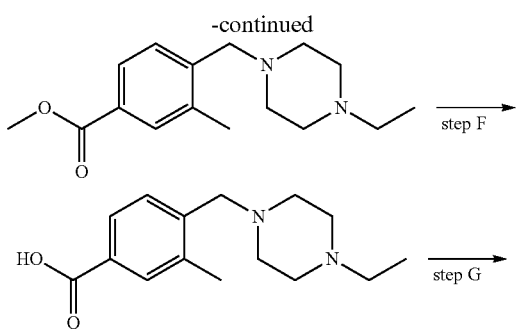
step F

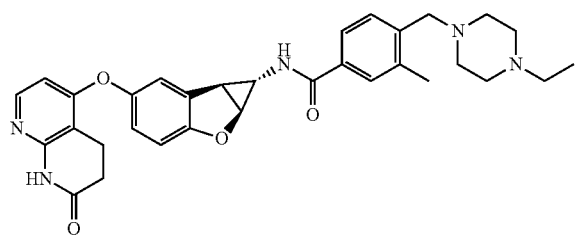
step G

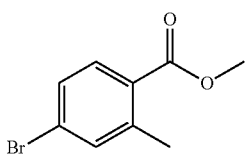

Step A: methyl 4-bromo-2-methylbenzoate

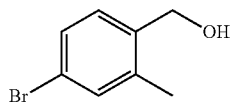

Conc. H₂SO₄ (2 mL) was dissolved in MeOH (10 mL), then 4-bromo-2-methyl benzoic acid (1.1 g, 5.11 mmol) was added. After the addition, the reaction mixture was refluxed for 5 hours. The reaction mixture was concentrated to give the residue, which was dissolved in EtOAc (20 mL) and washed with aq. NaHCO₃, brine, dried over Na₂SO₄ and concentrated to give (1.12 g, 95.7%) as yellow oil. $^1$H NMR (400 MHz, CDCl₃) δ 7.78 (d, J=8.4 Hz, 1H), 7.42 (s, 1H), 7.40-7.35 (d, J=8.4 Hz, 1H), 3.98-3.80 (m, 3H), 2.58 (s, 3H).

Step B: (4-bromo-2-methylphenyl)methanol

LiAlH₄ (0.37 g, 9.78 mmol) was suspended in THF (10 mL) and a solution of the product of Step A (1.12 g, 4.89 mmol) in THF (5 mL) was added dropwise at 0° C. After the addition, the reaction mixture was stirred for 2 hours at room temperature. The reaction was quenched with H₂O (0.37 mL), aq. NaOH (15%, 1 mL), H₂O (1.11 mL), then filtered. The filtrate was concentrated to give target compound (0.88 g, 88.6%) as yellow oil.

Step C: methyl 4-(hydroxymethyl)-3-methylbenzoate

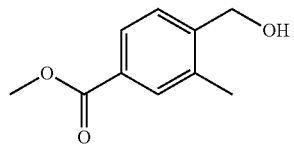

A mixture of the product of Step B (700 mg, 3.45 mmol), Pd(OAc)₂ (77.2 mg, 0.345 mmol), Xant-phos (398 mg, 0.69 mmol) and K₂CO₃ (2.4 g, 217.3 mmol) in MeOH/DMF (10 mL/10 mL) was stirred at 85° C. under CO gas (1 atm) for 6 hours. The reaction mixture was concentrated to remove the solvent; the residue was treated with H₂O/EtOAc (10 mL/10 mL). The organic layer was separated and the aqueous layer was extracted with EtOAc (5 mL×2). The combined organic layers were washed with brine, dried over Na₂SO₄, concentrated and purified by column chromatography (silica gel: 10 g, petroleum ether/EtOAc=5:1) to give target compound (280 mg, 45%) as yellow oil. MS: M/e 181 (M+1)⁺.

Step D: methyl 3-methyl-4-(((methylsulfonyl)oxy)methyl)benzoate

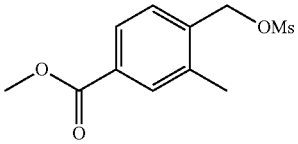 [SMILES: COC(=O)c1ccc(COS(C)(=O)=O)c(C)c1]

A solution of methylsulfonyl chloride (MsCl) (38 mg, 0.34 mmol) in THF (1 mL) was added dropwise to a stirred solution of product of Step C (50 mg, 0.28 mmol) and Et₃N (40 mg, 036 mmol) in THF (5 mL) at 0° C. After the addition, the reaction mixture was stirred for 2 hours. The reaction mixture was poured into H₂O (10 mL) and extracted with EtOAc (5 mL×3). The combined organic layers were washed with brine, dried over Na₂SO₄ and concentrated to give target compound (crude, 100%) as colorless oil, which was directly used to the next step. MS: M/e 259 (M+1)⁺.

Step E: methyl 4-((4-ethylpiperazin-1-yl)methyl)-3-methylbenzoate

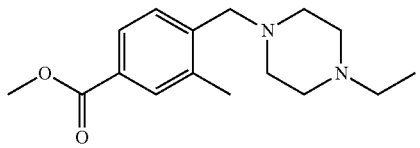 [SMILES: CCN1CCN(Cc2ccc(C(=O)OC)cc2C)CC1]

To a stirred suspension of the product of Step D (77 mg, 0.28 mmol) and K₂CO₃ (77.3 mg, 0.36 mmol) in EtOH (5 mL) was added 1-ethylpiperazine (63.8 mg, 0.56 mmol) at 0° C. After the addition, the reaction mixture was stirred overnight. Most EtOH was removed in vacuo, the residue was treated with CH$_2$Cl$_2$ and filtered, purified by prep-TLC (CH$_2$Cl$_2$/MeOH=10:1) to give target compound (25 mg, 32.3%) as a white solid. MS: M/e 277 (M+1)$^+$.

Step F: 4-((4-ethylpiperazin-1-yl)methyl)-3-methylbenzoic acid

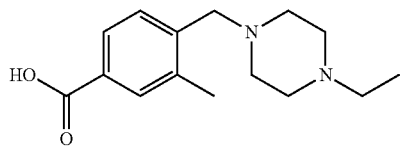 [SMILES: CCN1CCN(Cc2ccc(C(=O)O)cc2C)CC1]

NaOH (7.24 mg, 0.18 mmol) was added to a mixture of the product of Step E (25 mg, 0.09 mmol) in MeOH/H$_2$O (2 mL/2 mL). After the addition, the reaction mixture was stirred for 2 hours. The reaction mixture was acidified to pH=6~7 with aq. HCl and concentrated to give the residue, which was washed with CH$_2$Cl$_2$/MeOH (5 mL/2 mL) and filtered. The filtrate was concentrated to give target compound (20 mg, 84.2%) as a white solid. MS: M/e 263 (M+1)$^+$.

Step G: 4-((4-ethylpiperazin-1-yl)methyl)-3-methyl-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)benzamide (Compound 1.57)

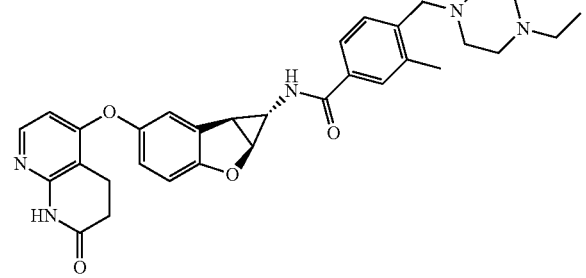

A mixture of the product of Step F (20 mg, 0.08 mmol), Intermediate I (27.6 mg, 0.08 mmol), HATU (36.5 mg, 0.096 mmol) and DIPEA (0.1 mL) in DMF (2 mL) was stirred for 2 hours. The reaction mixture was concentrated to give the residue, which was purified by prep-HPLC to give target compound (15 mg, 34%) as a white solid. $^1$H NMR (400 MHz, CD$_3$OD) δ 8.47 (s, 1H, CF$_3$COOH), 7.92 (d, J=6.0 Hz, 1H), 7.65 (s, 1H), 7.61 (d, J=8.0 Hz, 1H), 7.36 (d, J=8.0 Hz, 1H), 7.21 (s, 1H), 6.89 (s, 2H), 6.32 (d, J=6.0 Hz, 1H), 4.99 (d, J=5.6 Hz, 1H), 3.60 (s, 2H), 3.23-2.84 (m, 9H), 2.80-2.53 (m, 5H), 2.48 (d, J=1.6 Hz, 1H), 2.42 (s, 3H), 1.25 (t, J=7.2 Hz, 3H) ppm. MS: M/e 554 (M+1)$^+$.

Compound 1.58 was prepared according to the procedures described for Compound 1.57 under appropriate conditions that could be recognized by one skilled in the art.

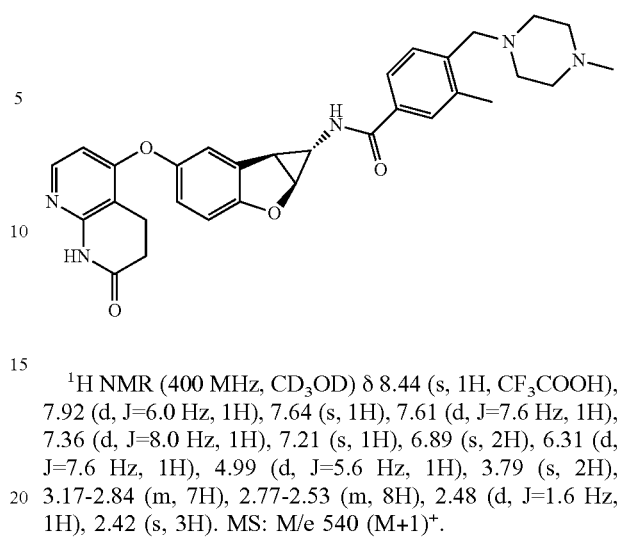

$^1$H NMR (400 MHz, CD$_3$OD) δ 8.44 (s, 1H, CF$_3$COOH), 7.92 (d, J=6.0 Hz, 1H), 7.64 (s, 1H), 7.61 (d, J=7.6 Hz, 1H), 7.36 (d, J=8.0 Hz, 1H), 7.21 (s, 1H), 6.89 (s, 2H), 6.31 (d, J=7.6 Hz, 1H), 4.99 (d, J=5.6 Hz, 1H), 3.79 (s, 2H), 3.17-2.84 (m, 7H), 2.77-2.53 (m, 8H), 2.48 (d, J=1.6 Hz, 1H), 2.42 (s, 3H). MS: M/e 540 (M+1)$^+$.

Compound 1.59: 4-(hydroxymethyl)-3-methyl-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)benzamide

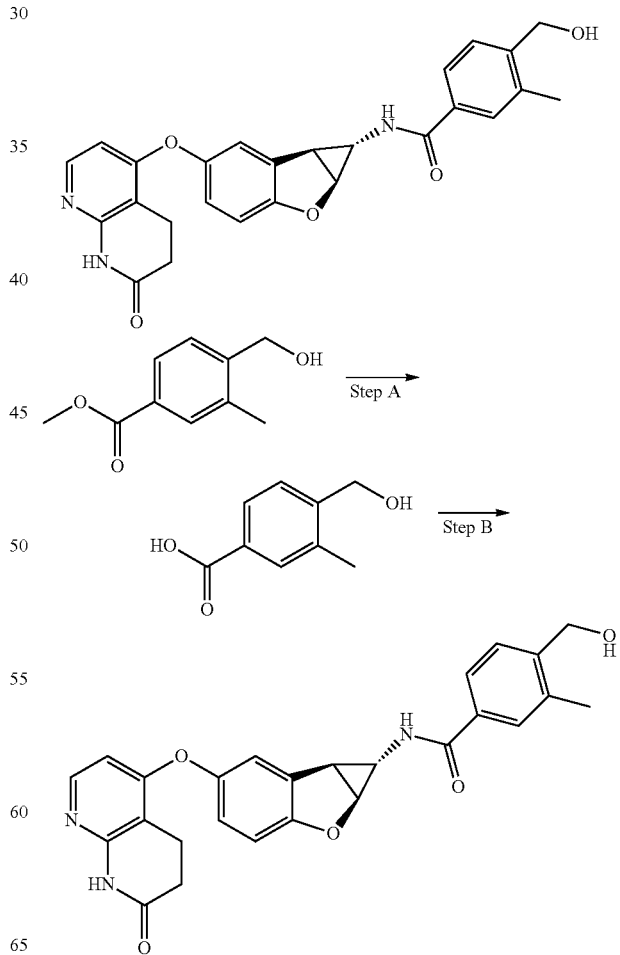

Step A: methyl 4-((4-ethylpiperazin-1-yl)methyl)-3-methylbenzoate

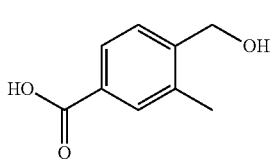

NaOH (22 mg, 0.56 mmol) was added to a mixture of the product of Step C in synthesis of Compound 1.57 (50 mg, 0.28 mmol) in MeOH/H$_2$O (5 mL/5 mL). After the addition, the reaction mixture was stirred for 2 hours. The reaction mixture was acidified to pH=6-7 with aq. HCl and concentrated to give the residue, which was washed with CH$_2$Cl$_2$/MeOH (5 mL/2 mL) and filtered. The filtrate was concentrated to give target compound (45 mg, 96%) as a white solid. MS: M/e 167 (M+1)$^+$.

Step B: 4-((4-ethylpiperazin-1-yl)methyl)-3-methyl-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)benzamide (Compound 1.59)

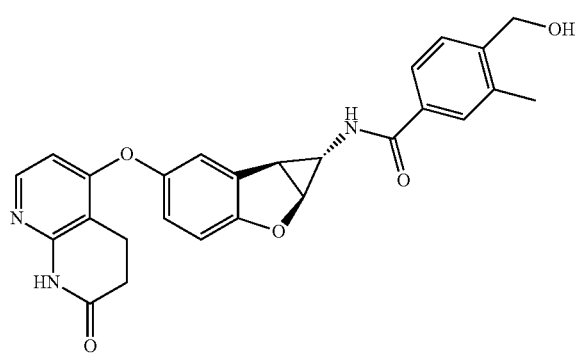 [SMILES: Cc1cc(C(=O)N[C@@H]2[C@H]3Oc4ccc(Oc5ccnc6c5CCC(=O)N6)cc4[C@@H]23)ccc1CO]

A mixture of product of Step A (20 mg, 0.12 mmol), Intermediate I (41 mg, 0.12 mmol), HATU (54.3 mg, 0.143 mmol) and DIPEA (0.1 mL) in DMF (2 mL) was stirred for 2 hours. The reaction mixture was concentrated to give the residue, which was purified by prep-HPLC to give target compound (15 mg, 27.3%) as a white solid. $^1$H NMR (400 MHz, CD$_3$OD) δ 8.66 (s, 1H, CF$_3$COOH), 7.94 (d, J=6.0 Hz, 1H), 7.68-7.59 (m, 2H), 7.46 (d, J=7.6 Hz, 1H), 7.22 (s, 1H), 6.89 (s, 2H), 6.35 (d, J=6.0 Hz, 1H), 5.00 (d, J=5.6 Hz, 1H), 4.65 (s, 2H), 3.07 (t, J=7.6 Hz, 2H), 3.02 (d, J=5.6 Hz, 1H), 2.65 (t, J=7.6 Hz, 2H), 2.51-2.46 (m, 1H), 2.35 (s, 3H) ppm. MS: M/e 458 (M+1)$^+$.

Compounds 1.60-1.63 were prepared according to the procedures described for Compound 1.1 under appropriate conditions that could be recognized by one skilled in the art.

Compound 1.60

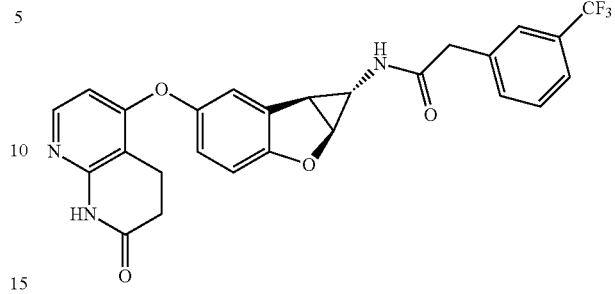

$^1$H NMR (400 MHz, DMSO-d6) δ 10.55 (s, 1H), 8.51 (d, J=3.6 Hz, 1H), 7.95 (d, J=6.0 Hz, 1H), 7.65-7.51 (m, 4H), 7.22 (d, J=1.2 Hz, 1H), 6.97-6.86 (m, 2H), 6.25 (d, J=6.0 Hz, 1H), 4.93 (d, J=6.0 Hz, 1H), 3.55 (s, 2H), 2.97-2.88 (m, 3H), 2.54 (t, J=7.6 Hz, 2H), 2.35-2.29 (m, 1H). MS: M/e 496 (M+1)$^+$.

Compound 1.61

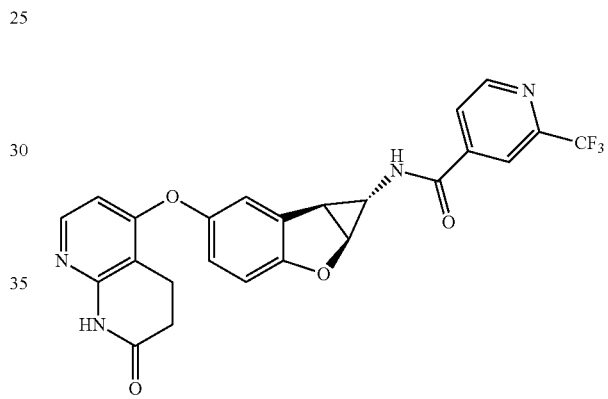

$^1$H NMR (400 MHz, DMSO-d6) δ 10.53 (s, 1H), 9.25 (d, J=3.6 Hz, 1H), 8.96 (d, J=5.2 Hz, 1H), 8.24 (s, 1H), 8.09 (d, J=5.2 Hz, 1H), 7.97 (d, J=5.6 Hz, 1H), 7.29 (d, J=2.4 Hz, 1H), 7.01-6.92 (m, 2H), 6.27 (d, J=5.6 Hz, 1H), 5.11 (d, J=5.6 Hz, 1H), 3.14 (dd, J=5.6, 2.0 Hz, 1H), 2.95 (t, J=7.6 Hz, 2H), 2.62-2.52 (m, 3H) ppm. MS: M/e 483 (M+1)$^+$.

Compound 1.62

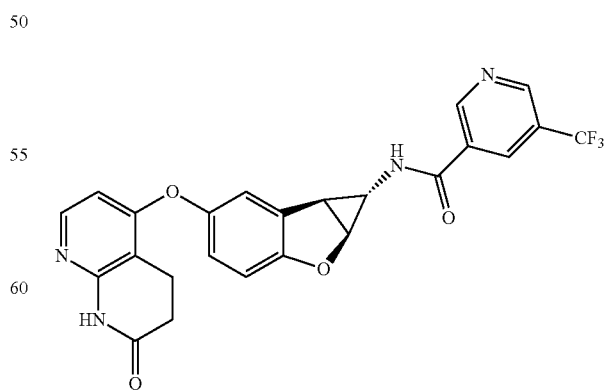

$^1$H NMR (400 MHz, DMSO-d6) δ 10.52 (s, 1H), 9.28 (d, J=2.0 Hz, 1H), 9.21-9.10 (m, 2H), 8.56 (s, 1H), 7.97 (d,

J=6.0 Hz, 1H), 7.29 (d, J=2.4 Hz, 1H), 7.00-6.92 (m, 2H), 6.27 (d, J=6.0 Hz, 1H), 5.10 (d, J=5.6 Hz, 1H), 3.13 (dd, J=5.6, 2.0 Hz, 1H), 2.95 (t, J=7.6 Hz, 2H), 2.59-2.52 (m, 3H) ppm. MS: M/e 483 (M+1)+.

Compound 1.63

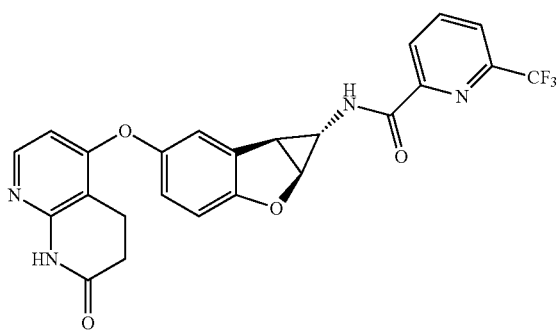 [SMILES: O=C1CCc2c(Oc3ccc4c(c3)[C@H]3[C@H](NC(=O)c5cccc(C(F)(F)F)n5)[C@H]3O4)ccnc2N1]

¹H NMR (400 MHz, DMSO-d6) δ 10.51 (s, 1H), 9.05 (d, J=4.0 Hz, 1H), 8.36-8.25 (m, 2H), 8.19-8.11 (m, 1H), 7.96 (d, J=6.0 Hz, 1H), 7.25 (d, J=2.0 Hz, 1H), 7.00-6.91 (m, 2H), 6.27 (d, J=6.0 Hz, 1H), 5.24 (d, J=5.6 Hz, 1H), 3.21 (dd, J=5.6, 2.0 Hz, 1H), 2.94 (t, J=7.6 Hz, 2H), 2.60-2.57 (m, 1H), 2.55 (t, J=7.6 Hz, 2H) ppm. MS: M/e 483 (M+1)+.

Compound 1.64 was prepared according to the procedures described for Compound 1.51 under appropriate conditions that could be recognized by one skilled in the art.

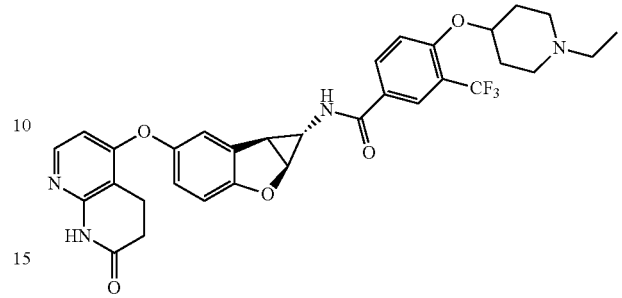

¹H NMR (400 MHz, CD₃OD) δ 8.19-8.07 (m, 2H), 8.01-7.92 (m, 1H), 7.42-7.32 (m, 1H), 7.24 (s, 1H), 6.99-6.84 (m, 2H), 6.48-6.37 (m, 1H), 5.10 (s, 1H), 5.02 (d, J=5.6 Hz, 1H), 3.70-3.48 (m, 2H), 3.26-3.06 (m, 6H), 3.06-3.00 (m, 1H), 2.75-2.65 (m, 2H), 2.50 (d, J=2.0 Hz, 1H), 2.46-1.87 (m, 4H), 1.35 (t, J=7.2 Hz, 3H) ppm. MS: M/e 609 (M+1)+.

Compound 1.65: 4-((3,5-dimethylpiperazin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

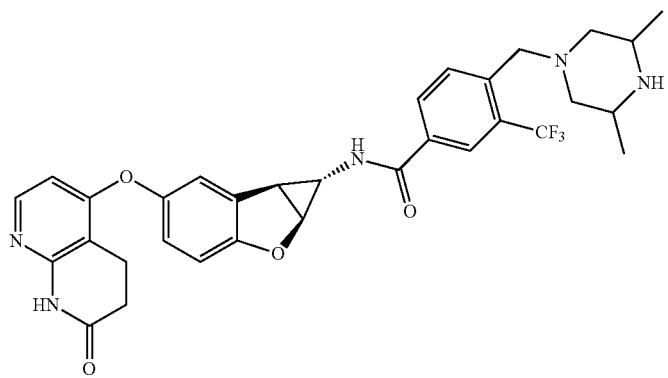

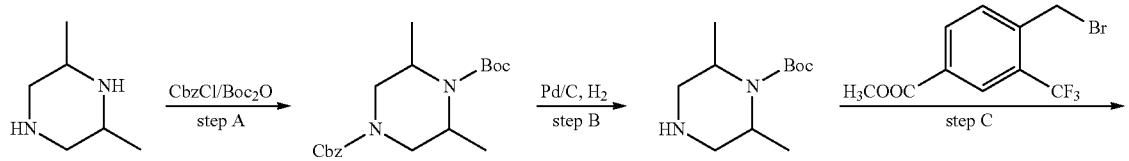

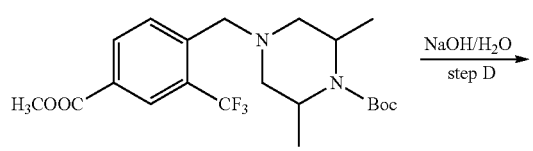

-continued

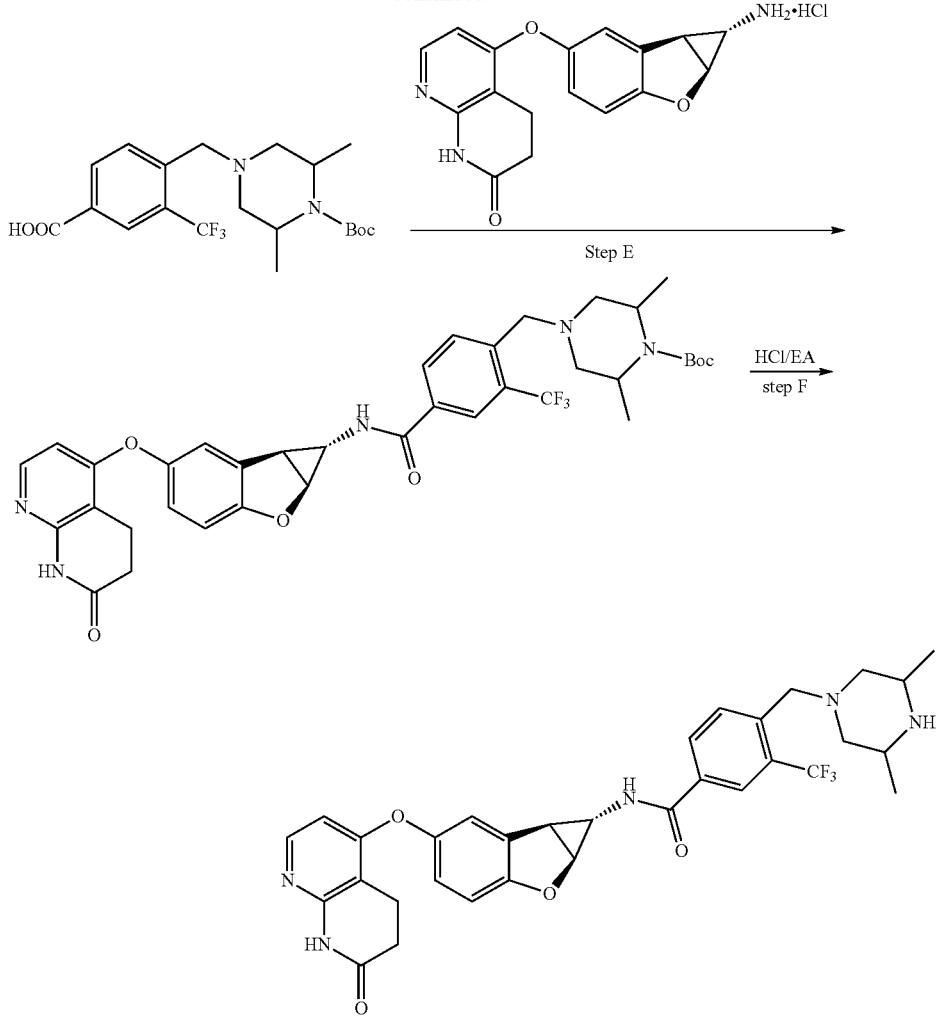

Step A: 4-benzyl 1-tert-butyl 2,6-dimethylpiperazine-1,4-dicarboxylate

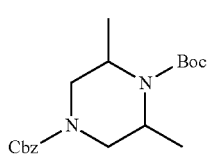

To a solution of 2,6-dimethylpiperazine (1.14 g, 10 mmol) in DCM (10 mL) was added benzylchloroformate (1.5 mL) dropwise at 0° C. The mixture was stirred at 0° C. for 1 hour then at room temperature for another 2 hours. The mixture was cooled to ° C., Diisopropylethylamine (2.5 mL) was added and followed by (Boc)₂O (2.4 g, 11 mmol). The mixture was stirred at room temperature overnight. The resulting solution was concentrated under reduced pressure. The residue was diluted with water and extracted with EA (5 mL×3). The combined organic layer was dried over Na₂SO₄ and concentrated under reduced pressure. The residue was purified by silica gel column chromatography (weight of silicon: 3 g; eluted with PE/EA=10/1) to get the title compound (1.17 g, yield: 33%) as colorless oil. MS: M/e 371 (M+Na)⁺.

Step B: tert-butyl 2,6-dimethylpiperazine-1-carboxylate

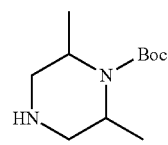

A solution of the product of Step A (1.17 g, 3.36 mmol) in methanol (5 mL) was added 117 mg of Pd/C (Palladium 10% on Carbon) and stirred at room temperature under 4 atm H₂ atmosphere overnight. The resulting solution was filtered and the filtrate was concentrated to give the title product (713 mg, yield: 100%) as colorless oil which was used into next step directly.

Step C: tert-butyl 4-(4-(methoxycarbonyl)-2-(trifluoromethyl)benzyl)-2,6-dimethylpiperazine-1-carboxylate

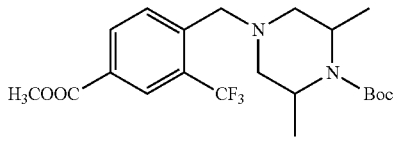

A mixture of the product of Step B (309 mg, 1.44 mmol), the product of Step B in synthesis of Compound 1.1 (357 mg, 1.20 mmol) and triethylamine (242 mg, 2.40 mmol) in DCM (10 mL) was stirred at room temperature for 1 hour. The reaction was completed according to the TLC plate. The resulting solution was concentrated and the residue was purified by silica gel column chromatography (weight of silicon: 3 g; eluted with PE/EA=5/1) to get the title compound (242 mg, yield: 47%) as yellow oil. MS: M/e 431 (M+1)$^+$.

Step D: 4-((4-(tert-butoxycarbonyl)-3,5-dimethylpiperazin-1-yl)methyl)-3-(trifluoromethyl)benzoic acid

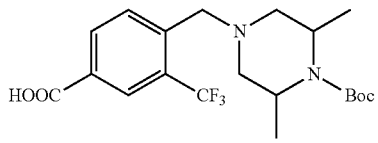 [SMILES: CC1CN(Cc2ccc(C(=O)O)cc2C(F)(F)F)CC(C)N1C(=O)OC(C)(C)C]

To a solution of the product of Step C (240 mg, 0.56 mmol) in MeOH (10 mL) was add NaOH aqueous solution (2 ml, 2N, 4 mmol). The solution was stirred at room temperature for 0.5 hour and concentrated under reduced pressure. The residue was dissolved into water (2 mL) and modified pH about 5-6 by 2N HCl aqueous solution. The mixture was extracted with DCM (5 mL×3). The combined organic layer was dried over Na$_2$SO$_4$ and concentrated under reduced pressure to get the crude product (100 mg, yield: 43%) as a yellow solid. MS: M/e 417 (M+1)$^+$.

Step E: tert-butyl 2,6-dimethyl-4-(4-(((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)carbamoyl)-2-(trifluoromethyl)benzyl)piperazine-1-carboxylate

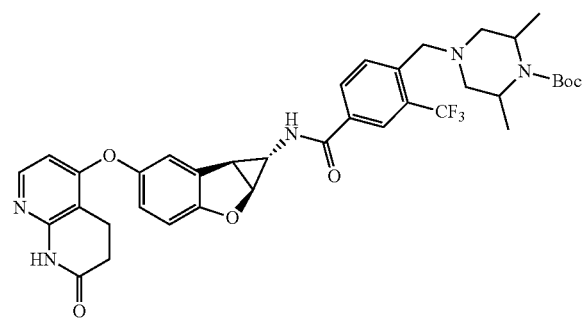 [SMILES: CC1CN(Cc2ccc(C(=O)N[C@@H]3[C@H]4Oc5ccc(Oc6ccnc7c6CCC(=O)N7)cc5[C@@H]34)cc2C(F)(F)F)CC(C)N1C(=O)OC(C)(C)C]

A mixture of the product of Step D (100 mg, 0.24 mmol), HATU (88 mg, 0.28 mmol) and DIPEA (93 mg, 0.732 mmol) in DMF (10 mL) was stirred at room temperature for 10 min. Then Intermediate I (100 mg, 0.28 mmol) was added. The final solution was stirred at room temperature overnight. The resulting solution was concentrated under reduced pressure. The residue was diluted with water (10 mL) and extracted with DCM (5 mL×3). The combined organic layer was dried over Na$_2$SO$_4$ and concentrated under reduced pressure. The residue was purified by silica gel column chromatography (weight of silicon: 3 g; eluted with DCM/MeOH=20/1) to get the title compound (150 mg, yield: 89%) as yellow oil. MS: M/e 708 (M+1)$^+$.

Step F: 4-((3,5-dimethylpiperazin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide (Compound 1.65)

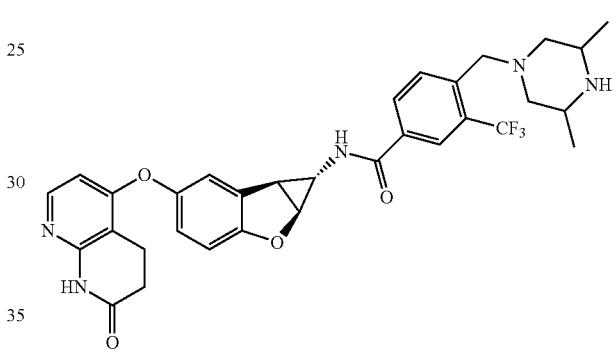

To a solution of the product of Step E (150 mg, 0.21 mmol) in EA (2 mL) was added a solution of HCl/EA (5 mL) dropwisely. The solution was stirred at room temperature for 1 hour. The resulting solution was concentrated under reduced pressure to remove excess solvents. The residue was diluted with water (10 mL) and extracted with DCM (5 mL×2). The aqueous layer was neutralized by NaHCO$_3$ aqueous solution till pH=7-8, then extracted with DCM (5 mL×2). The combined organic layer was dried over Na$_2$SO$_4$ and concentrated to get the title compound (50 mg, yield: 38%) as white solid. $^1$H NMR (400 MHz, DMSO-d6) δ 10.48 (s, 1H), 8.94 (d, J=3.6 Hz, 1H), 8.15 (s, 1H), 8.11 (d, J=8.0 Hz, 1H), 7.96 (d, J=5.6 Hz, 1H), 7.88 (d, J=8.0 Hz, 1H), 7.27 (d, J=2.0 Hz, 1H), 7.00-6.89 (m, 2H), 6.25 (d, J=5.6 Hz, 1H), 5.08 (d, J=5.6 Hz, 1H), 3.61 (s, 2H), 3.09 (dd, J=5.6, 2.0 Hz, 1H), 2.94 (t, J=7.6 Hz, 2H), 2.80 (s, 2H), 2.62 (d, J=9.6 Hz, 2H), 2.56-2.52 (m, 3H), 1.62-1.56 (m, 2H), 0.91 (d, J=6.0 Hz, 6H) ppm. MS: M/e 608 (M+1)$^+$.

Compounds 1.66-1.70 were prepared according to the procedures described for Compound 1.1 under appropriate conditions that could be recognized by one skilled in the art.

Compound 1.66

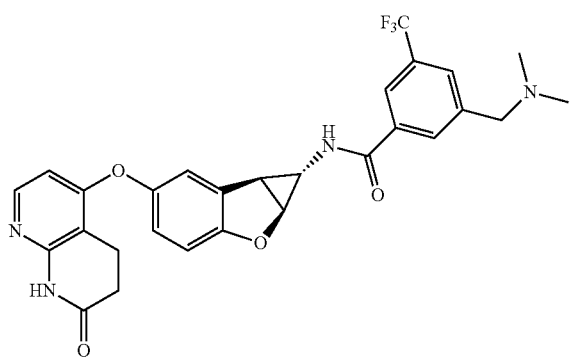 [SMILES: CN(C)Cc1cc(C(=O)N[C@@H]2[C@H]3Oc4ccc(Oc5ccnc6c5CCC(=O)N6)cc4[C@@H]23)cc(C(F)(F)F)c1]

$^1$H NMR (400 MHz, DMSO-d6) δ 10.50 (br.s, 1H), 10.09-9.80 (m, 1H, CF$_3$COOH), 9.10 (s, 1H), 8.31 (s, 2H), 8.12 (s, 1H), 7.97 (d, J=6.0 Hz, 1H), 7.28 (d, J=2.0 Hz, 1H), 7.01-6.92 (m, 2H), 6.26 (d, J=6.0 Hz, 1H), 5.10 (d, J=6.0 Hz, 1H), 4.46 (s, 2H), 3.12 (dd, J=6.0, 2.0 Hz, 1H), 2.94 (t, J=7.6 Hz, 2H), 2.77 (s, 6H), 2.62-2.52 (m, 3H) ppm. MS: M/e 539 (M+1)$^+$.

Compound 1.67

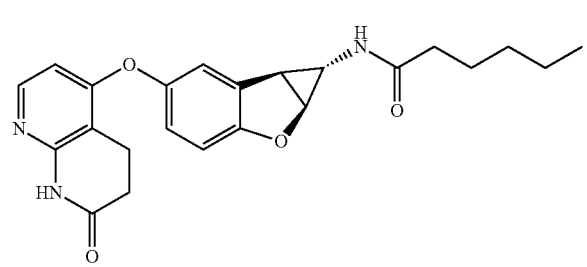 [SMILES: CCCCCC(=O)N[C@@H]1[C@H]2Oc3ccc(Oc4ccnc5c4CCC(=O)N5)cc3[C@@H]12]

$^1$H NMR (400 MHz, DMSO-d6) δ 10.56-10.50 (m, 1H), 8.13 (d, J=3.6 Hz, 1H), 7.96 (d, J=5.6 Hz, 1H), 7.23-7.20 (m, 1H), 6.94-6.88 (m, 2H), 6.25 (d, J=5.6 Hz, 1H), 4.88 (d, J=5.6 Hz, 1H), 2.93 (t, J=7.6 Hz, 2H), 2.87 (dd, J=6.0, 2.4 Hz, 1H), 2.54 (t, J=7.6 Hz, 2H), 2.31-2.27 (m, 1H), 2.05 (t, J=8.0 Hz, 2H), 1.55-1.44 (m, 2H), 1.33-1.16 (m, 4H), 0.86 (t, J=7.2 Hz, 3H) ppm. MS: M/e 408 (M+1)$^+$ Compound 1.68

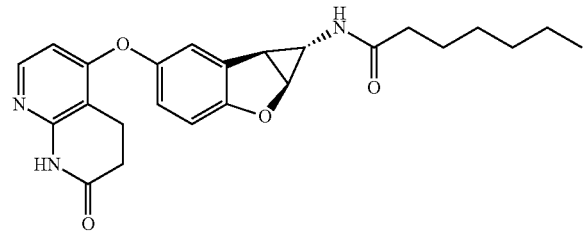 [SMILES: CCCCCCC(=O)N[C@@H]1[C@H]2Oc3ccc(Oc4ccnc5c4CCC(=O)N5)cc3[C@@H]12]

$^1$H NMR (400 MHz, DMSO-d6) δ 10.49 (s, 1H), 8.12 (d, J=3.6 Hz, 1H), 7.95 (d, J=6.0 Hz, 1H), 7.21 (s, 1H), 6.92 (m, 2H), 6.24 (d, J=6.0 Hz, 1H), 4.87 (d, J=5.6 Hz, 1H), 3.05-2.76 (m, 3H), 2.53 (t, J=8.0 Hz, 2H), 2.30-2.25 (m, 1H), 2.05 (t, J=7.6 Hz, 2H), 1.54-1.40 (m, 2H), 1.30-1.15 (m, 6H), 0.86 (t, J=7.6 Hz, 3H) ppm. MS: M/e 422 (M+1)$^+$.

Compound 1.69

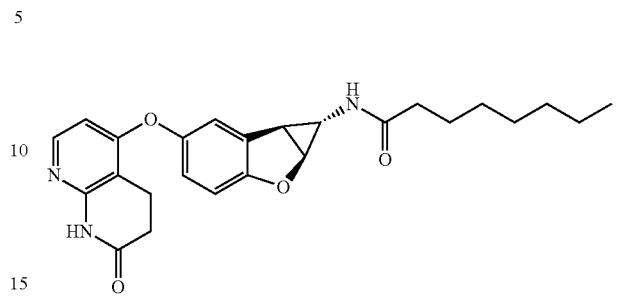

$^1$H NMR (400 MHz, DMSO-d6) δ 10.54-10.49 (m, 1H), 8.12 (d, J=3.6 Hz, 1H), 7.95 (d, J=6.0 Hz, 1H), 7.23-7.20 (m, 1H), 6.94-6.88 (m, 2H), 6.25 (d, J=6.0 Hz, 1H), 4.87 (d, J=5.6 Hz, 1H), 2.93 (t, J=7.6 Hz, 2H), 2.86 (dd, J=5.6, 2.0 Hz, 1H), 2.54 (t, J=8.0 Hz, 2H), 2.30-2.27 (m, 1H), 2.05 (t, J=7.6 Hz, 2H), 1.53-1.44 (m, 2H), 1.30-1.18 (m, 8H), 0.86 (t, J=6.8 Hz, 3H) ppm. MS: M/e 436 (M+1)$^+$ Compound 1.70

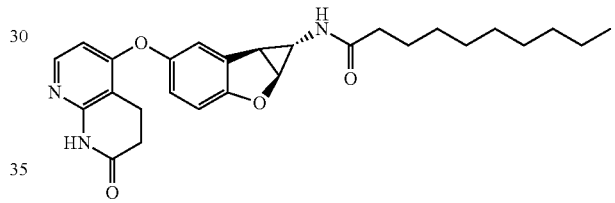

$^1$H NMR (400 MHz, DMSO-d6) δ 10.50 (s, 1H), 8.12 (d, J=3.6 Hz, 1H), 7.95 (d, J=6.0 Hz, 1H), 7.22-7.20 (m, 1H), 6.94-6.88 (m, 2H), 6.24 (d, J=6.0 Hz, 1H), 4.87 (d, J=5.6 Hz, 1H), 2.93 (t, J=7.6 Hz, 2H), 2.86 (dd, J=5.6, 2.0 Hz, 1H), 2.54 (t, J=7.6 Hz, 2H), 2.30-2.27 (m, 1H), 2.05 (t, J=7.6 Hz, 2H), 1.54-1.41 (m, 2H), 1.36-1.19 (m, 12H), 0.85 (t, J=6.8 Hz, 3H) ppm. MS: M/e 464 (M+1)$^+$.

Compound 1.71 was prepared according to the procedures described for Compound 1.47 under appropriate conditions that could be recognized by one skilled in the art.

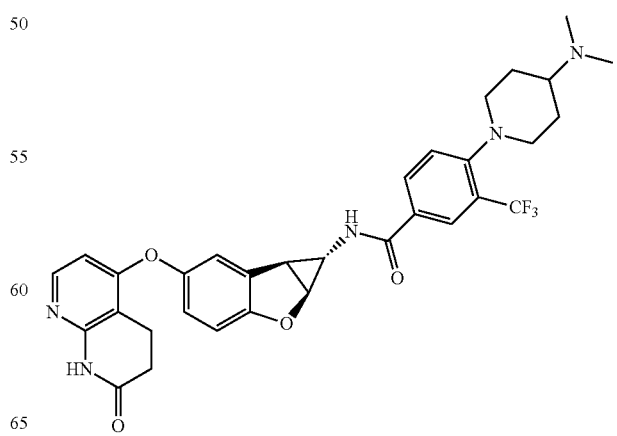

¹H NMR (400 MHz, CD₃OD) δ 8.48 (br.s, 1H, CF₃COOH), 8.15 (d, J=2.0 Hz, 1H), 8.06 (d, J=8.4 Hz, 1H), 7.92 (d, J=6.0 Hz, 1H), 7.52 (d, J=8.4 Hz, 1H), 7.21 (s, 1H), 6.90 (s, J=10.4 Hz, 2H), 6.32 (d, J=6.0 Hz, 1H), 5.00 (d, J=5.8 Hz, 1H), 3.26-3.15 (m, 3H), 3.09-3.02 (m, 3H), 2.91 (t, J=11.6 Hz, 2H), 2.83 (s, 6H), 2.65 (t, J=7.8 Hz, 2H), 2.50 (d, J=1.6 Hz, 1H), 2.15 (d, J=12.0 Hz, 2H), 1.92-1.77 (m, 2H) ppm. MS: M/e 608 (M+1)⁺.

Compounds 1.72-1.73 were prepared according to the procedures described for Compound 1.1 under appropriate conditions that could be recognized by one skilled in the art.

Compound 1.72

¹H NMR (400 MHz, CD₃OD) δ 8.43 (s, 1H, HCOOH), 7.92 (d, J=6.0 Hz, 1H), 7.45-7.40 (m, 3H), 7.22-7.20 (m, 1H), 6.89 (d, J=1.2 Hz, 2H), 6.32 (d, J=6.0 Hz, 1H), 5.01 (d, J=5.6 Hz, 1H), 3.89 (s, 3H), 3.70 (s, 2H), 3.13-2.90 (m, 7H), 2.80-2.60 (m, 9H), 2.50 (d, J=1.6 Hz, 1H) ppm. MS: M/e 556 (M+1)⁺.

Compound 1.73

¹H NMR (400 MHz, CD₃OD) δ 8.48 (s, 1H, HCOOH), 7.92 (d, J=6.0 Hz, 1H), 7.45-7.40 (m, 3H), 7.22-7.19 (m, 1H), 6.89 (s, 2H), 6.32 (d, J=6.0 Hz, 1H), 5.01 (d, J=5.6 Hz, 1H), 3.89 (s, 3H), 3.70 (s, 2H), 3.09-2.86 (m, 9H), 2.84-2.60 (m, 6H) 2.49 (d, J=2.0 Hz, 1H), 1.23 (t, J=7.2 Hz, 3H) ppm. MS: M/e 570 (M+1)⁺

Compound 1.74: 4-((1-ethylpiperidin-4-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

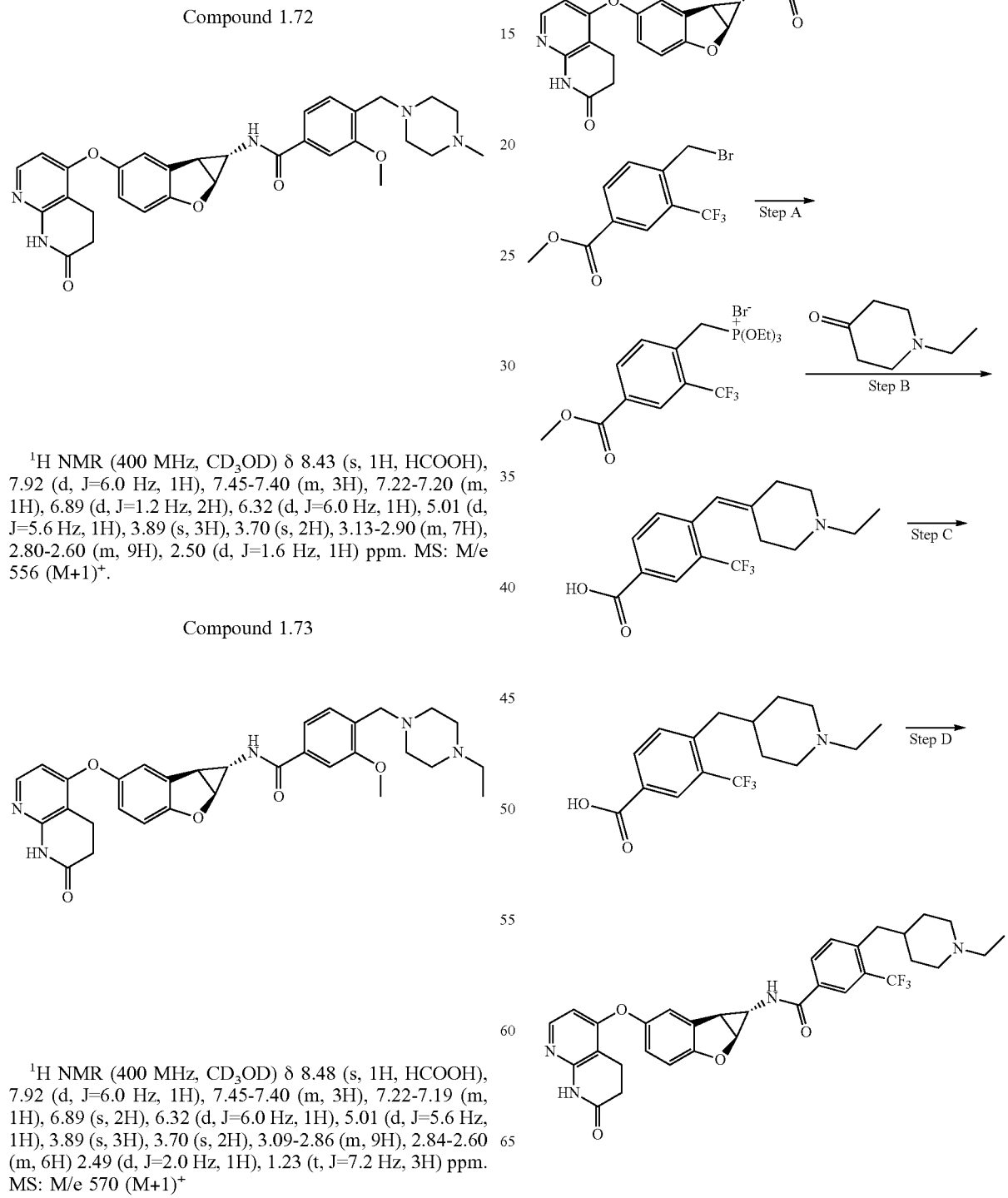

Step A: triethoxy(4-(methoxycarbonyl)-2-(trifluoromethyl)benzyl)phosphonium bromide

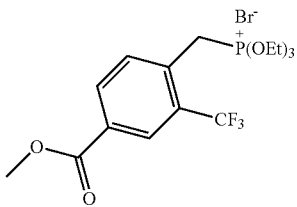

The mixture of methyl 4-(bromomethyl)-3-(trifluoromethyl)benzoate (500 mg, 1.69 mmol) and triethyl phosphate (0.32 mL, 1.86 mmol) in toluene (10 mL) was stirred at reflux overnight. The solvent was removed under reduced pressure. The residue (780 mg, crude) was used into next step without further purification.

Step B: 4-((1-ethylpiperidin-4-ylidene)methyl)-3-(trifluoromethyl)benzoic acid

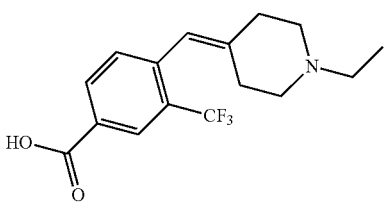 [SMILES: CCN1CCC(=Cc2ccc(C(=O)O)cc2C(F)(F)F)CC1]

To a mixture of the product of Step A (780 mg, 1.69 mmol) in THF (10 mL) was added Sodium hydride (78 mg, 2.03 mmol, 60% dispersion in mineral oil) at 0° C. The mixture was stirred at room temperature for 30 mins. Then 1-ethylpiperidin-4-one (191 mg, 169 mmol) was added to the reaction. The reaction was stirred at room temperature overnight.

NaOH aqueous (2 mL, 2M) was added to the mixture. The mixture was stirred at room temperature for 2 hours. The solvent was removed under reduced pressure. The residue was dissolved into water (20 mL). The mixture was neutralized with HCl (2M) and concentrated under reduced pressure. The residue was dissolved into MeOH/DCM (1/10, 30 mL). The mixture was filtered through a celite pad and the filtrate was concentrated. The residue (320 mg, crude) was used into next step directly with further purification. MS: M/e 314 (M+1)$^+$.

Step C: 4-((1-ethylpiperidin-4-yl)methyl)-3-(trifluoromethyl)benzoic acid

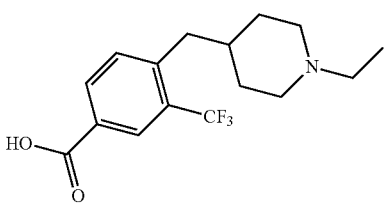 [SMILES: CCN1CCC(Cc2ccc(C(=O)O)cc2C(F)(F)F)CC1]

The mixture of the product of Step B (300 mg, 0.96 mmol) and Pd/C (30 mg, 10% Palladium on activated carbon) in MeOH was stirred at room temperature under hydrogen atmosphere. The mixture was stirred at room temperature overnight. The reaction was filtered through a celite pad and the filtrate was concentrated under reduced pressure. The residue (105 mg, yield: 34.8%) was used into next step directly. MS: M/e 316 (M+1)$^+$ Step D: 4-((1-ethylpiperidin-4-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide (Compound 1.74)

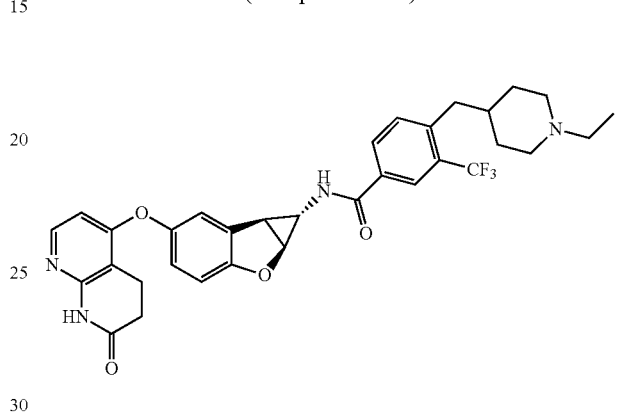

The mixture of the product of Step C (105 mg, 0.33 mmol), Intermediate I (102 mg, 0.33 mmol), HATU (126 mmol, 0.33 mmol) and DIEA (0.2 mL) in DMF (2 mL) was stirred at room temperature for 3 hours. Water (20 mL) was added to the reaction. The mixture was filtered and the solid was purified by prep-HPLC to afford the title compound (20 mg, yield: 10%) as a white solid. $^1$H NMR (400 MHz, DMSO-d6) δ 10.50 (s, 1H), 9.02-8.92 (m, 2H, CF$_3$COOH), 8.18 (s, 1H), 8.10 (d, J=8.0 Hz, 1H), 7.96 (d, J=6.0 Hz, 1H), 7.63 (d, J=8.0 Hz, 1H), 7.26 (d, J=2.0 Hz, 1H), 7.01-6.92 (m, 2H), 6.26 (d, J=6.0 Hz, 1H), 5.08 (d, J=5.6 Hz, 1H), 3.43 (d, J=11.2 Hz, 2H), 3.15-3.01 (m, 3H), 2.98-2.74 (m, 6H), 2.60-2.53 (m, 3H), 1.91 (s, 1H), 1.80-1.64 (m, 2H), 1.50-1.36 (m, 2H), 1.19 (t, J=7.2 Hz, 3H) ppm. MS: M/e 607 (M+1)$^+$.

Compound 1.75: 4-((1-ethylpiperidin-4-ylidene)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

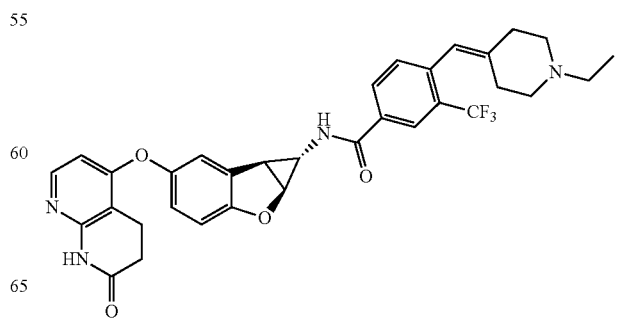

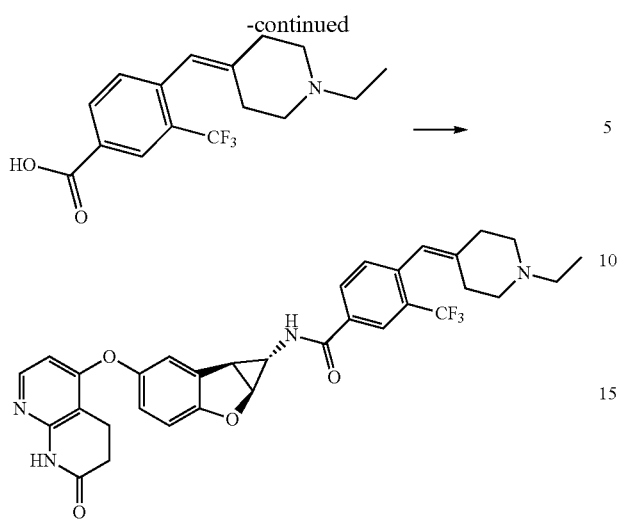

The mixture of the product of Step B in synthesis of Compound 1.74 (72 mg, 0.23 mmol), Intermediate I (70 mg, 0.23 mmol), HATU (86 mg, 0.23 mmol) and DIEA (0.2 mL) in DMF (2 mL) was stirred at room temperature for 3 hours. Water (20 mL) was added to the reaction. The mixture was filtered and the solid was purified by prep-HPLC to afford the title compound (12 mg, yield: 10%) as a white solid. $^1$H NMR (400 MHz, DMSO-d6) δ 10.49 (s, 1H), 9.42 (s, 1H, CF$_3$COOH), 9.00 (d, J=3.6 Hz, 1H), 8.22 (s, 1H), 8.13 (d, J=8.0 Hz, 1H), 7.96 (d, J=6.0 Hz, 1H), 7.53 (d, J=8.0 Hz, 1H), 7.27 (d, J=2.0 Hz, 1H), 7.00-6.90 (m, 2H), 6.63 (s, 1H), 6.26 (d, J=6.0 Hz, 1H), 5.08 (d, J=6.0 Hz, 1H), 3.22-3.07 (m, 4H), 3.01-2.79 (m, 5H), 2.74-2.62 (m, 2H), 2.62-2.52 (m, 4H), 2.41-2.30 (m, 1H), 1.27-1.23 (m, 4H) ppm. MS: M/e 605 (M+1)$^+$.

Compound 1.76: 4-(hydroxymethyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide

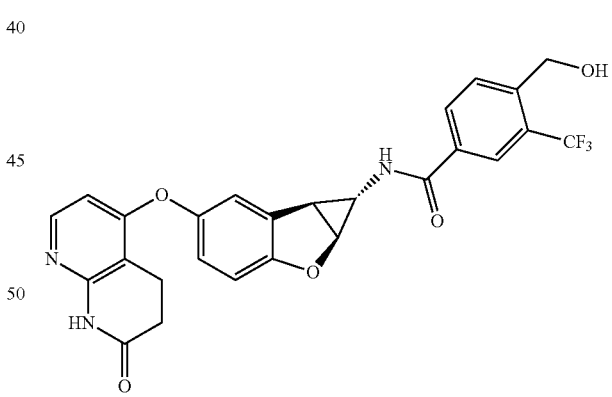

Step A:
4-(hydroxymethyl)-3-(trifluoromethyl)benzoic acid

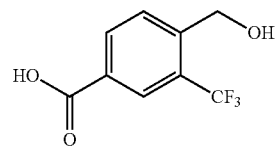 [SMILES: O=C(O)c1ccc(CO)c(C(F)(F)F)c1]

The mixture of methyl 4-(bromomethyl)-3-(trifluoromethyl)benzoate (500 mg, 1.69 mmol) and NaOH aqueous (10 mL, 2M) in 1,4-dioxane was stirred at reflux overnight. The reaction was cooled to room temperature. The solvent was removed under reduced pressure. The residue was dissolved into water (20 mL). The mixture was neutralized with HCl (2M) and the solid was precipitated from the system. The solid (371 mg, yield: 100%) was dried in air and used into next step directly. $^1$H NMR (400 MHz, DMSO-d6) δ 8.23 (d, J=8.0 Hz, 1H), 8.14 (s, 1H), 7.95 (d, J=8.0 Hz, 1H), 4.74 (s, 2H) ppm. MS: M/e 221 (M+1)$^+$.

Step B: 4-(hydroxymethyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethyl)benzamide The mixture of the product of Step A (36 mg, 0.16 mmol), Intermediate I (50 mg, 0.16 mmol), HATU (86 mg, 0.16 mmol) and DIEA (0.2 mL) in DMF (2 mL) was stirred at room temperature for 3 hours. Water (20 mL) was added to the reaction. The mixture was filtered and the brown solid was purified by prep-HPLC to afford the title compound (15 mg, yield: 18.1%) as a white solid. $^1$H NMR (400 MHz, DMSO-d6) δ 10.57 (s, 1H), 8.97 (d, J=3.6 Hz, 1H), 8.20-8.11 (m, 2H), 7.98 (d, J=6.0 Hz, 1H), 7.90 (d, J=8.0 Hz, 1H), 7.28 (d, J=2.0 Hz, 1H), 7.01-6.90 (m, 2H), 6.29 (d, J=6.0 Hz, 1H), 5.10 (d, J=5.6 Hz, 1H), 4.72 (s, 2H), 3.11 (dd, J=5.6, 2.0 Hz, 1H), 2.96 (t, J=7.6 Hz, 2H), 2.61-2.52 (m, 3H) ppm. MS: M/e 512 (M+1)$^+$.

Compound 1.77: N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-4-((1,2,2,6,6-pentamethylpiperidin-4-yl)oxy)-3-(trifluoromethyl)benzamide
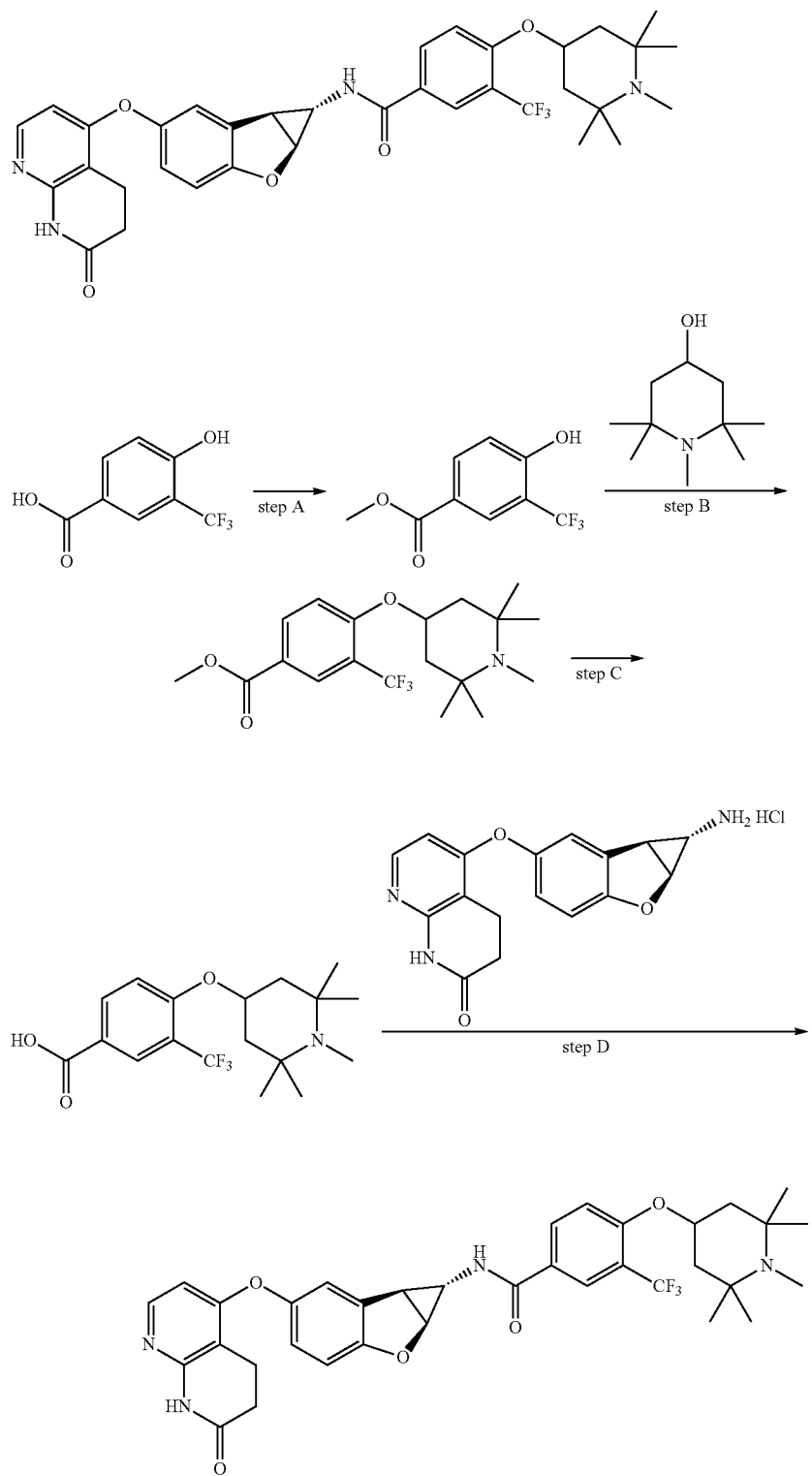

Step A: methyl 4-hydroxy-3-(trifluoromethyl)benzoate

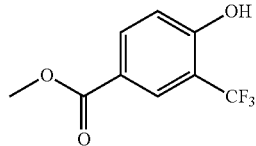

conc. H₂SO₄ (1.5 mL) was dissolved in MeOH (20 mL) and 4-hydroxy-3-(trifluoromethyl)benzoic acid (2.0 g, 9.7 mmol) was added. After the addition, the reaction was refluxed overnight. Most MeOH was removed to give the residue, which was treated with EtOAc (20 mL) and washed with aq. K₂CO₃, brine, dried over Na₂SO₄ and concentrated to give target compound (2.1 g, 98.4%) as a white solid. MS: M/e 221 (M+1)⁺.

Step B: methyl 4-((1,2,2,6,6-pentamethylpiperidin-4-yl)oxy)-3-(trifluoromethyl)benzoate

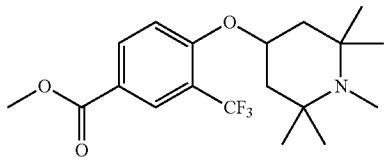

The product of step A (100 mg, 0.45 mmol) and 1,2,2,6,6-pentamethyl piperidin-4-ol (77 mg, 0.45 mmol) were dissolved in dry CH₂Cl₂ (10 mL), di-tert-butyl azodicarboxylate (DTBAD, 207 mg, 0.9 mmol) and PPh₃ (236 mg, 0.9 mmol) were added at 0° C. under N₂. After the addition, the reaction mixture was stirred overnight. The reaction mixture was concentrated and purified by column chromatography (EtOAc~CH₂Cl₂/MeOH=10:1) to give target compound (100 mg, 59.6%) as colorless oil. MS: M/e 374 (M+1)⁺.

Step C: 4-((1,2,2,6,6-pentamethylpiperidin-4-yl)oxy)-3-(trifluoromethyl)benzoic acid

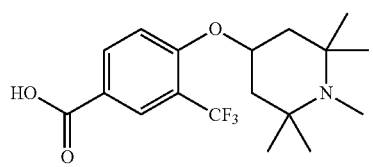 [SMILES: CN1C(C)(C)CC(Oc2ccc(C(=O)O)cc2C(F)(F)F)CC1(C)C]

A mixture of product of step C (100 mg, 0.268 mmol) and NaOH (21.4 mg, 0.536 mmol) in MeOH/H₂O (5 mL/3 mL) was stirred for 2 hours. The reaction mixture was acidified to pH=5-6 with aq. HCl, concentrated to give the residue, which was treated with CH₂Cl₂/MeOH (10 mL/3 mL) and filtered. The filtrate was concentrated to give target compound (86.7 mg, 89.3%) as a white solid. MS: M/e 360 (M+1)⁺.

Step D: N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-4-((1,2,2,6,6-pentamethylpiperidin-4-yl)oxy)-3-(trifluoromethyl)benzamide (Compound 1.77)

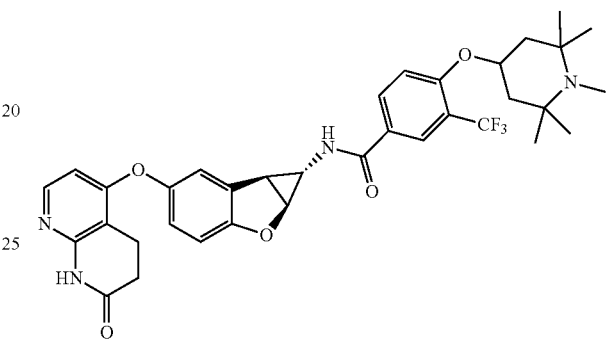

A mixture of Intermediate I (15 mg, 0.043 mmol), the product of step C (15.5 mg, 0.043 mmol), HATU (19.6 mg, 0.052 mmol) and DIPEA (0.2 mL) in DMF (2 mL) was stirred for 2 hours. The reaction mixture was concentrated to give the residue, which was purified by prep-HPLC to give the target compound (7 mg) as a white solid (TFA salt). ¹H NMR (400 MHz, CD₃OD) δ 8.16-8.07 (m, 2H), 7.92 (d, J=5.6 Hz, 1H), 7.38 (d, J=8.4 Hz, 1H), 7.21 (s, 1H), 6.89 (s, 2H), 6.32 (d, J=5.6 Hz, 1H), 5.10 (s, 1H), 5.00 (d, J=5.6 Hz, 1H), 3.05 (dd, J=14.0, 6.4 Hz, 3H), 2.80 (s, 3H), 2.65 (t, J=7.6 Hz, 2H), 2.49 (s, 1H), 2.39 (br.s, 2H), 1.86 (br.s, 2H), 1.50 (d, J=8.0 Hz, 12H) ppm. MS: M/e 651 (M+1)⁺.

Compound 1.78: 4-((4-ethylpiperazin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethoxy)benzamide

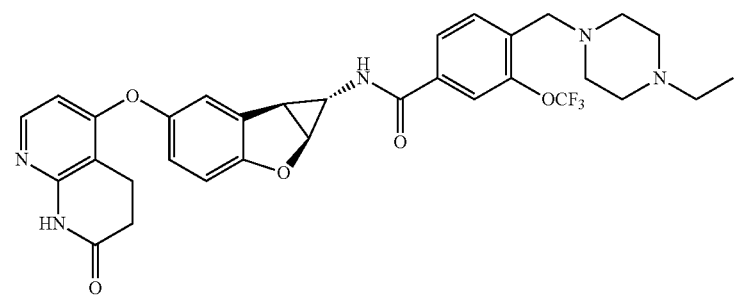

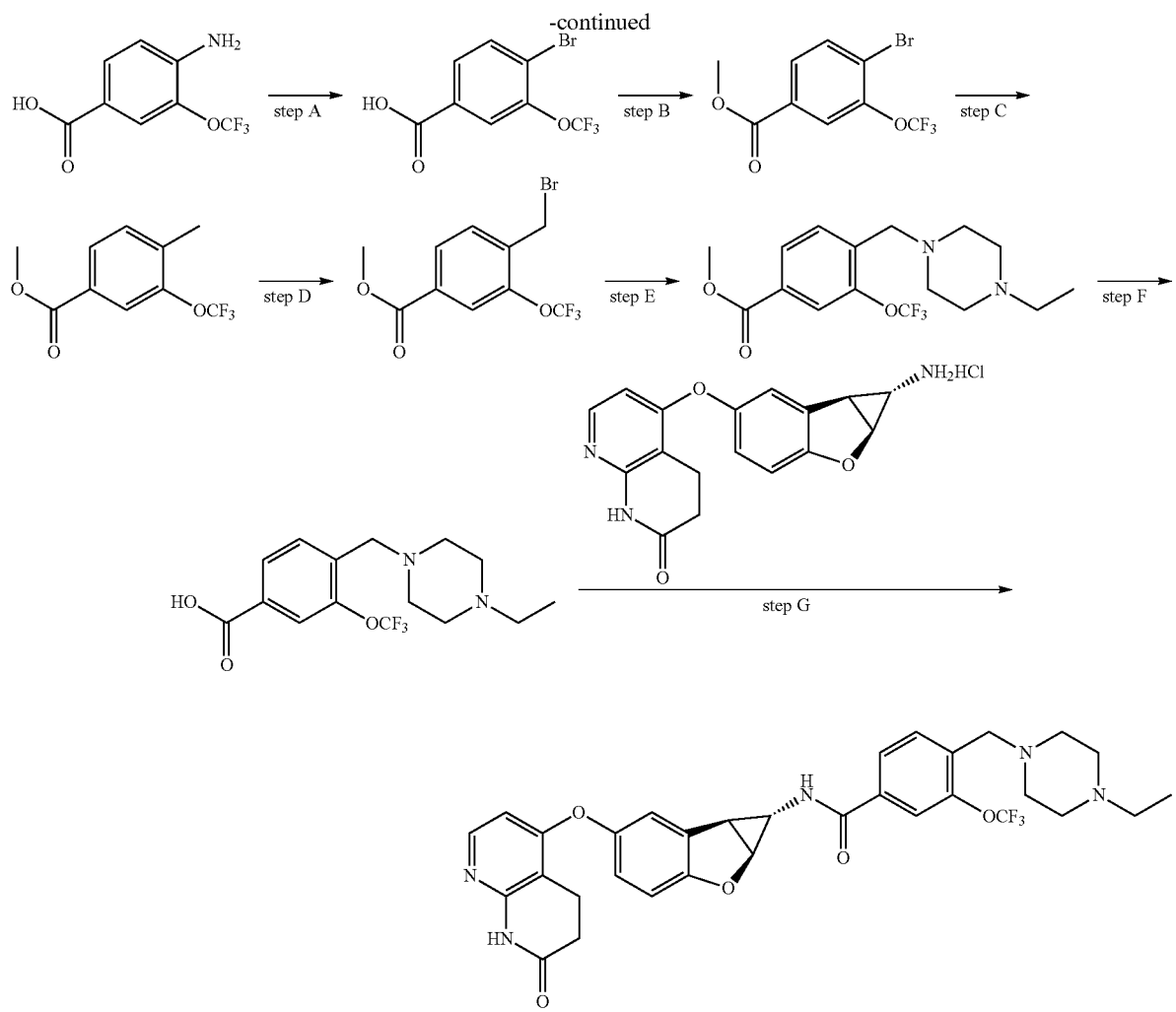

Step A: 4-bromo-3-(trifluoromethoxy)benzoic acid

Step B: methyl 4-bromo-3-(trifluoromethoxy)benzoate

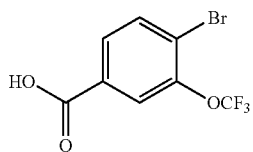 [SMILES: O=C(O)c1ccc(Br)c(OC(F)(F)F)c1]

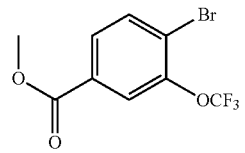 [SMILES: COC(=O)c1ccc(Br)c(OC(F)(F)F)c1]

To a solution of 4-amino-3-(trifluoromethoxy)benzoic acid (2.2 g, 10 mmol) in CH$_3$CN (25 mL) was added HBr solution (7 mL) at 0° C. Then a solution of NaNO$_2$ (759 mg, 11 mmol) in water (3 mL) was added drop wise to keep the temperature below 5° C. After addition, CuBr$_2$ (2.56 g, 11.5 mmol) was added in some portions and the resulting mixture was heated at 70° C. for 0.5 h. The mixture was cooled to room temperature, diluted with water (30 mL), extracted with EA (40 mL×2). The combined organic layer was washed with brine, dried over Na$_2$SO$_4$, filtered and concentrated to give target compound (3.3 g, crude) as a yellow solid which used directly for next step without further purification.

To a solution of the product of step A (3.3 g, crude) in CH$_3$OH (30 mL) was added conc H$_2$S$_4$ (0.5 mL). The reaction was heated to reflux for 6 hrs. The mixture was concentrated, diluted with water (30 mL), extracted with EA (60 mL). The combined organic layer was washed with brine, dried over Na$_2$SO$_4$, filtered and concentrated. The residue was purified by column chromatography (EA/PE=1: 40~1:20) to give target compound (2.1 g, 70% for two steps) as light yellow oil. $^1$H NMR (400 MHz, CD$_3$Cl) δ 7.96 (t, J=1.2 Hz, 1H), 7.38 (dd, J=8.0, 1.2 Hz, 1H), 7.75 (d, J=8.0 Hz, 1H), 3.94 (s, 3H) ppm.

Step C: methyl 4-methyl-3-(trifluoromethoxy)benzoate

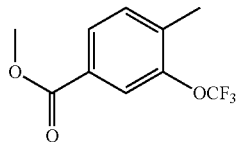 [SMILES: COC(=O)c1ccc(C)c(OC(F)(F)F)c1]

To a mixture of the product of step B (596 mg, 2 mmol) and methylboronic acid (144 mg, 2.4 mmol) in dioxane/water (7/5 mL) was added $Cs_2CO_3$ (1.28 g, 4 mmol) and $Pd(PPh_3)_4$ (115 mg, 1 mmol). The resulting mixture was heated at 100° C. for 5 hrs under $N_2$ protect. The mixture was cooled to room temperature, diluted with water (30 mL), extracted with EA (50 mL). The combined organic layer was washed with brine, dried over $Na_2SO_4$, filtered and concentrated. The residue was purified by column chromatography (EA/PE=1:30) to give target compound (0.1 g, 21%) as yellow oil.

$^1$H NMR (400 MHz, $CD_3Cl$) δ 7.87 (d J=8.4 Hz, 1H), 7.86 (s, 1H), 7.33 (d, J=8.4 Hz, 1H), 3.92 (s, 3H), 2.38 (s, 3H) ppm. MS: M/e 235 (M+1)+.

Step D: methyl 4-(bromomethyl)-3-(trifluoromethoxy)benzoate

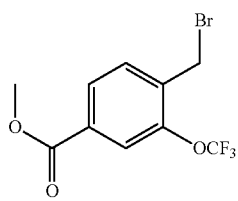 [SMILES: COC(=O)c1ccc(CBr)c(OC(F)(F)F)c1]

To a mixture of the product of step C (100 mg, 0.43 mmol) in $CCl_4$ (5 mL) was added NBS (92 mg, 0.52 mmol) and Benzoyl peroxide (BPO 10 mg, 0.043 mmol). The resulting mixture was heated at 80° C. for 8 hrs. The mixture was concentrated, diluted with water (10 mL), extracted with EA (15 mL×3). The combined organic layer was washed with brine, dried over $Na_2SO_4$, filtered and concentrated to give target compound (0.15 g, crude) which used directly for next step without further purification.

Step E: methyl 4-((4-ethylpiperazin-1-yl)methyl)-3-(trifluoromethoxy)benzoate

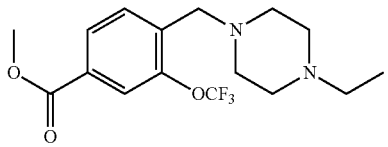 [SMILES: CCN1CCN(Cc2ccc(C(=O)OC)cc2OC(F)(F)F)CC1]

To a mixture of the product of step D (150 mg, crude) in $CH_3CN$ (5 mL) was added 1-ethylpiperazine (60 mg, 0.52 mmol) and $Cs_2CO_3$ (0.28 g, 0.86 mmol). The resulting mixture was heated at 80° C. for 4 hrs. The mixture was cooled, diluted with water (20 mL), extracted with EA (40 mL). The combined organic layer was washed with brine, dried over $Na_2SO_4$, filtered and concentrated to give target compound (0.2 g, crude) which used directly for next step without further purification. MS: M/e 347 (M+1)+.

Step F: 4-((4-ethylpiperazin-1-yl)methyl)-3-(trifluoromethoxy)benzoic acid

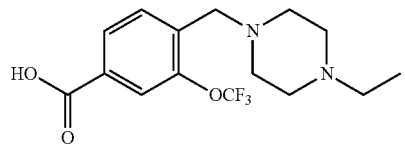 [SMILES: CCN1CCN(Cc2ccc(C(=O)O)cc2OC(F)(F)F)CC1]

To a mixture of the product of step E (200 mg, crude) in THF (5 mL) was added 2N NaOH (1 mL). The resulting mixture was heated at 60° C. for 5 hrs. The mixture was cooled, 2N HCl aqueous solution was add to pH=4, extracted with EA (30 mL). The aqueous layer was concentrated to give target compound (0.1 g, crude) as a yellow solid which used directly for next step without further purification. MS: M/e 333 (M+1)+.

Step G: 4-((4-ethylpiperazin-1-yl)methyl)-N-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(trifluoromethoxy)benzamide (Compound 1.78)

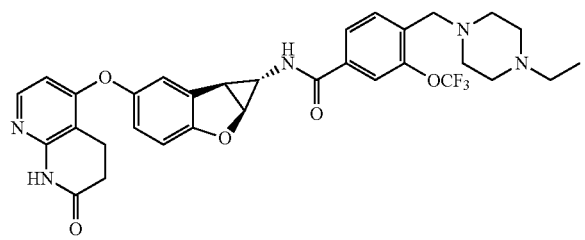 [SMILES: CCN1CCN(Cc2ccc(C(=O)N[C@@H]3[C@H]4Oc5ccc(Oc6ccnc7c6CCC(=O)N7)cc5[C@@H]34)cc2OC(F)(F)F)CC1]

A mixture of 5-(((1S,1aS,6bS)-1-amino-1a,6b-dihydro-1H-cyclopropa[b]benzofuran-5-yl)oxy)-3,4-dihydro-1,8-naphthyridin-2(1H)-one hydrochloride (Intermediate I, 50 mg, 0.143 mmol), the product of step F (100 mg, crude), HATU (57 mg, 0.15 mmol) and DIPEA (64 mg, 0.5 mmol) in DMF (1 mL) was stirred at room temperature overnight. The mixture was diluted with water (30 mL), extracted with EA (30 mL). The organic layer was washed with brine, dried over $Na_2SO_4$, filtered and concentrated. The residue was purified by prep-HPLC to give target compound (15 mg) as a white solid (TFA salt). $^1$H NMR (400 MHz, DMSO-$d_6$) δ 10.49 (s, 1H), 9.16 (br.s, 1H), 8.92 (d, J=3.2 Hz, 1H), 7.96 (d, J=6.0 Hz, 1H), 7.91 (dd, J=8.0, 1.2 Hz, 1H), 7.83 (s, 1H), 7.69 (d, J=8.4 Hz, 1H), 7.26 (d, J=2.4 Hz, 1H), 7.00-6.92 (m, 2H), 6.25 (d, J=5.6 Hz, 1H), 5.08 (d, J=5.6 Hz, 1H), 3.69 (s, 2H), 3.50-3.35 (m, 2H), 3.20-3.08 (m, 3H), 3.02-2.88 (m, 6H), 2.58-2.50 (m, 3H), 2.44-2.30 (m, 2H), 1.12 (t, J=7.2 Hz, 3H) ppm. MS: M/e 624 (M+1)+.

EXAMPLE 2: Synthesis of Compounds 2.1-2.7

Compound 2.1: 4-((4-ethylpiperazin-1-yl)methyl)-N-((1S,1aS,6bS)-5-((2-oxo-2,4-dihydro-1H-pyrido[2,3-d][1,3]oxazin-5-yl)oxy)-1a,6b-dihydro-1H-cyclopropa[b]benzofuran-1-yl)-3-(trifluoromethyl)benzamide

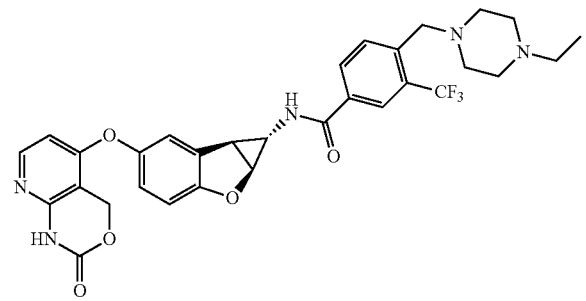

Intermediate II: (1S,1aS,6bR)-5-hydroxy-1a,6b-dihydro-1H-cyclopropa[b]benzofuran-1-carboxylic acid

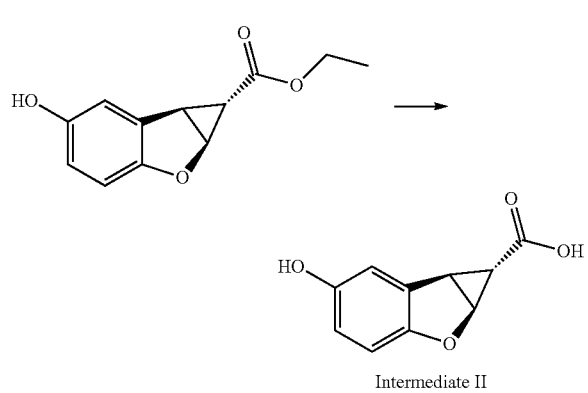

A mixture of (1S,1aS,6bR)-ethyl 5-hydroxy-1a,6b-dihydro-1H-cyclopropa[b]benzofuran-1-carboxylate (the product of Step G in synthesis of Intermediate I, 4.4 g, 20 mmol) in NaOH (2N, 20 mL) in THF (40 mL) was stirred at 60° C. for 2 hours. The solvent was removed under reduced pressure and the residue was dissolved into water. The aqueous phase was adjusted to pH=3-4 by HCl (2 mol/L). The white solid was collected and dried in air to afford the title compound (3.8 g, 99%). $^1$H NMR (400 MHz, DMSO-d6) δ 12.51 (s, 1H), 9.03 (s, 1H), 6.88 (d, J=2.4 Hz, 1H), 6.71 (d, J=8.8 Hz, 1H), 6.54 (dd, J=8.8, 2.4 Hz, 1H), 5.07 (dd, J=5.6, 1.2 Hz, 1H), 3.21 (dd, J=5.6, 3.2 Hz, 1H), 1.06 (dd, J=3.2, 1.2 Hz, 1H) ppm.

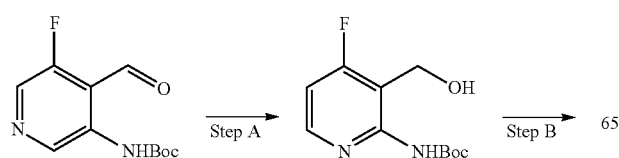

-continued

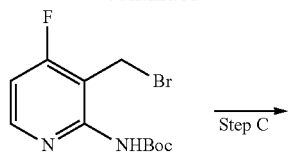

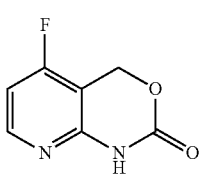

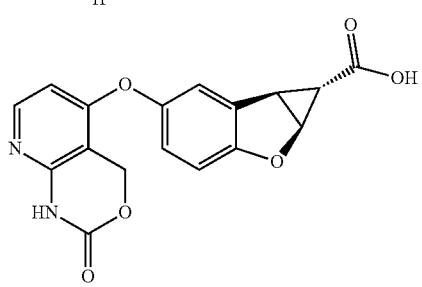

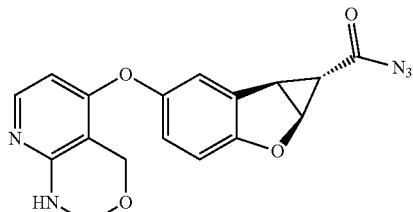

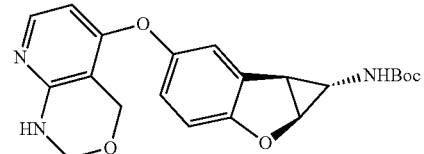

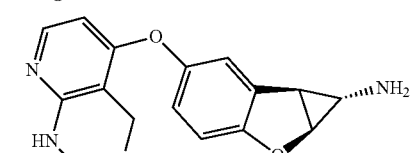

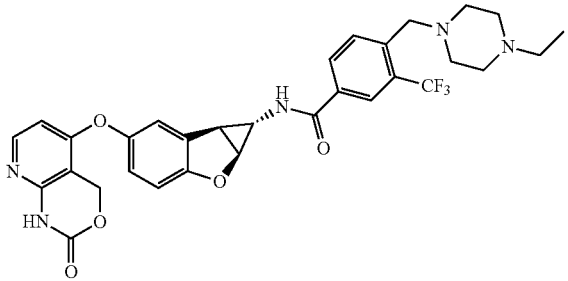

Step A: tert-butyl 4-fluoro-3-(hydroxymethyl)pyridin-2-ylcarbamate

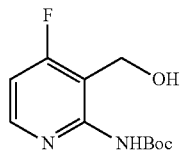

To a solution of tert-butyl (4-fluoro-3-formylpyridin-2-yl)carbamate (480 mg, 2 mmol) in MeOH (3 mL) was added NaBH$_4$ (76 mg, 2 mmol) at 0° C. The reaction was stirred at 0° C. for 30 min. The reaction was quenched with saturated NH$_4$Cl (1 mL) and water (5 mL) and extracted with ethyl acetate (2×15 mL). The combined organic phase was dried over anhydrous sodium sulfate, filtered and concentrated under reduced pressure to obtain the target compound (460 mg, 95%) as a white solid which was used directly into the next step. $^1$HNMR (600 MHz, DMSO-d$_6$) δ 9.20 (s, 1H), 8.31-8.28 (m, 1H), 7.11-7.09 (m, 1H), 5.26 (t, J=6.0 Hz, 1H), 4.48 (d, J=6.0 Hz, 2H), 1.45 (s, 9H) ppm. MS: M/e 243 (M+1)$^+$.

Step B: tert-butyl 3-(bromomethyl)-4-fluoropyridin-2-ylcarbamate

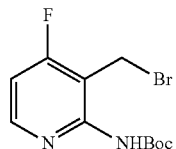 [SMILES: CC(C)(C)OC(=O)Nc1nccc(F)c1CBr]

CBr$_4$ (531 mg, 1.6 mmol) was added to a solution of the product from Step A (242 mg, 1 mmol) in THF (3 mL). Then a solution of triphenylphosphine in THF (1 mL) was added dropwise and the mixture was stirred at room temperature for 3 hours. The mixture was loaded onto a silica gel column. Eluted with (EA:PE=1:3) to afford the title compound (160 mg, 52%) as a white solid. $^1$H-NMR (400 MHz, CDCl$_3$) δ 8.38-8.35 (m, 1H), 7.09 (s, 1H), 6.90-6.86 (m, 1H), 4.61 (s, 2H), 1.54 (s, 9H) ppm MS: M/e 305 (M+1)$^+$.

Step C: 5-fluoro-1H-pyrido[2,3-d][1,3]oxazin-2(4H)-one

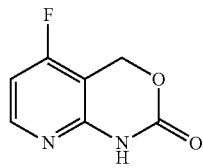 [SMILES: O=C1Nc2nccc(F)c2CO1]

The solution of the product from Step B (120 mg, 0.4 mmol) in DMSO (1 mL) was stirred at 60° C. for 4 hours under N$_2$. Then water (10 mL) was added and extracted with ethyl acetate (3×15 mL). The combined organic phase was washed with brine, dried over anhydrous sodium sulfate and concentrated under reduce pressure. The residue was purified by prep-TLC (EtOAc:PE=1:1) to give the title compound (20 mg, 30%) as a light yellow solid. $^1$H-NMR (600 MHz, DMSO-d$_6$) δ 10.95 (s, 1H), 8.21-8.18 (m, 1H), 6.97-6.94 (m, 1H), 5.37 (s, 2H) ppm. MS: M/e 169 (M+1)$^+$.

Step D: (1S,1aS,6bR)-5-((2-oxo-2,4-dihydro-1H-pyrido[2,3-d][1,3]oxazin-5-yl)oxy)-1a,6b-dihydro-1H-cyclopropa[b]benzofuran-1-carboxylic acid

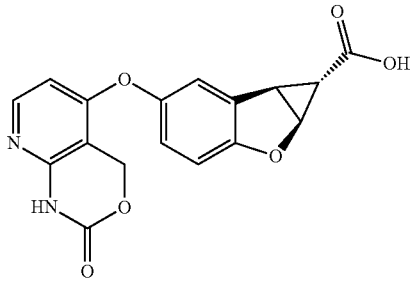 [SMILES: O=C1Nc2nccc(Oc3ccc4c(c3)[C@@H]3[C@H](O4)[C@H]3C(=O)O)c2CO1]

A mixture of Intermediate II (103 mg, 0.536 mmol), the product from Step C (90 mg, 0.536 mmol) and Cs$_2$CO$_3$ (528 mg, 1.61 mmol) in DMF (3 mL) was stirred at 100° C. for 2 hours. Most of DMF was removed to give the residue, which was treated with H$_2$O (10 mL). The mixture was acidified to pH about 3-4 with aq. HCl (2.0 M) and extracted with EA (30 mL×4). The combined organic layers were washed with brine, dried over Na$_2$SO$_4$ and concentrated under reduced pressure. The residue was purified by prep-HPLC to give the target compound (30 mg, 16.5%) as a white solid. MS: M/e 341 (M+1)$^+$.

Step E: (1S,1aS,6bR)-5-((2-oxo-2,4-dihydro-1H-pyrido[2,3-d][1,3]oxazin-5-yl)oxy)-1a,6b-dihydro-1H-cyclopropa[b]benzofuran-1-carbonyl azide

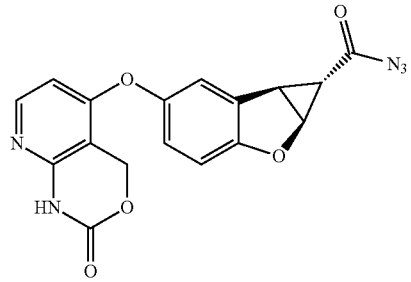 [SMILES: [N-]=[N+]=NC(=O)[C@@H]1[C@H]2Oc3ccc(Oc4ccnc5c4COC(=O)N5)cc3[C@H]21]

The product from Step D (30 mg, 0.088 mmol) and Et$_3$N (8.9 mg, 0.088 mmol) were dissolved in DMF (2 mL), and then DPPA (24 mg, 0.088 mmol) was added at room temperature. After the addition, the reaction was stirred for 4 hours at room temperature. The reaction mixture was treated with H$_2$O (20 mL) and extracted with EA (15 mL×3). The combined organic layers were washed with brine, dried over Na$_2$SO$_4$ and concentrated to give crude product (100%), which was directly used into the next step. MS: M/e 366 (M+1)$^+$.

Step F: tert-butyl ((1S,1aS,6bS)-5-((2-oxo-2,4-dihydro-1H-pyrido[2,3-d][1,3]oxazin-5-yl)oxy)-1a,6b-dihydro-1H-cyclopropa[b]benzofuran-1-yl)carbamate

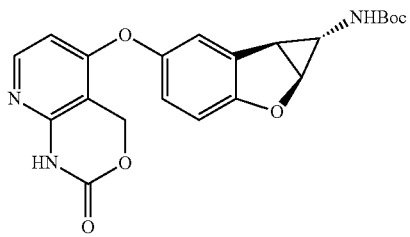 [SMILES: CC(C)(C)OC(=O)N[C@@H]1[C@H]2Oc3ccc(Oc4ccnc5c4COC(=O)N5)cc3[C@@H]12]

A mixture of the product from Step E (crude, 0.588 mmol) in t-BuOH (2 mL) was stirred at 85° C. for 2 hours. The reaction mixture was concentrated to give the residue, which was treated with CH$_2$Cl$_2$ (5 mL) and filtered. The filtrate was concentrated and purified by prep-TLC (petroleum ether/EtOAc=1:1) to give the target compound (27 mg, 11.1%) as a white solid. MS: M/e 412 (M+1)$^+$.

Step G: 5-(((1S,1aS,6bS)-1-amino-1a,6b-dihydro-1H-cyclopropa[b]benzofuran-5-yl)oxy)-1H-pyrido[2,3-d][1,3]oxazin-2(4H)-one

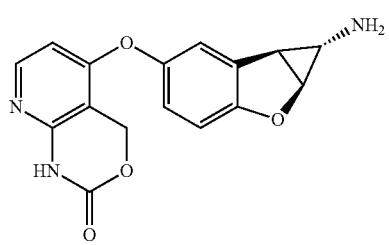 [SMILES: N[C@@H]1[C@H]2Oc3ccc(Oc4ccnc5c4COC(=O)N5)cc3[C@@H]12]

To a stirred solution of the product from Step F (27 mg, 0.066 mmol) in CH$_2$Cl$_2$ (2 mL) was added EtOAc/HCl(g) (2 mL, 6N). After stirred for 2 hours, the reaction mixture was concentrated to give the target compound, which was directly used into the next step without further purification. MS: M/e 312 (M+1)$^+$.

Step H: 4-((4-ethylpiperazin-1-yl)methyl)-N-((1S,1aS,6bS)-5-((2-oxo-2,4-dihydro-1H-pyrido[2,3-d][1,3]oxazin-5-yl)oxy)-1a,6b-dihydro-1H-cyclopropa[b]benzofuran-1-yl)-3-(trifluoromethyl)benzamide (Compound 2.1)

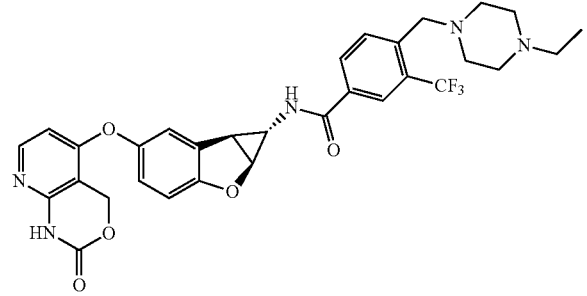

A mixture of the product from Step G (11 mg, 0.033 mmol), 4-((4-ethylpiperazin-1-yl)methyl)-3-(trifluoromethyl)benzoic acid (10.4 mg), HATU (15 mg, 0.039 mmol) and DIPEA (0.1 mL) in DMF (2 mL) was stirred for 2 hours. The reaction was concentrated to give the residue, which was purified by prep-HPLC to give the target compound (7.38 mg, 30.9%) as a white solid (TFA salt). $^1$HNMR (400 MHz, CD$_3$OD) δ 8.18 (s, 1H), 8.08 (d, J=8.0 Hz, 1H), 7.99 (d, J=6.0 Hz, 1H), 7.93 (d, J=8.4 Hz, 1H), 7.25 (d, J=2.4 Hz, 1H), 6.97-6.87 (m, 2H), 6.34 (d, J=6.0 Hz, 1H), 5.49 (s, 2H), 5.02 (d, J=5.6 Hz, 1H), 3.83 (s, 2H), 3.53 (d, J=12.4 Hz, 2H), 3.25-3.17 (m, J=7.2 Hz, 2H), 3.16-2.97 (m, 5H), 2.58-2.41 (m, 3H), 1.33 (t, J=7.6 Hz, 3H) ppm. MS: M/e 305.5 (M/2+1)$^+$.

Compound 2.2 was prepared according to the procedures described for Compound 2.1 under appropriate conditions that could be recognized by one skilled in the art.

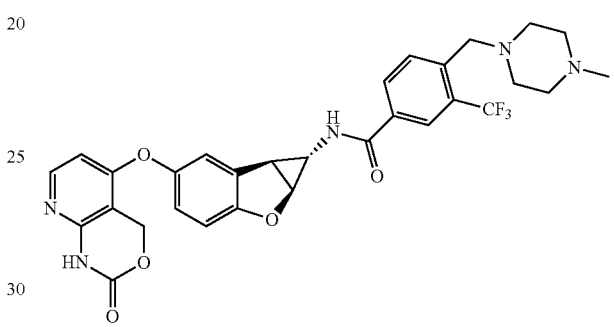

$^1$H NMR (400 MHz, CD3OD) δ 8.09 (s, 1H), 8.00 (d, J=8.0 Hz, 1H), 7.91 (d, J=6.0 Hz, 1H), 7.84 (d, J=8.0 Hz, 1H), 7.17 (d, J=2.4 Hz, 1H), 6.88-6.79 (m, 2H), 6.26 (d, J=6.0 Hz, 1H), 5.41 (s, 2H), 4.94 (d, J=5.2 Hz, 1H), 3.75 (s, 2H), 3.44-3.32 (m, 2H), 3.17-3.01 (m, 2H), 3.00-2.87 (m, 3H), 2.82 (s, 3H), 2.49-2.33 (m, 3H) ppm. MS: M/e 298.5 (M/2+1)$^+$.

Compound 2.3: 4-(((1S,1aS,6bS)-1-(4-((4-ethylpiperazin-1-yl)methyl)-3-(trifluoromethyl)benzamido)-1a,6b-dihydro-1H-cyclopropa[b]benzofuran-5-yl)oxy)-N-methylpicolinamide

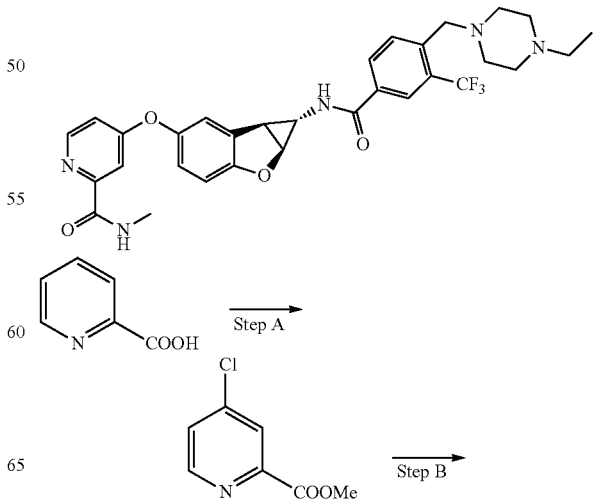

169
-continued

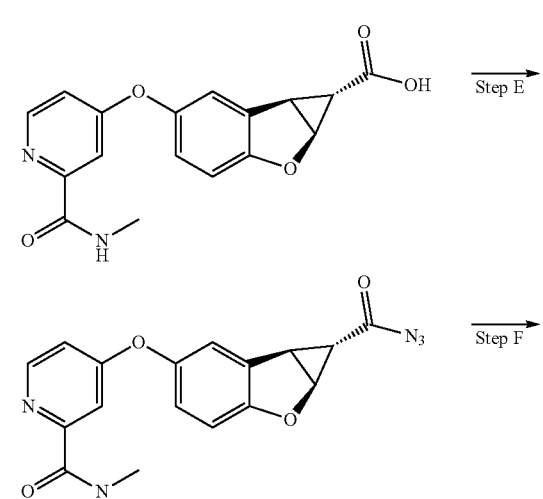

170

Step A: methyl 4-chloropicolinate

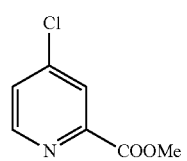 [SMILES: COC(=O)c1cc(Cl)ccn1]

Anhydrous DMF (1 mL) was slowly added to sulfurous dichloride (30 mL) at 45° C. The solution was stirred at room temperature for 10 min, and then picolinic acid (10 g, 81 mmol) was added over 30 min. The resulting solution was heated at 72° C. for 16 hours to generate a yellow solid. The mixture was cooled to room temperature, diluted with toluene (50 mL) and concentrated to 20 mL. The toluene addition/concentration process was repeated twice. The resulted solid was added into 20 mL methanol at ice bath to keep the internal temperature below 55° C. The mixture was stirred at room temperature for 45 min, cooled to 5° C. and treated with ethyl ether (20 mL) dropwise. The resulted solid was filtered, washed with ethyl ether (20 mL) and dried under 35° C. to provide a white yellow solid. After the solid was solvated with hot water (50 mL, 45° C.), sodium bicarbonate aqueous solution was added to adjust pH to 8-9. The mixture was extracted with ethyl acetate (2×30 mL) and the organic phase was concentrated to give desired compound (5.5 g, yield: 39.6%) as a off-white solid.

Step B: 4-chloro-N-methylpicolinamide

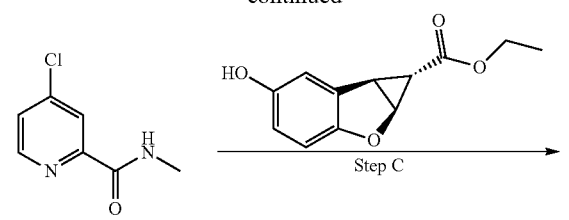

To a solution of the product of Step A (5.5 g, 32.2 mmol) in methanol (60 mL) was added methylamine in methanol (2.2 mL) at 5° C. The mixture was stirred at 0-5° C. for 2 hours. The solvent was evaporated at 40~50° C. to give the title compound (6.2 g, yield: 90%) as a yellow solid. $^1$H NMR (400 MHz, DMSO-d6) δ 8.85 (br.s, 1H), 8.63 (d, J=5.2 Hz, 1H), 8.05-8.02 (m, 1H), 7.76 (dd, J=5.2, 2.0 Hz, 1H), 2.85 (d, J=4.8 Hz, 3H). MS: M/e 171 (M+1)$^+$.

Step C: (1S,1aS,6bR)-ethyl 5-((2-(methylcarbamoyl)pyridin-4-yl)oxy)-1a,6b-dihydro-1H-cyclopropa[b]benzofuran-1-carboxylate

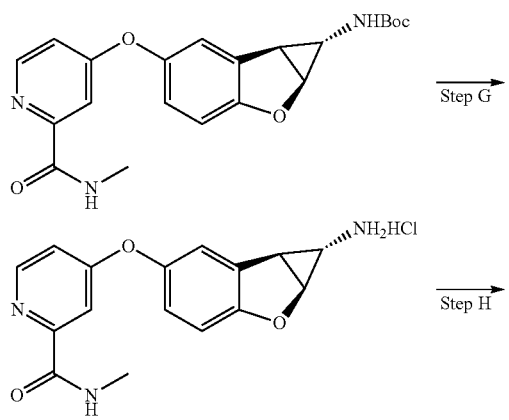

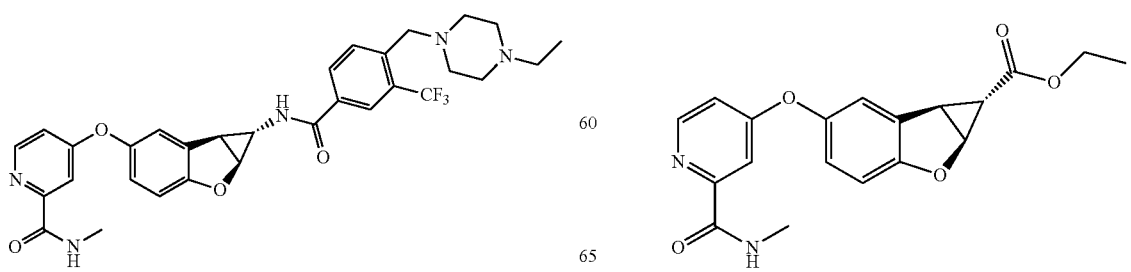

The mixture of the product of Step B (1.5 g, 8.82 mmol), the product obtained from Step G in synthesis of Intermediate I (1.94 g, 8.82 mmol) and Cesium carbonate (3.45 g, 10.6 mmol) in DMF (20 mL) was stirred at 110° C. for 2 hours. Water (20 mL) was added to quench the reaction which was extracted with ethyl acetate (2×20 mL). The combined organic phase was washed with brine, dried over anhydrous sodium sulfate and concentrated under reduced pressure. The residue was purified by silica gel chromatography (silica gel weight: 30 g, elute: EA/PE: 1/3) to afford the title product (1.4 g, yield: 44.9%) as a yellow solid. MS: M/e 355 (M+1)$^+$.

Step D: (1S,1aS,6bR)-5-((2-(methylcarbamoyl)pyridin-4-yl)oxy)-1a,6b-dihydro-1H-cyclopropa[b]benzofuran-1-carboxylic acid

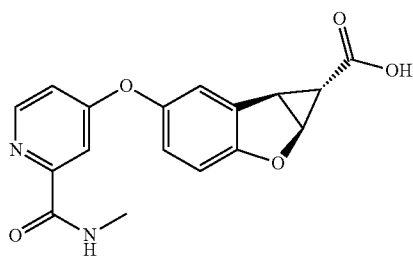 [SMILES: CNC(=O)c1cc(Oc2ccc3c(c2)[C@@H]2[C@H](O3)[C@H]2C(=O)O)ccn1]

To a stirred solution of the product of step C (1.4 g, 4.0 mmol) in THF/H$_2$O (8 mL/2 mL) was added sodium hydroxide aqueous solution (4 mL, 2 mol/L) at room temperature. The mixture was stirred at 60° C. for 2 hours. The solvent was concentrated and the residue was dissolved into 20 mL water. Hydrochloric acid (2 mol/L) was added to adjust pH to 7. The mixture was extracted with ethyl acetate (2×20 mL). The organic phase was washed with brine, dried over anhydrous sodium sulfate and concentrated under reduced pressure. The residue (800 mg, yield: 61.5%) as a yellow solid which was used into next step directly. MS: M/e 327 (M+1)$^+$.

Step E: (1S,1aS,6bR)-5-((2-(methylcarbamoyl)pyridin-4-yl)oxy)-1a,6b-dihydro-1H-cyclopropa[b]benzofuran-1-carbonyl azide

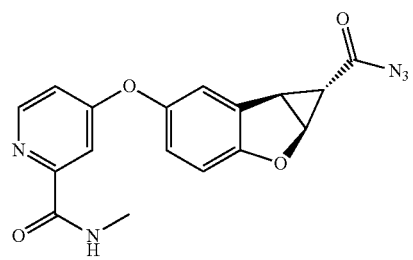 [SMILES: CNC(=O)c1cc(Oc2ccc3c(c2)[C@@H]2[C@H](O3)[C@H]2C(=O)N=[N+]=[N-])ccn1]

To a solution of the product of Step D (400 mg, 1.23 mmol) in DMF (10 mL) was added Et$_3$N and followed by DPPA at 0° C. The resulted mixture was warmed to room temperature and stirred for 5 hours. Water (20 mL) was added and the mixture was extracted with ethyl acetate (3×20 mL). The combined extracted phase was washed with brine, dried over anhydrous sodium sulfate and concentrated under reduced pressure. The residue (300 mg, yield: 69.8%) as yellow oil was used into next step directly. $^1$H NMR (400 MHz, DMSO-d6) δ 8.90-8.71 (m, 1H), 8.60-8.41 (m, 1H), 7.55-7.33 (m, 2H), 7.26-7.03 (m, 3H), 5.58-5.34 (m, 1H), 3.77-3.49 (m, 1H), 3.01-2.66 (m, 4H) ppm. MS: M/e 352 (M+1)$^+$.

Step F: tert-butyl ((1S,1aS,6bS)-5-((2-(methylcarbamoyl)pyridin-4-yl)oxy)-1a,6b-dihydro-1H-cyclopropa[b]benzofuran-1-yl)carbamate

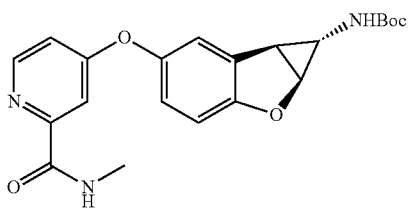 [SMILES: CNC(=O)c1cc(Oc2ccc3c(c2)[C@H]2[C@H](NC(=O)OC(C)(C)C)[C@H]2O3)ccn1]

The mixture of the product of Step E (300 mg, 0.85 mmol) in t-butanol (5 mL) was stirred at 100° C. for 5 hours. The solvent was removed under reduced pressure and the residue was used into next step directly. The residue (310 mg, yield: 92%) was used into next step directly as yellow oil. MS: M/e 398 (M+1)$^+$.

Step G: 4-(((1S,1aS,6bS)-1-amino-1a,6b-dihydro-1H-cyclopropa[b]benzofuran-5-yl)oxy)-N-methylpicolinamide hydrochloride

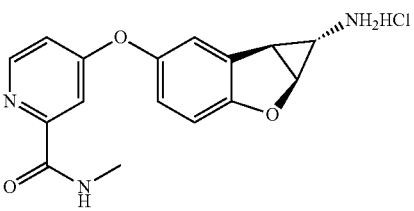

To a stirred solution of the product of Step F (100 mg, 0.25 mmol) in EA (3 mL) was added dropwise HCl/EA (1 mL, 6N) at room temperature. The white solid was precipitated from the solution immediately. The mixture was filtered. The solid (80 mg, yield: 96.4%) was dried in air and used into next step directly. MS: M/e 334 (M+1)$^+$.

Step H: 4-(((1S,1aS,6bS)-1-(4-((4-ethylpiperazin-1-yl)methyl)-3-(trifluoromethyl)benzamido)-1a,6b-dihydro-1H-cyclopropa[b]benzofuran-5-yl)oxy)-N-methylpicolinamide (Compound 2.3)

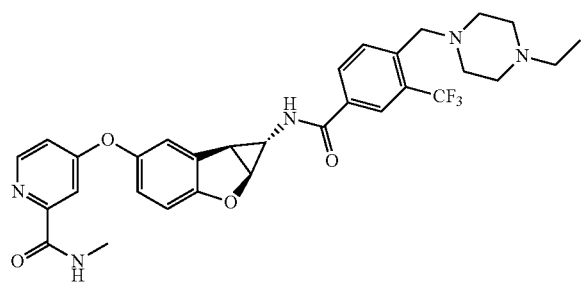 [SMILES: CCN1CCN(Cc2ccc(C(=O)N[C@@H]3[C@H]4Oc5ccc(Oc6ccnc(C(=O)NC)c6)cc5[C@@H]34)cc2C(F)(F)F)CC1]

The mixture of the product of Step G (40 mg, 0.12 mmol), 4-((4-ethylpiperazin-1-yl)methyl)-3-(trifluoromethyl)benzoic acid (38 mg, 0.12 mmol), DIEA (0.5 mL) and HATU (45.6 mg, 0.21 mmol) in DMF (2 mL) was stirred at room temperature for 3 hours. The solvent was removed under reduced pressure. The residue was added water (4 mL) and the solid was precipitated from the system. The solid was purified by prep-HPLC to afford the title compound as a white solid (13.5 mg, yield: 10.8%). $^1$HNMR (400 MHz, DMSO-d6) δ 9.31 (brs, 1H, CF$_3$COOH), 9.00 (d, J=3.6 Hz, 1H), 8.78 (d, J=4.8 Hz, 1H), 8.50 (d, J=5.6 Hz, 1H), 8.20 (s, 1H), 8.15 (d, J=8.4 Hz, 1H), 7.89 (d, J=8.4 Hz, 1H), 7.38 (d, J=2.4 Hz, 1H), 7.34 (s, 1H), 7.14 (dd, J=5.6, 2.4 Hz, 1H), 7.01 (d, J=1.2 Hz, 2H), 5.11 (d, J=5.6 Hz, 1H), 3.78 (s, 2H), 3.46 (d, J=12.0 Hz, 2H), 3.19-2.85 (m, 7H), 2.79 (d, J=4.8 Hz, 3H), 2.62-2.55 (m, 1H), 2.42 (t, J=12.0 Hz, 2H), 1.21 (t, J=7.2 Hz, 3H) ppm. MS: M/e 596 (M+1)$^+$.

Compound 2.4 was prepared according to the procedures described for Compound 2.3 under appropriate conditions that could be recognized by one skilled in the art.

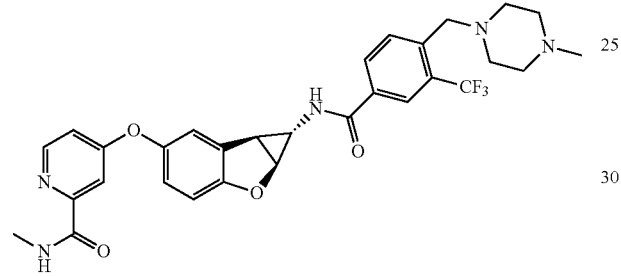

$^1$H NMR (400 MHz, DMSO-d6) δ 9.58 (s, 1H, CF$_3$COOH), 9.01 (d, J=3.2 Hz, 1H), 8.83-8.73 (m, 1H), 8.50 (d, J=5.6 Hz, 1H), 8.20 (s, 1H), 8.15 (d, J=8.4 Hz, 1H), 7.88 (d, J=8.4 Hz, 1H), 7.38 (d, J=2.4 Hz, 1H), 7.34 (s, 1H), 7.14 (dd, J=5.6, 2.4 Hz, 1H), 7.02 (d, J=1.0 Hz, 2H), 5.11 (d, J=5.6 Hz, 1H), 3.76 (s, 2H), 3.40 (d, J=11.6 Hz, 2H), 3.12 (dd, J=5.6, 2.0 Hz, 1H), 3.10-2.98 (m, 2H), 2.90 (d, J=12.8 Hz, 2H), 2.83-2.75 (m, 6H), 2.59 (s, 1H), 2.40 (t, J=11.6 Hz, 2H). MS: M/e 582 (M+1)$^+$.

Compound 2.5: N-((1S,1aS,6bS)-5-((2-aminopyridin-4-yl)oxy)-1a,6b-dihydro-1H-cyclopropa[b]benzofuran-1-yl)-4-((4-ethylpiperazin-1-yl)methyl)-3-(trifluoromethyl)benzamide

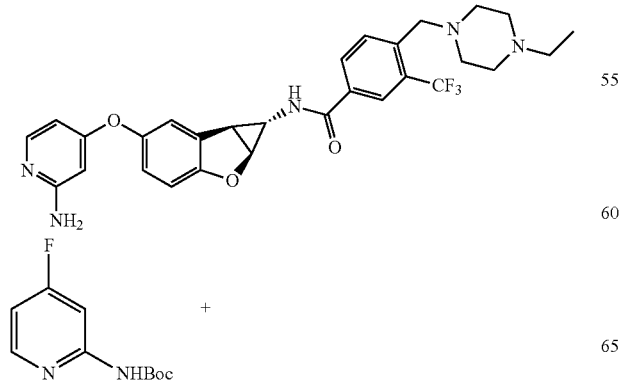

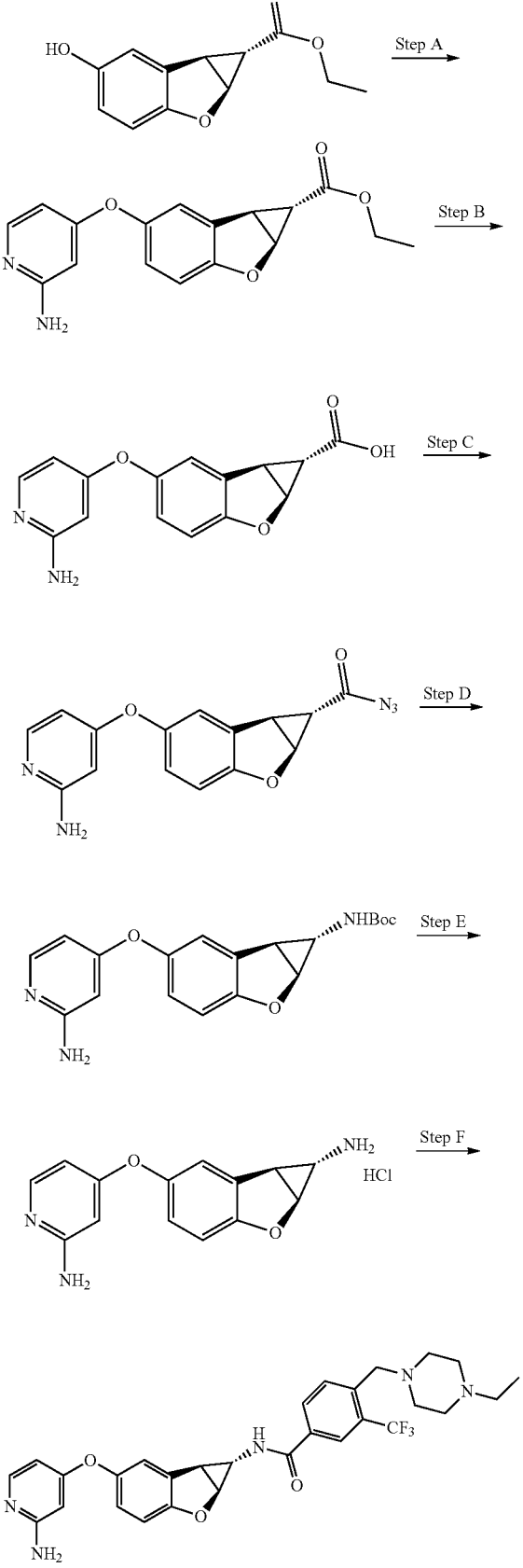

Step A: (1S,1aS,6bR)-ethyl 5-((2-aminopyridin-4-yl)oxy)-1a,6b-dihydro-1H-cyclopropa[b]benzofuran-1-carboxylate

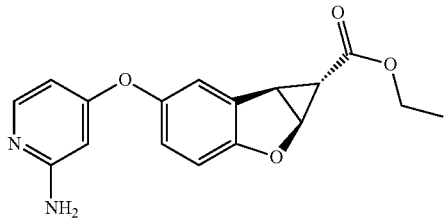 [SMILES: CCOC(=O)[C@@H]1[C@H]2Oc3ccc(Oc4ccnc(N)c4)cc3[C@H]21]

The mixture of (1S,1aS,6bR)-ethyl 5-hydroxy-1a,6b-dihydro-1H-cyclopropa [b]benzofuran-1-carboxylate (the product of Step G in synthesis of the product obtained from Step G in synthesis of Intermediate I (2.2 g, 10 mmol), tert-butyl (4-fluoropyridin-2-yl)carbamate (2.1 g, 10 mmol) and cesium carbonate (6.5 g, 20 mmol) in DMF (50 mL) was stirred at 100° C. for 2 hours. The reaction was filtered through a celite pad. The filtrate was concentrated under reduced pressure. The residue was diluted with EA (300 mL), washed with brine (100 mL×3), dried over anhydrous sodium sulfate and concentrated under reduced pressure. The residue was purified by silica gel chromatography (silica weight: 20 g, eluted with petroleum ether/EA: 2/3, 1500 mL) to give the target compound (1.0 g, 30%) as brown oil. $^1$H NMR (400 MHz, DMSO-d6) δ 7.83 (d, J=6.0 Hz, 1H), 7.37 (d, J=2.4 Hz, 1H), 7.08-6.96 (m, 2H), 6.16 (dd, J=6.0, 2.4 Hz, 1H), 5.95 (s, 2H), 5.81 (d, J=2.4 Hz, 1H), 5.35 (dd, J=5.2, 1.2 Hz, 1H), 4.17 (q, J=7.2 Hz, 2H), 3.44 (dd, J=5.2, 3.2 Hz, 1H), 1.39 (dd, J=3.2, 1.2 Hz, 1H), 1.27 (t, J=7.2 Hz, 3H) ppm.

Step B: (1S,1aS,6bR)-5-((2-aminopyridin-4-yl)oxy)-1a,6b-dihydro-1H-cyclopropa[b]benzofuran-1-carboxylic acid

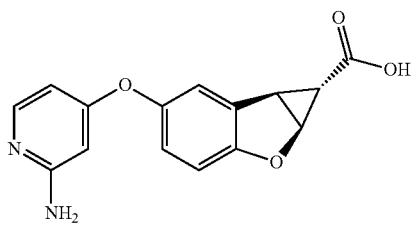 [SMILES: Nc1cc(Oc2ccc3c(c2)[C@@H]2[C@H](O3)[C@H]2C(=O)O)ccn1]

A mixture of the product of Step A (600 mg, 2 mmol) in sodium hydroxide aqueous solution (2 mol/L, 2 mL, 4 mmol) and THF (8 mL) was stirred at 60° C. for 2 hours. The solvent was removed under reduced pressure, the residue was diluted with water (8 mL) and adjusted to pH about 6 by HCl (2 mol/L). The solid was collected and dried in air to afford the title compound (500 mg, yield: 88%) as a white solid. $^1$H NMR (400 MHz, DMSO-d6) δ 7.73 (d, J=5.6 Hz, 1H), 7.27 (d, J=2.4 Hz, 1H), 6.97-6.88 (m, 2H), 6.09 (dd, J=5.6, 2.4 Hz, 1H), 5.90 (s, 2H), 5.71 (d, J=2.0 Hz, 1H), 5.19 (d, J=5.2 Hz, 1H), 3.27 (dd, J=5.2, 2.8 Hz, 1H), 1.15-1.13 (m, 1H) ppm.

Step C: (1S,1aS,6bR)-5-((2-aminopyridin-4-yl)oxy)-1a,6b-dihydro-1H-cyclopropa[b]benzofuran-1-carbonyl azide

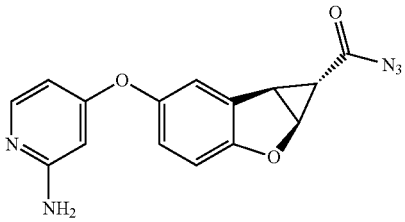 [SMILES: [N-]=[N+]=NC(=O)[C@@H]1[C@H]2Oc3ccc(Oc4ccnc(N)c4)cc3[C@H]21]

To a solution of the product of Step B (100 mg, 0.35 mmol) and Et$_3$N (89 mg, 0.88 mmol) in DMF (5 mL) was added DPPA (116 mg, 0.42 mmol) at room temperature. The reaction mixture was stirred at room temperature for 2 hours. The resulting mixture was diluted with EA (60 mL) and washed with brine (20 mL×3). The organic phase was dried over anhydrous sodium sulfate and concentrated under reduced pressure to afford the crude product (100 mg, 93%) which was directly used in the next step. $^1$H NMR (400 MHz, DMSO-d6) 7.78 (d, J=5.6 Hz, 1H), 7.35-7.31 (m, 1H), 7.06-7.03 (m, 1H), 7.01-6.97 (m, 1H), 6.14 (dd, J=5.6, 2.0 Hz, 1H), 6.03 (s, 2H), 5.78 (d, J=2.0 Hz, 1H), 5.43 (dd, J=5.2, 1.2 Hz, 1H), 3.58 (dd, J=5.2, 3.2 Hz, 1H), 1.45 (dd, J=3.2, 1.2 Hz, 1H) ppm.

Step D: tert-butyl ((1S,1aS,6bS)-5-((2-aminopyridin-4-yl)oxy)-1a,6b-dihydro-1H-cyclopropa[b]benzofuran-1-yl)carbamate

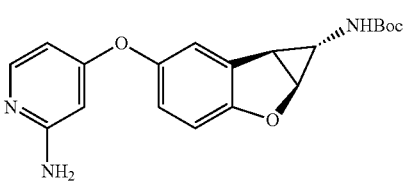 [SMILES: CC(C)(C)OC(=O)N[C@@H]1[C@H]2Oc3ccc(Oc4ccnc(N)c4)cc3[C@@H]12]

A mixture of the product of Step C (200 mg, 0.53 mmol) in n-BuOH (10 mL) was refluxed for 5 h. The reaction was concentrated and directly purified by column chromatography (petroleum ether/EtOAc 1:2 200 mL) and further purified by prep-HPLC to afford the product (45 mg, 26%) as a white solid.

Step E: 4-(((1S,1aS,6bS)-1-amino-1a,6b-dihydro-1H-cyclopropa[b]benzofuran-5-yl)oxy) pyridin-2-amine hydrochloride

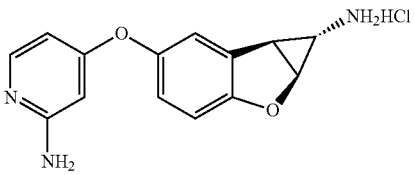

A mixture of the product of Step D (45 mg, 0.13 mmol) in HCl (g)/EtOAc (6M, 5 mL) was stirred at room temperature for 30 min. The reaction mixture was concentrated to afford the product (40 mg, 100%) as a white solid. The crude product was directly used in the next step.

Step F: N-((1S,1aS,6bS)-5-((2-aminopyridin-4-yl)oxy)-1a,6b-dihydro-1H-cyclopropa[b]benzofuran-1-yl)-4-((4-ethylpiperazin-1-yl)methyl)-3-(trifluoromethyl)benzamide (Compound 2.5)

A mixture of the product of Step E (40 mg, 0.14 mmol), 4-((4-ethylpiperazin-1-yl)methyl)-3-(trifluoromethyl)benzoic acid (49 mg, 0.154 mmol), HATU (64 mg, 0.168 mmol) and DIEA (72 mg, 0.56 mmol) in DMF (2 mL) was stirred at room temperature for 2 hours. The reaction was concentrated and water (10 mL) was added to the residue. The precipitate was collected and purified by prep-HPLC to get the title compound (25 mg, 32%) as a white solid. $^1$H NMR (400 MHz, CD$_3$OD) δ 8.10 (s, 1H), 8.00 (d, J=8.0 Hz, 1H), 7.85 (d, J=8.0 Hz, 1H), 7.70 (d, J=7.2 Hz, 1H), 7.21 (d, J=2.0 Hz, 1H), 6.92-6.84 (m, 2H), 6.53 (dd, J=7.2, 2.4 Hz, 1H), 6.05 (d, J=2.4 Hz, 1H), 4.98 (d, J=5.6 Hz, 1H), 3.75 (s, 2H), 3.55-3.35 (m, 2H), 3.12 (t, J=7.2 Hz, 2H), 3.07-2.89 (m, 5H), 2.50-2.35 (m, 3H), 1.25 (t, J=7.2 Hz, 3H) ppm. MS: M/e 554 (M+1)$^+$ Compound 2.6: 4-((4-ethylpiperazin-1-yl)methyl)-N-((1S,1aS,6bS)-5-((2-oxo-1,2,3,4-tetrahydropyrido[2,3-d]pyrimidin-5-yl)oxy)-1a,6b-dihydro-1H-cyclopropa[b]benzofuran-1-yl)-3-(trifluoromethyl)benzamide

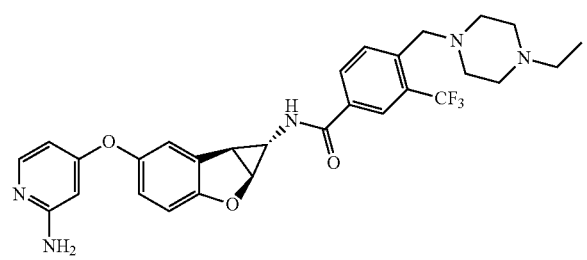 [SMILES: CCN1CCN(Cc2ccc(C(=O)N[C@@H]3[C@H]4Oc5ccc(Oc6ccnc(N)c6)cc5[C@@H]34)cc2C(F)(F)F)CC1]

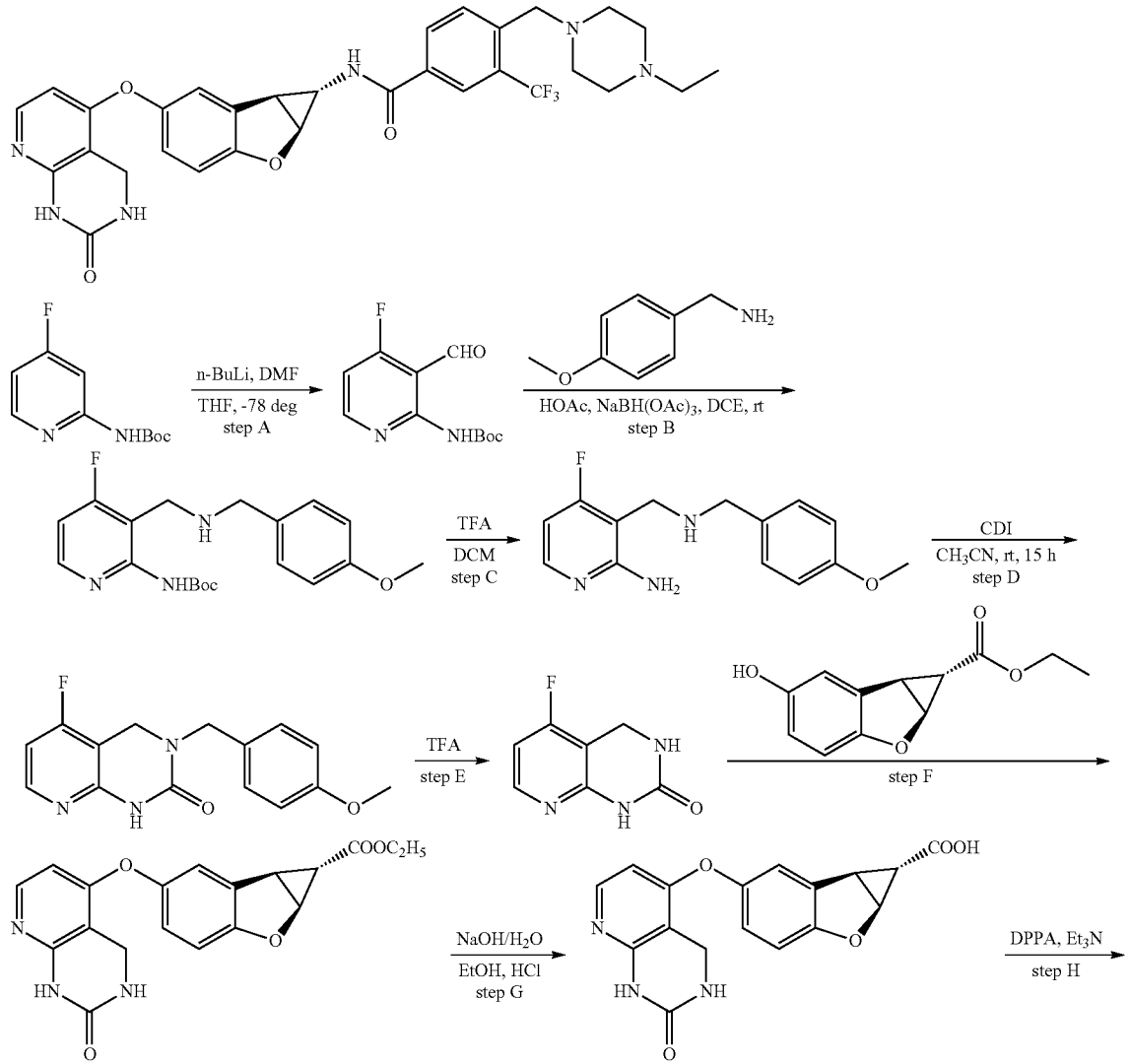

-continued

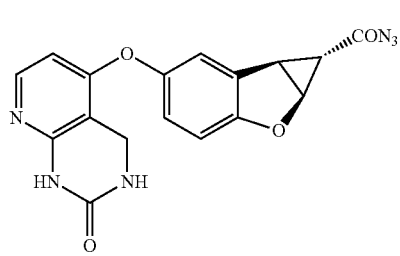 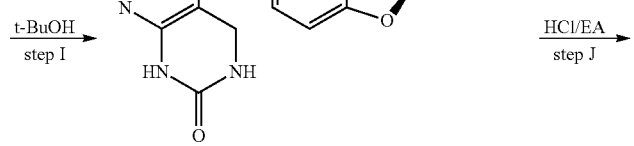

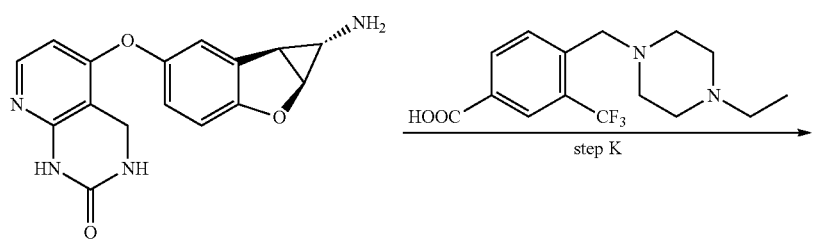

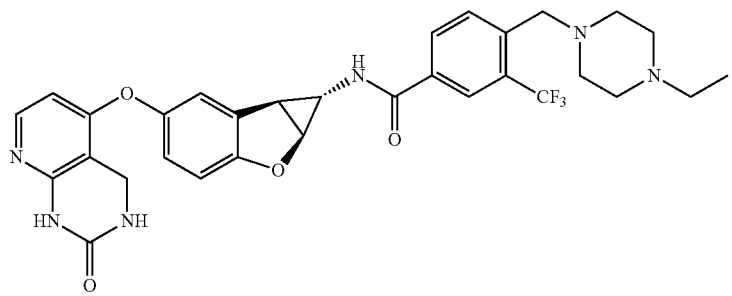

Step A: tert-butyl (4-fluoro-3-formylpyridin-2-yl)carbamate

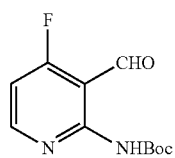 [SMILES: CC(C)(C)OC(=O)Nc1nccc(F)c1C=O]

To a solution of tert-butyl (4-fluoropyridin-2-yl)carbamate (10.0 g, 47.12 mmol) in 100 mL of tetrahydrofuran was added dropwise 49 mL of n-Butyllithium (2.4 M, 117.80 mmol) at −78° C. under N$_2$. The mixture was stirred for 1 hour at −78° C. Then DMF (6.88 g, 94.24 mmol) was added dropwise at −78° C. in 0.5 hour. The mixture was stirred at −70° C. for 1 hour (monitored by TLC) and quenched by 2N HCl (100 mL) at −60° C. Make sure the pH of mixture solution was under 6. Then the solution was warmed to rt, washed by water (200 mL), extracted with EtOAc (100 mL×3). The combined organic phase was dried over Na$_2$SO$_4$, concentrated and purified by silica gel column chromatography (eluting with PE:EA=1:1) to get the title compound (5.0, yield: 45%) as a white solid. $^1$H NMR (400 MHz, CDCl$_3$) δ 10.54 (s, 1H), 10.37 (s, 1H), 8.62 (dd, J=8.4, 5.6 Hz, 1H), 6.80 (dd, J=10.0, 5.6 Hz, 1H), 1.55 (s, 9H).

Step B: tert-butyl (4-fluoro-3-(((4-methoxybenzyl)amino)methyl)pyridin-2-yl)carbamate

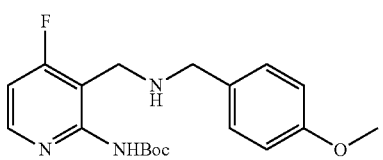 [SMILES: COc1ccc(CNCc2c(F)ccnc2NC(=O)OC(C)(C)C)cc1]

To the solution of the product of Step A (6.0 g, 24.98 mmol) and (4-methoxyphenyl)methanamine (4.11 g, 29.98 mmol) in 1,2-dichloroethane (60 mL) was added acetic acid (1.5 g, 24.98 mmol). The solution was stirred at room temperature for 10 min. To this solution was added NaHB(OAc)$_3$ (26.47 g, 124.90 mmol). The solution was stirred at room temperature for 15 hours. TLC (PE/EA=1/1) showed the reaction was completed. The resulting solution was quenched by NaHCO$_3$ aqueous solution, extracted with DCM (100 mL×3). The combined organic layers were dried over Na$_2$SO$_4$, concentrated and purified by silica gel column chromatography (eluting with PE:EA=1:1) to get the title compound (6 g, yield: 67%) as yellow oil. MS: M/e 362 (M+1)$^+$.

Step C: 4-fluoro-3-(((4-methoxybenzyl)amino)methyl)pyridin-2-amine

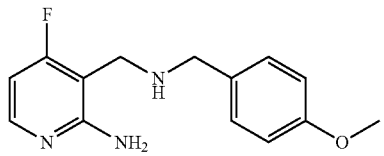 [SMILES: COc1ccc(CNCc2c(F)ccnc2N)cc1]

To the solution of the product of Step B (6 g, 16.60 mmol) in DCM (10 mL) was added TFA (20 mL). The solution was stirred at room temperature for 5 hours. TLC (DCM/MeOH=20/1) showed the reaction was completed. The resulting solution was concentrated under reduced pressure, the residue was neutralized by NaHCO$_3$ aqueous solution till pH=7-8, then extracted with DCM (50 mL×3). The combined organic layer was dried over Na$_2$SO$_4$, concentrated and purified by silica gel column chromatography (weight of silica: 50 g, eluting with DCM/MeOH=20:1) to get the title compound (2.4 g, yield=56%) as yellow oil. MS: M/e 262 (M+1)$^+$.

Step D: 5-fluoro-3-(4-methoxybenzyl)-3,4-dihydropyrido[2,3-d]pyrimidin-2(1H)-one

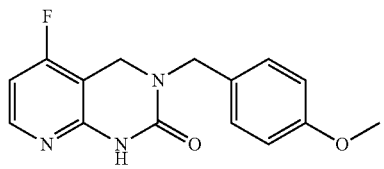 [SMILES: COc1ccc(CN2Cc3c(F)ccnc3NC2=O)cc1]

A mixture of the product of Step C (2.4 g, 9.19 mmol), CDI (4.47 g, 27.56 mmol) in CH$_3$CN (20 mL) was stirred at 50° C. under N$_2$ for 2 hours. TLC (PE/EA=1/1) showed the reaction was completed. The resulting solution was filtered, the solid was washed by water (10 mL) followed by methanol (10 mL) to get the title compound (1.42 g, yield: 57%) as a white solid. MS: M/e 288 (M+1)$^+$.

Step E: 5-fluoro-3,4-dihydropyrido[2,3-d]pyrimidin-2(1H)-one

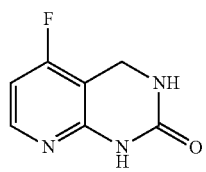 [SMILES: O=C1NCc2c(F)ccnc2N1]

The product of Step D (1.42 g, 4.94 mmol) was dissolved in TFA (5 mL) in sealing tube. The solution was stirred at 85° C. overnight. The resulting solution was cooled, concentrated under reduced pressure. The residue was neutralized by 2N NaOH aqueous solution till pH=7. The mixture was filtered, the solid was dried to get the title compound (825 mg, yield: 98%) as a white solid. $^1$H NMR (400 MHz, DMSO) δ 9.76 (s, 1H), 8.08 (dd, J=8.8, 5.6 Hz, 1H), 7.10 (s, 1H), 6.84 (dd, J=8.8, 5.6 Hz, 1H), 4.36 (s, 2H) ppm. MS: M/e 168 (M+1)$^+$.

Step F: (1S,1aS,6bR)-ethyl 5-((2-oxo-1,2,3,4-tetrahydropyrido[2,3-d]pyrimidin-5-yl)oxy)-1a,6b-dihydro-1H-cyclopropa[b]benzofuran-1-carboxylate

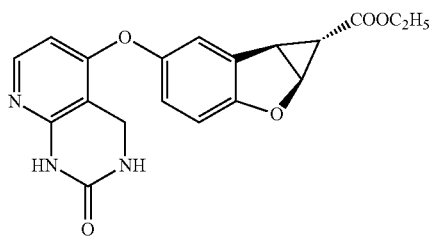

A mixture of the product of Step E (825 mg, 4.94 mmol), (1S,1aS,6bR)-ethyl 5-hydroxy-1a,6b-dihydro-1H-cyclopropa[b]benzofuran-1-carboxylate (the product of Step G in synthesis of Intermediate I, 1.09 g, 4.94 mmol) and Potassium tert-butoxide (581 mg, 5.19 mmol) in DMF (15 mL) was stirred at 120° C. for 2 hours (monitored by LC_MS). The resulting solution was concentrated under reduced pressure to remove excess solvent, the residue was washed by water (5 mL), the black solid was formed and filtered to get the crude product (1.8 g, yield: 100%) which was used in next step directly. MS: M/e 368 (M+1)$^+$.

Step G: (1S,1aS,6bR)-5-((2-oxo-1,2,3,4-tetrahydropyrido[2,3-d]pyrimidin-5-yl)oxy)-1a,6b-dihydro-1H-cyclopropa[b]benzofuran-1-carboxylic acid

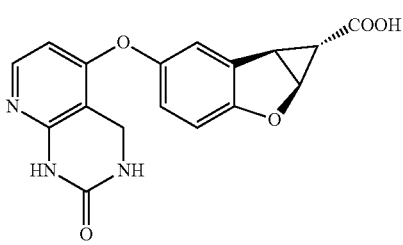

The product of Step F (1.8 g, 4.89 mmol) was diluted in ethanol (20 mL), added NaOH (392 mg, 9.80 mmol) in H$_2$O (2 mL) dropwise. The solution was stirred at room temperature for 2 hours, then added HCl (2 mol/L) aqueous solution till pH=5~6. The resulting solution was concentrated and the residue was washed by water (5 mL). The solid was formed and filtered to get the title compound (1.29 g, yield: 77%) as a brown solid, which was used into next step directly. MS: M/e 340 (M+1)$^+$.

Step H: (1S,1aS,6bR)-5-((2-oxo-1,2,3,4-tetrahydro-pyrido[2,3-d]pyrimidin-5-yl)oxy)-1a,6b-dihydro-1H-cyclopropa[b]benzofuran-1-carbonyl azide

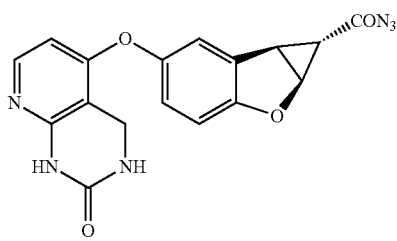

To a 0° C. solution of the product of Step G (500 mg, 1.47 mmol) in 1,4-dioxane (10 mL) was added Et₃N (371 mg, 3.68 mmol) followed by DPPA (486 mg, 1.77 mmol). The resulted mixture was warmed to ambient temperature and stirred for 5 hours under $N_2$. The resulting solution was poured into water (20 mL), extracted with DCM (10 mL×3). The combined organic layer dried over $Na_2SO_4$ was concentrated to get crude title compound (530 mg, yield: 99%) as a brown solid, which was used in next step directly. MS: M/e 365 (M+1)⁺.

Step I: tert-butyl ((1S,1aS,6bS)-5-((2-oxo-1,2,3,4-tetrahydropyrido[2,3-d]pyrimidin-5-yl)oxy)-1a,6b-dihydro-1H-cyclopropa[b]benzofuran-1-yl)carbamate

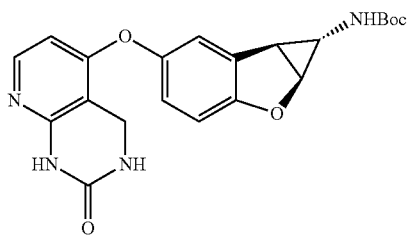

The solution of the product of Step H (530 mg, 1.47 mmol) in t-BuOH (10 mL) was stirred at reflux for 3 hours (monitored by LC-MS). The resulting solution was filtered, the filtrate was concentrated and the residue (180 mg) was used in next step directly. MS: M/e 411 (M+1)⁺.

Step J: 5-(((1S,1aS,6bS)-1-amino-1a,6b-dihydro-1H-cyclopropa[b]benzofuran-5-yl)oxy)-3,4-dihydro-pyrido[2,3-d]pyrimidin-2(1H)-one

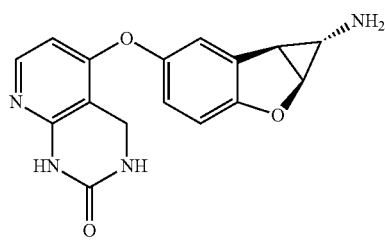

To a 6 N HCl/EA (5 mL) solution was added the solution of the product of Step H (180 mg, 0.44 mmol) in EA (5 mL) dropwise. The final solution was stirred at room temperature for 2 hours (monitored by LC-MS). The resulting mixture was filtered. The solid was diluted in water (5 mL), neutralized by 2N NaOH aqueous solution till pH=7-8, then extracted with DCM (5 mL×3). The combined organic layer was dried over $Na_2SO_4$, filtered and concentrated to get title compound (54 mg, 40%) as a yellow solid. MS: M/e 311 (M+1)⁺.

Step K: 4-((4-ethylpiperazin-1-yl)methyl)-N-((1S,1aS,6bS)-5-((2-oxo-1,2,3,4-tetrahydropyrido[2,3-d]pyrimidin-5-yl)oxy)-1a,6b-dihydro-1H-cyclopropa[b]benzofuran-1-yl)-3-(trifluoromethyl)benzamide (Compound 2.6)

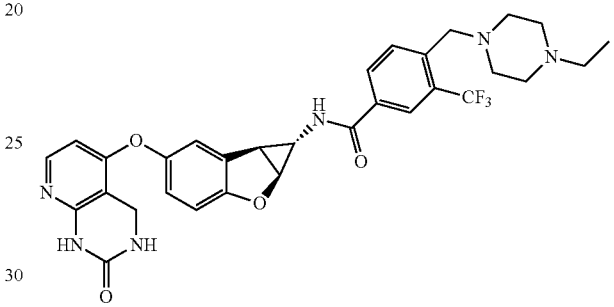

A mixture of the product of Step J (27 mg, 0.09 mmol), 4-((4-ethylpiperazin-1-yl)methyl)-3-(trifluoromethyl)benzoic acid (23 mg, 0.07 mmol), HATU (28 mg, 0.09 mmol) and DIPEA (35 mg, 0.27 mmol) in DMF (5 mL) was stirred at room temperature for 1.5 hours (monitored by LC-MS). The resulting solution was concentrated and purified by prep-HPLC to get title compound (930 mg, yield: 75%) as a white solid. ¹H NMR (400 MHz, DMSO-d6) δ 9.55 (s, 1H), 9.31 (s, 1H—CF₃COOH), 8.99 (d, J=3.2 Hz, 1H), 8.19 (s, 1H), 8.14 (d, J=8.0 Hz, 1H), 7.92 (d, J=6.0 Hz, 1H), 7.89 (d, J=8.0 Hz, 1H), 7.28 (s, 1H), 7.05 (s, 1H), 7.00-6.91 (m, 2H), 6.15 (d, J=6.0 Hz, 1H), 5.08 (d, J=5.6 Hz, 1H), 4.41 (s, 2H), 3.77 (s, 2H), 3.46 (d, J=12.4 Hz, 2H), 3.21-3.12 (m, 2H), 3.10 (dd, J=5.6, 2.0 Hz, 1H), 3.07-2.96 (m, 2H), 2.92 (d, J=12.4 Hz, 2H), 2.59-2.53 (m, 1H), 2.41 (t, J=11.6 Hz, 2H), 1.21 (t, J=7.6 Hz, 3H) ppm. MS: M/e 609 (M+1)⁺.

Compound 2.7 was prepared according to the procedures described for Compound 2.6 under appropriate conditions that could be recognized by one skilled in the art.

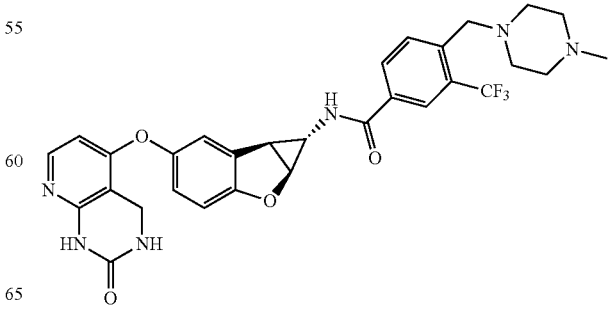

¹H NMR (400 MHz, DMSO-d6) δ 9.55 (s, 1H), 9.48 (s, 1H—CF₃COOH), 8.99 (d, J=3.6 Hz, 1H), 8.19 (s, 1H), 8.14 (d, J=8.4 Hz, 1H), 7.92 (d, J=6.0 Hz, 1H), 7.87 (d, J=8.4 Hz, 1H), 7.28 (s, 1H), 7.05 (s, 1H), 7.01-6.90 (m, 2H), 6.15 (d, J=6.0 Hz, 1H), 5.08 (d, J=6.0 Hz, 1H), 4.41 (s, 2H), 3.76 (s, 2H), 3.40 (d, J=12.0 Hz, 2H), 3.13-2.98 (m, 3H), 2.90 (d, J=12.0 Hz, 2H), 2.81 (s, 3H), 2.59-2.53 (m, 1H), 2.39 (t, J=11.46 Hz, 2H) ppm. MS: M/e 595 (M+1)⁺.

Raf IC₅₀ Assay Protocol

Compounds disclosed herein were tested against B-Raf (V600E) (PV3849, from Invitrogen) or C-Raf (Y340D/Y341D) (PV3805, from Invitrogen) in a time-resolved fluorescence energy transfer assay. The assay was carried out in reactions (10 μL) containing 0.0625 nM B-Raf or 0.5 nM C-Raf, 25 mM Tris pH7.4, 10 mM MgCl₂, 0.5 mM EGTA, 0.5 mM Na₃VO4, 5 mM beta-glycerophosphate, 0.01% Triton X-100, 2.5 mM DTT, 0.1% BSA, 0.1 mM ATP, 13.7 nM GST-tagged MEK1 (Full-length protein with K97R mutation, recombinant protein purified from bacterial expression system) and 0-5 μM compounds disclosed herein (final concentration of 1% DMSO). The enzyme was incubated with the compounds disclosed herein at room temperature for 60 minutes and the reactions were initiated by the addition of ATP and GST-MEK1. After reaction at room temperature for 60 minutes, an equal volume of stop/detection solution was added according to the manufacture's instruction (CisBio Bioassays). The stop/detection solution contained Eu³⁺ cryptate-conjugated anti-phospho MEK1/2 (Ser217/221) rabbit polyclonal antibody and d2-conjugated anti-GST mouse monoclonal antibody in buffer containing 25 mM Tris pH7.4, 400 mM KF, 50 mM EDTA, 0.01% BSA and 0.01% Triton X-100. Plates were sealed and incubated at room temperature for 2 hours, and the TR-FRET signals (ratio of fluorescence emission at 665 nm over emission at 620 nm with excitation at 337 nm wavelength) were recorded on a PHERAstar FS plate reader (BMG Labtech). Phosphorylation of MEK1 led to the binding of anti-phospho-MEK1/2 antibody to GST-MEK1 protein that place fluorescent donor (Eu³⁺ crypate) in close proximity to the accepter d2 on the anti-GST antibody, thus resulting in a high degree of fluorescence resonance energy transfer from the donor fluorophore (at 620 nm) to the acceptor fluorophore (at 665 nm). Inhibition of RAF kinase activity resulted in decrease of the TR-FRET signal. The IC₅₀ for each compound was derived from fitting the dose-response % inhibition data to the four-parameter logistic model by Graphpad Prism software.

WT BRaf IC₅₀ Assay Protocol

Compounds disclosed herein were tested against wild type B-Raf (PV3848, from Invitrogen) in a time-resolved fluorescence energy transfer assay. The assay was carried out in reactions (10 μL) containing 0.5 nM B-Raf, 25 mM Tris pH7.4, 10 mM MgCl₂, 0.5 mM EGTA, 0.5 mM Na₃VO₄, 5 mM beta-glycerophosphate, 0.01% Triton X-100, 2.5 mM DTT, 0.1% BSA, 2.9 μM or 2.5 mM ATP, 10 nM GST-tagged MEK1 (Full-length protein with K97R mutation, recombinant protein purified from bacterial expression system) and 0-10 μM compounds disclosed herein (final concentration of 1% DMSO). The enzyme was incubated with the compounds disclosed herein at room temperature for 120 minutes and the reactions were initiated by the addition of ATP and GST-MEK1. After incubating at room temperature for 60 minutes, an equal volume of stop buffer containing 25 mM Tris pH7.4, 400 mM KF, 50 mM EDTA, 0.1% BSA, 0.01% Triton X-100, 1 test of Eu3+ Cryptate-conjugated rabbit polyclonal antibody anti-Phospho MEK1/2 (Ser217/221) and 1 test of d2-conjugated mouse monoclonal antibody anti-glutathione S-transferase was added to stop the reactions. Plates were sealed and incubated at room temperature for 1.5 hours, and then the TR-FRET signals were read on BMG PHERAstar FS instrument. The IC₅₀ for each compound was calculated by non linear regression by Graphpad Prism software.

EGFR Enzymatic Assay

Compounds disclosed herein were tested against WT EGFR kinase domain (aa.669-1210, Carna Biosciences, 08-115), EGFR T790M/L858R kinase domain (aa.669-1210, Carna Biosciences, 08-510) and EGFR L858R kinase domain (aa.669-1210, Carna Biosciences, 08-502) in assays based on time-resolved fluorescence-resonance energy transfer methodology. The assay was carried out in 384-well low volume black plate in a reaction mixture containing EGFR kinases, 20 LM for EGFR WT and T790M/L858R, and 125 LM for EGFR L858R), biotin-TK substrate and 0-5 LM compounds in buffer containing 50 mM HEPES pH7.5, 10 mM MgCl₂, 1 mM EGTA, 0.01% Brij-35, 2.5 mM DTT, 0.1% BSA. The kinase was incubated with the compounds disclosed herein at room temperature for 120 minutes and the reaction was initiated by the addition of ATP and biotin-TK substrate. After reaction at room temperature for 30 minutes, an equal volume of stop/detection solution was added according to the manufacture's instruction (CisBio Bioassays). The stop/detection solution contained TK-Antibody-Cryptate and Streptavidin-XL665 in buffer containing 25 mM Tris pH7.4, 400 mM KF, 50 mM EDTA, 0.01% BSA, 0.01% Triton X-100. Plates were sealed and incubated at room temperature for 1 hour, and the TR-FRET signals were read on BMG PHERAstar FS instrument. The IC₅₀ of an inhibitor was derived from fitting the % inhibition data at each compound concentration to the four-parameter logistic equation by Graphpad Prism software.

Compounds 1.1-1.78 and 2.1-2.7 inhibited BRAF and/or EGFR kinases with IC₅₀ values ranging from 0.01 nM to 10 μM.

TABLE 1

| | | | | IC₅₀s (nM) | | | |
|---|---|---|---|---|---|---|---|
| Compound No. | BRAF-V600E | CRAF | Braf-WT Km ATP | Braf-WT 2.5 mM ATP | EGFR-WT | EGFR-L858R | EGFR-L858R/T790M |
| 1.1 | 5.3 | 0.94 | 9.5 | 27 | 0.50 | 0.11 | 0.10 |
| 1.2 | 27 | | | | 249 | 292 | 813 |
| 1.3 | 7.1 | 1.9 | 14 | 36 | 0.70 | 0.079 | 0.088 |
| 1.4 | 8.1 | 1.5 | 7.9 | 31 | 1.4 | 0.46 | 2.3 |
| 1.5 | 12 | 2.1 | 15 | 39 | 2.3 | 1.0 | 7.1 |
| 1.6 | 1.7 | | | | 2.9 | 7.0 | 138 |
| 1.7 | 36 | 3.5 | 36 | 130 | 9.8 | 16 | 54 |
| 1.8 | 41 | 18 | 96 | 380 | 70 | 100 | 504 |

TABLE 1-continued

| | IC$_{50}$s (nM) | | | | | | |
|---|---|---|---|---|---|---|---|
| Compound No. | BRAF-V600E | CRAF | Braf-WT Km ATP | Braf-WT 2.5 mM ATP | EGFR-WT | EGFR-L858R | EGFR-L858R/T790M |
| 1.9 | 17 | | 32 | | 1.6 | 0.30 | 0.30 |
| 1.10 | 14 | | | | 1.6 | 0.67 | 3.1 |
| 1.11 | 5.9 | | | | 1.28 | 0.57 | 18 |
| 1.12 | 9 | 1.3 | 9.4 | 33 | 0.67 | 0.16 | 0.21 |
| 1.13 | 86 | | | | 59 | 11 | 47 |
| 1.14 | 20 | 1.7 | 20 | | 5.1 | 3.3 | 36 |
| 1.15 | 28 | 6.2 | 64 | 130 | 4.4 | 6.8 | 49 |
| 1.16 | 30 | | | | 4.2 | 5.8 | 30 |
| 1.17 | 10.4 | | | | 1.4 | 0.26 | 0.76 |
| 1.18 | 5.7 | | | | 0.70 | <0.25 | 0.65 |
| 1.19 | 5.4 | | | | 0.55 | 0.27 | 1.1 |
| 1.20 | 11 | 2.1 | 16 | | 1.3 | 0.27 | 0.42 |
| 1.21 | 8.8 | | | | 1.3 | 0.28 | 3.0 |
| 1.22 | 4.8 | | | | 0.80 | 0.23 | 0.47 |
| 1.23 | 5.4 | | | | 1.1 | 0.24 | 0.52 |
| 1.24 | 14 | 1.4 | 34 | | 2.7 | 1.2 | 8.1 |
| 1.25 | 0.71 | 0.25 | 1.4 | 3.4 | 0.48 | 0.15 | 1.2 |
| 1.26 | 2.2 | 0.52 | 5.7 | | 1.7 | 1.3 | 9.4 |
| 1.27 | 27.2 | 3 | 63 | 120 | 1.3 | 0.31 | 0.54 |
| 1.28 | | | | | 809 | 287 | 885 |
| 1.29 | 6.2 | 1.1 | 9.1 | | 0.61 | 0.14 | 0.30 |
| 1.30 | | | | | 0.69 | 0.46 | 2.7 |
| 1.31 | 15 | 0.78 | 10 | | 0.99 | 0.44 | 1.9 |
| 1.32 | 13 | 2.5 | 21 | | 1.5 | 0.47 | 1.3 |
| 1.33 | 16 | 0.47 | 35 | | 774 | 146 | 293 |
| 1.34 | 11 | | | | 254 | 29 | 119 |
| 1.35 | 1.2 | 0.33 | 4.4 | 12 | 18 | 9.7 | 47 |
| 1.36 | 1.4 | | 96% at 100 nM | | 93 | 60 | 538 |
| 1.37 | 7.5 | | 80% at 100 nM | | 1242 | 529 | >5000 |
| 1.38 | 4.7 | | 84% at 100 nM | | 425 | 79 | 3194 |
| 1.39 | 0.76 | 0.15 | 0.9 | | 75 | 30 | 692 |
| 1.40 | 8.1 | 0.64 | 5.7 | | 13 | 12 | 84 |
| 1.41 | 1.2 | | 100% at 100 nM | | 59 | 29 | 648 |
| 1.42 | 9.2 | | 102% at 100 nM | | 5.3 | 5.3 | 182 |
| 1.43 | 4.1 | 0.34 | 4.4 | | 13 | 11 | 38 |
| 1.44 | 4.8 | | 93% at 100 nM | | 243 | 63 | >5000 |
| 1.45 | 3.1 | | 101% at 100 nM | | 8.5 | 5.4 | 104 |
| 1.46 | 2.5 | | 1.4 | | 85 | 52 | 316 |
| 1.47 | 10 | 1.2 | 8.5 | | 1.4 | 0.39 | 6.6 |
| 1.48 | 16 | | | | 1.7 | 0.91 | 5.3 |
| 1.49 | 9.5 | 2.6 | 13 | | 5.1 | 4.6 | 38 |
| 1.50 | 11 | | | | 6.3 | 7.1 | 25 |
| 1.51 | 14 | 1.61 | 9.8 | | 1.1 | 0.24 | 0.21 |
| 1.52 | 14 | 2.5 | 15 | | 9.6 | 12 | 32 |
| 1.53 | 16 | | 86% at 100 nM | | 678 | 68 | 1144 |
| 1.54 | 4.9 | | 93% at 100 nM | | 326 | 152 | 757 |
| 1.55 | 18 | | | | 2.2 | 0.35 | 0.40 |
| 1.56 | 21 | | | | 2.5 | 0.40 | 0.47 |
| 1.57 | 6.4 | | | | 1.5 | 0.50 | 3.1 |
| 1.58 | 5.5 | | | | 1.2 | 0.31 | 1.8 |
| 1.59 | 1 | | | | 19 | 4.8 | 6.2 |
| 1.60 | 1.5 | | | | 3448 | 949 | 2551 |
| 1.61 | 1.5 | | | | 132 | 76 | 237 |
| 1.62 | 1.3 | | | | 42 | 28 | 114 |
| 1.63 | 2.5 | | | | 1140 | 296 | 234 |
| 1.64 | 12 | | | | 1.1 | <0.25 | 0.46 |
| 1.65 | 8.1 | | | | 1.9 | 1.1 | 11 |
| 1.66 | 3.6 | | | | 9.3 | 13 | 81 |
| 1.67 | 0.6 | | | | 385 | 182 | 1412 |
| 1.68 | 0.77 | | | | 98 | 71 | 95 |
| 1.69 | 2 | | | | 118 | 116 | 782 |
| 1.70 | 24 | | | | 628 | 230 | 1302 |
| 1.71 | 10 | | | | 2.7 | 2.1 | 21 |
| 1.72 | 7.7 | | | | 3.0 | 1.0 | 32 |
| 1.73 | 6.9 | | | | 1.8 | 0.91 | 34 |
| 1.74 | 10 | | | | 0.74 | 0.17 | 0.2 |
| 1.75 | 21 | | | | 1.3 | 0.26 | 0.18 |
| 1.76 | 3.7 | | | | 4.2 | 18 | 31 |
| 1.77 | 13 | | | | 19 | 9.5 | >50 |
| 1.78 | 10 | | | | 1.2 | 0.79 | 8.0 |
| 2.1 | 16 | 2.3 | 15 | | 1.8 | 0.38 | 0.25 |
| 2.2 | 11 | | | | 1.5 | 0.29 | 0.49 |
| 2.3 | 54 | 12 | 52 | | 7.1 | 4.7 | 22 |
| 2.4 | 49 | | | | 6.8 | 4.1 | 7.3 |

TABLE 1-continued

| | | | | IC$_{50}$s (nM) | | | |
|---|---|---|---|---|---|---|---|
| Compound No. | BRAF-V600E | CRAF | Braf-WT Km ATP | Braf-WT 2.5 mM ATP | EGFR-WT | EGFR-L858R | EGFR-L858R/T790M |
| 2.5 | 58 | | | | 4.1 | 0.47 | 0.82 |
| 2.6 | 17 | | | | 0.43 | 0.085 | 0.076 |
| 2.7 | 16 | | | | 0.67 | 0.15 | 0.084 |
| Intermediate I | 2839 | 277 | −2% at 100 nM | | | | |

What is claimed is:

1. A compound selected from compounds of Formula I:

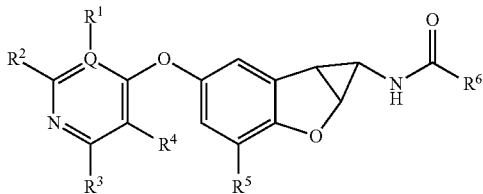

I or a stereoisomer thereof or a pharmaceutically acceptable salt thereof,
wherein:
Q is selected from C and N;
$R^1$, $R^2$, $R^3$ and $R^4$ which may be the same or different, are each selected from hydrogen, halogen, haloalkyl, alkyl, alkenyl, cycloalkyl, aryl, heterocyclyl, heteroaryl, alkynyl, —CN, —NR$^{10}$R$^{11}$, —OR$^{10}$, —COR$^{10}$, —CO$_2$R$^{10}$, —CONR$^{10}$R$^{11}$, —C(═NR$^{10}$)NR$^{11}$R$^{12}$, —NR$^{10}$COR$^{11}$, —NR$^{10}$CONR$^{11}$R$^{12}$, —NR$^{10}$CO$_2$R$^{11}$, —SO$_2$R$^{10}$, —NR$^{10}$SO$_2$NR$^{11}$R$^{12}$, and —NR$^{10}$SO$_2$R$^{11}$, wherein the alkyl, alkenyl, alkynyl, cycloalkyl, heteroaryl, aryl, and heterocyclyl are optionally substituted with at least one substituent $R^{13}$, or ($R^1$ and $R^2$), and/or ($R^3$ and $R^4$), together with the ring to which they are attached, form a fused ring selected from heterocyclyl, and heteroaryl rings optionally substituted with at least one substituent $R^{14}$;
provided that $R^1$ is absent when Q is N;
$R^5$ is selected from hydrogen, halogen and CH$_3$;
$R^6$ is selected from haloalkyl, alkyl, alkenyl, cycloalkyl, aryl, heterocyclyl, heteroaryl, alkynyl, wherein the alkyl, alkenyl, cycloalkyl, heteroaryl, aryl, and heterocyclyl are optionally substituted with at least one substituent $R^{15}$;
$R^{10}$, $R^{11}$, $R^{12}$, $R^{13}$ and $R^{14}$ are each selected from hydrogen, halogen, haloalkyl, alkyl, alkenyl, cycloalkyl, aryl, heteroaryl, heterocyclyl, alkynyl, oxo, —CN, —OR', —NR'R", —COR', —CO$_2$R', —CONR'R", —C(═NR')NR"R'", —NR'COR", —NR'CONR'R"', —NR'CO$_2$R", —SO$_2$R', —SO$_2$aryl, —NR'SO$_2$NR"R'", and NR'SO$_2$R", wherein R', R", and R'" are independently selected from H, haloalkyl, alkyl, alkenyl, alkynyl, cycloalkyl, heterocyclyl, aryl, and heteroaryl, or (R' and R"), and/or (R" and R'") together with the atoms to which they are attached, form a ring selected from heterocyclyl, and heteroaryl rings;
$R^{15}$ is selected from hydrogen, halogen, haloalkyl, alkyl, cycloalkyl, aryl, heteroaryl, heterocyclyl, —CN, —OR', —O—(CH$_2$)$_{0-2}$-(heterocyclyl), —NR'R", CH$_2$NR'R", C(Me)$_2$NR'R",

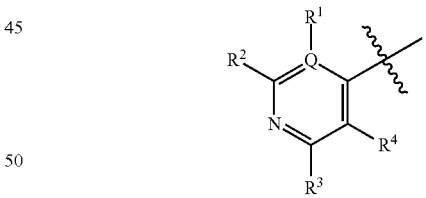

wherein R' and R" are independently selected from H, haloalkyl, alkyl, cycloalkyl, heterocyclyl, aryl, and heteroaryl, or (R' and R") together with the atoms to which they are attached, form a ring selected from heterocyclyl, and heteroaryl rings, wherein any of the alkyl, cycloalkyl, aryl, heteroaryl and heterocyclyl groups in $R^{15}$, R' and R" is optionally substituted.

2. The compound of claim 1, wherein Q is C.
3. The compound of claim 1, wherein $R^1$ is H.
4. The compound of claim 1, wherein $R^2$ is H.
5. The compound of claim 1, wherein both $R^1$ and $R^2$ are H.
6. The compound of claim 1, wherein $R^3$ is —NR$^{10}$R$^{11}$ or —CONR$^{10}$R$^{11}$.
7. The compound of claim 1, wherein $R^4$ is H.
8. The compound of claim 1, wherein $R^3$ is —NR$^{10}$R$^{11}$ or —CONR$^{10}$R$^{11}$, and $R^4$ is hydrogen.
9. The compound of claim 1, wherein $R^{10}$ and $R^{11}$ are each selected from H and alkyl.
10. The compound of claim 8, wherein the moiety

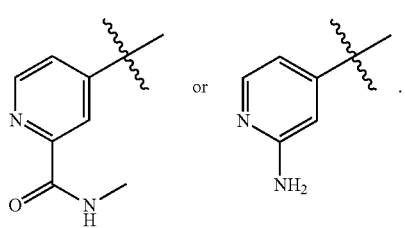 [SMILES: *c1ccnc(C(=O)NC)c1 ; *c1ccnc(N)c1]

in Formula I is:

11. The compound of claim 1, wherein $R^3$ and $R^4$, together with the ring to which they are attached, form a fused heterocyclyl or heteroaryl ring optionally substituted with at least one substituent $R^{14}$.

12. The compound of claim 1, wherein $R^3$ and $R^4$, together with the ring to which they are attached, form a fused heterocyclyl or heteroaryl ring selected from the group consisting of naphthyridinyl, pyridooxazinyl and pyridopyrimidinyl which are optionally hydrogenated and optionally substituted with at least one substituent $R^{14}$.

13. The compound of claim 12, wherein $R^{14}$ is oxo.
14. The compound of claim 1, wherein $R^5$ is H or $CH_3$.
15. The compound of claim 1, wherein $R^6$ is selected from alkyl, alkenyl, aryl and heteroaryl, wherein the alkyl, alkenyl, aryl and heteroaryl are optionally substituted with at least one substituent $R^{15}$.
16. The compound of claim 15, wherein $R^6$ is pyridinyl or furanyl substituted with one, two or three substituent $R^{15}$.
17. The compound of claim 1, wherein $R^{15}$ is selected from halogen, haloalkyl, optionally substituted alkyl, optionally substituted cycloalkyl, optionally substituted aryl, —OR', —O—$(CH_2)_{0-2}$-(optionally substituted heterocyclyl), —NR'R", $CH_2NR'R"$ and $C(Me)_2NR'R"$.
18. The compound of claim 17, wherein R' and R" are independently selected from H, alky and haloalkyl.
19. The compound of claim 17, wherein (R' and R") together with the atoms to which they are attached, form a ring selected from optionally substituted heterocyclyl, and optionally substituted heteroaryl rings.
20. The compound of claim 1, wherein the compound is in the following configuration:

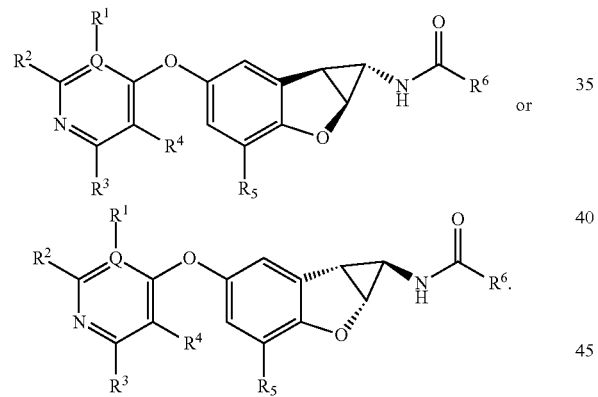

or

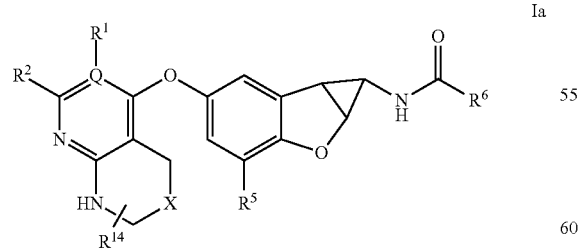

21. The compound of claim 1 having Formula Ia:

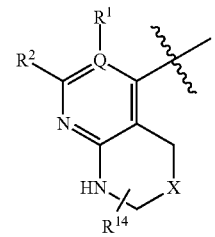

Ia or a stereoisomer thereof or a pharmaceutically acceptable salt thereof,
wherein
X is selected from the group consisting of $C(R^{16})_2$, $N(R^{16})$ and O;

$R^{16}$ is selected from the group consisting of H and alkyl; and $R^1$, $R^2$, $R^5$, $R^6$ and $R^{14}$ are defined as in claim 1.

22. The compound of claim 21, wherein $R^{14}$ is oxo.
23. The compound of claim 21, wherein the moiety

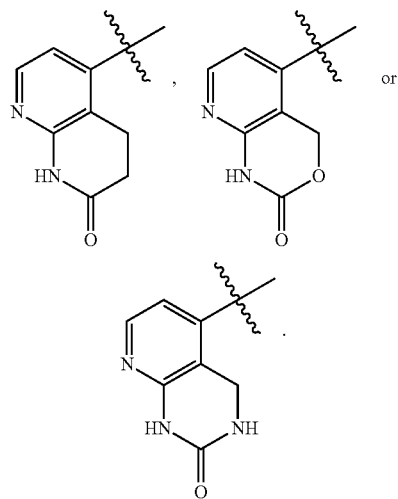

in Formula Ia is:

, or

.

24. The compound of claim 21, wherein the compound is in the following configuration:

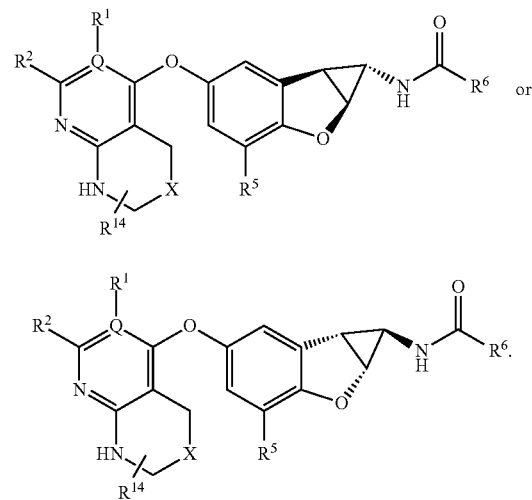

or

.

25. The compound of claim 21 having Formula Ia-1:

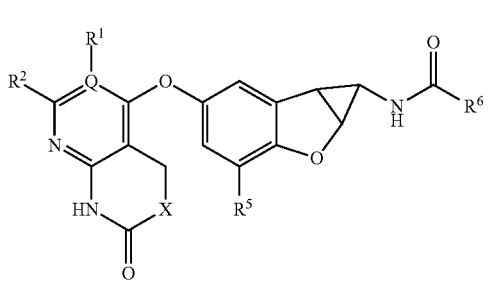

or a stereoisomer thereof or a pharmaceutically acceptable salt thereof,
wherein
$R^1$, $R^2$, $R^5$, $R^6$ and X are defined as in claim 21.

26. The compound of claim 21 having Formula Ia-1a:

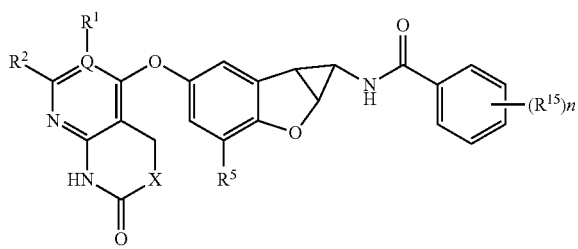

or a stereoisomer thereof or a pharmaceutically acceptable salt thereof,
wherein
n=1, 2 or 3; and
$R^1$, $R^2$, $R^5$, $R^{15}$ and X are defined as in claim 21.

27. The compound of claim having Formula Ia-1b:

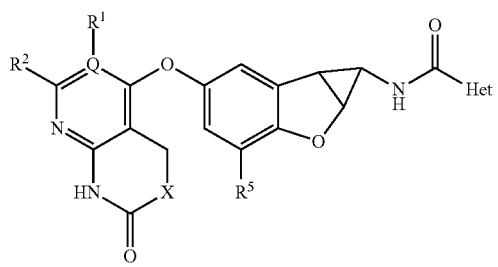

or a stereoisomer thereof or a pharmaceutically acceptable salt thereof,
wherein
Het is a 5- or 6-membered heteroaryl comprising 1, 2 or 3 heteroatoms selected from the group consisting of N, O and S and substituted with one, two or three substituent $R^{15}$; and
$R^1$, $R^2$, $R^5$, $R^{15}$ and X are defined as in claim 25.

28. The compound of claim 1 having Formula Ic:

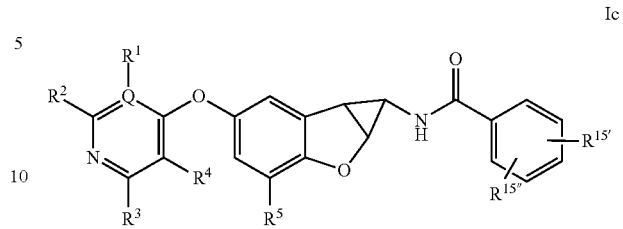

or a stereoisomer thereof or a pharmaceutically acceptable salt thereof,
wherein
$R^{15'}$ is —Y—NR'R";
Y is absent, or is -alkyl-, -cycloalkyl- or —O-alkyl-;
$R^{15''}$ is defined as $R^{15}$ in claim 1; and
$R^1$-$R^5$, R' and R" are defined as in claim 1.

29. The compound of claim 1 having Formula (II):

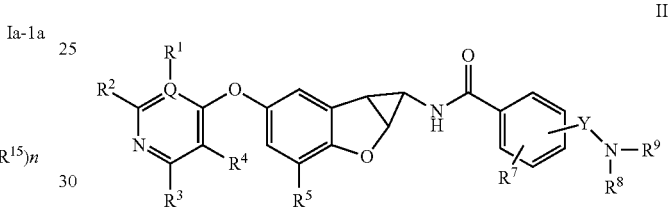

or a stereoisomer thereof or a pharmaceutically acceptable salt thereof,
wherein:
Q is selected from C and N;
Y is selected from $CH_2$, $C(CH_3)_2$, cyclopropyl, $CH_2$-alkyl, $CH_2$-cycloalkyl, $CH_2$-heterocyclyl, O-alkyl, O-cycloalkyl, O-heterocyclyl or absent;
$R^1$, $R^2$, $R^3$ and $R^4$ which may be the same or different, are each selected from hydrogen, halogen, haloalkyl, alkyl, alkenyl, cycloalkyl, aryl, heterocyclyl, heteroaryl, alkynyl, —CN, —$NR^{10}R^{11}$, —$OR^{10}$, —$COR^{10}$, —$CO_2R^{10}$, —$CONR^{10}R^{11}$, —$C(=NR^{10})NR^{11}R^{12}$, —$NR^{10}COR^{11}$, —$NR^{10}CONR^{11}R^{12}$, —$NR^{10}CO_2R^{11}$, —$SO_2R^{10}$, —$NR^{10}SO_2NR^{11}R^{12}$, and —$NR^{10}SO_2R^{11}$, wherein the alkyl, alkenyl, alkynyl, cycloalkyl, heteroaryl, aryl, and heterocyclyl are optionally substituted with at least one substituent $R^{13}$, or ($R^1$ and $R^2$), and/or ($R^3$ and $R^4$), together with the ring to which they are attached, form a fused ring selected from heterocyclyl, and heteroaryl rings optionally substituted with at least one substituent $R^{14}$;
provided that $R^1$ is absent when Q is N;
$R^7$ is selected from hydrogen, halogen, alkyl, cycloalkyl, haloalkyl, cyanoalkyl, halocycloalkyl and cyanocycloalkyl;
$R^8$ and $R^9$ which may be the same or different, are each selected from hydrogen, haloalkyl, alkyl, cycloalkyl, heterocyclyl, wherein the alkyl, cycloalkyl, and heterocyclyl are optionally substituted with at least one substituent $R^{13}$, or ($R^8$ and $R^9$) together with the ring to which they are attached, form a fused ring selected from heterocyclyl, and heteroaryl rings optionally substituted with at least one substituent $R^{14}$;
$R^{10}$, $R^{11}$, $R^{12}$, $R^{13}$ and $R^{14}$ are each selected from hydrogen, halogen, haloalkyl, alkyl, alkenyl, cycloalkyl, aryl, heteroaryl, heterocyclyl, alkynyl, oxo, —CN, —OR', —NR'R", —COR', —CO₂R', —CONR'R", —C(=NR')NR"R'", —NR'COR", —NR'CONR'R", —NR'CO₂R", —SO₂R', —SO₂aryl, —NR'SO₂NR"R'", and NR'SO₂R", wherein R', R", and R'" are independently selected from H, haloalkyl, alkyl, alkenyl, alkynyl, cycloalkyl, heterocyclyl, aryl, and heteroaryl, or (R' and R"), and/or (R" and R'") together with the atoms to which they are attached, form a ring selected from heterocyclyl, and heteroaryl rings.

30. A compound selected from

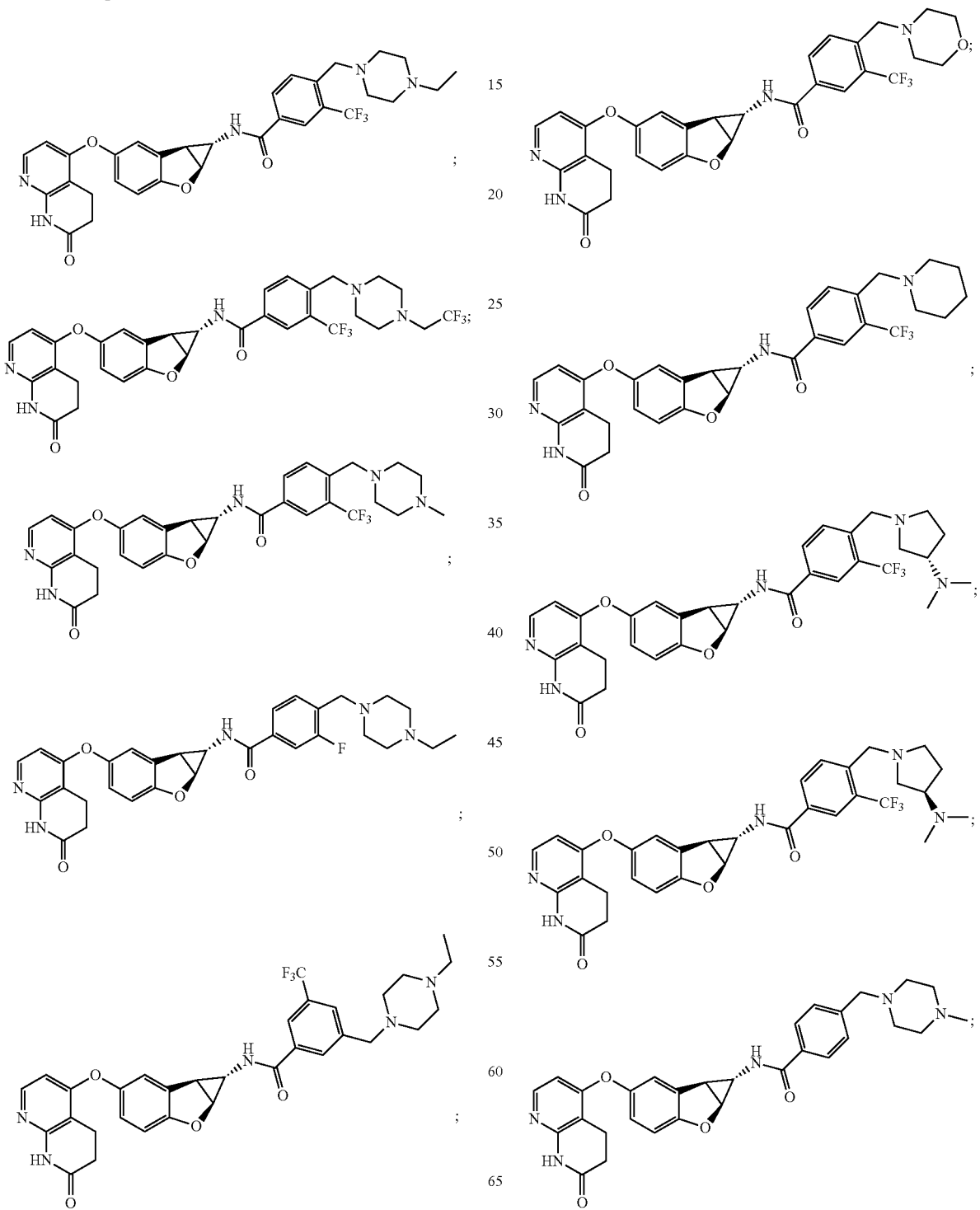

197
-continued
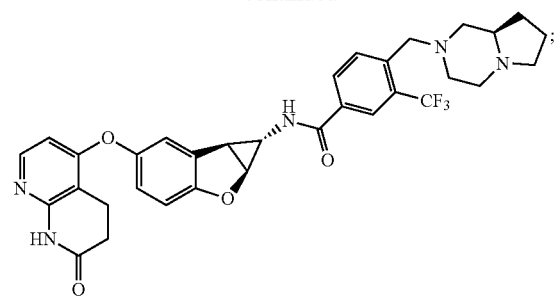
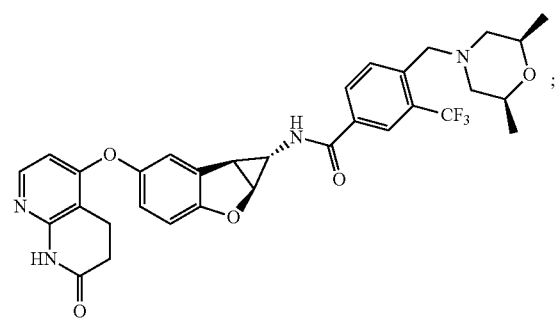
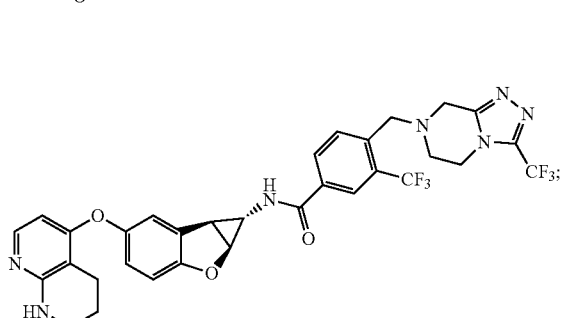
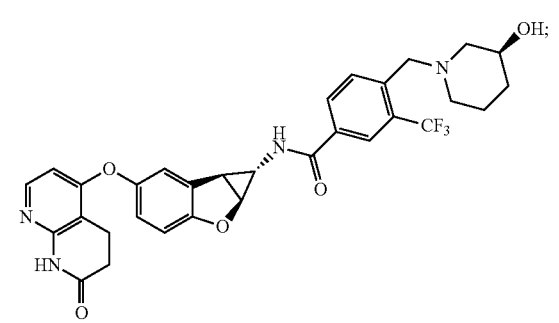
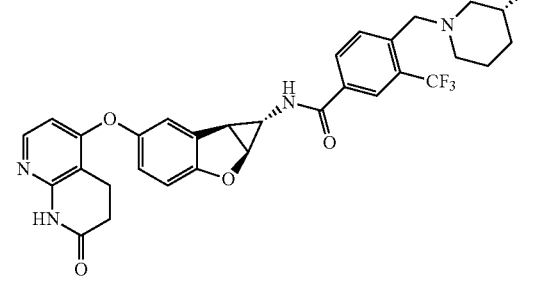
198
-continued
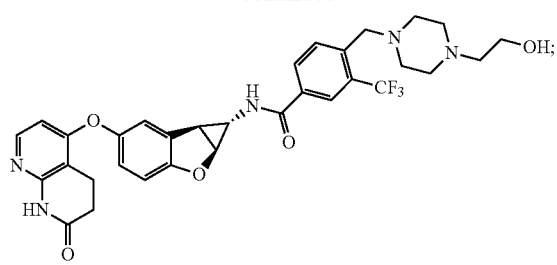
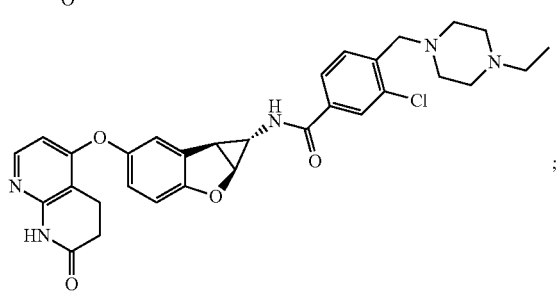
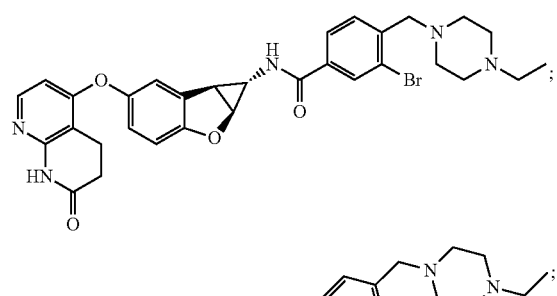
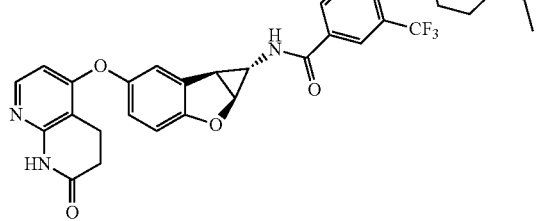
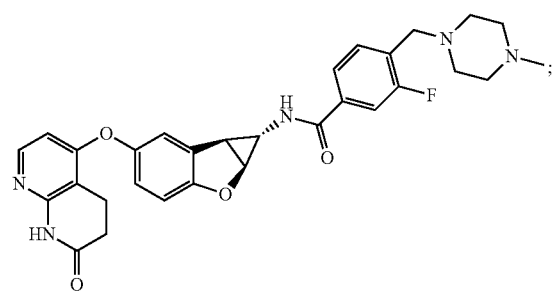
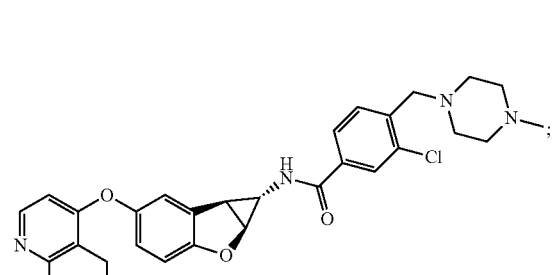

199
-continued
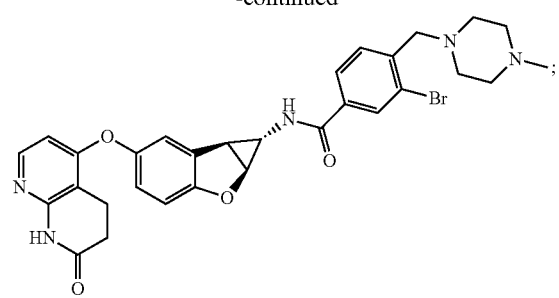
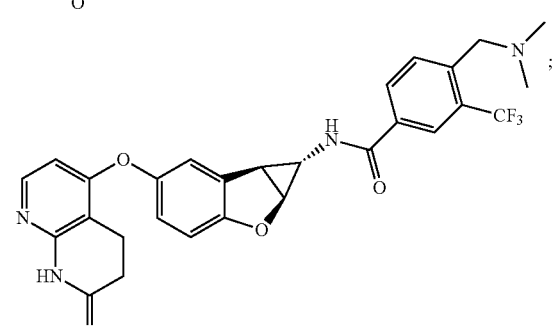
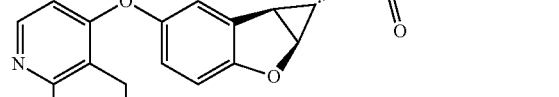
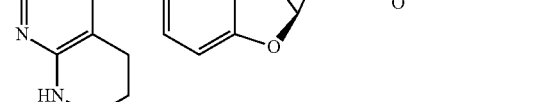
200
-continued
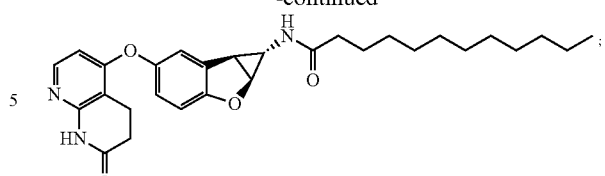
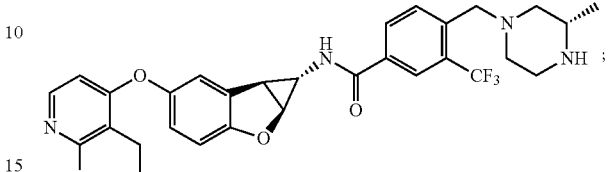
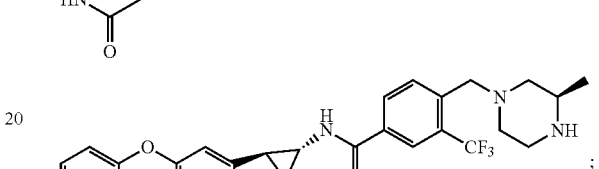
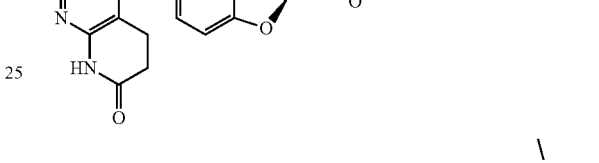
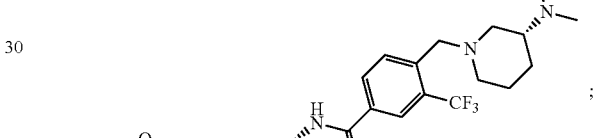
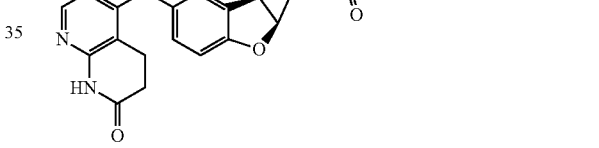
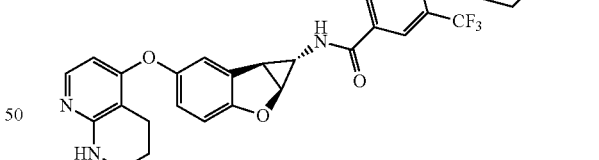
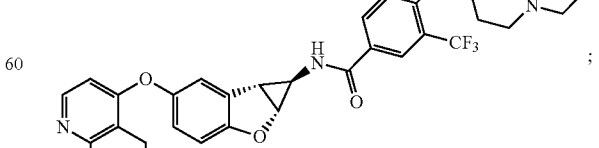

201
-continued
202
-continued
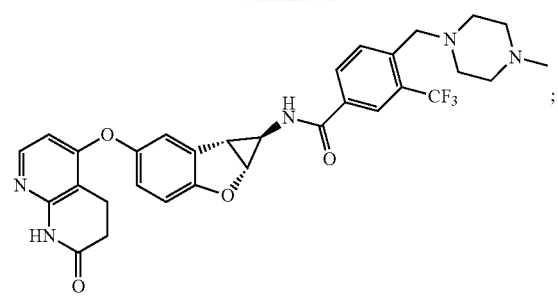
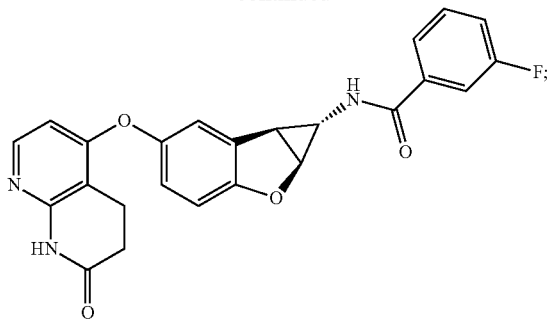

203
-continued
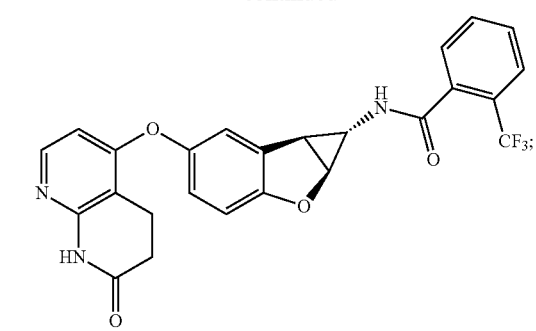
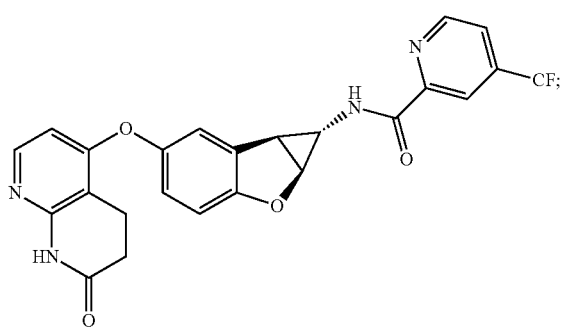
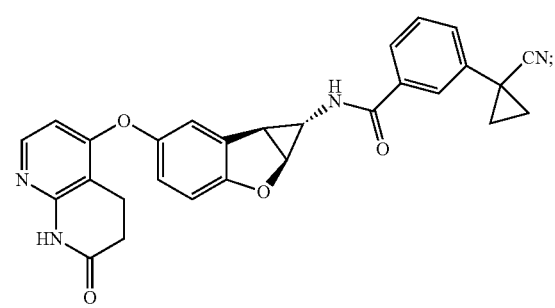
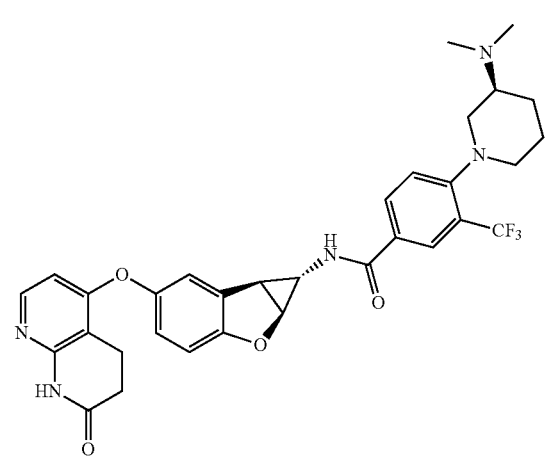
204
-continued
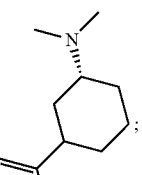
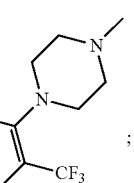
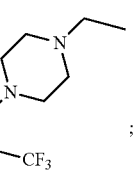
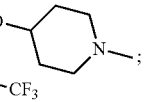

205
-continued
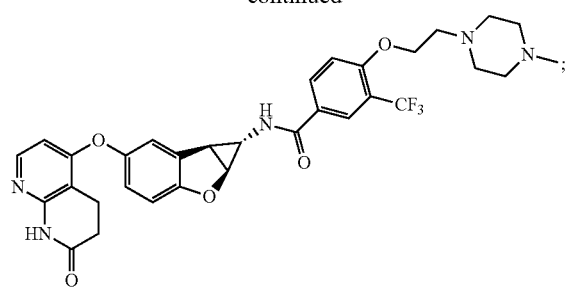
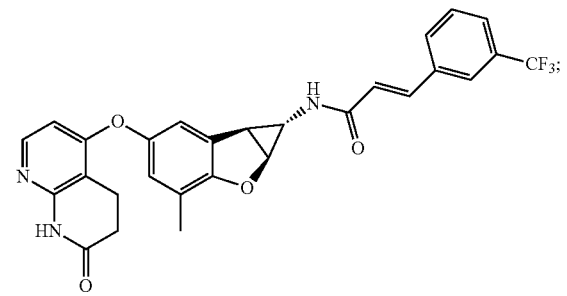
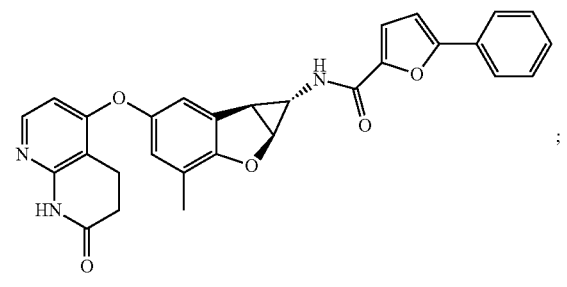
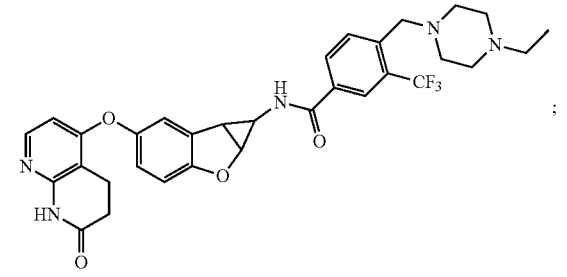
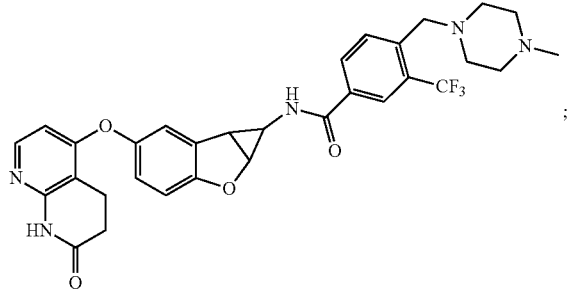
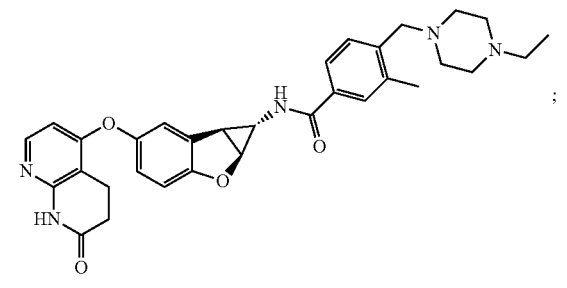
206
-continued
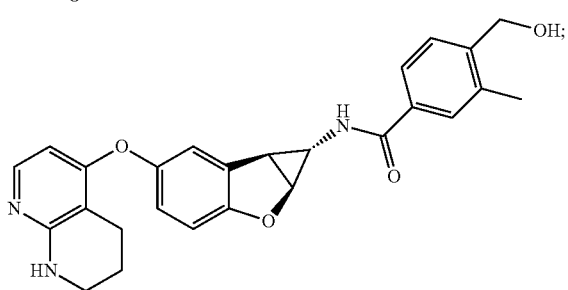
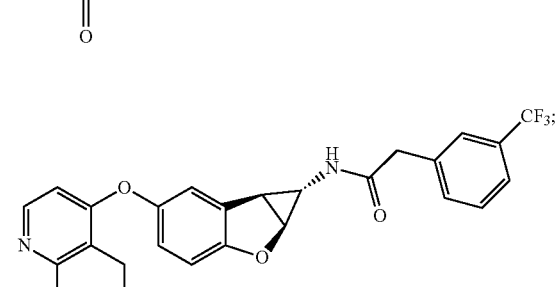
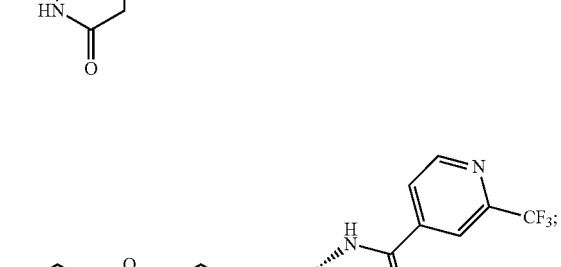
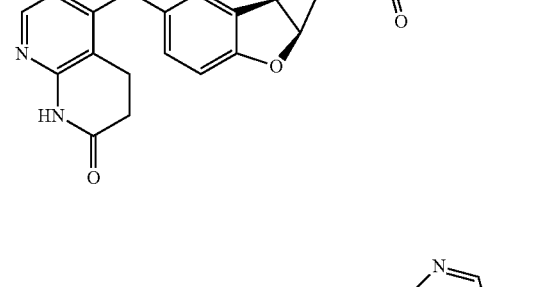
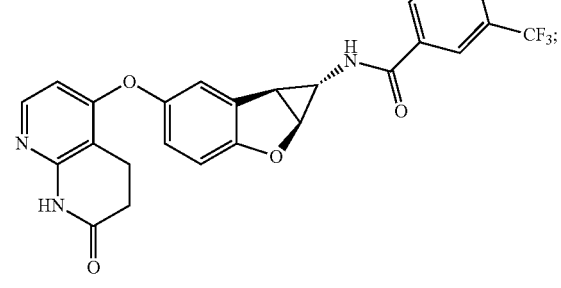

207
-continued
208
-continued
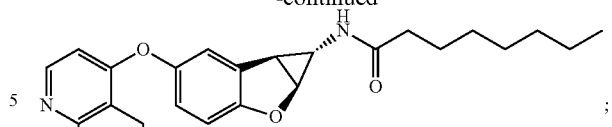
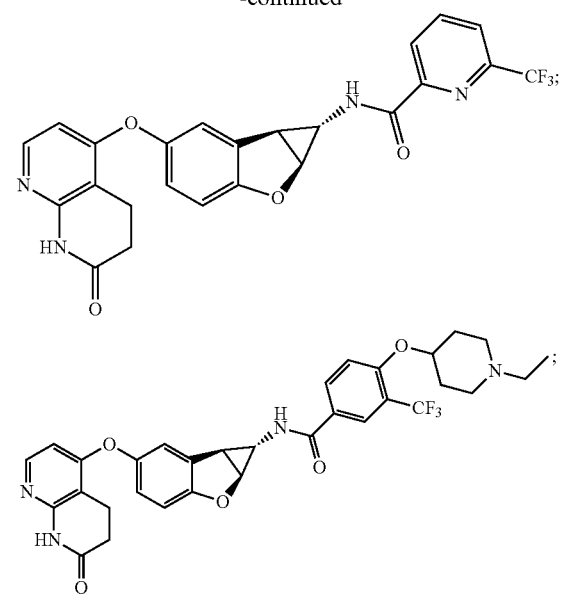
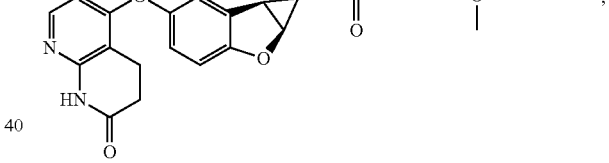
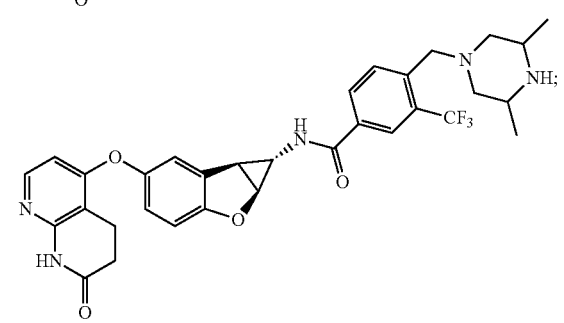
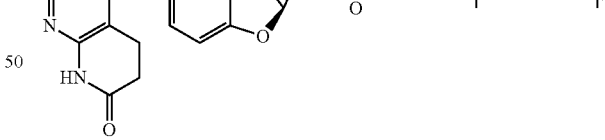
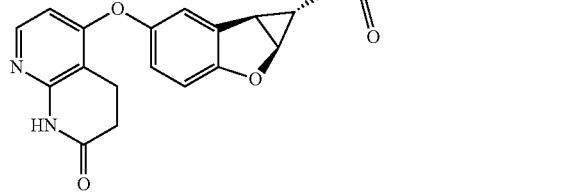
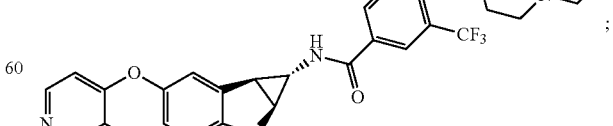
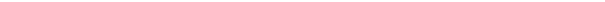

-continued

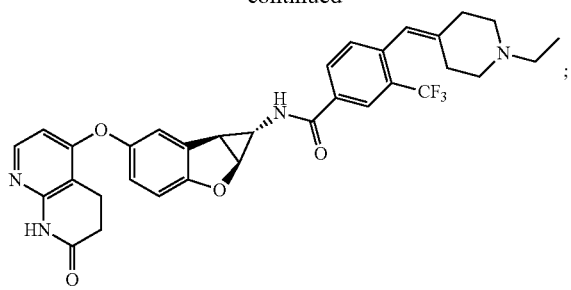
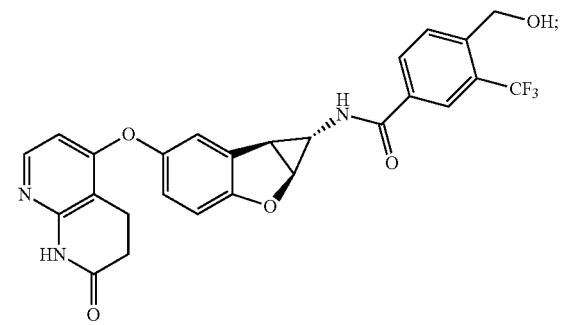
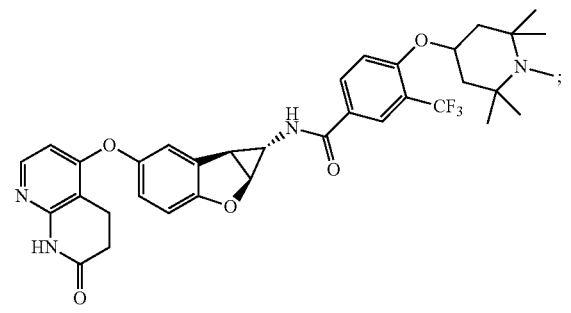
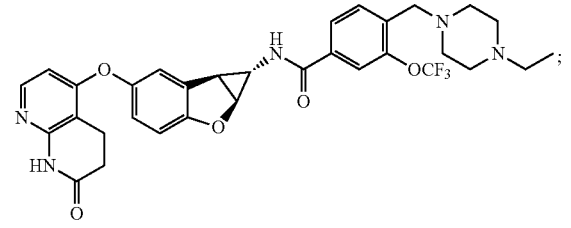
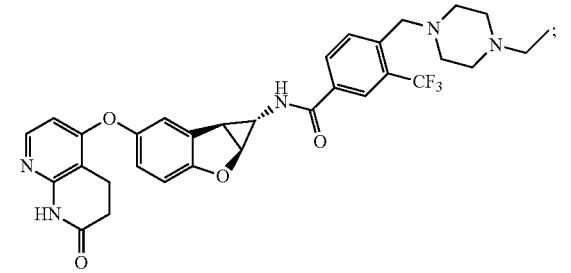
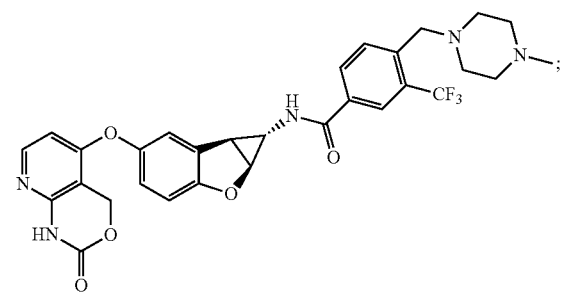

-continued

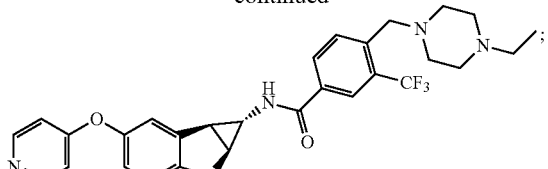
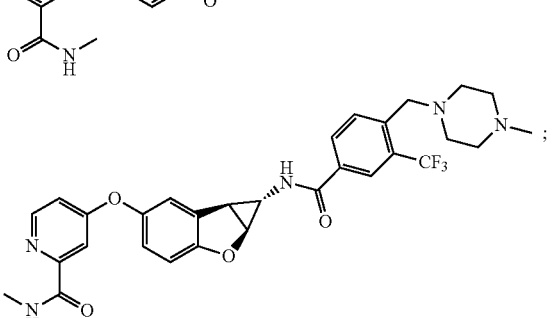
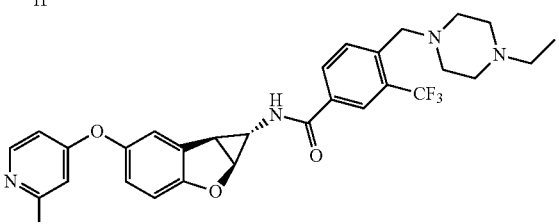
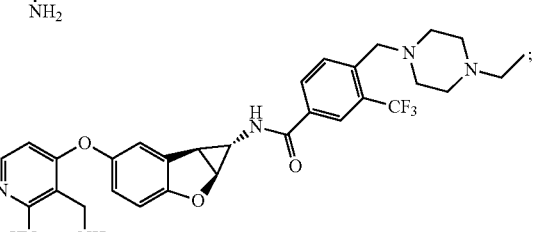
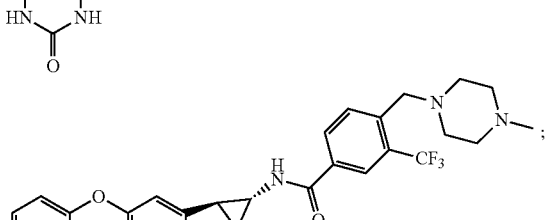
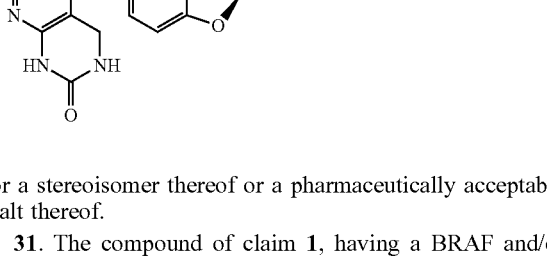

or a stereoisomer thereof or a pharmaceutically acceptable salt thereof.

31. The compound of claim 1, having a BRAF and/or EGFR-T790M-inhibiting activity corresponding to a $IC_{50}$ of 10 μM or less in a BRAF and/or EGFR-T790M enzyme assay.

32. A pharmaceutical composition comprising at least one pharmaceutically acceptable carrier and as an active ingredient a therapeutically effective amount of at least one compound of claim 1.

33. A method of treating cancer responsive to inhibition of BRAF and/or EGFR-T790M kinase comprising administering to a subject in recognized need thereof at least one compound of any one of claim 1 in an amount effective to inhibit said BRAF and/or EGFR-T790M kinase.

34. A method for making a medicament for inhibiting the activity of BRAF and/or EGFR-T790M kinase, comprising including into the medicament at least one compound of any one of claim 1.

35. The method of claim 33 wherein the cancer is selected from one or more of the group consisting of melanomas and thyroid cancers, Barret's adenocarcinoma, breast cancer, cervical cancer, cholangiocarcinoma, glioblastoma, colorectal cancer, gastric cancer, lung cancer, ovarian cancer, pancreatic cancer, prostate cancer, and hematologic cancers.

36. A compound having the following structure

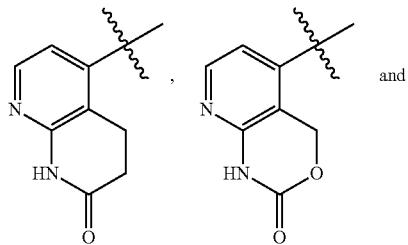

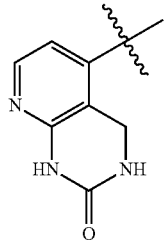

or a pharmaceutically acceptable salt or stereoisomer thereof.

37. A pharmaceutical composition comprising the compound of claim 36 and at least one pharmaceutically acceptable carrier.

* * * * *

UNITED STATES PATENT AND TRADEMARK OFFICE
CERTIFICATE OF CORRECTION

PATENT NO.       : 9,670,231 B2                                      Page 1 of 1
APPLICATION NO.  : 14/901556
DATED            : June 6, 2017
INVENTOR(S)      : Changyou Zhou et al.

It is certified that error appears in the above-identified patent and that said Letters Patent is hereby corrected as shown below:

On the Title Page

Left column, line reciting "(71) Applicant", please replace:
"Camana Bay, KY (US)" with -- Camana Bay (KY) --.

In the Claims

In Claim 36, Column 211, Line 12 to Column 212, Line 12, please replace:

" 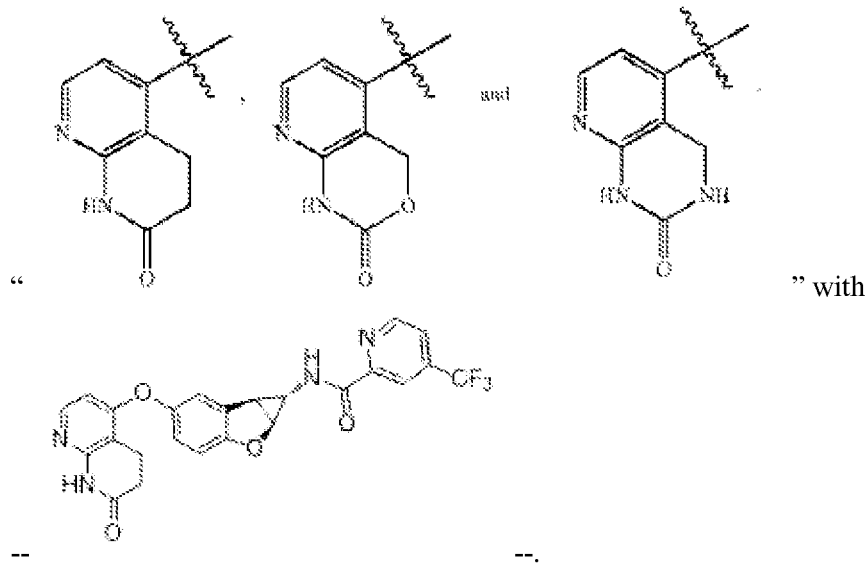 " with

-- --.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*